(12) United States Patent
Manoharan et al.

(10) Patent No.: US 8,507,455 B2
(45) Date of Patent: Aug. 13, 2013

(54) FOLATE CONJUGATES

(75) Inventors: Muthiah Manoharan, Weston, MA (US); Kallanthottathil G. Rajeev, Wayland, MA (US); Muthusamy Jayaraman, Sharon, MA (US); Jayaprakash K. Narayanannair, Wakefield, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 1154 days.

(21) Appl. No.: 12/328,537

(22) Filed: Dec. 4, 2008

(65) Prior Publication Data

US 2009/0247614 A1    Oct. 1, 2009

Related U.S. Application Data

(60) Provisional application No. 60/992,309, filed on Dec. 4, 2007, provisional application No. 61/013,597, filed on Dec. 13, 2007.

(51) Int. Cl.
    C12N 15/11    (2006.01)
    A61K 48/00    (2006.01)
    C07H 21/02    (2006.01)
    C07H 21/04    (2006.01)

(52) U.S. Cl.
    USPC ........................................ 514/44 A; 536/24.5

(58) Field of Classification Search
    USPC ............................ 536/23.1, 24.3, 24.33, 24.5
    See application file for complete search history.

(56) References Cited

U.S. PATENT DOCUMENTS

| | | | |
|---|---|---|---|
| 5,994,517 | A  | 11/1999 | Ts'o et al. |
| 6,906,182 | B2 | 6/2005  | Ts'o et al. |
| 7,109,165 | B2 | 9/2006  | Matulic-Adamic et al. |
| 7,491,805 | B2 | 2/2009  | Vargeese et al. |
| 2002/0086356 | A1 | 7/2002 | Tuschl et al. |
| 2003/0148928 | A1 | 8/2003 | Beigelman et al. |
| 2004/0110296 | A1 | 6/2004 | Vargeese et al. |
| 2004/0259247 | A1 | 12/2004 | Tuschl et al. |
| 2006/0148740 | A1 | 7/2006 | Platenburg |
| 2009/0325297 | A1 | 12/2009 | Tian et al. |

FOREIGN PATENT DOCUMENTS

| | | |
|---|---|---|
| EP | 0 957 107 A    | 11/1999 |
| WO | WO 90/12096    | 10/1990 |
| WO | WO 99/52932 A  | 10/1999 |
| WO | 9965925 A1     | 12/1999 |
| WO | WO 00/44914    | 8/2000  |
| WO | WO 02/085908 A | 10/2002 |
| WO | 02094185       | 11/2002 |
| WO | 2004024757 A2  | 3/2004  |
| WO | WO 2004/080406 A3 | 9/2004 |
| WO | WO 2004/090108 A2 | 10/2004 |
| WO | 2004094595 A2  | 11/2004 |
| WO | WO 2006/020768 A | 2/2006 |
| WO | WO 2006/078278 A | 7/2006 |

OTHER PUBLICATIONS

Kim et al. (Journal of Controlled Release, 2005 vol. 104:223-232).*

Biessen, E.A., et al.: "The Cholesterol Derivative of a Triantennary Galactoside with High Affinity for Hepatic Asialoglycoprotein Receptor: A Potent Cholesterol Lowering Agent", Journal of Medicinal Chemistry, vol. 38(11), 1995, pp. 1846-1852.

Biessen, Erik A. L., et al.: "Synthesis of Cluster Galactosides with High Affinity for the Hepatic Asialoglycoprotein Receptor", Journal of Medicinal Chemistry, vol. 38(9), 1995, pp. 1538-1546.

Choi, Youngseon, et al.: "Targeting Cancer Cells with DNA-Assembled Dendrimers: A Mix and Match Strategy for Cancer", Cell Cycle, vol. 4(5), 2005, pp. 669-671.

Crossman, Arthur Jr., et al.: "Synthesis of Some Second-Generation Substrate Analogues of Early Intermediates in the Biosynthetic Pathway of Glycosylphosphatidylinositol Membrane Anchors", Carbohydrate Research, vol. 321(1-2), 1999, pp. 42-51.

Dubber, Michael, et al.: "Solid-Phase Synthesis of Multivalent Glycoconjugates on a DNA Synthesizer", Bioconjugate Chemistry, vol. 14(1), 2003, pp. 239-246.

Guo, S., et al.: "Construction of Folate-Conjugated pRNA of Bateriophase phi29 DNA Packaging Motor for Delivery of Chimeric siRNA to Nasopharyngeal Carcinoma Cells", Gene Therapy, vol. 13(10), 2006, pp. 814-820.

Ikeda, Yutaka, et al.: "Ligand-Targeted Delivery of Therapeutic siRNA", Pharmaceutical Research, vol. 23(8), 2006, pp. 1631-1640.

Karskela, Marika, et al.: "Synthesis and Cellular Uptake of Fluorescently Labeled Multivalent Hyaluronan Disaccharide Conjugates of Oligonucleotide Phosphorothioates", Bioconjugate Chemistry, vol. 19(12), 2008, pp. 2549-2558.

Katajisto, Johanna, et al.: "An Aminooxy-Functionalized Non-Nucleosidic Phosphoramidite for the Construction of Multiantennary Oligonucleotide Glycoconjugates on a Solid Support", Current Protocols in Nucleic Acid Chemistry, 2005, pp. 4.26.1-4.26.16.

Katajisto, Johanna, et al.: "Solid-Phase Synthesis of Oligonucleotide Glycoconjugates Bearing Three Different Glycosyl Groups: Orthoganally Protected Bis (Hydroxymethyl)-N, N'-bis(3-Hydroxyproply)Malondiamide Phosphoramidite as Key Building Block", Journal of Organic Chemistry, vol. 69(22), 2004, pp. 7609-7615.

Katajisto, Johanna, et al.: "Solid-Phase Synthesis of Multiantennary Oligonucleotide Glycoconjugates Utilizing On-Support Oximation", Bioconjugate chemistry, vol. 15(4), 2004, pp. 890-896.

Li, Song, et al.: "Folate-Mediated Targeting of Antisense Oligodeoxynucleotides to Ovarian Cancer Cells", Pharmaceutical Research, vol. 15(10), 1998, pp. 1540-1545.

Liu, J., et al.: "Targeted Drug Delivery to Chemoresistant Cells: Folic Acid Derivatization of FdUMP [10] Enhances Cytotoxicity Toward 5-FU-Resistant Human Colorector Tumor Cells", Journal of Organic Chemistry, vol. 66(17), 2001, pp. 5655-5663.

Mahato, R. I., et al.: "Modulation of Gene Expression by Antisense and Antigene Oligodeoxynucleotides and Small Interfering RNA", Expert Opinion on Drug Delivery, 2005, vol. 2(1), pp. 3-28.

Murata, J. et al.: "Design of Quaternary Chitosan Conjugate Having Antennary Galactose Residues as a Gene Delivery Tool", Carbohydrate Polymers, vol. 32(2), 1997, pp. 105-109.

Rensen, Patrick, C. N., et al.: "Design and Synthesis of Novel N-Acetylgalactosamine-Terminated Glycolipids for Targeting of Lipoproteins to the Hepatic Asialoglycoprotein Receptor", Journal of Medicinal Chemistry, vol. 47(23), 2004, pp. 5798-5808.

Sioud, M.: "On the Delivery of Small Interfering RNAs into Mammalian Cells", Expert Opinion on Drug Delivery, vol. 2(4), 2005, pp. 639-651.

Six, L., et al.: "An Efficient and Stereoselective Synthesis of 1, 2-0-Dialkyl-3-0-Beta-D-Glycosyl-SN-Glycerols", Tetrahedron Letters, vol. 24(12), 1983, pp. 1229-1232.

Six, L., et al.: "Influence of Carbohydrate Moities on Monolayer Properties of Dialkylglyceryletherglycosides, Simple Model Compounds of the Glycolipids of Halophilic Bacteria", Journal of Colloid and Interface Science, vol. 93(1), 1983, pp. 109-114.

Sliedregt, Leo A. J. M., et al.: "Design and Synthesis of Novel Amphiphilic Dendritic Galactosides for Selective Targeting of Liposomes to the Hepatic Asialoglycoprotein Receptor", Journal of Medicinal Chemistry, vol. 42(4), 1999, pp. 609-618.

Vaino, A. R., et al.: "Synthesis of a D-Lactosyl Cluster-Nucleoside Conjugate", Chemical Communications, No. 19, 1997, pp. 1871-1872.

Wong, A., et al.: "Lipid, Sugar and Liposaccharide Based Delivery Systems", Current Medicinal Chemistry, vol. 8(9), 2001, pp. 1123-1136.

Zatsepin, Timofei S., et al.: "Synthesis and Applications of Oligonucleotide-Carbohydrate Conjugates", Chemistry & Biodiversity, vol. 1(10), 2004, pp. 1401-1417.

Zimmerman, T. S., et al.: "RNAi-Mediated Gene Silencing in Non-Human Primates", Nature, vol. 441(7089), 2006, pp. 111-114.

Erik A. L. Biessen et al., "Synthesis of Cluster Galactosides with High Affinity for the Hepatic Asialoglycoprotein Receptor", Journal of Medical Chemistry, 1995, pp. 1538-1546, vol. 38, No. 9.

A. Paul Krapcho et al., "Mono-Protected Diamines N-tert-Butoxycarbonyl-α,β-Alkanediamines from-α,β-Alkanediamines", Synthetic Communications, 1990, pp. 2559-2564.

Ya-Lin Chiu et al., "RNAi in Human Cells: Basic Structural and Functional Features of Small Interfering RNA", Molecular Cell, 2002, pp. 549-561, vol. 10.

Daniel T. Connolly et al., "Binding and Endocytosis of Cluster Glycosides by Rabbit Hepatocytes", The Journal of Biological Chemistry, 1982, pp. 939-645, vol. 257, No. 2.

Hamzavi R. et al., "Modulation of the Pharmacokinetic Properties of PNA: Preparation of Galactosyl, Mannosyl, Fucosyl, N-Acetylgalactosaminyl, and N-Acetylglucosaminyl Derivatives of Aminoethylglycine Peptide Nucleic Acid Monomers and Their Incorporation into PNA Oligomers", Bioconjugate Chemistry, ACS, Washington, DC, US, vol. 14, Jan. 1, 2003, pp. 941-954, XP002270930; ISSN: 1043-1802.

Zheng, Sun-Jen et al., "Distribution and anti-HBV effects of antisense oligodeoxynucleotides conjugated to galactosylated poly-L-lysine", World Journal of Gastroenterology, vol. 9, No. 6, 2003, pp. 1251-1255, XP002510287.

Mahato, R.I. et al., "Physicochemical and Disposition Characteristics of Antisense Oligonucleotides Complexed with Glycosylated Poly(L-lysine)", Biochemical Pharmacology, Pergamon, Oxford, GB, vol. 53, Jan. 1, 1997, pp. 887-895, XP000197861, ISSN: 0006-2952.

Maier, M.A. et al., "Synthesis of Antisense Oligonucleotides Conjugated to a Multivalent Carbohydrate Cluster for Cellular Targeting", Bioconjugate Chemistry, vol. 14, 2003, pp. 18-29, XP002510288.

Sliedregt et al., "Design and Synthesis of Novel Amphiphilic Dendritic Galactosides for Selective Targeting of Liposomes to the Hepatic Asialoglycoprotein Receptor", J. Med. Chem., 1999, 42:609-618.

Wolfrum et al., "Mechanisms and optimization of in vivo delivery of lipophilic siRNAs", Nature Biotechnology 25(10):1149-57 (2007).

* cited by examiner

*Primary Examiner* — Terra Cotta Gibbs
(74) *Attorney, Agent, or Firm* — Jeffrey N. Townes; LeClairRyan

(57) ABSTRACT

The present invention provides iRNA agent including at least one monomer having the structure shown in formula (I')

$$X-A \atop \underset{\underset{\text{Linker-R}}{|}}{N} B-Y \qquad (I')$$

wherein: A and B are each independently for each occurrence O, N(R$^N$) or S; X is H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, —P(Z')(Z")O-L$^6$-Q'-L$^7$-OP(Z''')(Z'''')O-oligonucleotide, a nucleotide, or an oligonucleotide; Y is H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a lipophile, a polymer, —P(Z')(Z")O-L$^6$-Q'-L$^7$-OP(Z''')(Z'''')O-oligonucleotide, a nucleotide, or an oligonucleotide; R is folate, a folate analog a folate mimic or a folate receptor binding ligand; $L^6$ and $L^7$ are each independently for each occurrence —$(CH_2)_n$—, —$C(R')(R'')(CH_2)_n$—, —$(CH_2)_nC(R')(R'')$—, —$(CH_2CH_2O)_mCH_2CH_2$—, or —$(CH_2CH_2O)_mCH_2CH_2NH$—; Q' is NH, O, S, $CH_2$, C(O)O, C(O)NH, —NH—CH($R^a$)—C(O)—, —C(O)—CH($R^a$)—NH—, CO,

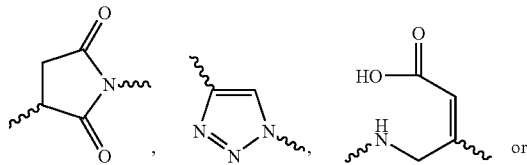

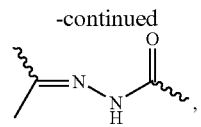

where $R^a$ is H or amino acid side chain;

R' and R'' are each independently H, $CH_3$, OH, SH, $NH_2$, NH(Alkyl=Me, Et, Pr, isoPr, Bu, Bn) or N(diAlkyl=$Me_2$, $Et_2$, $Bn_2$); Z', Z'', Z''' and Z'''' are independently O or S; n represent independently for each occurrence 1-20; and m represent independently for each occurrence 0-50.

14 Claims, 17 Drawing Sheets

Cholesterol-C18-folate conjugated siRNA

-Quasar-Cholesterol-C18-folate conjugated siRNA (A)

(B)

(A)

(B)

SEQUENCE LISTING

```
<160> NUMBER OF SEQ ID NOS: 178

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Ala Leu Ala
1

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Leu Glu Ala Leu Ala Glu Ala Leu Glu Ala Leu Ala Glu Ala
1               5                   10                  15

Leu Glu Ala Leu Ala Glu Ala Ala Ala Gly Gly Cys
            20                  25

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Ala Leu Ala Glu Ala Leu Ala Glu Ala Leu Ala Glu Ala Leu Ala
1               5                   10                  15
```

Glu Ala Leu Ala Glu Ala Leu Ala Ala Ala Gly Gly Cys
            20                  25                  30

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Leu Glu Ala Leu Ala Glu Ala Leu Glu Ala Leu Ala Glu Ala
1               5                   10                  15

<210> SEQ ID NO 5
<211> LENGTH: 22
<212> TYPE: PRT
<213> ORGANISM: Influenza A virus

<400> SEQUENCE: 5

Gly Leu Phe Glu Ala Ile Glu Gly Phe Ile Glu Asn Gly Trp Glu Gly
1               5                   10                  15

Met Ile Trp Asp Tyr Gly
            20

<210> SEQ ID NO 6
<211> LENGTH: 23
<212> TYPE: PRT
<213> ORGANISM: Influenza A virus

<400> SEQUENCE: 6

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 7
<211> LENGTH: 24
<212> TYPE: PRT
<213> ORGANISM: Influenza A virus

<400> SEQUENCE: 7

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 8
<211> LENGTH: 22
<212> TYPE: PRT
<213> ORGANISM: Influenza A virus

<400> SEQUENCE: 8

Gly Leu Phe Glu Ala Ile Glu Gly Phe Ile Glu Asn Gly Trp Glu Gly
1               5                   10                  15

Met Ile Asp Gly Gly Cys
            20

<210> SEQ ID NO 9
<211> LENGTH: 35
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
                20                  25                  30

Gly Ser Cys
        35

<210> SEQ ID NO 10
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
                20                  25                  30

Ser Cys

<210> SEQ ID NO 11
<211> LENGTH: 21
<212> TYPE: PRT
<213> ORGANISM: Influenza A virus
<220> FEATURE:
<221> NAME/KEY: MOD_RES
<222> LOCATION: (17)..(17)
<223> OTHER INFORMATION: Norleucine

<400> SEQUENCE: 11

Gly Leu Phe Glu Ala Ile Glu Gly Phe Ile Glu Asn Gly Trp Glu Gly
1               5                   10                  15

Leu Ile Asp Gly Lys
                20

<210> SEQ ID NO 12
<211> LENGTH: 20
<212> TYPE: PRT
<213> ORGANISM: Influenza A virus
<220> FEATURE:
<221> NAME/KEY: MOD_RES
<222> LOCATION: (17)..(17)
<223> OTHER INFORMATION: Norleucine

<400> SEQUENCE: 12

Gly Leu Phe Glu Ala Ile Glu Gly Phe Ile Glu Asn Gly Trp Glu Gly
1               5                   10                  15

Leu Ile Asp Gly
                20

<210> SEQ ID NO 13
<211> LENGTH: 16
<212> TYPE: PRT
<213> ORGANISM: Drosophila sp.

<400> SEQUENCE: 13

Arg Gln Ile Lys Ile Trp Phe Gln Asn Arg Arg Met Lys Trp Lys Lys
1               5                   10                  15

```
<210> SEQ ID NO 14
<211> LENGTH: 13
<212> TYPE: PRT
<213> ORGANISM: Human immunodeficiency virus 1

<400> SEQUENCE: 14

Gly Arg Lys Lys Arg Arg Gln Arg Arg Pro Pro Gln
1               5                   10

<210> SEQ ID NO 15
<211> LENGTH: 27
<212> TYPE: PRT
<213> ORGANISM: Human immunodeficiency virus 1

<400> SEQUENCE: 15

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 16
<211> LENGTH: 18
<212> TYPE: PRT
<213> ORGANISM: Mus sp.

<400> SEQUENCE: 16

Leu Leu Ile Ile Leu Arg Arg Arg Ile Arg Lys Gln Ala His Ala His
1               5                   10                  15

Ser Lys

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Leu Ala Leu Lys Leu Ala Leu Lys Ala Leu Lys Ala Ala Leu Lys
1               5                   10                  15

Leu Ala

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19
```

```
Arg Arg Arg Arg Arg Arg Arg Arg
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Phe Phe Lys Phe Phe Lys Phe Phe Lys
1               5                   10

<210> SEQ ID NO 21
<211> LENGTH: 37
<212> TYPE: PRT
<213> ORGANISM: Homo sapiens

<400> SEQUENCE: 21

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 22
<211> LENGTH: 31
<212> TYPE: PRT
<213> ORGANISM: Ascaris suum

<400> SEQUENCE: 22

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 23
<211> LENGTH: 30
<212> TYPE: PRT
<213> ORGANISM: Homo sapiens

<400> SEQUENCE: 23

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 24
<211> LENGTH: 36
<212> TYPE: PRT
<213> ORGANISM: Homo sapiens

<400> SEQUENCE: 24

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35
```

```
<210> SEQ ID NO 25
<211> LENGTH: 12
<212> TYPE: PRT
<213> ORGANISM: Unknown
<220> FEATURE:
<223> OTHER INFORMATION: Description of Unknown: Unknown bactenecin
      peptide

<400> SEQUENCE: 25

Arg Lys Cys Arg Ile Val Val Ile Arg Val Cys Arg
1               5                  10

<210> SEQ ID NO 26
<211> LENGTH: 42
<212> TYPE: PRT
<213> ORGANISM: Sus scrofa

<400> SEQUENCE: 26

Arg Arg Arg Pro Arg Pro Pro Tyr Leu Pro Arg Pro Arg Pro Pro
1               5                  10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 27
<211> LENGTH: 13
<212> TYPE: PRT
<213> ORGANISM: Unknown
<220> FEATURE:
<223> OTHER INFORMATION: Description of Unknown: Unknown indolicidin
      peptide

<400> SEQUENCE: 27

Ile Leu Pro Trp Lys Trp Pro Trp Trp Pro Trp Arg Arg
1               5                  10

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ala Val Ala Leu Leu Pro Ala Val Leu Leu Ala Leu Leu Ala Pro
1               5                  10                  15

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Leu Leu Pro Val Leu Leu Ala Ala Pro
1               5                  10

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
            oligonucleotide

<400> SEQUENCE: 30
ccacaugaag cagcacgacu u                                              21

<210> SEQ ID NO 31
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
aagucgugcu gcuucaugug guc                                            23

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
accgaaaggu cuuaccggat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
uccgguaaga ccuuucggut t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 34
cuuacgcuga guacuucgat t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
```
ucgaaguacu cagcguaagt t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 36
cuuacgcuga guacuucgat t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
ucgaaguacu cagcguaagt t                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ccacaugaag cagcacgacu u                                              21

<210> SEQ ID NO 39
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aagucgugcu gcuucaugug guc                                            23

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 40
cuggcugaau uucagagcat t                                              21

<210> SEQ ID NO 41
<211> LENGTH: 21

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 41
ugcucugaaa uucagccagt t                                             21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42
accgaaaggu cuuaccggat t                                             21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 43
uccgguaaga ccuuucggut t                                             21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44
cuggcugaau uucagagcat t                                             21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
ugcucugaaa uucagccagt t                                             21

<210> SEQ ID NO 46
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 46
cuggcugaau uucagagcat t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 47
ugcucugaaa uucagccagt t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48
cuggcugaau uucagagcat t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
ugcucugaaa uucagccagt t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50
cuggcugaau uucagagcat t                                              21

<210> SEQ ID NO 51
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
ugcucugaaa uucagccagt t                                            21

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
cuggcugaau uucagagcat t                                            21

<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 53
ugcucugaaa uucagccagt t                                            21

<210> SEQ ID NO 54
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 54
cuggcugaau uucagagcat t                                            21

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 55
ugcucugaaa uucagccagt t                                            21

<210> SEQ ID NO 56
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 56
cuggcugaau uucagagcat t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 57
ugcucugaaa uucagccagt t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 58
cuggcugaau uucagagcat t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 59
ugcucugaaa uucagccagt t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 60
cuggcugaau uucagagcat t                                              21

<210> SEQ ID NO 61
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 61
ugcucugaaa uucagccagt t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 62
cuggcugaau uucagagcat t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 63
ugcucugaaa uucagccagt t                                              21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cuggcugaau uucagagcau u                                              21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ugcucugaaa uucagccagu u                                              21

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 66
aaccgtggtc atgctcc                                                  17

<210> SEQ ID NO 67
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ccacaugaag cagcacgacu uuu                                           23

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ugcucugaaa uucagccagu u                                             21

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aaccgtggtc atgctcc                                                  17

<210> SEQ ID NO 70
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 70
cuggcugaau uucagagcat t                                             21

<210> SEQ ID NO 71
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 71
ugcucugaaa uucagccagt t                                             21

<210> SEQ ID NO 72
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 72
acaugaagca gcacgacuut t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 73
aagucgugcu gcuucaugut t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 74
acaugaagca gcacgacuut t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 75
aagucgugcu gcuucaugut t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 76
acaugaagca gcacgacuut t                                              21

<210> SEQ ID NO 77
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 77
aagucgugcu gcuucaugut t                                              21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ccacaugaag cagcacgacu u                                              21

<210> SEQ ID NO 79
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
aagucgugcu gcuucaugug guc                                            23

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ccacaugaag cagcacgacu u                                              21

<210> SEQ ID NO 81
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
aagucgugcu gcuucaugug guc                                            23

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ccacaugaag cagcacgacu u                                              21

<210> SEQ ID NO 83
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 83
aagucgugcu gcuucaugug guc                                            23

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ccacaugaag cagcacgacu u                                              21

<210> SEQ ID NO 85
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
aagucgugcu gcuucaugug guc                                            23

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ccacaugaag cagcacgacu u                                              21

<210> SEQ ID NO 87
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
aagucgugcu gcuucaugug guc                                            23

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 88
acaugaagca gcacgacuut t                                              21

<210> SEQ ID NO 89
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 89
aagucgugcu gcuucaugut t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 90
acaugaagca gcacgacuut t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 91
aagucgugcu gcuucaugut t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 92
acaugaagca gcacgacuut t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 93
aagucgugcu gcuucaugut t                                              21

<210> SEQ ID NO 94
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 94
acaugaagca gcacgacuut t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 95
aagucgugcu gcuucaugut t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 96
acaugaagca gcacgacuut t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 97
aagucgugcu gcuucaugut t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 98
acaugaagca gcacgacuut t                                              21

<210> SEQ ID NO 99
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 99
aagucgugcu gcuucaugut t                                             21

<210> SEQ ID NO 100
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 100
acaugaagca gcacgacuut t                                             21

<210> SEQ ID NO 101
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 101
aagucgugcu gcuucaugut t                                             21

<210> SEQ ID NO 102
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 102
acaugaagca gcacgacuut t                                             21

<210> SEQ ID NO 103
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 103
aagucgugcu gcuucaugut t                                             21

<210> SEQ ID NO 104
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 104
acaugaagca gcacgacuut t                                             21

<210> SEQ ID NO 105
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 105
aagucgugcu gcuucaugut t                                             21

<210> SEQ ID NO 106
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 106
acaugaagca gcacgacuut t                                             21

<210> SEQ ID NO 107
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 107
aagucgugcu gcuucaugut t                                             21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
ccacaugaag cagcacgacu u                                             21

<210> SEQ ID NO 109
<211> LENGTH: 23
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 109
aagucgugcu gcuucaugug guc                                              23

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
ccacaugaag cagcacgacu u                                                21

<210> SEQ ID NO 111
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
aagucgugcu gcuucaugug guc                                              23

<210> SEQ ID NO 112
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 112
acaugaagca gcacgacuut t                                                21

<210> SEQ ID NO 113
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 113
aagucgugcu gcuucaugut t                                                21

<210> SEQ ID NO 114
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 114
acaugaagca gcacgacuut t                                                21

<210> SEQ ID NO 115
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 115
aagucgugcu gcuucaugut t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 116
acaugaagca gcacgacuut t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 117
aagucgugcu gcuucaugut t                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 118
acaugaagca gcacgacuut t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 119
aagucgugcu gcuucaugut t                                              21

```
<210> SEQ ID NO 120
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 120
acaugaagca gcacgacuut t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 121
aagucgugcu gcuucaugut t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 122
acaugaagca gcacgacuut t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 123
aagucgugcu gcuucaugut t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 124
acaugaagca gcacgacuut t                                              21
```

<210> SEQ ID NO 125
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 125
aagucgugcu gcuucaugut t                                                 21

<210> SEQ ID NO 126
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
ggagcaugac cacgg                                                        15

<210> SEQ ID NO 127
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 127
cugaagaccu gaagacaaut t                                                 21

<210> SEQ ID NO 128
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 128
auugucuuca ggucuucagt t                                                 21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gaacugugug ugagaggucc u                                                 21

<210> SEQ ID NO 130
<211> LENGTH: 21
<212> TYPE: RNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 130
gaacugugug ugagaggucc u                                          21

<210> SEQ ID NO 131
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 131
cugaagaccu gaagacaaut t                                          21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gaacugugug ugagaggucc u                                          21

<210> SEQ ID NO 133
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 133
cuuacgcuga guacuucgat t                                          21

<210> SEQ ID NO 134
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 134
cuuacgcuga guacuucgat t                                          21

<210> SEQ ID NO 135
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

-continued

<400> SEQUENCE: 135
cuuacgcuga guacuucgat t                                              21

<210> SEQ ID NO 136
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 136
cuuacgcuga guacuucgat t                                              21

<210> SEQ ID NO 137
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 137
cuuacgcuga guacuucgat t                                              21

<210> SEQ ID NO 138
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 138
cuuacgcuga guacuucgat t                                              21

<210> SEQ ID NO 139
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 139
cuuacgcuga guacuucgat t                                              21

<210> SEQ ID NO 140
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide <210> SEQ ID NO 141
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 140
cuuacgcuga guacuucgat t           21

<210> SEQ ID NO 141
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 141
cugaagaccu gaagacaaut t           21

<210> SEQ ID NO 142
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 142
cugaagaccu gaagacaaut t           21

<210> SEQ ID NO 143
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 143
cugaagaccu gaagacaaut t           21

<210> SEQ ID NO 144
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 144
cugaagaccu gaagacaaut t           21

<210> SEQ ID NO 145
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide -continued

<400> SEQUENCE: 145
cuuacgcuga guacuucgat t                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 146
ucgaaguacu cagcguaagt t                                              21

<210> SEQ ID NO 147
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 147
cuuacgcuga guacuucgat t                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 148
ucgaaguacu cagcguaagt t                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 149
cuggcugaau uucagagcat t                                              21

<210> SEQ ID NO 150
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 150
accgaaaggu cuuaccggat t                                             21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
ccacaugaag cagcacgacu u                                             21

<210> SEQ ID NO 152
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 152
ugcucugaaa uucagccagt t                                             21

<210> SEQ ID NO 153
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 153
uccgguaaga ccuuucggut t                                             21

<210> SEQ ID NO 154
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
aagucgugcu gcuucaugug guc                                           23

<210> SEQ ID NO 155
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 155
uccgguaaga ccuuucggut t                                             21
```

```
<210> SEQ ID NO 156
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
aagucgugcu gcuucaugug guc                                                23

<210> SEQ ID NO 157
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 157
ugcucugaaa uucagccagt t                                                  21

<210> SEQ ID NO 158
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 158
ugcucugaaa uucagccagt t                                                  21

<210> SEQ ID NO 159
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 159
cuuacgcuga guacuucgat t                                                  21

<210> SEQ ID NO 160
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 160
ucgaaguacu cagcguaagt t                                                  21

<210> SEQ ID NO 161
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 161
cuuacgcuga guacuucgat t                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 162
ucgaaguacu cagcguaagt t                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 163
cuuacgcuga guacuucgat t                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 164
ucgaaguacu cagcguaagt t                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 165
cuggcugaau uucagagcat t                                              21

<210> SEQ ID NO 166
<211> LENGTH: 21
<212> TYPE: DNA
```

<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 166
ugcucugaaa uucagccagt t                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 167
cuggcugaau uucagagcat t                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Combined DNA/RNA Molecule: Synthetic oligonucleotide
<220> FEATURE:
<223> OTHER INFORMATION: Description of Artificial Sequence: Synthetic oligonucleotide

<400> SEQUENCE: 168
ugcucugaaa uucagccagt t                                              21

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 169
ccacaugaag cagcacgacu u                                              21

<210> SEQ ID NO 170
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 170
aagucgugcu gcuucaugug guc                                            23

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 171
ccacaugaag cagcacgacu u     21

<210> SEQ ID NO 172
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 172
aagucgugcu gcuucaugug guc     23

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 173
ccacaugaag cagcacgacu u     21

<210> SEQ ID NO 174
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 174
aagucgugcu gcuucaugug guc     23

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 175
ccacaugaag cagcacgacu u     21

<210> SEQ ID NO 176
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 176
aagucgugcu gcuucaugug guc     23

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 177
ccacaugaag cagcacgacu u     21

```
<210> SEQ ID NO 178
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
aagucgugcu gcuucaugug guc                                              23
```

FOLATE CONJUGATES

RELATED APPLICATIONS

This application claims the benefit of priority to U.S. Provisional Patent Application Ser. No. 60/992,309, filed Dec. 4, 2007; and U.S. Provisional Patent Application Ser. No. 61/013,597 filed Dec. 13, 2007.

GOVERNMENT SUPPORT

This invention was made with government support under contract number HHSN266200600012C, awarded by the National Institute of Allergy and Infection Diseases/National Institutes of Health/Department of Health and Human Services (NIAID/NIH/DHHS) and contract number[s] HDTRA-1-07-C-0082, awarded by the Department of Defense and Defense Threat Reduction Agency (DOD/DTRA). The government has certain rights in the invention.

BACKGROUND

Oligonucleotide compounds have important therapeutic applications in medicine. Oligonucleotides can be used to silence genes that are responsible for a particular disease. Gene-silencing prevents formation of a protein by inhibiting translation. Importantly, gene-silencing agents are a promising alternative to traditional small, organic compounds that inhibit the function of the protein linked to the disease. siRNA, antisense RNA, and micro-RNA are oligonucleotides that prevent the formation of proteins by gene-silencing.

RNA interference or "RNAi" is a term initially coined by Fire and co-workers to describe the observation that double-stranded RNA (dsRNA) can block gene expression when it is introduced into worms (Fire et al. (1998) Nature 391, 806-811). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

siRNA compounds are promising agents for a variety of diagnostic and therapeutic purposes. siRNA compounds can be used to identify the function of a gene. In addition, siRNA compounds offer enormous potential as a new type of pharmaceutical agent which acts by silencing disease-causing genes. Research is currently underway to develop interference RNA therapeutic agents for the treatment of many diseases including central-nervous-system diseases, inflammatory diseases, metabolic disorders, oncology, infectious diseases, and ocular disease.

siRNA has been shown to be extremely effective as a potential anti-viral therapeutic with numerous published examples appearing recently. siRNA molecules directed against targets in the viral genome dramatically reduce viral titers by orders of magnitude in animal models of influenza (Ge et. al., Proc. Natl. Acd. Sci. USA, 101:8676-8681 (2004); Tompkins et. al., Proc. Natl. Acd. Sci. USA, 101:8682-8686 (2004); Thomas et. al., Expert Opin. Biol. Ther. 5:495-505 (2005)), respiratory synctial virus (RSV) (Bitko et. al., Nat. Med. 11:50-55 (2005)), hepatitis B virus (HBV) (Morrissey et. al., Nat. Biotechnol. 23:1002-1007 (2005)), hepatitis C virus (Kapadia, Proc. Natl. Acad. Sci. USA, 100:2014-2018 (2003); Wilson et. al., Proc. Natl. Acad. Sci. USA, 100:2783-2788 (2003)) and SARS coronavirus (Li et. al., Nat. Med. 11:944-951 (2005)).

Antisense methodology is the complementary hybridization of relatively short oligonucleotides to mRNA or DNA such that the normal, essential functions, such as protein synthesis, of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally-occurring events that alter the expression level of the target sequence, discussed by Cohen (*Oligonucleotides: Antisense Inhibitors of Gene Expression*, CRC Press, Inc., 1989, Boca Raton, Fla.) are thought to be of two types. The first, hybridization arrest, describes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller et al. (1987) *Anti-Cancer Drug Design*, 2:117-128), and α-anomer oligonucleotides are the two most extensively studied antisense agents which are thought to disrupt nucleic acid function by hybridization arrest.

Another means by which antisense oligonucleotides alter the expression level of target sequences is by hybridization to a target mRNA, followed by enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

The opportunity to use these and other nucleic acid based therapies holds significant promise, providing solutions to medical problems that could not be addressed with current, traditional medicines. The location and sequences of an increasing number of disease-related genes are being identified, and clinical testing of nucleic acid-based therapeutics for a variety of diseases is now underway.

Despite the advances in application of oligonucleotides and oligonucleotide analogs as therapeutics, the need exists for oligonucleotides having improved pharmacologic properties. Efforts aimed at improving the transmembrane delivery of nucleic acids and oligonucleotides have utilized protein carriers, antibody carriers, liposomal delivery systems, electroporation, direct injection, cell fusion, viral vectors, and calcium phosphate-mediated transformation. However, many of these techniques are limited by the types of cells in which transmembrane transport is enabled and by the conditions needed for achieving such transport. Some progress has been made on increasing the cellular uptake of single-stranded oligonucleotides, including increasing the membrane permeability via conjugates and cellular delivery of oligonucleotides. In U.S. Pat. No. 6,656,730, M. Manoharan describes compositions in which a ligand that binds serum, vascular, or cellular proteins may be attached via an optional linking moiety to one or more sites on an oligonucleotide. These sites include one or more of, but are not limited to, the 2'-position, 3'-position, 5'-position, the internucleotide linkage, and a nucleobase atom of any nucleotide residue.

Unlike many of the methods mentioned above, receptor mediated endocytotic activity can be used successfully both in vitro and in vivo. This mechanism of uptake involves the movement of ligands bound to membrane receptors into the interior of an area that is enveloped by the membrane via invagination of the membrane structure. This process is initiated via activation of a cell-surface or membrane receptor following binding of a specific ligand to the receptor. Many receptor-mediated endocytotic systems are known and have been studied, including those that recognize sugars such as galactose, mannose, mannose-6-phosphate, peptides and proteins such as transferrin, asialoglycoprotein, vitamin B12, insulin and epidermal growth factor (EGF). The Asialoglycoprotein receptor (ASGP-R) is a high capacity receptor, which is highly abundant on hepatocytes. The ASGP-R shows a 50-fold higher affinity for N-Acetyl-D-Galactosylamine (GalNAc) than D-Gal. Previous work has shown that multivalency is required to achieve nM affinity, while spacing among sugars is also crucial. Multivalent GalNAc clusters and galactosylated carrier systems have been successfully used to target small molecules to hepatocytes in vivo and in vitro.

Receptor mediated endocytosis has been well studied and is known to be a critical pathway for the uptake and internalization of a variety of cellular nutrients. These are highly developed mechanisms because of their critical role in providing nutrients to cells and in maintaining cellular physiology. Thus many examples of the utilization of receptor mediated endocytosis pathways for the delivery of drugs, proteins, nucleic acids and other molecules to cells are known.

One way in which this has been applied is the conjugation of essential nutrients that are actively transported into cells with the drug or molecule of interest. The transporters or receptors involved in the uptake are capable of recognizing the nutrient portion of the conjugate and ferrying the entire conjugate into the cell. Examples of nutrients that are actively transported into cells and that may be of use in conjugates include, but are not limited to, folic acid, vitamin B6, cholesterol and vitamin B12. Such molecules have been conjugated to macromolecules such as nucleic acids and oligonucleotides to afford conjugates that exhibit improved cellular penetration. Manorharan et al., PCT Application WO 93/07883; Low et al., U.S. Pat. Nos. 5,108,921, 5,416,016.

Folic acid and its various forms, such as dihydrofolate and tetrahydrofolate, are essential vitamins that are crucial for the biosynthesis of nucleic acids and therefore are critical to the survival and proliferation of cells. Folate cofactors play an important role in the one-carbon transfers that are critical for the biosynthesis of pyrimidine nucleosides. Cells therefore have a sophisticated system of transporting folates into the cytoplasm. Uptake of folates occurs by two different pathways depending on the cell type. Cells expressing a carrier or transporter for folate that exhibits a low affinity (Kd~$10^{-6}$ M) for the vitamin prefer reduced over oxidized forms of folate. Cells that express membrane receptors called folate binding protein (FBP), in contrast, exhibit high binding affinity (Kd~$10^{-9}$ M) and prefer the oxidized form of the vitamin. This latter receptor is believed to mediate the uptake of folates into the cytoplasm via endocytosis.

The use of biotin conjugates and also folic acid conjugates to enhance transmembrane transport of exogenous molecules, including oligonucleotides, has been reported by Low et al., U.S. Pat. Nos. 5,108,921; 5,416,016; PCT Application WO 90/12096. Folic acid was conjugated to 3'-aminoalkyl-oligonucleotides at their 3'-terminus via carbodiimide chemistry. The multiplicity of folate receptors on membrane surfaces of most cells and the associated receptor mediated endocytotic processes were implicated in the enhanced transport of these oligonucleotide-folic acid conjugates into cells. There are however, several limitations to this approach for the conjugation of folic acid to oligonucleotides.

Folic acid and many related folates and antifolates exhibit very poor solubility that hinders the effective conjugation of folic acid to oligonucleotides and subsequent purification of oligonucleotide-folic acid conjugates. Further folic acid bears two reactive carboxylic acid groups that are just as likely to react with the terminal amino group of the 3-aminoalkyl-oligonucleotide. Thus conjugation will typically result in a mixture of a- and g-conjugates arising from the reaction of the a-carboxylate and the g-carboxylate of the glutamic acid portion of the folic acid molecule. This poses difficulties from the standpoint of characterizing the conjugate and further from the standpoint of polyglutamylation of folates. Polyglutamylation of folates is a well recognized phenomenon that has significant implications on the transport, localization and activity of folates. Since polyglutamylation rates differ significantly between the α- and γ-carboxylates, the use of poorly defined mixtures of oligonucleotide-folate conjugates, as obtained from the Low et al. procedure, U.S. Pat. No. 5,108,921, will lead to variable transport and concentration of the conjugate. Further, the conjugation of folates onto one end of an oligonucleotide may be a disadvantage because of the known propensity of exonucleases to rapidly cleave oligonucleotides by excising the terminal residues. Also, it has been observed that oligonucleotide-folic acid conjugates prepared in this fashion are light sensitive.

Therefore, there is a clear need for new oligonucleotide-folate conjugates, oligonucleotide-carbohydrate conjugates and methods for their preparation, that address the shortcomings of oligonucleotide conjugates as described above. The present invention is directed to this very important end.

SUMMARY OF THE INVENTION

The present invention provides compounds of formula I

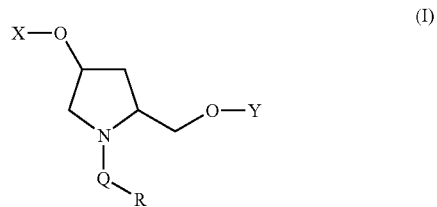

wherein:

X is H, a hydroxyl protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, —P(Z')(Z")O-L$^6$-Q'-L$^7$-OP(Z''')(Z'''')O-oligonucleotide, a nucleotide, or an oligonucleotide;

Y is H, a hydroxyl protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a lipophile, a polymer, —P(Z')(Z")O-L$^6$-Q'-L$^7$-OP(Z''')(Z'''')O-oligonucleotide, a nucleotide, or an oligonucleotide;

Q is a tether;

R is folate, a folate analog, a folate mimic, a folate receptor binding ligand;

Z', Z", Z''' and Z'''' are independently O or S;

n represent independently for each occurrence 1-20;

m represent independently for each occurrence 0-50;

$L^6$ and $L^7$ are each independently for each occurrence $-(CH_2)_n-$, $-C(R')(R'')(CH_2)_n-$, $-(CH_2)_nC(R')(R'')-$, $-(CH_2CH_2O)_mCH_2CH_2-$, or $-(CH_2CH_2O)_mCH_2CH_2NH-$;

Q' is NH, O, S, $CH_2$, C(O)O, C(O)NH, $-NH-CH(R^a)-C(O)-$, $-C(O)-CH(R^a)-NH-$, CO,

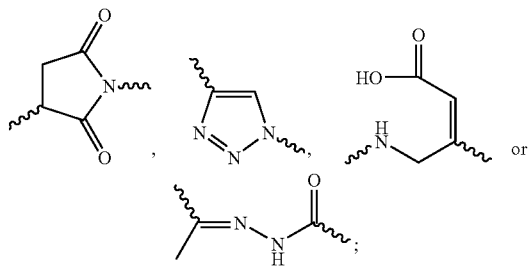

$R^a$ is H or amino acid side chain.

In some preferred embodiments R is folate, a folate analog, a folate mimic or a folate receptor binding ligand.

In some embodiments, R is

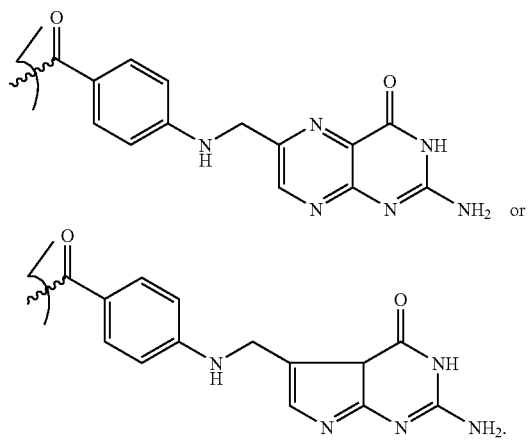

Embodiments can include one or more of the features described above.

In a further aspect, this invention features an iRNA agent having a first strand and a second strand, wherein at least one subunit having a formula (I) is incorporated into at least one of said strands.

In one aspect, this invention features an iRNA agent having a first strand and a second strand, wherein at least two subunits having a formula (I) are incorporated into at least one of said strands.

In another aspect, this invention provides a method of making an iRNA agent described herein having a first strand and a second strand in which at least one subunit of formula (I) is incorporated in the strands. The method includes contacting the first strand with the second strand.

In a further aspect, this invention provides a method of modulating expression of a target gene, the method includes administering an iRNA agent described herein having a first strand and a second strand in which at least one subunit of formula (I) is incorporated in the strands to a subject.

In one aspect, this invention features a pharmaceutical composition having an iRNA agent described herein having a first strand and a second strand in which at least one subunit of formula (I) is incorporated in the strands and a pharmaceutically acceptable carrier.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
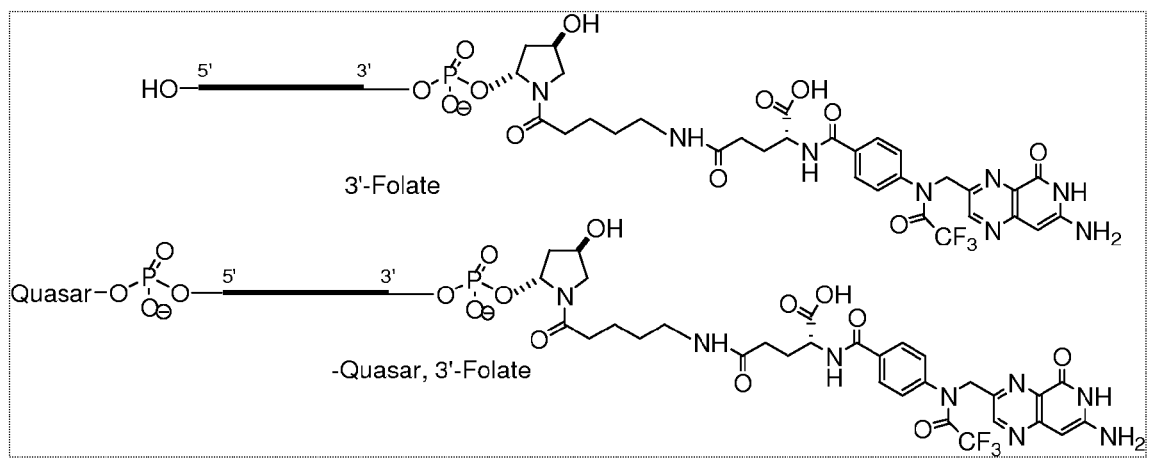
FIG. 1. Graphical representation of folate conjugated sequences.

The inventor has discovered, inter alia, that attachment of a folic acid moiety to an iRNA agent can optimize one or more properties of the iRNA agent. In many cases, the folic acid will be attached to a modified subunit of the iRNA agent. E.g., the ribose sugar of one or more ribonucleotide subunits of an iRNA agent can be replaced with another moiety, e.g., a non-carbohydrate (preferably cyclic) carrier to which is attached a folic acid. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The carriers further include (i) at least two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" in some embodiments refers to a constituent ring atom of the cyclic carrier, e.g., a carbon atom or a heteroatom (distinct from an atom which provides a backbone attachment point), that connects a selected moiety. The moiety can be, e.g., a folic acid, folic acid analog, a folic acid mimic or a ligand capable of binding to the folate receptor. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In addition to the cyclic carriers described herein, RRMS can include cyclic carriers described in copending co-owned U.S. application Ser. No. 10/916,185 filed Aug. 10, 2004, and U.S. application Ser. No. 10/946,873 filed Sep. 21, 2004, both of which are hereby incorporated by reference.

Accordingly, in one aspect, the invention features, a monomer having the structure shown in formula (I')

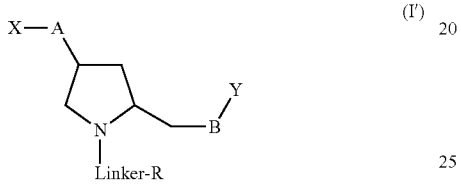

wherein:

A and B are each independently for each occurrence O, $N(R^N)$ or S;

X is H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, —P(Z')(Z")O-$L^6$-Q'-$L^7$-OP(Z''')(Z'''')O-oligonucleotide, a nucleotide, or an oligonucleotide;

Y is H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a lipophile, a polymer, —P(Z')(Z")O-$L^6$-Q'-$L^7$-OP(Z''')(Z'''')O-oligonucleotide, a nucleotide, or an oligonucleotide;

R is folate, a folate analog a folate mimic or a folate receptor binding ligand;

$L^6$ and $L^7$ are each independently for each occurrence —(CH$_2$)$_n$—, —C(R')(R")(CH$_2$)$_n$—, —(CH$_2$)$_n$C(R')(R")—, —(CH$_2$CH$_2$O)$_m$CH$_2$CH$_2$—, or —(CH$_2$CH$_2$O)$_m$CH$_2$CH$_2$NH—;

Q' is NH, O, S, CH$_2$, C(O)O, C(O)NH, —NH—CH($R^a$)—C(O)—, —C(O)—CH($R^a$)—NH—, CO,

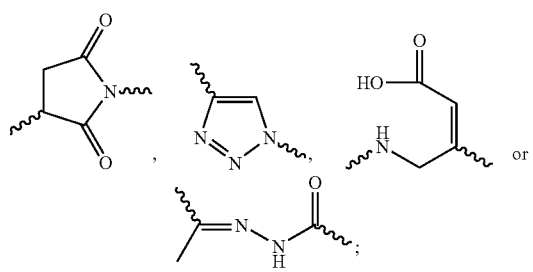

$R^a$ is H or amino acid side chain;

R' and R" are each independently H, CH3, OH, SH, NH2, NH(Alkyl=Me, Et, Pr, isoPr, Bu, Bn) or N(diAlkyl=Me$_2$, Et$_2$, Bn$_2$);

Z', Z", Z''' and Z'''' are independently O or S;

n represent independently for each occurrence 1-20; and m represent independently for each occurrence 0-50.

Accordingly, in one aspect, the invention features, a monomer having the structure shown in formula (I).

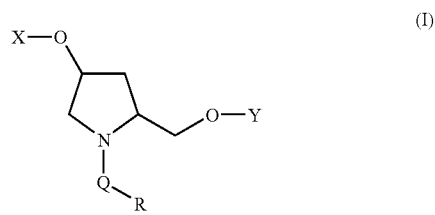

wherein:

X is H, a hydroxyl protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, —P(Z')(Z")O-$L^6$-Q'-$L^7$-OP(Z''')(Z'''')O-oligonucleotide, a nucleotide, or an oligonucleotide;

Y is H, a hydroxyl protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a lipophile, a polymer, —P(Z')(Z")O-$L^6$-Q'-$L^7$-OP(Z''')(Z'''')O-oligonucleotide, a nucleotide, or an oligonucleotide;

Q is a tether;

R is folate, a folate analog, a folate mimic, a folate receptor binding ligand;

n represent independently for each occurrence 1-20;

m represent independently for each occurrence 0-50;

$L^6$ and $L^7$ are each independently for each occurrence —(CH$_2$)$_n$—, —C(R')(R")(CH$_2$)$_n$—, —(CH$_2$)$_n$C(R')(R")—, —(CH$_2$CH$_2$O)$_m$CH$_2$CH$_2$—, or —(CH$_2$CH$_2$O)$_m$CH$_2$CH$_2$NH—;

Q' is NH, O, S, CH$_2$, C(O)O, C(O)NH, —NH—CH($R^a$)—C(O)—, —C(O)—CH($R^a$)—NH—, CO,

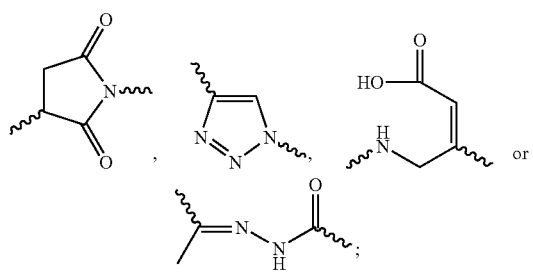

$R^a$ is H or amino acid side chain.

In some embodiments, R is
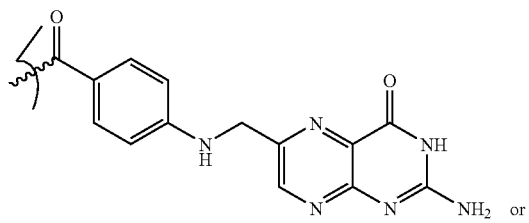
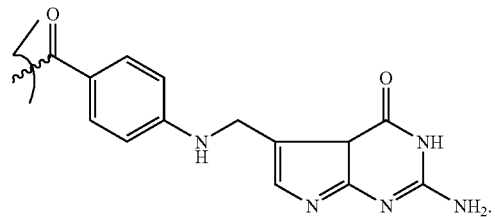 or
In some embodiments, R is one of
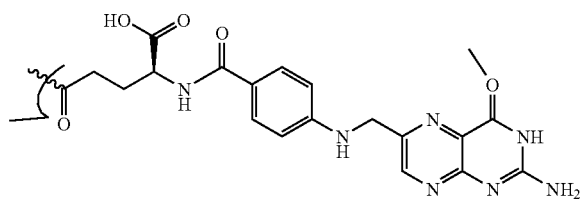
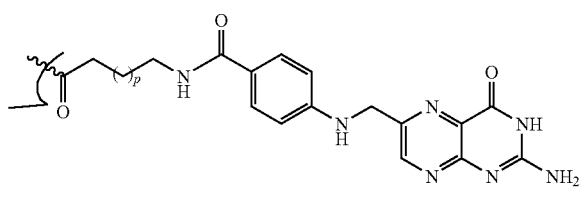
p = 1, 3, 8, 13, 19
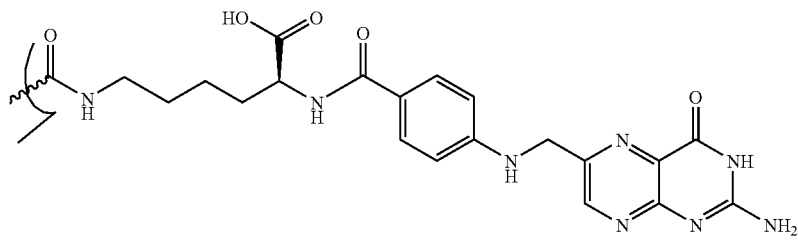
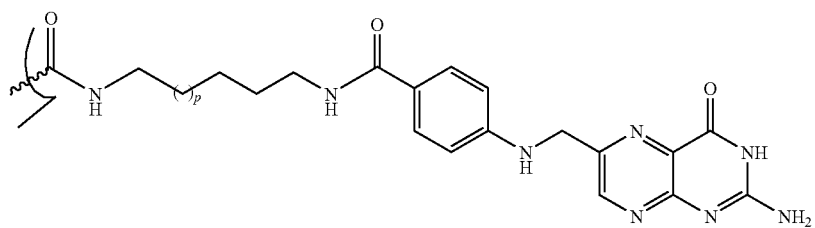
p = 1, 2, 7, 12, 18
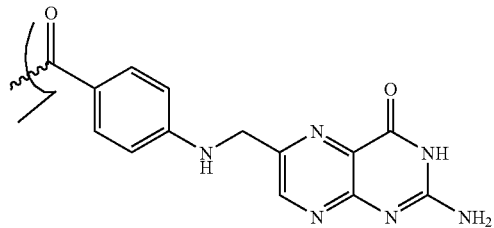
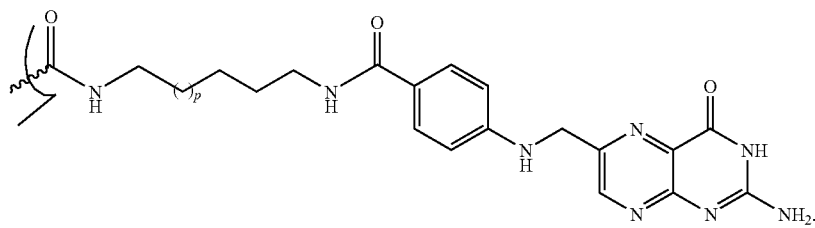
p = 1, 2, 7, 12, 18

In some embodiments, R is one of
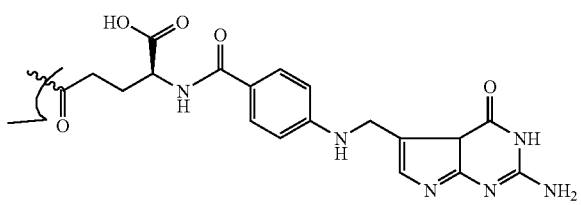
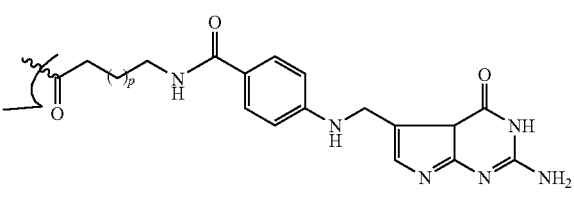
p = 1, 3, 8, 13, 19
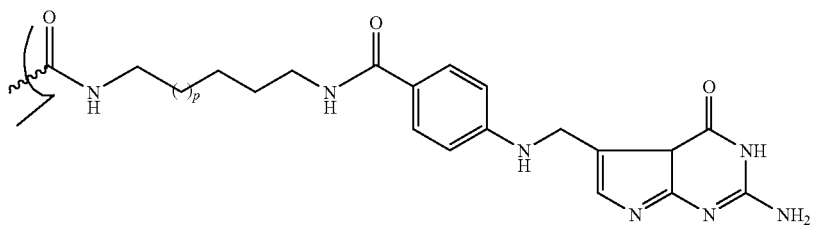
p = 1, 2, 7, 12, 18
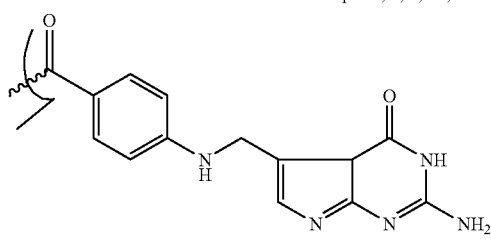
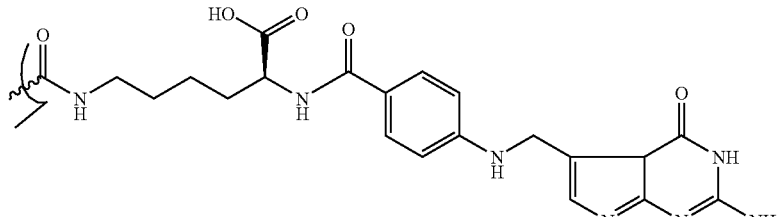
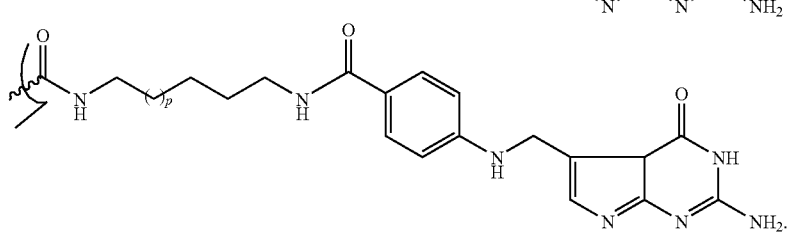
p = 1, 2, 7, 12, 18
In some embodiments, R is one of
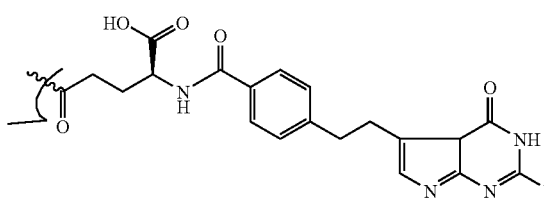
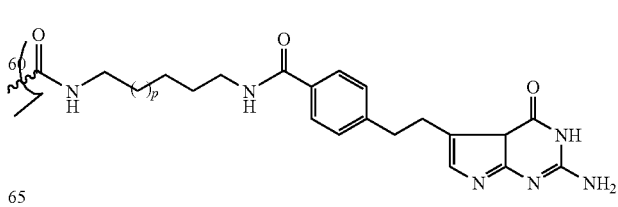
p = 1, 2, 7, 12, 18

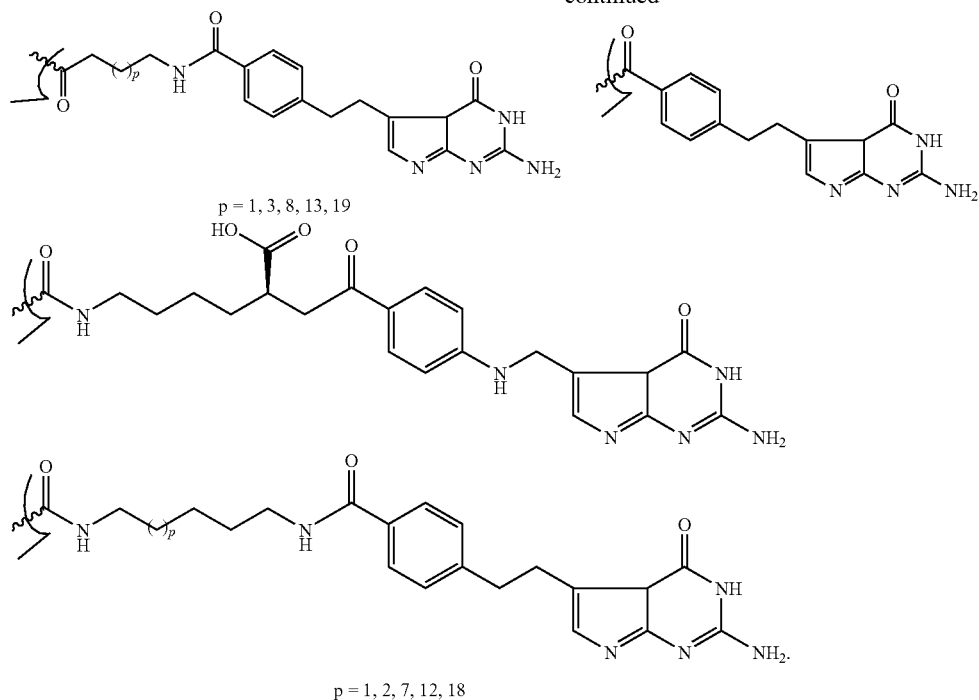
In some embodiments, R is
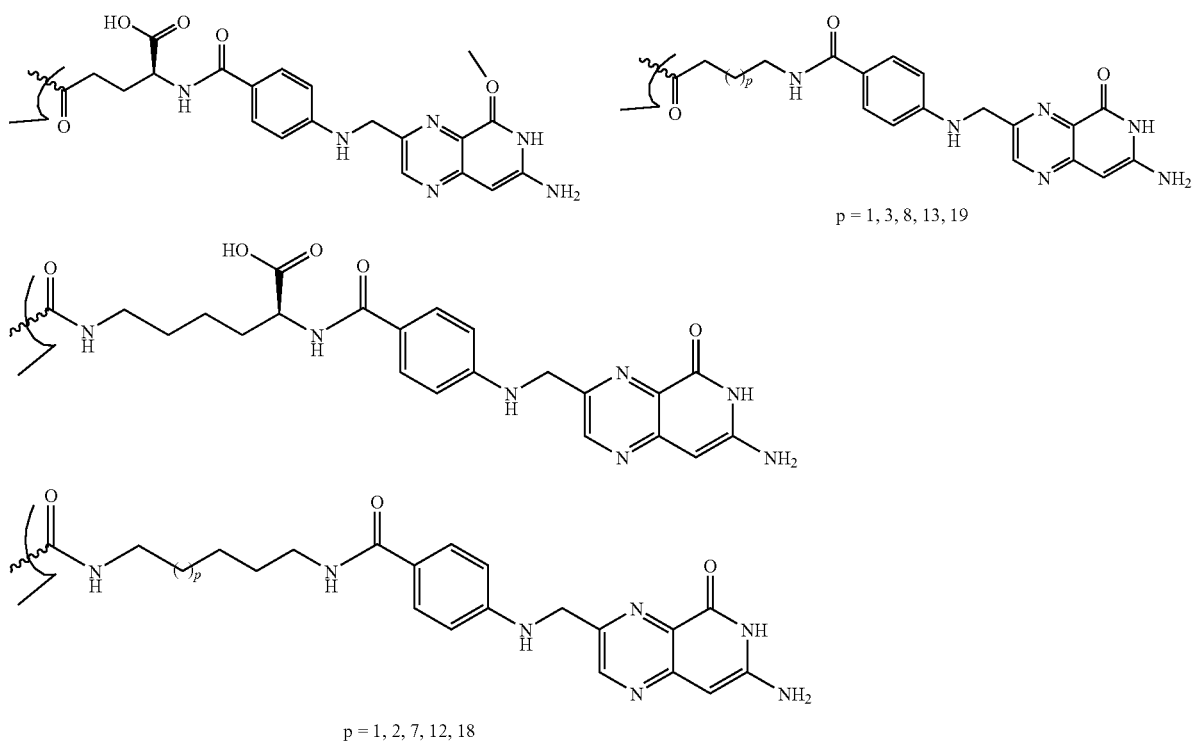

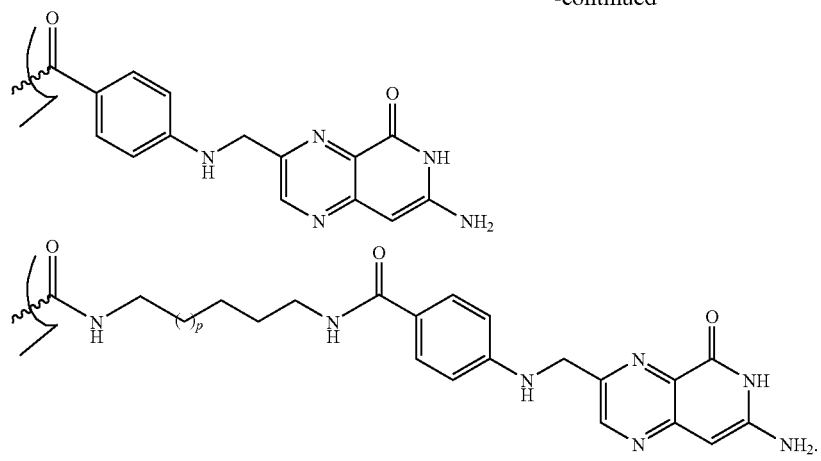
p = 1, 2, 7, 12, 18
In some embodiments, the RRMS has the structure
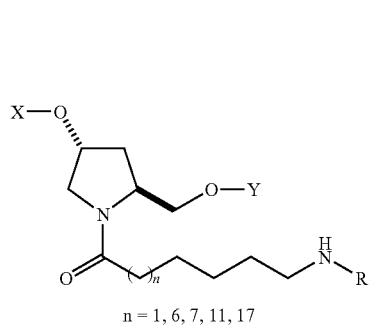
n = 1, 6, 7, 11, 17
In some embodiments, the RRMS has the structure
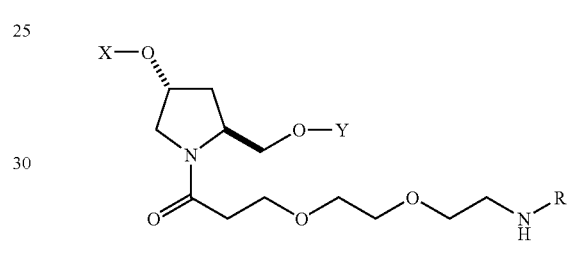
m = 0 or 1, n = 1, 2, 3, 4
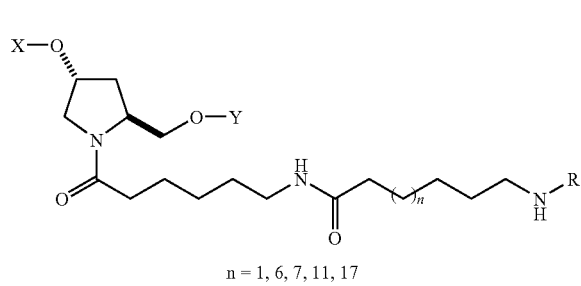
n = 1, 6, 7, 11, 17
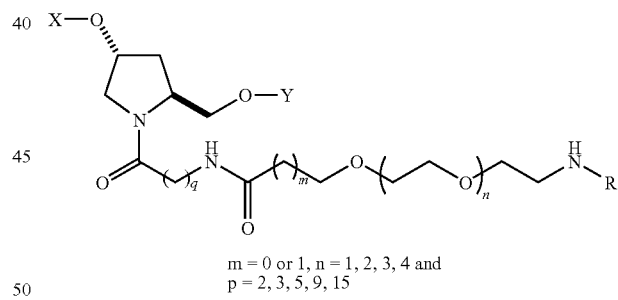
m = 0 or 1, n = 1, 2, 3, 4 and
p = 2, 3, 5, 9, 15
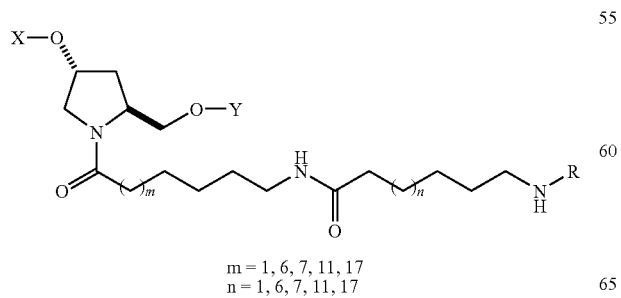
m = 1, 6, 7, 11, 17
n = 1, 6, 7, 11, 17
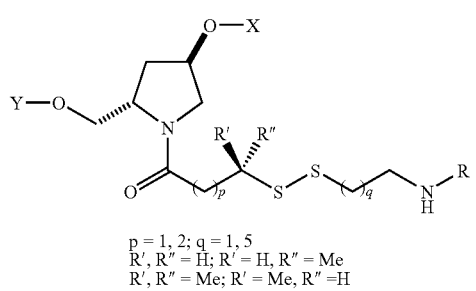
p = 1, 2; q = 1, 5
R', R'' = H; R' = H, R'' = Me
R', R'' = Me; R' = Me, R'' = H In some embodiments, RRMS has the structure

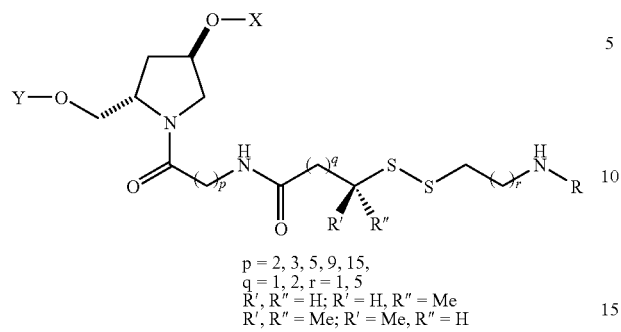

p = 2, 3, 5, 9, 15,
q = 1, 2, r = 1, 5
R', R" = H; R' = H, R" = Me
R', R" = Me; R' = Me, R" = H

-continued

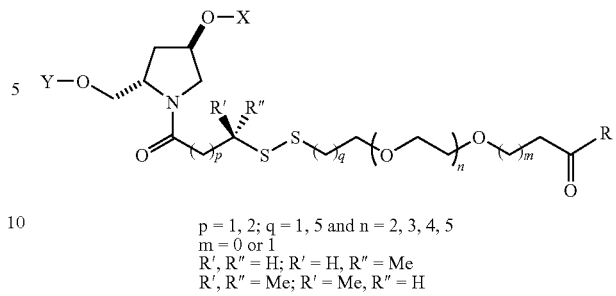

p = 1, 2; q = 1, 5 and n = 2, 3, 4, 5
m = 0 or 1
R', R" = H; R' = H, R" = Me
R', R" = Me; R' = Me, R" = H In some embodiments, RRMS has the structure

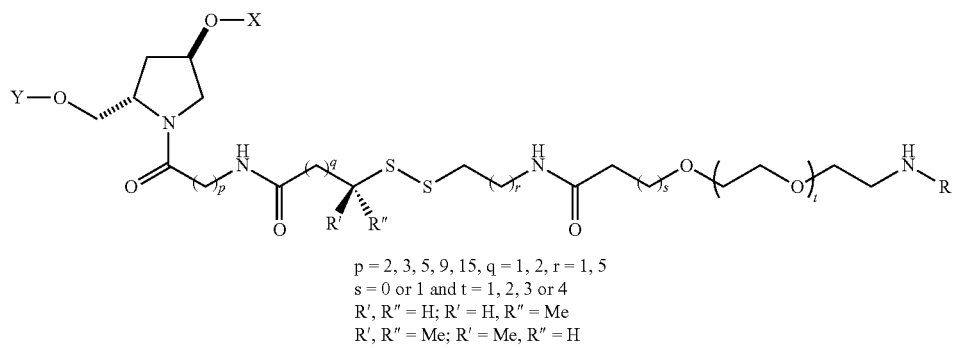

p = 2, 3, 5, 9, 15, q = 1, 2, r = 1, 5
s = 0 or 1 and t = 1, 2, 3 or 4
R', R" = H; R' = H, R" = Me
R', R" = Me; R' = Me, R" = H -continued

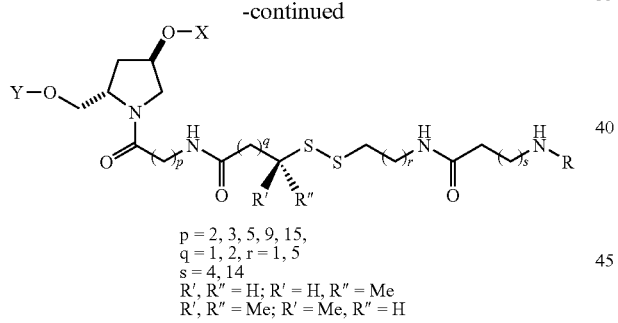

p = 2, 3, 5, 9, 15,
q = 1, 2, r = 1, 5
s = 4, 14
R', R" = H; R' = H, R" = Me
R', R" = Me; R' = Me, R" = H

In some embodiments, RRMS has the structure

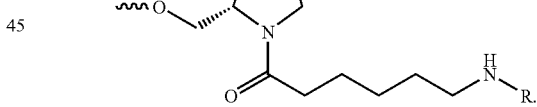

In some embodiments, RRMS has the structure

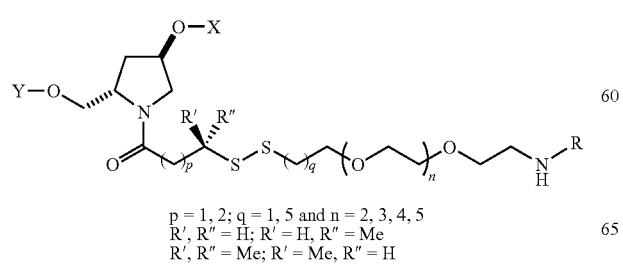

p = 1, 2; q = 1, 5 and n = 2, 3, 4, 5
R', R" = H; R' = H, R" = Me
R', R" = Me; R' = Me, R" = H In some embodiments, RRMS has the structure

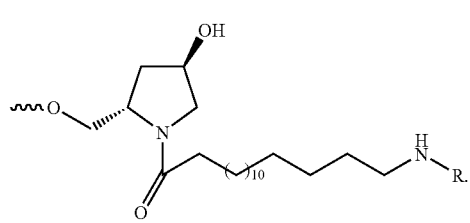

In some embodiments, RRMS has the structure

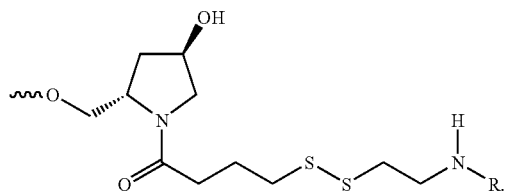

In some embodiments, RRMS has the structure

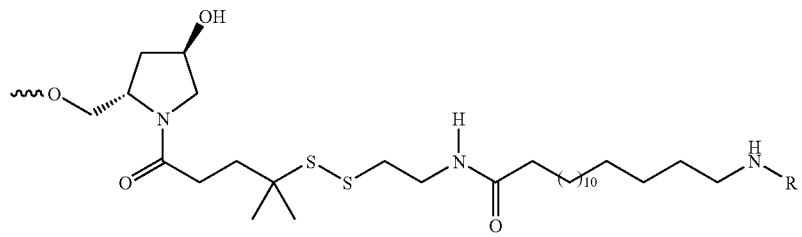

In one aspect, the invention features, a compound having the structure shown in formula (CI)

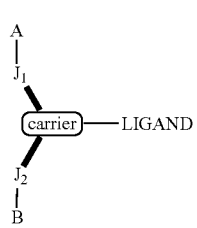

A and B are independently for each occurrence hydrogen, protecting group, optionally substituted aliphatic, optionally substituted aryl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O— nucleoside, or —P(Z$^1$)(Z$^2$)—O— oligonucleotide; wherein Z$^1$ and Z$^2$ are each independently for each occurrence O, S, N(alkyl) or optionally substituted alkyl;

J$_1$ and J$_2$ are independently O, S, NR$^N$, optionally substituted alkyl, OC(O)NH, NHC(O)O, C(O)NH, NHC(O), OC(O), C(O)O, OC(O)O, NHC(O)NH, NHC(S)NH, OC(S)NH, OP(N(R$^P$)$_2$)O, or OP(N(R$^P$)$_2$); and is cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In preferred embodiments, ligand is a folate or folate analog. As used herein, the term "folate" is meant to refer to folate and folate derivatives, including pteroic acid derivatives and analogs. The analogs and derivatives of folic acid suitable for use in the present invention include, but are not limited to, antifolates, dihy-drofloates, tetrahydrofolates, tetrahydroproteins, folinic acid, pteropolyglutamic acid, 1-deza, 3-deaza, 5-deaza, 8-deaza, 10-deaza, 1,5-deaza, 5,10 dideaza, 8,10-dideaza, and 5,8-dideaza folates, antifolates, and pteroic acid derivatives. Additional folate analogs are described in published US publication US2004/0,242,582 (published Dec. 2, 2004).

In one embodiment, the compound is a pyrroline ring system as shown in formula (CII)

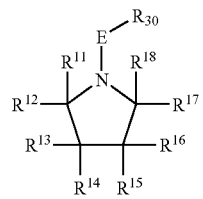

wherein E is absent or C(O), C(O)O, C(O)NH, C(S), C(S)NH, SO, SO$_2$, or SO$_2$NH;

R$^{11}$, R$^{12}$, R$^{13}$, R$^{14}$, R$^{15}$, R$^{16}$, R$^{17}$, and R$^{18}$ are each independently for each occurrence H, —CH$_2$OR$^a$, or OR$^b$, R$^a$ and R$^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O-nucleoside, —P(Z$^1$)(Z$^2$)—O-oligonucleotide, —P(Z$^1$)(O-linker-R$^L$)—O-nucleoside, or —P(Z$^1$)(O-linker-R$^L$)—O-oligonucleotide;

R$^{30}$ is independently for each occurrence -linker-R$^L$ or R$^{31}$;

R$^L$ is hydrogen or a ligand;

R$^{31}$ is —C(O)CH(N(R$^{32}$)$_2$)(CH$_2$)$_h$N(R$^{32}$)$_2$;

R$^{32}$ is independently for each occurrence H, —R$^L$, -linker-R$^L$ or R$^{31}$;

Z$^1$ is independently for each occurrence O or S;

Z$^2$ is independently for each occurrence O, S, N(alkyl) or optionally substituted alkyl; and h is independently for each occurrence 1-20.

For the pyrroline-based click-carriers, R$^{11}$ is —CH$_2$OR$^a$ and R$^3$ is OR$^b$; or R$^{11}$ is —CH$_2$OR$^a$ and R$^9$ is OR$^b$; or R$^{11}$ is —CH$_2$OR$^a$ and R$^{17}$ is OR$^b$; or R$^{13}$ is —CH$_2$OR$^a$ and R$^{11}$ is $OR^b$; or $R^{13}$ is —$CH_2OR^a$ and $R^{15}$ is $OR^b$; or $R^{13}$ is —$CH_2OR^a$ and $R^{17}$ is $OR^b$. In certain embodiments, $CH_2OR^a$ and $OR^b$ may be germinally substituted. For the 4-hydroxyproline-based carriers, $R^{11}$ is —$CH_2OR^a$ and $R^{17}$ is $OR^b$. The pyrroline- and 4-hydroxyproline-based compounds may therefore contain linkages (e.g., carbon-carbon bonds) wherein bond rotation is restricted about that particular linkage, e.g. restriction resulting from the presence of a ring. Thus, $CH_2OR^a$ and $OR^b$ may be cis or trans with respect to one another in any of the pairings delineated above Accordingly, all cis/trans isomers are expressly included. The compounds may also contain one or more asymmetric centers and thus occur as racemates and racemic mixtures, single enantiomers, individual diastereomers and diastereomeric mixtures. All such isomeric forms of the compounds are expressly included (e.g., the centers bearing $CH_2OR^a$ and $OR^b$ can both have the R configuration; or both have the S configuration; or one center can have the R configuration and the other center can have the S configuration and vice versa).

In one embodiment, $R^{11}$ is $CH_2OR^a$ and $R^9$ is $OR^b$.

In one embodiment, $R^b$ is a solid support.

In one embodiment, carrier of formula (CII) is a phosphoramidite, i.e., one of $R^a$ or $R^b$ is —$P(O\text{-alkyl})N(\text{alkyl})_2$, e.g., —$P(OCH_2CH_2CN)N(\text{i-propyl})_2$. In one embodiment, $R^b$ is —$P(O\text{-alkyl})N(\text{alkyl})_2$.

In embodiment, the compound is a ribose ring system as shown in formula (CIII).

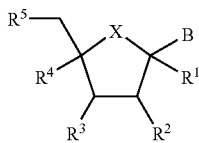

Formula (CIII)

wherein:

X is O, S, $NR^N$ or $CR^P{}_2$;

B is independently for each occurrence hydrogen, optionally substituted natural or non-natural nucleobase, optionally substituted natural nucleobase conjugated with -linker-$R^L$ or optionally substituted non-natural nucleobase conjugated with -linker-$R^L$;

$R^1$, $R^2$, $R^3$, $R^4$ and $R^5$ are each independently for each occurrence H, $OR^6$, F, $N(R^N)_2$, or -J-linker-$R_L$;

J is absent, O, S, $NR^N$, OC(O)NH, NHC(O)O, C(O)NH, NHC(O), NHSO, $NHSO_2$, $NHSO_2NH$, OC(O), C(O)O, OC(O)O, NHC(O)NH, NHC(S)NH, OC(S)NH, $OP(N(R^P)_2)$O, or $OP(N(R^P)_2)$;

$R^6$ is independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —$P(Z^1)(Z^2)$—O-nucleoside, —$P(Z^1)(Z^2)$—O-oligonucleotide, —$P(Z^1)(Z^2)$-formula (CIII), —$P(Z^1)$(O-linker-$R^L$)—O-nucleoside, —$P(Z^1)$(O-linker-$R^L$)—O-oligonucleotide, or —$P(Z^1)$(O-linker-$R^L$)—O-formula (CIII);

$R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

$R^P$ is independently for each occurrence H, optionally substituted alkyl, optionally substituted alkenyl, optionally substituted alkynyl, optionally substituted aryl, optionally substituted cycloalkyl or optionally substituted heteroaryl;

$R^L$ is hydrogen or a ligand;

$Z^1$ and $Z^2$ are each independently for each occurrence O, S N(alkyl) or optionally substituted alkyl; and provided that $R^L$ is present at least once and further provided that $R^L$ is a ligand at least once.

In one embodiment, the carrier of formula (CI) is an acyclic group and is termed an "acyclic carrier". Preferred acyclic carriers can have the structure shown in formula (CIV) or formula (CV) below.

In one embodiment, the compound is an acyclic carrier having the structure shown in formula (CIV).

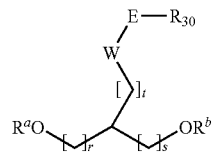

Formula (CIV)

wherein:

W is absent, O, S and $N(R^N)$, where $R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

E is absent or C(O), C(O)O, C(O)NH, C(S), C(S)NH, SO, $SO_2$, or $SO_2NH$;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —$P(Z^1)(Z^2)$—O-nucleoside, —$P(Z^1)(Z^2)$—O-oligonucleotide, —$P(Z^1)$(O-linker-$R^L$)—O-nucleoside, or —$P(Z^1)$(O-linker-$R^L$)-O-oligonucleotide;

$R^{30}$ is independently for each occurrence -linker-$R^L$ or $R^{31}$;

$R^L$ is hydrogen or a ligand;

$R^{31}$ is —$C(O)CH(N(R^{32})_2)(CH_2)_nN(R^{32})_2$;

$R^{32}$ is independently for each occurrence H, —$R^L$, -linker-$R^L$ or $R^{31}$;

$Z^1$ is independently for each occurrence O or S;

$Z^2$ is independently for each occurrence O, S, N(alkyl) or optionally substituted alkyl;

h is independently for each occurrence 1-20; and r, s and t are each independently for each occurrence 0, 1, 2 or 3.

When r and s are different, then the tertiary carbon can be either the R or S configuration. In preferred embodiments, x and y are one and z is zero (e.g. carrier is based on serinol). The acyclic carriers can optionally be substituted, e.g. with hydroxy, alkoxy, perhaloalky.

In one embodiment, the compound is an acyclic carrier having the structure shown in formula (CV)

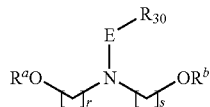

Formula (CV)

wherein E is absent or C(O), C(O)O, C(O)NH, C(S), C(S)NH, SO, SO$_2$, or SO$_2$NH;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O-nucleoside, —P(Z$^1$)(Z$^2$)—O-oligonucleotide, —P(Z$^1$)(Z$^2$)-formula (I), —P(Z$^1$)(O-linker-R$^L$)—O-nucleoside, or —P(Z$^1$)(O-linker-R$^L$)—O-oligonucleotide;

R$^{30}$ is independently for each occurrence -linker-R$^L$ or R$^{31}$;
R$^L$ is hydrogen or a ligand;
R$^{31}$ is —C(O)CH(N(R$^{32}$)$_2$)(CH$_2$)$_h$N(R$^{32}$)$_2$;
R$^{32}$ is independently for each occurrence H, —R$^L$, -linker-R$^L$ or R$^{31}$;
Z$^1$ is independently for each occurrence O or S;
Z$^2$ is independently for each occurrence O, S, N(alkyl) or optionally substituted alkyl; and
h is independently for each occurrence 1-20; and
r and s are each independently for each occurrence 0, 1, 2 or 3.

Other carrier compounds amenable to the invention are described in copending applications U.S. Ser. No. 10/916,185, filed Aug. 10, 2004; U.S. Ser. No. 10/946,873, filed Sep. 21, 2004; U.S. Ser. No. 10/985,426, filed Nov. 9, 2004; U.S. Ser. No. 10/833,934, filed Aug. 3, 2007; U.S. Ser. No. 11/115,989 filed Apr. 27, 2005 and U.S. Ser. No. 11/119,533, filed Apr. 29, 2005, which are incorporated by reference in their entireties for all purposes.

In some embodiments, ligand is chosen from a group consisting of

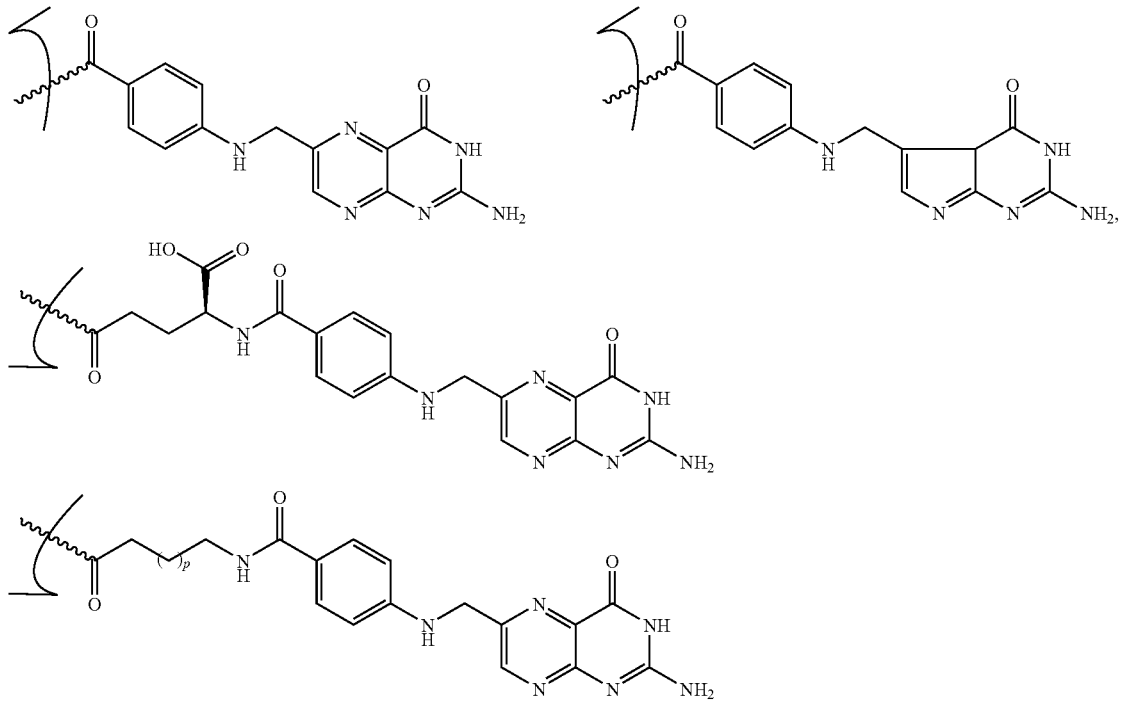

p = 1, 3, 8, 13, 19

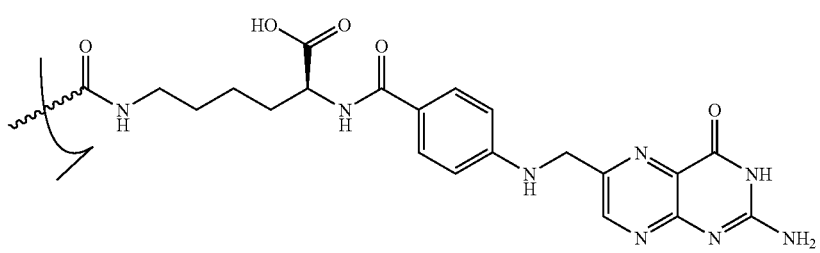

-continued
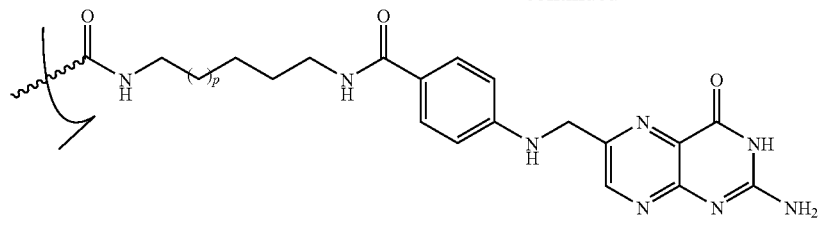
p = 1, 2, 7, 12, 18
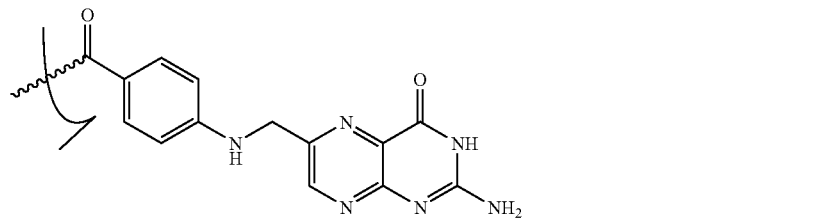
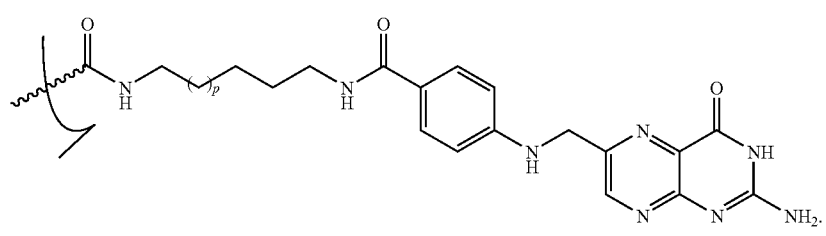
p = 1, 2, 7, 12, 18
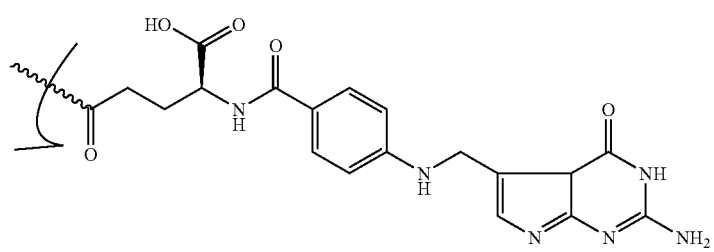
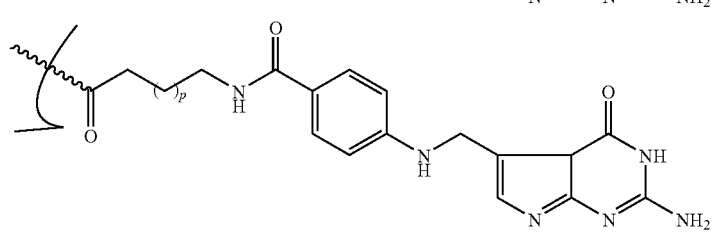
p = 1, 3, 8, 13, 19
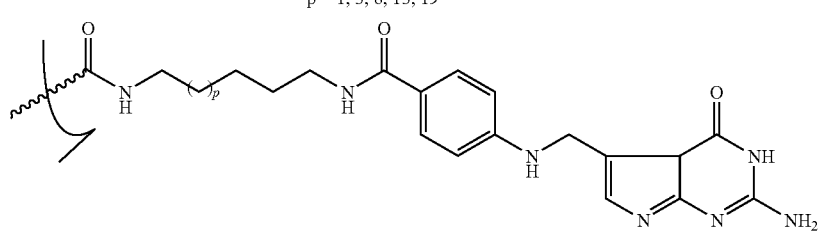
p = 1, 2, 7, 12, 18
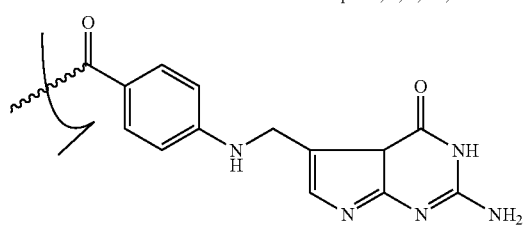

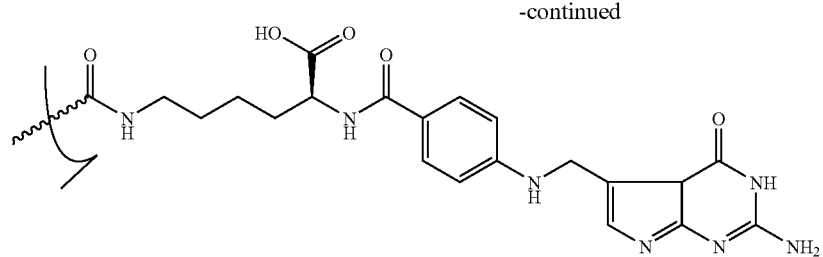
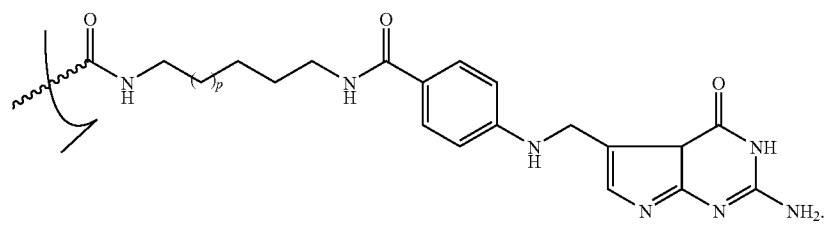
p = 1, 2, 7, 12, 18
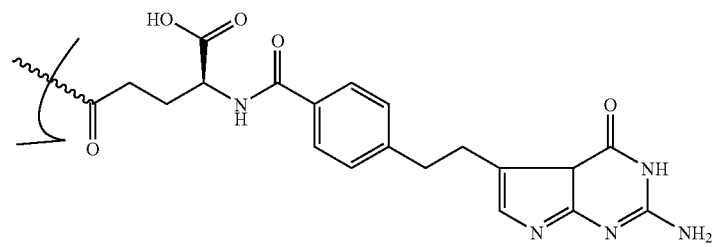
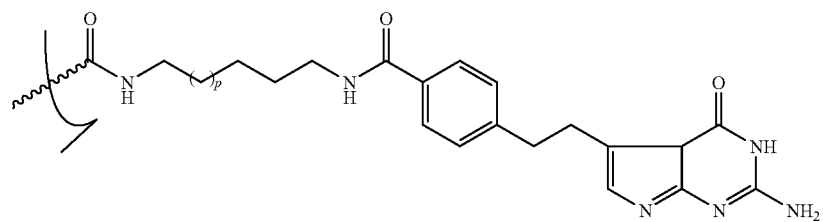
p = 1, 2, 7, 12, 18
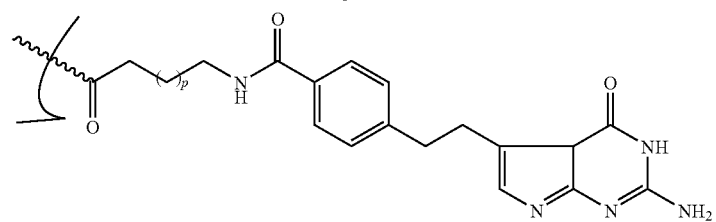
p = 1, 3, 8, 13, 19
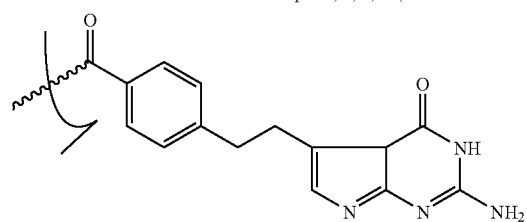
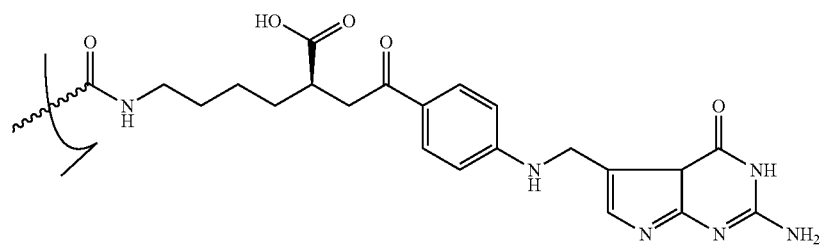

-continued
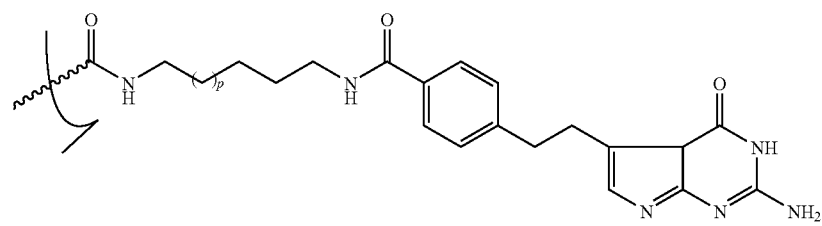
p = 1, 2, 7, 12, 18
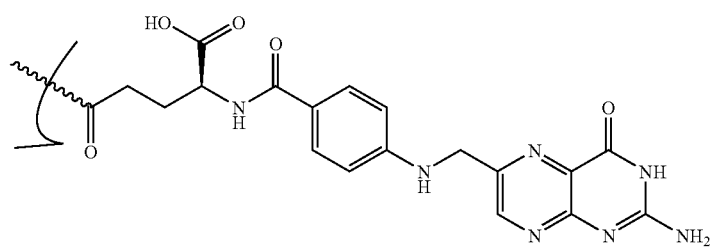
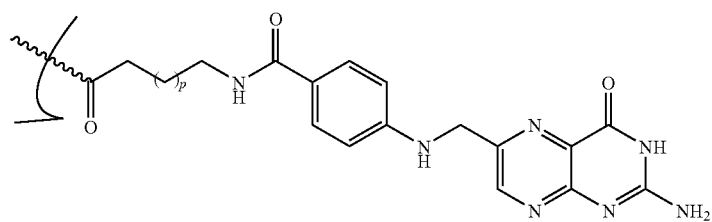
p = 1, 3, 8, 13, 19
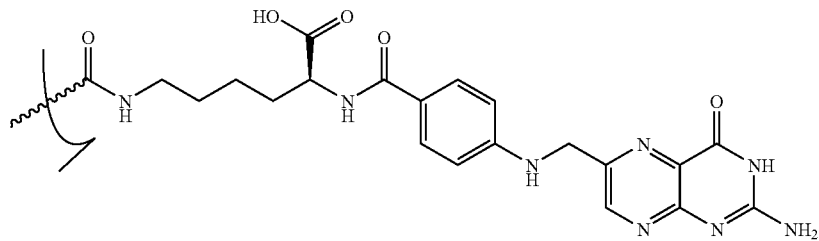
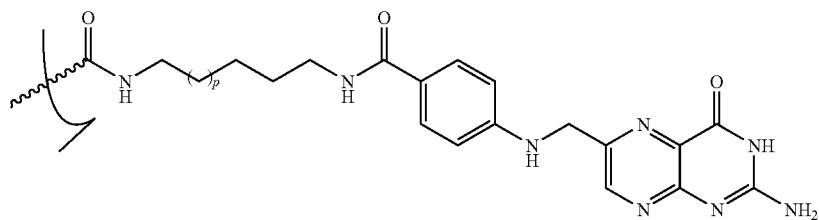
p = 1, 2, 7, 12, 18
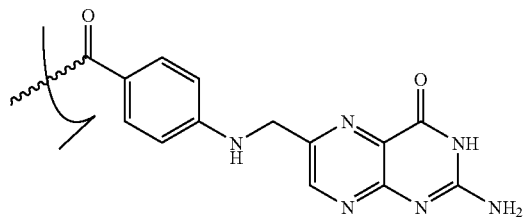

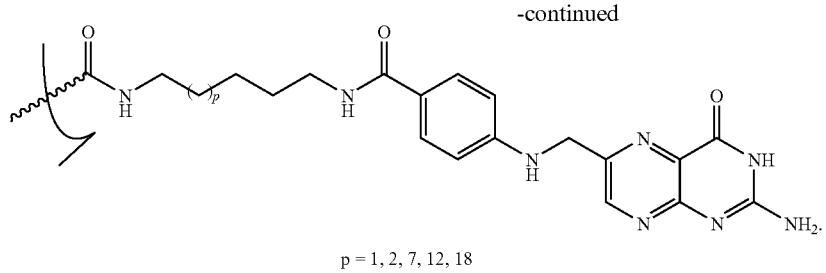

p = 1, 2, 7, 12, 18

Embodiments can include one or more of the features described above.

In a further aspect, this invention features an iRNA agent having a first strand and a second strand, wherein at least one subunit having a formula (I) is incorporated into at least one of said strands.

In one aspect, this invention features an iRNA agent having a first strand and a second strand, wherein at least two subunits having a formula (I) are incorporated into at least one of said strands.

In another aspect, this invention provides a method of making an iRNA agent described herein having a first strand and a second strand in which at least one subunit of formula (I) is incorporated in the strands. The method includes contacting the first strand with the second strand.

In a further aspect, this invention provides a method of modulating expression of a target gene, the method includes administering an iRNA agent described herein having a first strand and a second strand in which at least one subunit of formula (I) is incorporated in the strands to a subject.

In one aspect, this invention features a pharmaceutical composition having an iRNA agent described herein having a first strand and a second strand in which at least one subunit of formula (I) is incorporated in the strands and a pharmaceutically acceptable carrier.

RRMS monomers described herein may be incorporated into any double-stranded RNA-like molecule described herein, e.g., an iRNA agent. An iRNA agent may include a duplex comprising a hybridized sense and antisense strand, in which the antisense strand and/or the sense strand may include one or more of the RRMSs described herein. An RRMS can be introduced at one or more points in one or both strands of a double-stranded iRNA agent. An RRMS can be placed at or near (within 1, 2, or 3 positions) of the 3' or 5' end of the sense strand or at near (within 1, 2 or 3 positions of) the 3' end of the antisense strand. In some embodiments it is preferred to not have an RRMS at or near (within 1, 2, or 3 positions of) the 5' end of the antisense strand. An RRMS can be internal, and will preferably be positioned in regions not critical for antisense binding to the target.

In an embodiment, an iRNA agent may have an RRMS at (or within 1, 2, or 3 positions of) the 3' end of the antisense strand. In an embodiment, an iRNA agent may have an RRMS at (or within 1, 2, or 3 positions of) the 3' end of the antisense strand and at (or within 1, 2, or 3 positions of) the 3' end of the sense strand. In an embodiment, an iRNA agent may have an RRMS at (or within 1, 2, or 3 positions of) the 3' end of the antisense strand and an RRMS at the 5' end of the sense strand, in which both RRMS are located at the same end of the iRNA agent.

In an embodiment, an iRNA agent may have an RRMS at (or within 1, 2, or 3 positions of) the 3' end of the antisense strand and an RRMS at the 5' end of the sense strand, in which both RRMSs may share the same ligand (e.g., folic acid) via connection of their individual tethers to separate positions on the ligand. A ligand shared between two proximal RRMSs is referred to herein as a "hairpin ligand."

In other embodiments, an iRNA agent may have an RRMS at the 3' end of the sense strand and an RRMS at an internal position of the sense strand. An iRNA agent may have an RRMS at an internal position of the sense strand; or may have an RRMS at an internal position of the antisense strand; or may have an RRMS at an internal position of the sense strand and an RRMS at an internal position of the antisense strand.

In preferred embodiments the iRNA agent includes a first and second sequences, which are preferably two separate molecules as opposed to two sequences located on the same strand, have sufficient complementarity to each other to hybridize (and thereby form a duplex region), e.g., under physiological conditions, e.g., under physiological conditions but not in contact with a helicase or other unwinding enzyme.

It is preferred that the first and second sequences be chosen such that the double stranded iRNA agent includes a single strand or unpaired region at one or both ends of the molecule. Thus, a double stranded iRNA agent contains first and second sequences, preferably paired to contain an overhang, e.g., one or two 5' or 3' overhangs but preferably a 3' overhang of 2-3 nucleotides. Most embodiments will have a 3' overhang. Preferred iRNA agents will have single-stranded overhangs, preferably 3' overhangs, of 1 or preferably 2 or 3 nucleotides in length at each end. The overhangs can be the result of one strand being longer than the other, or the result of two strands of the same length being staggered. 5' ends are preferably phosphorylated.

Other modifications to sugars, bases, or backbones can be incorporated into the iRNA agents.

The iRNA agents can take an architecture or structure described herein. The iRNA agents can be palindromic, or double targeting, as described herein.

The iRNA agents can have a sequence such that a non-cannonical or other than cannonical Watson-Crick structure is formed between two monomers of the iRNA agent or between a strand of the iRNA agent and another sequence, e.g., a target or off-target sequence, as is described herein.

The iRNA agent can be selected to target any of a broad spectrum of genes, including any of the genes described herein.

In a preferred embodiment the iRNA agent has an architecture (architecture refers to one or more of overall length, length of a duplex region, the presence, number, location, or length of overhangs, single strand versus double strand form) described herein. E.g., the iRNA agent can be less than 30 nucleotides in length, e.g., 21-23 nucleotides. Preferably, the iRNA is 21 nucleotides in length and there is a duplex region of about 19 pairs. In one embodiment, the iRNA is 21 nucleotides in length, and the duplex region of the iRNA is 19 nucleotides. In another embodiment, the iRNA is greater than 30 nucleotides in length.

In some embodiment the duplex region of the iRNA agent will have, mismatches. Preferably it will have no more than 1, 2, 3, 4, or 5 bases, which do not form canonical Watson-Crick pairs or which do not hybridize. Overhangs are discussed in detail elsewhere herein but are preferably about 2 nucleotides in length. The overhangs can be complementary to the gene sequences being targeted or can be other sequence. TT is a preferred overhang sequence. The first and second iRNA agent sequences can also be joined, e.g., by additional bases to form a hairpin, or by other non-base linkers.

In addition to the RRMS-containing bases the iRNA agents described herein can include nuclease resistant monomers (NRMs) described in copending co-owned U.S. Provisional application Ser. No. 10/553,659 filed on Apr. 14, 2006 and International Application No. PCT/US04/07070, both of which are hereby incorporated by reference.

In some embodiments, the iRNA agent will have a monomer with the structure shown in formula (LI) in addition to monomer of formula (I) or formula (I').

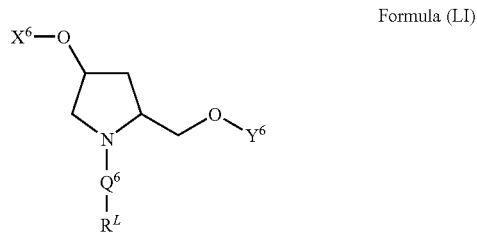

Formula (LI)

wherein $X^6$ and $Y^6$ are each independently H, a hydroxyl protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, —P(Z')(Z")O—$R^1$-Q'-$R^2$—OP(Z''')(Z'''')O-oligonucleotide, a nucleotide, or an oligonucleotide, —P(Z')(Z")-formula (I) or —P(Z')(Z")—;

$Q^6$ is absent or —($P^6$-$Q^6$-$R^6$)$_v$-$T^6$-;

$P^6$ and $T^6$ are each independently for each occurrence absent, CO, NH, O, S, OC(O), NHC(O), $CH_2$, $CH_2$NH or $CH_2$O;

$Q^6$ is independently for each occurrence absent, substituted alkylene wherein one or more methylenes can be interrupted or terminated by one or more of O, S, S(O), $SO_2$, N($R^N$), C(R')=C(R'), C≡C or C(O);

$R^6$ is independently for each occurrence absent, NH, O, S, $CH_2$, C(O)O, C(O)NH, NHCH($R^a$)C(O), —C(O)—CH($R^a$)—NH—, CO, CH=N—O,

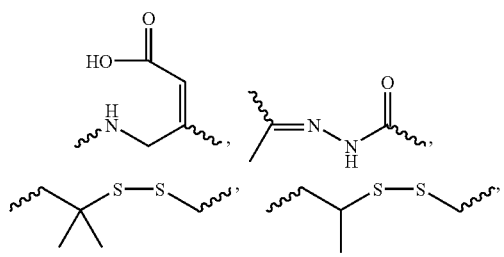

or heterocyclyl;

R' and R" are each independently H, $C_1$-$C_6$ alkyl OH, SH, N($R^N$)$_2$;

$R^N$ is independently for each occurrence hydrogen, methyl, ethyl, propyl, isopropyl, butyl or benzyl;

$R^a$ is H or amino acid side chain;

Z', Z", Z''' and Z'''' are each independently for each occurrence O or S;

v represent independently for each occurrence 0-20;

$R^L$ is a lipophile (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, Friedelin, epifriedelanol derivatized lithocholic acid), or a cationic lipid.

In some embodiments, one or more, e.g., 1, 2, 3, 4 or 5, monomers of formula (LI) in addition to one or more, e.g. 1, 2, 3, 4, or 5, monomers of formula (I) or formula (I') are present in the iRNA agent.

In some preferred embodiments only 1 monomer of formula (I) or formula (I') and 1 monomer of formula (LI) are present in the iRNA agent.

In some embodiments, $R^L$ is cholesterol.

In some embodiments, $R^L$ is lithocholic.

In some embodiments, $R^L$ is oleyl lithocholic.

In a preferred embodiment, the iRNA agent targets an exogenous gene of a genetically modified cell. An exogenous gene can be, for example, a viral or bacterial gene that derives from an organism that has invaded or infected the cell, or the exogenous gene can be any gene introduced into the cell by natural or artificial means, such as by a genetic recombination event. An iRNA agent can target a viral gene, for example, such as a hepatitis viral gene (e.g., a gene of an HAV, HBV, or HCV). Alternatively, or in addition, the iRNA agent can silence a reporter gene, such as GFP or beta galatosidase and the like. These iRNA agents can be used to silence exogenous genes in an adherent tumor cell line.

In another aspect, the invention provides, methods of silencing a target gene by providing an iRNA agent to which a folic acid, folic acid analog or folic acid mimic is conjugated. In a preferred embodiment the conjugated iRNA agent can be used to silence a target gene in an organism, e.g., a mammal, e.g., a human, or to silence a target gene in a cell line or in cells which are outside an organism. In the case of a whole organism, the method can be used to silence a gene, e.g., a gene described herein, and treat a condition mediated by the gene. In the case of use on a cell which is not part of an organism, e.g., a primary cell line, secondary cell line, tumor cell line, or transformed or immortalized cell line, the iRNA agent to which a folic acid, folic acid analog or folic acid mimic is conjugated can be used to silence a gene, e.g., one described herein. Cells which are not part of a whole organism can be used in an initial screen to determine if an iRNA agent is effective in silencing a gene. A test in cells which are not part of a whole organism can be followed by testing the iRNA agent in a whole animal. In preferred embodiments, the iRNA agent which is conjugated to a carbohydrate, a steroid, or a steroid tethered to at least one carbohydrate is conjugated is administered to an organism, or contacted with a cell which is not part of an organism, in the absence of (or in a reduced amount of) other reagents that facilitate or enhance delivery, e.g., a compound which enhances transit through the cell membrane. (A reduced amount can be an amount of such reagent which is reduced in comparison to what would be needed to get an equal amount of nonconjugated iRNA agent into the target cell).

In a preferred embodiment the iRNA agent is suitable for delivery to a cell in vivo, e.g., to a cell in an organism. In another aspect, the iRNA agent is suitable for delivery to a cell in vitro, e.g., to a cell in a cell line.

An iRNA agent to which a folic acid, folic acid analog or folic acid mimic is attached can target any gene described herein and can be delivered to any cell type described herein, e.g., a cell type in an organism, tissue, or cell line. Delivery of the iRNA agent can be in vivo, e.g., to a cell in an organism, or in vitro, e.g., to a cell in a cell line.

In another aspect, the invention provides compositions of iRNA agents described herein, and in particular compositions of an iRNA agent to which a folate receptor binding ligand e.g. a folic acid, folic acid analog or folic acid mimic is conjugated, e.g., a lipophilic conjugated iRNA agent described herein. In a preferred embodiment the composition is a pharmaceutically acceptable composition.

In preferred embodiments, the composition, e.g., pharmaceutically acceptable composition, is free of, has a reduced amount of, or is essentially free of other reagents that facilitate or enhance delivery, e.g., compounds which enhance transit through the cell membrane. (A reduced amount can be an amount of such reagent which is reduced in comparison to what would be needed to get an equal amount of nonconjugated iRNA agent into the target cell). E.g., the composition is free of, has a reduced amount of, or is essentially free of: an additional lipophilic moiety; a transfection agent, e.g., concentrations of an ion or other substance which substantially alters cell permeability to an iRNA agent; a transfecting agent such as Lipofectamine™ (Invitrogen, Carlsbad, Calif.), Lipofectamine 2000™, TransIT-TKO™ (Mirus, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), and the like.

In a preferred embodiment the composition is suitable for delivery to a cell in vivo, e.g., to a cell in an organism. In another aspect, the iRNA agent is suitable for delivery to a cell in vitro, e.g., to a cell in a cell line.

The RRMS-containing iRNA agents can be used in any of the methods described herein, e.g., to target any of the genes described herein or to treat any of the disorders described herein. They can be incorporated into any of the formulations, modes of delivery, delivery modalities, kits or preparations, e.g., pharmaceutical preparations, described herein. E.g, a kit which includes one or more of the iRNA agents described herein, a sterile container in which the iRNA agent is disclosed, and instructions for use.

The methods and compositions of the invention, e.g., the RRSM-containing iRNA agents described herein, can be used with any of the iRNA agents described herein. In addition, the methods and compositions of the invention can be used for the treatment of any disease or disorder described herein, and for the treatment of any subject, e.g., any animal, any mammal, such as any human.

The methods and compositions of the invention, e.g., the RRMS-containing iRNA agents described herein, can be used with any dosage and/or formulation described herein, as well as with any route of administration described herein.

Definitions

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH (alkyl) and —N(alkyl)$_2$ radicals respectively. The term "aralkylamino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals respectively. The term "siloxy" refers to a $R_3SiO$— radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom can be substituted. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Fused rings are rings that share a common carbon-carbon bond or a common carbon atom (e.g., spiro-fused rings). Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), S(O), aryl (where n is 0-2), S(O), heteroaryl (where n is 0-2), S(O), heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

Ligand-Conjugated Monomers

Cyclic sugar replacement-based monomers, e.g., sugar replacement-based ligand-conjugated monomers, are also referred to herein as ribose replacement monomer subunit (RRMS) monomer compounds. Preferred carriers have the general formula (I) provided below. The carriers are an entity which can be incorporated into a strand. Thus, it is understood that the structures also encompass the situations wherein one (in the case of a terminal position) or two (in the case of an internal position) of the attachment points, e.g., either X or Y in case of terminal position and both X and Y in case of internal position, is connected to the phosphate, or modified phosphate, e.g., sulfur containing, backbone.

Tethers

In certain embodiments, a moiety, e.g., a ligand may be connected indirectly to the carrier via the intermediacy of an intervening tether. Tethers are connected to the carrier at a tethering attachment point (TAP) and may include any $C_1$–$C_{100}$ carbon-containing moiety, (e.g. $C_1$–$C_{75}$, $C_1$–$C_{50}$, $C_1$–$C_{20}$, $C_1$–$C_{10}$; $C_1$, $C_2$, $C_3$, $C_4$, $C_5$, $C_6$, $C_7$, $C_8$, $C_9$, or $C_{10}$), preferably having at least one nitrogen atom. In preferred embodiments, the nitrogen atom forms part of a terminal amino or amido (NHC(O)—) group on the tether, which may serve as a connection point for the ligand. Preferred tethers (underlined) include TAP-$(CH_2)_n$NH—; TAP-C(O)$(CH_2)_n$NH—; TAP-NR''''$(CH_2)_n$NH—, TAP-C(O)—$(CH_2)_n$—C(O)—; TAP-C(O)—$(CH_2)_n$—C(O)O—; TAP-C(O)—O—; TAP-C(O)—$(CH_2)_n$—NH—C(O)—; TAP-C(O)—$(CH_2)_n$—; TAP-C(O)—NH—; TAP-C(O)—; TAP-$(CH_2)_n$—C(O)—; TAP-$(CH_2)_n$—C(O)O—; TAP-$(CH_2)_n$—; or TAP-$(CH_2)_n$—NH—C(O)—; TAP-C(O)—$(CH_2)_n$—NH—C(O)—$(CH_2)_n$CH(R''')NH—; TAP-C(O)—$(CH_2)_n$—NH—C(O)—$(CH_2)_n$C(R')(R'')—SS—$(CH_2)_n$—NH—C(O)—$(CH_2)_n$CH(R''')NH—; TAP-C(O)—$(CH_2)_n$—NH—C(O)—$(CH_2)_n$—SS—$(CH_2)_n$CH(R''')—NH—C(O)—$(CH_2)_n$CH(R''')NH—; TAP-$(CH_2)_n$—NH—C(O)—$(CH_2)_n$C(R')(R'')—SS—$(CH_2)_n$—; in which each n is independently-20 (e.g., 1, 2, 3, 4, 5, 6, 7, 8, 9, 10, 11, 12, 13, 14, 15, 16, 17, 18, 19, or 20), R', R'' and R''' are described elsewhere and R'''' is $C_1$-$C_6$ alkyl. Preferably, n is 2, 5, 6, or 11. In other embodiments, the nitrogen may form part of a terminal oxyamino group, e.g., —$ONH_2$, or hydrazino group, —$NHNH_2$. The tether may optionally be substituted, e.g., with hydroxy, alkoxy, perhaloalkyl, and/or optionally inserted with one or more additional heteroatoms, e.g., N, O, or S. Preferred tethered ligands may include, e.g., TAP-$(CH_2)_n$NH(LIGAND); TAP-C(O)$(CH_2)_n$NH(LIGAND); TAP-NR''''$(CH_2)_n$NH(LIGAND); TAP-$(CH_2)_n$ONH(LIGAND); TAP-C(O)(CH)$_n$ONH(LIGAND); TAP-NR''''$(CH_2)_n$ONH(LIGAND); TAP-$(CH_2)_n$ NHNH$_2$(LIGAND), TAP-C(O)$(CH_2)_n$NHNH$_2$(LIGAND); TAP-NR''''$(CH_2)_n$NHNH$_2$(LIGAND); TAP-C(O)—$(CH_2)_n$—C(O)(LIGAND); TAP-C(O)—$(CH_2)_n$—C(O)O(LIGAND); TAP-C(O)—O(LIGAND); TAP-C(O)—$(CH_2)_n$—NH—C(O)(LIGAND); TAP-C(O)—$(CH_2)_n$(LIGAND); TAP-C(O)—NH(LIGAND); TAP-C(O)(LIGAND); TAP-$(CH_2)_n$—C(O)O(LIGAND); TAP-$(CH_2)_n$—C(O)O(LIGAND); TAP-$(CH_2)_n$(LIGAND); TAP-$(CH_2)_n$—NH—C(O)(LIGAND); TAP-C(O)—$(CH_2)_n$—NH—C(O)—$(CH_2)_n$CH(R''')NH(LIGAND); TAP-C(O)—$(CH_2)_n$—NH—C(O)—$(CH_2)_n$C(R')(R'')—SS—$(CH_2)_n$—NH—C(O)—$(CH_2)_n$CH(R''')NH(LIGAND); TAP-C(O)—$(CH_2)_n$—NH—C(O)—$(CH_2)_n$—SS—$(CH_2)_n$CH(R''')—

NH—C(O)—(CH$_2$)$_n$CH(R''')NH(LIGAND); TAP-(CH$_2$)$_n$—NH—C(O)—(CH$_2$)$_n$C(R')(R'')—SS—(CH$_2$)$_n$(LIGAND). In some embodiments, amino terminated tethers (e.g., NH$_2$, ONH$_2$, NH$_2$NH$_2$) can form an imino bond (i.e., C=N) with the ligand. In some embodiments, amino terminated tethers (e.g., NH$_2$, ONH$_2$, NH$_2$NH$_2$) can be acylated, e.g., with C(O)CF$_3$.

In some embodiments, the tether can terminate with a mercapto group (i.e., SH) or an olefin (e.g., CH=CH$_2$). For example, the tether can be TAP-(CH$_2$)—SH, TAP-C(O)(CH$_2$)$_n$SH, TAP-(CH$_2$)$_n$—(CH=CH$_2$)—, or TAP-C(O)(CH$_2$)$_n$(CH=CH$_2$), in which n can be as described elsewhere. The tether may optionally be substituted, e.g., with hydroxy, alkoxy, perhaloalkyl, and/or optionally inserted with one or more additional heteroatoms, e.g., N, O, or S. The double bond can be cis or trans or E or Z.

In other embodiments the tether may include an electrophilic moiety, preferably at the terminal position of the tether. Preferred electrophilic moieties include, e.g., an aldehyde, alkyl halide, mesylate, tosylate, nosylate, or brosylate, or an activated carboxylic acid ester, e.g. an NHS ester, or a pentafluorophenyl ester. Preferred tethers (underlined) include TAP-(CH$_2$)$_n$CHO; TAP-C(O)(CH$_2$)$_n$CHO; or TAP-NR''''(CH$_2$)$_n$CHO, in which n is 1-6 and R'''' is C$_1$-C$_6$ alkyl; or TAP-(CH$_2$)$_n$C(O)ONHS; TAP-C(O)(CH$_2$)$_n$C(O)ONHS; or TAP-NR''''(CH$_2$)$_n$C(O)ONHS, in which n is 1-6 and R'''' is C$_1$-C$_6$ alkyl; TAP-(CH$_2$)$_n$C(O)OC$_6$F$_5$; TAP-C(O)(CH$_2$)$_n$C(O) OC$_6$F$_5$; or TAP-NR''''(CH$_2$)$_n$C(O)OC$_6$F$_5$, in which n is 1-11 and R'''' is C$_1$-C$_6$ alkyl; or —(CH$_2$)$_n$CH$_2$LG; TAP-C(O)(CH$_2$)$_n$CH$_2$LG; or TAP-NR''''(CH$_2$)$_n$CH$_2$LG, in which n can be as described elsewhere and R'''' is C$_1$-C$_6$ alkyl (LG can be a leaving group, e.g., halide, mesylate, tosylate, nosylate, brosylate). Tethering can be carried out by coupling a nucleophilic group of a ligand, e.g., a thiol or amino group with an electrophilic group on the tether.

In other embodiments, it can be desirable for the monomer to include a phthalimido group (K) at the terminal position of the tether.

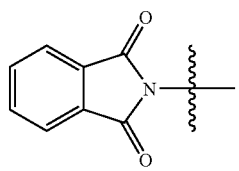

K

In other embodiments, other protected amino groups can be at the terminal position of the tether, e.g., alloc, monomethoxy trityl (MMT), trifluoroacetyl, Fmoc, or aryl sulfonyl (e.g., the aryl portion can be ortho-nitrophenyl or ortho, para-dinitrophenyl).

Any of the tethers described herein may further include one or more additional linking groups, e.g., —O—(CH$_2$)$_n$—, —(CH$_2$)$_n$—SS—, —(CH$_2$)$_n$—, or —(CH=CH)—.

Ligands

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. As discussed above, the ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-(CH$_2$)$_n$NH$_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipids, steroids (e.g., cholesterol, uvaol, hecigenin, diosgenin), terpenes (e.g., triterpenes, e.g., sarsasapogenin, Friedelin, epifriedelanol derivatized lithocholic acid), vitamins (e.g., folic acid, folic acid mimics, folate receptor binding ligands, vitamin A, vitamin E, biotin, pyridoxal), carbohydrates, proteins, protein binding agents, integrin targeting molecules, CCR5 receptor antagonists, CCR5 receptor binding ligands, polycationics (e.g., porphyrins), peptides, polyamines, peptide mimics, PEG. In some embodiments, the ligand can be one of the following:

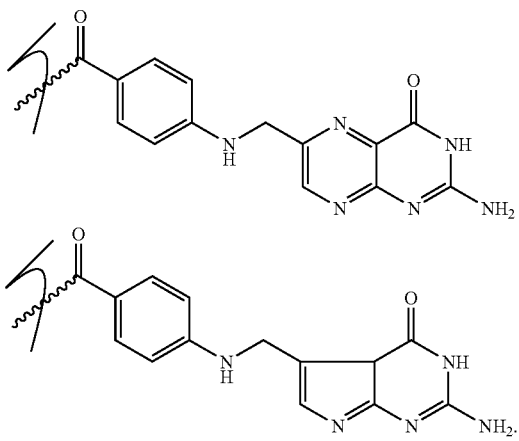

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In certain embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972), the EALA (SEQ ID NO: 1) peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component may contain a chemical group (e.g., an amino acid) which will undergo a change in charge or protonation in response to a change in pH. The endosomolytic component may be linear or branched. Exemplary primary sequences of peptide based endosomolytic ligands are shown in Table 1.

6. Oberhauser, B., Plank, C. et al. (1995). Enhancing endosomal exit of nucleic acids using pH-sensitive viral fusion peptides. Deliv. Strategies Antisense Oligonucleotide Ther. 247-66.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, insulin, cyclodextrin or hyaluronic acid); or a lipid. The

TABLE 1

List of peptides with endosomolytic activity.

| Name | Sequence (N to C) | Ref. | SEQ ID NO: |
|---|---|---|---|
| GALA | AALEALAEALEALAEALEALAEAAAAGGC | 1 | 2 |
| EALA (SEQ ID NO: 1) | AALAEALAEALAEALAEALAEALAAAAGGC | 2 | 3 |
|  | ALEALAEALEALAEA | 3 | 4 |
| INF-7 | GLFEAIEGFIENGWEGMIWDYG | 4 | 5 |
| Inf HA-2 | GLFGAIAGFIENGWEGMIDGWYG | 5 | 6 |
| diINF-7 | GLF EAI EGFI ENGW EGMI DGWYGC<br>GLF EAI EGFI ENGW EGMI DGWYGC | 5 | 7 |
| diINF3 | GLF EAI EGFI ENGW EGMI DGGC<br>GLF EAI EGFI ENGW EGMI DGGC | 6 | 8 |
| GLF | GLFGALAEALAEALAEHLAEALAEALEALAAGGSC | 6 | 9 |
| GALA-INF3 | GLFEAIEGFIENGWEGLAEALAEALEALAAGGSC | 6 | 10 |
| INF-5 | GLF EAI EGFI ENGW EGnI DG K<br>GLF EAI EGFI ENGW EGnI DG | 4 | 11<br>12 | n, norleucine

References
1. Subbarao et al., Biochemistry, 1987, 26: 2964-2972.
2. Vogel et al., J. Am. Chem. Soc., 1996, 118: 1581-1586
3. Turk, M. J., Reddy, J. A. et al. (2002). Characterization of a novel pH-sensitive peptide that enhances drug release from folate-targeted liposomes at endosomal pHs. Biochim. Biophys. Acta 1559, 56-68.
4. Plank, C. Oberhauser, B. Mechtler, K. Koch, C. Wagner, E. (1994). The influence of endosome-disruptive peptides on gene transfer using synthetic virus-like gene transfer systems, J. Biol. Chem. 269 12918-12924.
5. Mastrobattista, E., Koning, G. A. et al. (2002). Functional characterization of an endosome-disruptive peptide and its application in cytosolic delivery of immunoliposome-entrapped proteins. J. Biol. Chem. 277, 27135-43.

ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

TABLE 2

Targeting Ligands and their associated receptors

| Liver Cells | | Ligand | Receptor |
|---|---|---|---|
| | | Negatively charged molecules | Scavenger receptors |
| 1) | Parenchymal Cell (PC) (Hepatocytes) | Galactose | ASGP-R (Asiologlycoprotein receptor) |
| | | Gal NAc (n-acetyl-galactosamine) | ASPG-R Gal NAc Receptor |
| | | Lactose | |
| | | Asialofetuin | ASPG-r |
| 2) | Sinusoidal Endothelial Cell (SEC) | Hyaluronan | Hyaluronan receptor |
| | | Procollagen | Procollagen receptor |
| | | Mannose | Mannose receptors |
| | | N-acetyl Glucosamine | Scavenger receptors |
| | | Immunoglobulins | Fc Receptor |
| | | LPS | CD14 Receptor |
| | | Insulin | Receptor mediated transcytosis |
| | | Transferrin | Receptor mediated transcytosis |
| | | Albumins | Non-specific |
| | | Sugar-Albumin conjugates | |
| | | Mannose-6-phosphate | Mannose-6-phosphate receptor |
| 3) | Kupffer Cell (KC) | Mannose | Mannose receptors |
| | | Fucose | Fucose receptors |
| | | Albumins | Non-specific |
| | | Mannose-albumin conjugates | |

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the iRNA agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long (see Table 3, for example).

TABLE 3

Exemplary Cell Permeation Peptides.

| Cell Permeation Peptide | Amino acid Sequence | Reference | SEQ ID NO: |
|---|---|---|---|
| Penetratin | RQIKIWFQNRRMKWKK | Derossi et al., J. Biol. Chem. 269:10444, 1994 | 13 |
| Tat fragment (48-60) | GRKKRRQRRRPPQC | Vives et al., J. Biol. Chem., 272:16010, 1997 | 14 |
| Signal Sequence-based peptide | GALFLGWLGAAGSTMGAWSQPKKKRKV | Chaloin et al., Biochem. Biophys. Res. Commun., 243:601, 1998 | 15 |
| PVEC | LLIILRRRIRKQAHAHSK | Elmquist et al., Exp. Cell Res., 269:237, 2001 | 16 |
| Transportan | GWTLNSAGYLLKINLKALAALAKKIL | Pooga et al., FASEB J., 12:67, 1998 | 17 |
| Amphiphilic model peptide | KLALKLALKALKAALKLA | Oehlke et al., Mol. Ther., 2:339, 2000 | 18 |
| Arg$_9$ | RRRRRRRRR | Mitchell et al., J. Pept. Res., 56:318, 2000 | 19 |
| Bacterial cell wall permeating | KFFKFFKFFK | | 20 |
| LL-37 | LLGDFFRKSKEKIGKEFKRIVQRIKDFLRNLVPRTES | | 21 |
| Cecropin P1 | SWLSKTAKKLENSAKKRISEGIAIAIQGGPR | | 22 |
| α-defensin | ACYCRIPACIAGERRYGTCIYQGRLWAFCC | | 23 |
| b-defensin | DHYNCVSSGGQCLYSACPIFTKIQGTCYRGKAKCCK | | 24 |
| Bactenecin | RKCRIVVIRVCR | | 25 |
| PR-39 | RRRPRPPYLPRPRPPPFFPPRLPPRIPPGFPPRFPPRFPGKR-NH2 | | 26 |
| Indolicidin | ILPWKWPWWPWRR-NH2 | | 27 |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 28). An RFGF analogue (e.g., amino acid sequence AALLPVLLAAP (SEQ ID NO: 29)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 14)) and the Drosophila Antennapedia protein (RQIKIWFQNRRMKWKK (SEQ ID NO: 13)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $I_v\Theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\Theta_3$ integrin ligand. Generally, such ligands can be used to control proliferating cells and angiogeneis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Examplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligands amenable to the invention are described in copending applications U.S. Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115, 989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-$(CH_2)_n NH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative United States patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574, 142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; each of which is herein incorporated by reference.

The monomers and methods described herein can be used in the preparation of modified RNA, e.g., an iRNA agent, which incorporates a RRMS, such as those described herein and those described in copending co-owned U.S. application Ser. No. 10/916,185 filed Aug. 10, 2004, Ser. No. 10/946,873 filed Sep. 21, 2004, Ser. No. 10/985,426 filed Nov. 9, 2004 and Ser. No. 11/833,934 filed Aug. 3, 2007, all of which are hereby incorporated by reference.

Modified RNA molecules include e.g. those molecules containing a chemically or stereochemically modified nucleoside (e.g., having one or more backbone modifications, e.g., phosphorothioate or P-alkyl; having one or more sugar modifications, e.g., 2'-OCH$_3$ or 2'-F; and/or having one or more base modifications, e.g., 5-alkylamino or 5-allylamino) or a nucleoside surrogate.

Coupling of 5'-hydroxyl groups with phosphoramidites forms phosphite ester intermediates, which in turn are oxidized e.g., with iodine, to the phosphate diester. Alternatively, the phosphites may be treated with e.g., sulfur, selenium, amino, and boron reagents to form modified phosphate backbones. Linkages between the monomers described herein and a nucleoside or oligonucleotide chain can also be treated with iodine, sulfur, selenium, amino, and boron reagents to form unmodified and modified phosphate backbones respectively. Similarly, the monomers described herein may be coupled with nucleosides or oligonucleotides containing any of the modifications or nucleoside surrogates described herein.

The synthesis and purification of oligonucleotide ligand conjugates can be performed by established methods. See, for example, Trufert et al., Tetrahedron, 52:3005, 1996; and Manoharan, "Oligonucleotide Conjugates in Antisense Technology," in *Antisense Drug Technology*, ed. S. T. Crooke, Marcel Dekker, Inc., 2001.

iRNA Agent Structure

The monomers described herein can be used to make oligonucleotides which are useful as iRNA agents, e.g., RNA molecules, (double-stranded; single-stranded) that mediate RNAi, e.g., with respect to an endogenous gene of a subject or to a gene of a pathogen. In most cases the iRNA agent will incorporate momomers described herein together with naturally occurring nucleosides or nucleotides or with other modified nucleosides or nucleotides. The modified monomers can be present at any position in the iRNA agent, e.g., at the terminii or in the middle region of an iRNA agent or in a duplex region or in an unpaired region. In a preferred embodiment iRNA agent can have any architecture, e.g., architecture described herein. e.g., it can be incorporated into an iRNA agent having an overhang structure, a hairpin or other single strand structure or a two-strand structure, as described herein.

An "RNA agent" as used herein, is an unmodified RNA, modified RNA, or nucleoside surrogate, all of which are defined herein (see, e.g., the section below entitled RNA Agents). While numerous modified RNAs and nucleoside surrogates are described, preferred examples include those which have greater resistance to nuclease degradation than do unmodified RNAs. Preferred examples include those which have a 2' sugar modification, a modification in a single strand overhang, preferably a 3' single strand overhang, or, particularly if single stranded, a 5' modification which includes one or more phosphate groups or one or more analogs of a phosphate group.

An "iRNA agent" as used herein, is an RNA agent which can, or which can be cleaved into an RNA agent which can, down regulate the expression of a target gene, preferably an endogenous or pathogen target RNA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded iRNA agent. If the iRNA agent is a single strand it is particularly preferred that it include a 5' modification which includes one or more phosphate groups or one or more analogs of a phosphate group.

The RRMS-containing iRNA agent should include a region of sufficient homology to the target gene, and be of sufficient length in terms of nucleotides, such that the iRNA agent, or a fragment thereof, can mediate down regulation of the target gene. (For ease of exposition the term nucleotide or ribonucleotide is sometimes used herein in reference to one or more monomeric subunits of an RNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA agent is or includes a region which is at least partially, and in some embodiments fully, complementary to the target RNA. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA.

As discussed elsewhere herein, an iRNA agent will often be modified or include nucleoside surrogates in addition to the ribose replacement modification subunit (RRMS). Single stranded regions of an iRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an iRNA agent, e.g., against exonucleases, or to favor the antisense strand of the iRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

In addition to homology to target RNA and the ability to down regulate a target gene, an iRNA agent will preferably have one or more of the following properties:

(1) if single stranded it will preferably have a 5' modification which includes one or more phosphate groups or one or more analogs of a phosphate group;
(2) it will, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;
(3) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, an iRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties;
(4) regardless of the nature of the modification, and even though the RNA agent can contain deoxynucleotides or modified deoxynucleotides, particularly in overhang or other single strand regions, it is preferred that DNA molecules, or any molecule in which more than 50, 60, or 70% of the nucleotides in the molecule, or more than 50, 60, or 70% of the nucleotides in a duplexed region are deoxyribonucleotides, or modified deoxyribonucleotides which are deoxy at the 2' position, are excluded from the definition of RNA agent.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents are preferably antisense with regard to the target molecule. In preferred embodiments single strand iRNA agents are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)₂(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)₂(S)P—O-5'); 5'-monodithiophosphate (phosphorodithioate; (HO)(HS)(S)P—O-5'), 5'-phosphorothiolate ((HO)₂(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-). (These modifications can also be used with the antisense strand of a double stranded iRNA.)

It may be desirable to modify one or both of the antisense and sense strands of a double strand iRNA agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active sRNA/protein or RISC. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O—Me. Alternatively, a large bulky group may be added to the 5'-phosphate turning it into a phosphodiester linkage, though this may be less desirable as phosphodiesterases can cleave such a linkage and release a functional sRNA 5'-end. Antisense strand modifications include 5' phosphorylation as well as any of the other 5' modifications discussed herein, particularly the 5' modifications discussed above in the section on single stranded iRNA molecules.

In some cases the sense and the antisense strands will include different modifications. Multiple different modifications can be included on the sense and antisense strands. The modifications on each strand may differ from each other, and may also differ from the various modifications on the other strand. For example, the sense strand may have a modification, e.g., a modification described herein, and the antisense strand may have a different modification, e.g., a different modification described herein. In other cases, one strand, such as the sense strand may have two different modifications, and the antisense strand may include a modification that differs from the at least two modifications on the sense strand.

It is preferred that the sense and antisense strands be chosen such that the double stranded iRNA agent includes a single strand or unpaired region at one or both ends of the molecule. Thus, a double-stranded iRNA agent contains sense and antisense strands, preferable paired to contain an overhang, e.g., one or two 5' or 3' overhangs but preferably a 3' overhang of 2-3 nucleotides. Most embodiments will have a 3' overhang. Preferred sRNA agents will have single-stranded overhangs, preferably 3' overhangs, of 1 or preferably 2 or 3 nucleotides in length at each end. The overhangs can be the result of one strand being longer than the other, or the result of two strands of the same length being staggered. 5' ends are preferably phosphorylated.

Preferred lengths for the duplexed region is between 15 and 30, most preferably 18, 19, 20, 21, 22, and 23 nucleotides in length, e.g., in the sRNA agent range discussed above. sRNA agents can resemble in length and structure the natural Dicer processed products from long dsRNAs. Embodiments in which the two strands of the sRNA agent are linked, e.g., covalently linked are also included. Hairpin, or other single strand structures which provide the required double stranded region, and preferably a 3' overhang are also within the invention.

The monomers and methods described herein can also be used in the preparation of oligonucleotides other than iRNA agents. In the context of this invention, the term "oligonucleotide" refers to a polymer or oligomer of nucleotide or nucleoside monomers consisting of naturally occurring bases, sugars and intersugar (backbone) linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The oligonucleotides used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA, iRNA agents and other RNA interference reagents. Single-stranded nucleic acids include, e.g., antisense oligonucleotides, ribozymes, microRNA, and triplex-forming oligonucleotides. The oligonucleotides of this invention may include one or more of the oligonucleotide modifications described herein.

Nucleic acids of the present invention may be of various lengths, generally dependent upon the particular form of nucleic acid. For example, in particular embodiments, plasmids or genes may be from about 1,000 to 100,000 nucleotide residues in length. In particular embodiments, oligonucleotides may range from about 10 to 100 nucleotides in length. In various related embodiments, oligonucleotides, single-stranded, double-stranded, and triple-stranded, may range in length from about 10 to about 50 nucleotides, from about 20 to about 50 nucleotides, from about 15 to about 30 nucleotides, from about 20 to about 30 nucleotides in length.

In particular embodiments, an oligonucleotide (or a strand thereof) of the present invention specifically hybridizes to or is complementary to a target polynucleotide. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, in other embodiments, this oligonucleotide includes 1, 2, or 3 base substitutions, e.g. mismatches, as compared to the region of a gene or mRNA sequence that it is targeting or to which it specifically hybridizes. Some exemplary oligonucleotides include antisense oligonucleotide, ribozymes, apatamers, microRNAs and antagomirs.

As nucleic acids are polymers of subunits or monomers, many of the modifications described below occur at a position which is repeated within a nucleic acid, e.g., a modification of a base, or a phosphate moiety, or the a non-linking O of a phosphate moiety. In some cases the modification will occur at all of the subject positions in the nucleic acid but in many, and infact in most cases it will not. By way of example, a modification may only occur at a 3' or 5' terminal position, may only occur in a terminal regions, e.g. at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

In some embodiments it is particularly preferred, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the RNA components can confer improved properties, and, e.g., can render oligoribonucleotides more stable to nucleases. Unmodified oligoribonucleotides may also be less than optimal in terms of offering tethering points for attaching ligands or other moieties to an iRNA agent.

Modified nucleic acids and nucleotide surrogates can include one or more of:
  (i) alteration of the backbone, e.g., replacement, of one or both of the non-linking phosphate oxygens and/or of one or more of the linking phosphate oxygens in the backbone. For simplicity of terminology, except where otherwise noted, one of the three non-linking oxygens at the 5' end of a nucleic acid and at the 3' end of a nucleic acid, are within the term "linking phosphate oxygens" as used herein.);
  (ii) alteration, e.g., replacement, of a constituent of the ribose sugar, e.g., of the 2' hydroxyl on the ribose sugar, or wholesale replacement of the ribose sugar with a structure other than ribose, e.g., as described herein;
  (iii) wholesale replacement of the phosphate diester with "dephospho" linkers;
  (iv) modification or replacement of a naturally occurring base;
  (v) replacement or modification of the ribose-phosphate backbone (bracket II);
  (vi) modification of the 3' end or 5' end of the RNA, e.g., removal, modification or replacement of a terminal phosphate group or conjugation of a moiety, e.g. a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

The Phosphate Group

The phosphate group is a negatively charged species. The charge is distributed equally over the two non-linking oxygen atoms. However, the phosphate group can be modified by replacing one or both of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur.

The phosphate group can be replaced by non-phosphorus containing connectors While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

The Sugar Group

A modified RNA can include modification of all or some of the sugar groups of the ribonucleic acid. For example, the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The modification can also entail the wholesale replacement of a ribose structure with another entity at one or more sites in the iRNA agent.

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. A preferred surrogate is a PNA surrogate.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), crosslinkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Terminal modifications useful for modulating activity include modification of the 5' end with phosphate or phosphate analogs. E.g., in preferred embodiments iRNA agents, especially antisense strands, are 5' phosphorylated or include a phosphoryl analog at the 5' prime terminus. 5'-phosphate modifications include those which are compatible with RISC mediated gene silencing.

Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for crosslinking an RNA agent to another moiety; modifications useful for this include mitomycin C.

The Bases

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are less preferred for promoting stability, but they can be useful for other reasons, e.g., some, e.g., 2,6-diaminopurine and 2 amino purine, are fluorescent.

Modified bases can reduce target specificity. This should be taken into consideration in the design of iRNA agents.

Exemplary Modifications and Placement within an iRNA Agent

Some modifications may preferably be included on an iRNA agent at a particular location, e.g., on the sense strand or antisense strand, or on the 5' or 3' end of the sense or antisense strand of an iRNA agent. A preferred location of a modification on an iRNA agent, may confer preferred properties on the agent. For example, preferred locations of particular modifications may confer optimum gene silencing properties, or increased resistance to endonuclease or exonuclease activity. A modification described herein and below may be the sole modification, or the sole type of modification included on multiple ribonucleotides, or a modification can be combined with one or more other modifications described herein and below. For example, a modification on a sense strand of a dsRNA agent can be different than a modification on the antisense strand of an iRNA agent. Similarly, two different modifications on the sense strand can differ from a modification on the antisense strand. Other additional unique modifications, without limitation, can be incorporates into the sense and antisense strands.

An iRNA agent may include a backbone modification to any nucleotide on an iRNA strand. For example, an iRNA agent may include a phosphorothioate linkage or P-alkyl modification in the linkages between one or more nucleotides of an iRNA agent. The nucleotides can be terminal nucleotides, e.g., nucleotides at the last position of a sense or antisense strand, or internal nucleotides.

An iRNA agent can include a sugar modification, e.g., a 2' or 3' sugar modification. Exemplary sugar modifications include, for example, a 2'-O-methylated nucleotide, a 2'-deoxy nucleotide, (e.g., a 2'-deoxyfluoro nucleotide), a 2'-O-methoxyethyl nucleotide, a 2'-O-NMA, a 2'-DMAEOE, a 2'-aminopropyl, 2'-hydroxy, or a 2'-ara-fluoro or a locked nucleic acid (LNA), extended nucleic acid (ENA), hexose nucleic acid (HNA), or cyclohexene nucleic acid (CeNA). A 2' modification is preferably 2'OMe, and more preferably, 2'-deoxyfluoro. When the modification is 2'OMe, the modification is preferably on the sense strand. When the modification is a 2' fluoro, and the modification may be on the sense or antisense strand, or on both strands. A 2'-ara-fluoro modification will preferably be on the sense strand of the iRNA agent. An LNA modification will preferably be on the sense strand of the iRNA agent or on the An iRNA agent may include a 3' sugar modification, e.g., a 3'OMe modification. Preferably a 3'OMe modification is on the sense strand of the iRNA agent.

An iRNA agent may includes a 5'-methyl-pyrimidine (e.g., a 5'-methyl-uridine modification or a 5'-methyl-cytodine) modification.

The modifications described herein can be combined onto a single iRNA agent. For example, an iRNA agent may have a phosphorothioate linkage and a 2' sugar modification, e.g., a 2'OMe or 2'F modification. In another example, an iRNA agent may include at least one 5' Me-pyrimidine and a 2' sugar modification, e.g., a 2'F or 2'OMe modification.

An iRNA agent may include a nucleobase modification, such as a cationic modification, such as a 3'-abasic cationic modification. The cationic modification can be e.g., an alkylamino-dT (e.g., a C6 amino-dT), an allylamino conjugate, a pyrrolidine conjugate, a pthalamido, a porphyrin, or a hydroxyprolinol conjugate, on one or more of the terminal nucleotides of the iRNA agent. When an alkylamino-dT conjugate is attached to the terminal nucleotide of an iRNA agent, the conjugate is preferably attached to the 3' end of the sense or antisense strand of an iRNA agent. When a pyrrolidine linker is attached to the terminal nucleotide of an iRNA agent, the linker is preferably attached to the 3' or 5' end of the sense strand, or the 3' end of the antisense strand. When a pyrrolidine linker is attached to the terminal nucleotide of an iRNA agent, the linker is preferably on the 3' or 5' end of the sense strand, and not on the 5' end of the antisense strand.

One or more nucleotides of an iRNA agent may have a 2'-5' linkage. Preferably, the 2'-5' linkage is on the sense strand. When the 2'-5' linkage is on the terminal nucleotide of an iRNA agent, the 2'-5' linkage occurs on the 5' end of the sense strand.

The iRNA agent may include an L-sugar, preferably on the sense strand, and not on the antisense strand.

The iRNA agent may include a methylphosphonate modification. When the methylphosphonate is on the terminal nucleotide of an iRNA agent, the methylphosphonate is at the 3' end of the sense or antisense strands of the iRNA agent.

An iRNA agent may be modified by replacing one or more ribonucleotides with deoxyribonucleotides. Preferably, adjacent deoxyribonucleotides are joined by phosphorothioate linkages, and the iRNA agent does not include more than four consecutive deoxyribonucleotides on the sense or the antisense strands.

An iRNA agent may include a difluorotoluoyl (DFT) modification, e.g., 2,4-difluorotoluoyl uracil, or a guanidine to inosine substitution.

The iRNA agent may include at least one 5'-uridine-adenine-3' (5'-UA-3') dinucleotide wherein the uridine is a 2'-modified nucleotide, or a terminal 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. The chemically modified nucleotide in the iRNA agent may be a 2'-O-methylated nucleotide. In some embodiments, the modified nucleotide can be a 2'-deoxy nucleotide, a 2'-deoxyfluoro nucleotide, a 2'-O-methoxyethyl nucleotide, a 2'-O-NMA, a 2'-DMAEOE, a 2'-aminopropyl, 2'-hydroxy, or a 2'-arafluoro, or a locked nucleic acid (LNA), extended nucleic acid (ENA), hexose nucleic acid (HNA), or cyclohexene nucleic acid (CeNA). The iRNA agents including these modifications are particularly stabilized against exonuclease activity, when the modified dinucleotide occurs on a terminal end of the sense or antisense strand of an iRNA agent, and are otherwise particularly stabilized against endonuclease activity.

An iRNA agent may have a single overhang, e.g., one end of the iRNA agent has a 3' or 5' overhang and the other end of the iRNA agent is a blunt end, or the iRNA agent may have a double overhang, e.g., both ends of the iRNA agent have a 3' or 5' overhang, such as a dinucleotide overhang. In another alternative, both ends of the iRNA agent may have blunt ends.

The iRNA agent may further include a sense RNA strand and an antisense RNA strand, wherein the antisense RNA strand is 25 or fewer nucleotides in length, and includes an antisense nucleotide sequence having 18-25 nucleotides in length. The iRNA agent may further include a nucleotide overhang having 1 to 4 unpaired nucleotides, which may be at the 3'-end of the antisense RNA strand, and the nucleotide overhang may have the nucleotide sequence 5'-GC-3' or 5'-CGC-3'. The unpaired nucleotides may have at least one phosphorothioate dinucleotide linkage, and at least one of the unpaired nucleotides may be chemically modified in the 2'-position. The doublestrand region of the iRNA agent may include phosphorothioate dinucleotide linkages on one or both of the sense and antisense strands. The antisense RNA strand and the sense RNA strand may be connected with a linker, e.g., a chemical linker such as hexaethylene glycol linker, a poly-(oxyphosphinico-oxy-1,3-propandiol) linker, an allyl linker, or a polyethylene glycol linker.

References

General References

The oligoribonucleotides and oligoribonucleosides used in accordance with this invention may be with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein.

Modification described in WO 00/44895, WO01/75164, or WO02/44321 can be used herein.

The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. Nos. 5,256,775 or 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Bases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references can be disclosed in the above section on base modifications.

Nuclease Resistant Monomers

An iRNA agent can include monomers which have been modified so as to inhibit degradation, e.g., by nucleases, e.g., endonucleases or exonucleases, found in the body of a subject. These monomers are referred to herein as NRMs, or nuclease resistance promoting monomers or modifications. In many cases these modifications will modulate other properties of the iRNA agent as well, e.g., the ability to interact with a protein, e.g., a transport protein, e.g., serum albumin, or a member of the RISC(RNA-induced Silencing Complex), or the ability of the first and second sequences to form a duplex with one another or to form a duplex with another sequence, e.g., a target molecule.

The monomers and methods described herein can be used to prepare an RNA, e.g., an iRNA agent, that incorporates a nuclease resistant monomer (NRM), such as those described herein and those described in copending, co-owned U.S. Provisional application Ser. No. 10/553,659 filed on Apr. 14, 2006, and International Application No. PCT/US04/07070, both of which are hereby incorporated by reference.

Linkers

The term "linker" means an organic moiety that connects two parts of a compound. Linkers typically comprise a direct bond or an atom such as oxygen or sulfur, a unit such as NR$^1$, C(O), C(O)NH, SO, SO$_2$, SO$_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylheterocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), SO$_2$, N(R$^1$)$_2$, C(O), cleavable linking group, substituted or unsubstituted aryl, substituted or unsubstituted heteroaryl, substituted or unsubstituted heterocyclic; where R$^1$ is hydrogen, acyl, aliphatic or substituted aliphatic. It is further understood that the term "linker" also encompasses tethers. In one embodiment, the linker is —[(P-Q"-R)$_q$—X—(P'-Q'"—R')$_{q'}$]$_{q''}$-T-, wherein:

P, R, T, P', R' and T are each independently for each occurrence absent, CO, NH, O, S, OC(O), NHC(O), CH$_2$, CH$_2$NH, CH$_2$O; NHCH(R$^a$)C(O), —C(O)—CH(R$^a$)—NH—, CH=N—O,

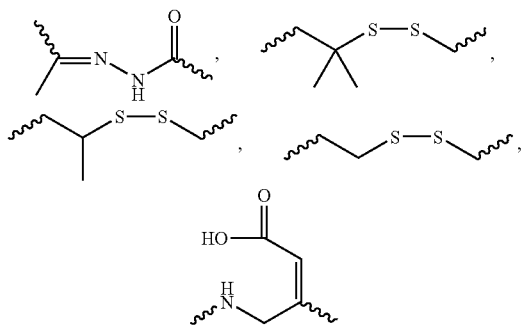

or heterocyclyl;

Q" and Q'" are each independently for each occurrence absent, —(CH$_2$)$_n$—, —C(R$^1$)(R$^2$)(CH$_2$)$_n$—, —(CH$_2$)$_n$C(R$^1$)(R$^2$)—, —(CH$_2$CH$_2$O)$_m$CH$_2$CH$_2$—, or —(CH$_2$CH$_2$O)$_m$CH$_2$CH$_2$NH—;

X is absent or a cleavable linking group;

R$^a$ is H or an amino acid side chain;

R$^1$ and R$^2$ are each independently for each occurrence H, CH$_3$, OH, SH or N(R$^N$)$_2$;

R$^N$ is independently for each occurrence H, methyl, ethyl, propyl, isopropyl, butyl or benzyl;

q, q' and q" are each independently for each occurrence 0-20 and wherein the repeating unit can be the same or different;

n is independently for each occurrence 1-20; and m is independently for each occurrence 0-50.

In one embodiment, the linker comprises at least one cleavable linking group.

In certain embodiments, the linker is a branched linker. The branchpoint of the branched linker may be at least trivalent, but may be a tetravalent, pentavalent or hexavalent atom, or a group presenting such multiple valencies. In certain embodiments, the branchpoint is, —N, —N(O)—C, —O—C, —S—C, —SS—C, —C(O)N(O)—C, —OC(O)N(O)—C, —N(O)C(O)—C, or —N(O)C(O)O—C; wherein Q is independently for each occurrence H or optionally substituted alkyl. In other embodiment, the branchpoint is glycerol or glycerol derivative.

In certain embodiments, the linker is a branched linker. The branchpoint of the branched linker may be at least trivalent, but may be a tetravalent, pentavalent or hexavalent atom, or a group presenting such multiple valencies. In certain embodiments, the branchpoint is, —N, —N(O)—C, —O—C, —S—C, —SS—C, —C(O)N(O)—C, —OC(O)N(O)—C, —N(O)C(O)—C, or —N(O)C(O)O—C; wherein Q is independently for each occurrence H or optionally substituted alkyl. In other embodiment, the branchpoint is glycerol or glycerol derivative.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NH-CHR$^B$C(O)—, where R$^A$ and R$^B$ are the R groups of the two adjacent amino acids. These candidates can be evaluated using methods analogous to those described above.

Synthesis

As can be appreciated by the skilled artisan, methods of synthesizing the compounds of the formulae herein will be evident to those of ordinary skill in the art. The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Pharmaceutical Compositions

In one embodiment, the invention relates to a pharmaceutical composition containing a modified iRNA agent, as described in the preceding sections, and a pharmaceutically acceptable carrier, as described below. A pharmaceutical composition including the modified iRNA agent is useful for treating a disease caused by expression of a target gene. In this aspect of the invention, the iRNA agent of the invention is formulated as described below. The pharmaceutical composition is administered in a dosage sufficient to inhibit expression of the target gene.

The pharmaceutical compositions of the present invention are administered in dosages sufficient to inhibit the expression or activity of the target gene. Compositions containing the iRNA agent of the invention can be administered at surprisingly low dosages. A maximum dosage of 5 mg iRNA agent per kilogram body weight per day may be sufficient to inhibit or completely suppress the expression or activity of the target gene.

In general, a suitable dose of modified iRNA agent will be in the range of 0.001 to 500 milligrams per kilogram body weight of the recipient per day (e.g., about 1 microgram per kilogram to about 500 milligrams per kilogram, about 100 micrograms per kilogram to about 100 milligrams per kilogram, about 1 milligrams per kilogram to about 75 milligrams per kilogram, about 10 micrograms per kilogram to about 50 milligrams per kilogram, or about 1 microgram per kilogram to about 50 micrograms per kilogram). The pharmaceutical composition may be administered once per day, or the iRNA agent may be administered as two, three, four, five, six or more sub-doses at appropriate intervals throughout the day. In that case, the iRNA agent contained in each sub-dose must be correspondingly smaller in order to achieve the total daily dosage. The dosage unit can also be compounded for delivery over several days, e.g., using a conventional sustained release formulation which provides sustained release of the iRNA agent over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the infection or disease, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNA agent encompassed by the invention can be made using conventional methodologies or on the basis of in vivo testing using an appropriate animal model, as described elsewhere herein.

Advances in mouse genetics have generated a number of mouse models for the study of various human diseases. For example, mouse repositories can be found at The Jackson Laboratory, Charles River Laboratories, Taconic, Harlan, Mutant Mouse Regional Resource Centers (MMRRC) National Network and at the European Mouse Mutant Archive. Such models may be used for in vivo testing of iRNA agent, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), ocular, rectal, vaginal and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

For oral administration, the iRNA agent useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of iRNA agent in the cells that harbor the target gene or virus. Such substances include, for example, micellar structures, such as liposomes or capsids, as described below. Although microinjection, lipofection, viruses, viroids, capsids, capsoids, or other auxiliary agents are required to introduce iRNA agent into cell cultures, surprisingly these methods and agents are not necessary for uptake of iRNA agent in vivo. The iRNA agent of the present invention are particularly advantageous in that they do not require the use of an auxiliary agent to mediate uptake of the iRNA agent into the cell, many of which agents are toxic or associated with deleterious side effects. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions can also include encapsulated formulations to protect the iRNA agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

Toxicity and therapeutic efficacy of iRNA agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. iRNA agents that exhibit high therapeutic indices are preferred.

The data obtained from cell culture assays and animal studies can be used in formulating a range of dosage for use in humans. The dosages of compositions of the invention are preferably within a range of circulating concentrations that include the ED50 with little or no toxicity. The dosage may vary within this range depending upon the dosage form employed and the route of administration utilized. For any iRNA agent used in the method of the invention, the therapeutically effective dose can be estimated initially from cell culture assays. A dose may be formulated in animal models to achieve a circulating plasma concentration range of the iRNA agent or, when appropriate, of the polypeptide product of a target sequence (e.g., achieving a decreased concentration of the polypeptide) that includes the IC50 (i.e., the concentration of the test iRNA agent which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, iRNA agents relating to the invention can be administered in combination with other known agents effective in treating viral infections and diseases. In any event, the administering physician can adjust the amount and timing of iRNA agent administration on the basis of results observed using standard measures of efficacy known in the art or described herein.

For oral administration, the iRNA agent useful in the invention will generally be provided in the form of tablets or capsules, as a powder or granules, or as an aqueous solution or suspension.

Methods for Treating Diseases Caused by Expression of a Target Gene

In one embodiment, the invention relates to a method for treating a subject having a disease or at risk of developing a disease caused by the expression of a target gene. In this embodiment, iRNA agents can act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method includes administering a pharmaceutical composition of the invention to the patient (e.g., a human), such that expression of the target gene is silenced. Because of their high efficiency and specificity, the iRNA agent of the present invention specifically target mRNA of target genes of diseased cells and tissues, as described below, and at surprisingly low dosages. The pharmaceutical compositions are formulated as described in the preceding section, which is hereby incorporated by reference herein.

Examples of genes which can be targeted for treatment include, without limitation, an oncogene (Hanahan, D. and R. A. Weinberg, *Cell* (2000) 100:57; and Yokota, J., *Carcinogenesis* (2000) 21(3):497-503); a cytokine gene (Rubinstein, M., et al., *Cytokine Growth Factor Rev.* (1998) 9(2):175-81); an idiotype (Id) protein gene (Benezra, R., et al., *Oncogene* (2001) 20(58):8334-41; Norton, J. D., *J. Cell Sci.* (2000) 113(22):3897-905); a prion gene (Prusiner, S. B., et al., *Cell* (1998) 93(3):337-48; Safar, J., and S. B. Prusiner, *Prog. Brain Res.* (1998) 117:421-34); a gene that expresses molecules that induce angiogenesis (Gould, V. E. and B. M. Wagner, *Hum. Pathol.* (2002) 33(11):1061-3); adhesion molecules (Chothia, C. and E. Y. Jones, *Annu. Rev. Biochem.* (1997) 66:823-62; Parise, L. V., et al., *Semin. Cancer Biol.* (2000) 10(6):407-14); cell surface receptors (Deller, M. C., and Y. E. Jones, *Curr. Opin. Struct. Biol.* (2000) 10(2):213-9); genes of proteins that are involved in metastasizing and/or invasive processes (Boyd, D., *Cancer Metastasis Rev.* (1996) 15(1):77-89; Yokota, J., *Carcinogenesis* (2000) 21(3):497-503); genes of proteases as well as of molecules that regulate apoptosis and the cell cycle (Matrisian, L. M., *Curr. Biol.* (1999) 9(20): R776-8; Krepela, E., *Neoplasma* (2001) 48(5):332-49; Basbaum and Werb, *Curr. Opin. Cell Biol.* (1996) 8:731-738; Birkedal-Hansen, et al., *Crit. Rev. Oral Biol. Med.* (1993) 4:197-250; Mignatti and Rifkin, *Physiol. Rev.* (1993) 73:161-195; Stetler-Stevenson, et al., *Annu. Rev. Cell Biol.* (1993) 9:541-573; Brinkerhoff, E., and L. M. Matrisan, *Nature Reviews* (2002) 3:207-214; Strasser, A., et al., *Annu. Rev. Biochem.* (2000) 69:217-45; Chao, D. T. and S. J. Korsmeyer, *Annu. Rev. Immunol.* (1998) 16:395-419; Mullauer, L., et al., *Mutat. Res.* (2001) 488(3):211-31; Fotedar, R., et al., *Prog. Cell Cycle Res.* (1996) 2:147-63; Reed, J. C., *Am. J. Pathol.* (2000) 157(5):1415-30; D'Ari, R., *Bioassays* (2001) 23(7): 563-5); genes that express the EGF receptor; Mendelsohn, J. and J. Baselga, *Oncogene* (2000) 19(56):6550-65; Normanno, N., et al., *Front. Biosci.* (2001) 6:D685-707); and the multi-drug resistance 1 gene, MDR1 gene (Childs, S., and V. Ling, *Imp. Adv. Oncol.* (1994) 21-36).

In the prevention of disease, the target gene may be one which is required for initiation or maintenance of the disease, or which has been identified as being associated with a higher risk of contracting the disease. In the treatment of disease, the iRNA agent can be brought into contact with the cells or tissue exhibiting the disease. For example, iRNA agent substantially identical to all or part of a mutated gene associated with cancer, or one expressed at high levels in tumor cells, may be brought into contact with or introduced into a cancerous cell or tumor gene.

Examples of cellular proliferative and/or differentiative disorders include cancer, e.g., a carcinoma, sarcoma, metastatic disorder or hematopoietic neoplastic disorder, such as a leukemia. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state or condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoietic origin, e.g., arising from myeloid, lymphoid or erythroid lineages, or precursor cells thereof.

The pharmaceutical compositions of the present invention can also be used to treat a variety of immune disorders, in particular those associated with overexpression or aberrant expression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

In another embodiment, the invention relates to methods for treating viral diseases, including but not limited to hepatitis C, hepatitis B, herpes simplex virus (HSV), HIV-AIDS, poliovirus, and smallpox virus. iRNA agent of the invention are prepared as described herein to target expressed sequences of a virus, thus ameliorating viral activity and replication. The iRNA agents can be used in the treatment and/or diagnosis of viral infected tissue, both animal and plant. Also, such iRNA agent can be used in the treatment of virus-associated carcinoma, such as hepatocellular cancer.

For example, the iRNA agent of the present invention are useful for treating a subject having an infection or a disease associated with the replication or activity of a (+) strand RNA virus having a 3'-UTR, such as HCV. In this embodiment, the iRNA agent can act as novel therapeutic agents for inhibiting replication of the virus. The method includes administering a pharmaceutical composition of the invention to the patient (e.g., a human), such that viral replication is inhibited. Examples of (+) strand RNA viruses which can be targeted for inhibition include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus O), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Beme virus). Arterivirus (equine arteritis virus) is the representative arteriviridus. Togavirises include alphavirus (Sindbis virus) and rubivirus (Rubella virus). Finally, the flaviviruses include flavivirus (Yellow fever virus), pestivirus (bovine diarrhea virus), and hepacivirus (hepatitis C virus). In a preferred embodiment, the virus is hepacivirus, the hepatitis C virus. Although the foregoing list exemplifies vertebrate viruses, the present invention encompasses the compositions and methods for treating infections and diseases caused by any (+) strand RNA virus having a 3'-UTR, regardless of the host. For example, the invention encompasses the treatment of plant diseases caused by sequiviruses, comoviruses, potyviruses, sobemovirus, luteoviruses, tombusviruses, tobavirus, tobravirus, bromoviruses, and closteroviruses.

The pharmaceutical compositions encompassed by the invention may be administered by any means known in the art including, but not limited to, oral or parenteral routes, including intravenous, intramuscular, intraperitoneal, subcutaneous, transdermal, airway (aerosol), ocular, rectal, vaginal, and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

Methods for Inhibiting Expression of a Target Gene.

In yet another aspect, the invention relates to a method for inhibiting the expression of a target gene in a cell or organism. In one embodiment, the method includes administering the inventive iRNA agent or a pharmaceutical composition containing the iRNA agent to a cell or an organism, such as a mammal, such that expression of the target gene is silenced. Because of their surprisingly improved stability and bioavailability, the iRNA agent of the present invention effectively inhibit expression or activity of target genes at surprisingly low dosages. Compositions and methods for inhibiting the expression of a target gene using iRNA agent can be performed as described in the preceding sections, particularly Sections 4 and 5.

In this embodiment, a pharmaceutical composition containing the iRNA agent may be administered by any means known in the art including, but not limited to oral or parenteral routes, including intravenous, intramuscular, intraperitoneal, subcutaneous, transdermal, airway (aerosol), ocular, rectal, vaginal, and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

The methods for inhibiting the expression of a target gene can be applied to any gene one wishes to silence, thereby specifically inhibiting its expression, provided the cell or organism in which the target gene is expressed includes the cellular machinery which effects RNA interference. Examples of genes which can be targeted for silencing include, without limitation, developmental genes including but not limited to adhesion molecules, cyclin kinase inhibitors, Wnt family members, Pax family members, Winged helix family members, Hox family members, cytokines/lymphokines and their receptors, growth/differentiation factors and their receptors, and neurotransmitters and their receptors; (2) oncogenes including but not limited to ABLI, BCL1, BCL2, BCL6, CBFA2, CBL, CSFIR, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES; (3) tumor suppresser genes including but not limited to APC, BRCA1, BRCA2, MADH4, MCC, NF1, NF2, RB1, TP53 and WT1; and (4) enzymes including but not limited to ACP desaturases and hydroxylases, ADP-glucose pyrophorylases, ATPases, alcohol dehydrogenases, amylases, amyloglucosidases, catalases, cellulases, cyclooxygenases, decarboxylases, dextrinases, DNA and RNA polymerases, galactosidases, glucanases, glucose oxidases, GTPases, helicases, hemicellulases, integrases, invertases, isomerases, kinases, lactases, lipases, lipoxygenases, lysozymes, pectinesterases, peroxidases, phosphatases, phospholipases, phosphorylases, polygalacturonases, proteinases and peptidases, pullanases, recombinases, reverse transcriptases, topoisomerases, and xylanases.

In addition to in vivo gene inhibition, the skilled artisan will appreciate that the iRNA agent of the present invention are useful in a wide variety of in vitro applications. Such in vitro applications, include, for example, scientific and commercial research (e.g., elucidation of physiological pathways, drug discovery and development), and medical and veterinary diagnostics. In general, the method involves the introduction of the iRNA agent into a cell using known techniques (e.g., absorption through cellular processes, or by auxiliary agents or devices, such as electroporation and lipofection), then maintaining the cell for a time sufficient to obtain degradation of an mRNA transcript of the target gene.

In one aspect the invention provides a method of modulating the expression of a target gene in a cell, comprising providing to said cell an iRNA agent of this invention. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Synthesis of Folate Conjugates 108 and 109

In order to conjugate the Folic acid to the siRNA the following strategy was used. Folic acid was conjugated to the 3' end using the solid support, 108 and to the 5' end using the amidite 109 as follows.

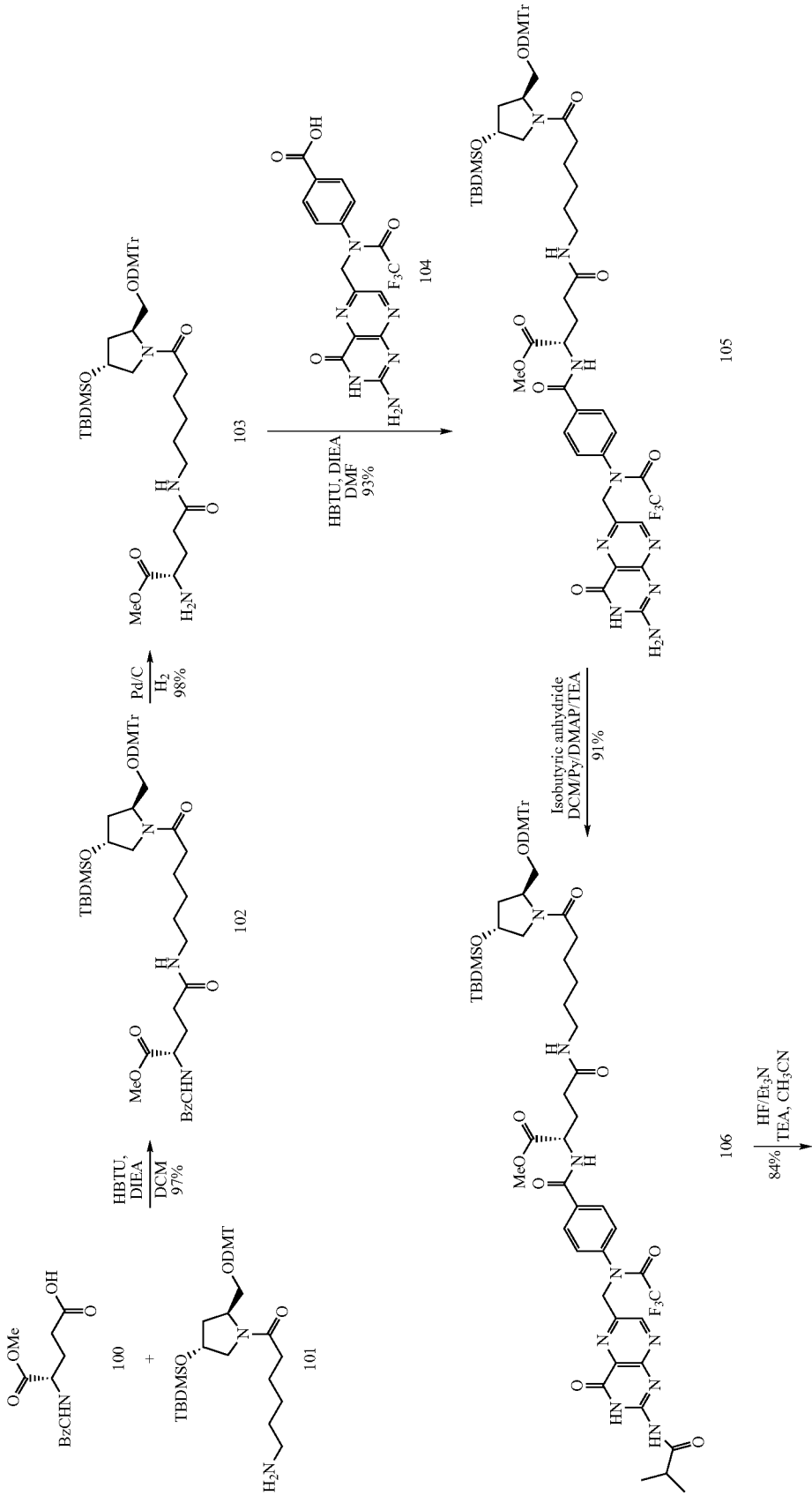

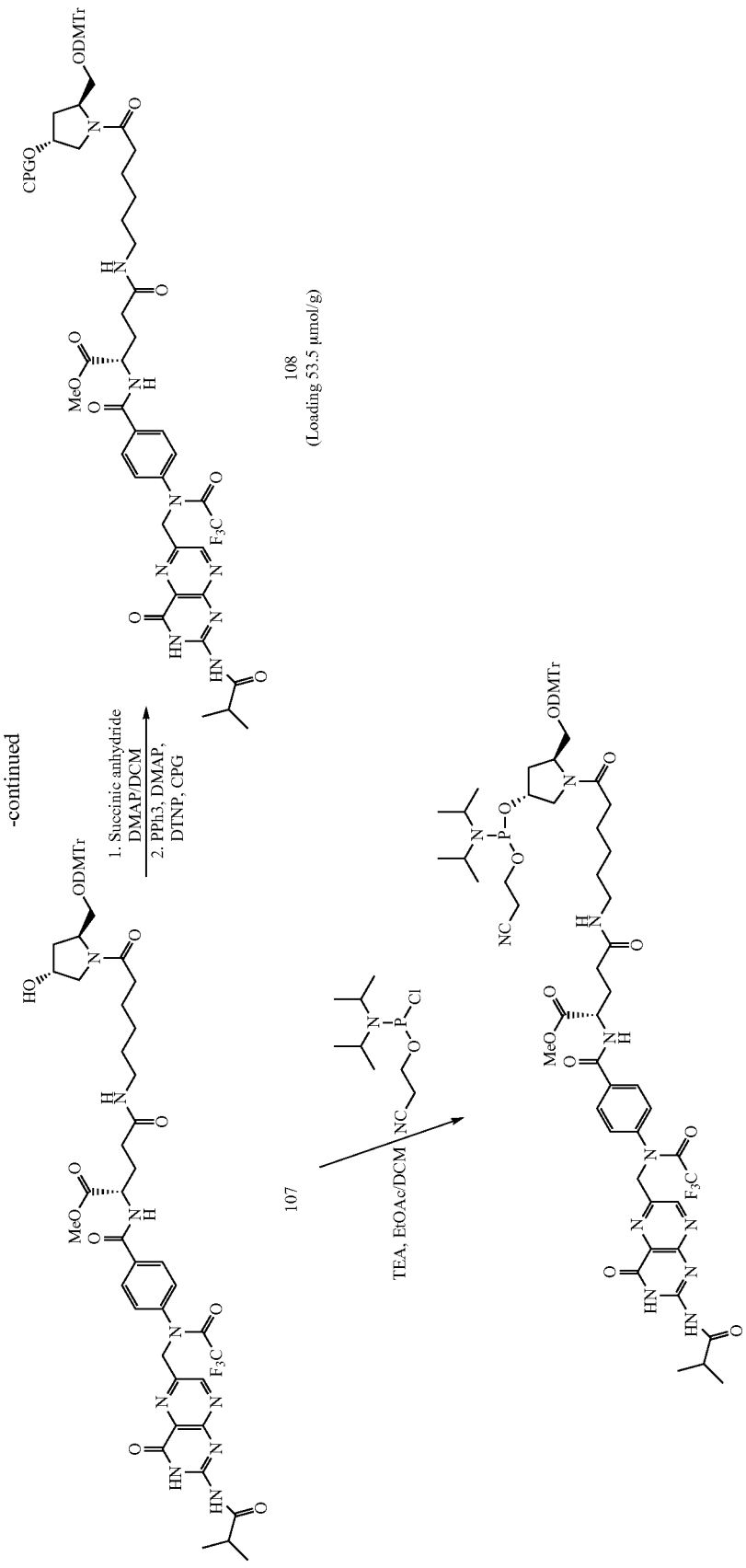

Preparation of 102: Glutamate 100 (2.05 g, 6.95 mmol) and amine 101 (4.50 g, 6.95 mmol) was taken together in a mixture of DCM/DMF (50 mL, 2:1). To this reaction mixture HBTU (3.42 g, 1.3 eq.) and DIEA (2.43 ml, 2 eq.) was added and stirred for 30 minutes at ambient temperature. The progress of the reaction was monitored by TLC (Ethyl acetate); solvents are removed under reduced pressure and the residue was extracted with dichloromethane, washed with water (2 times) and brine. The organic layer was dried over anhydrous sodium sulfate. Solvents were removed and residue was purified by chromatography (during the packing of column please add few drops of TEA, First elute with 1:1 ethyl acetate/hexane, followed ethyl acetate) to get the product 102 as yellow gum (Yield, 6.35 g, 97%). $^1$H NMR (DMSO-d$_6$, 400 MHz) δ=7.94 (bs, 1H), 7.70-7.77(m, 1H), 7.15-7.40(m, 14H), 6.80-6.90(m, 4H), 5.01(s, 2H), 4.69-4.50 (m, 1H), 4.01-4.15(m, 1H), 3.71(s, 6H), 3.61(s, 3H), 2.85-3.40(m, 5H), 2.46-2.52(m, 1H), 1.80-2.22(m, 7H), 0.89-1.50 (m, 6H), 0.83(s, 9H), 0.04-0.01(m, 6H). $^{13}$C NMR DMSO-d$_6$) δ=172.68, 170.91, 170.82, 170.80, 170.28, 164.56, 162.25, 158.11, 157.99, 156.05, 145.06, 144.74, 136.86, 135.77, 135.59, 135.33, 129.57, 128.89, 128.31, 127.78, 127.74, 127.69, 127.62, 127.51, 126.58, 113.08, 112.71, 85.49, 85.24, 70.32, 65.47, 63.36, 59.71, 54.99, 54.96, 54.86, 54.60, 53.48, 51.78, 38.33, 38.20, 36.78, 35.73, 33.93, 31.45, 30.71, 29.02, 26.65, 26.65, 26.14, 25.62, 24.12, 20.70, 17.65, 17.62, 14.04, −4.91, −4.93, −4.97. MS. Molecular weight calculated for C$_{52}$H$_{67}$N$_3$O$_9$Si, Cal. 906.19, Found 907.2 (MH$^+$).

Preparation of 103: The Cbz protected amine 102 (6.30 g 6.80 mmol) was dissolved in a mixture of MeOH/Ethyl acetate (1:3, 75 mL) and degassed with argon. Pd/C (0.80 g, 10 wt % Degussa wet type) was added and degassed and purged with hydrogen. The mixture was stirred under hydrogen (Balloon pressure) for 6-9 hrs. Reaction was monitored by TLC (Ethyl acetate, PMA stain). The TLC of the reaction mixture showed the complete disappearance of the starting Cbz protected amine. The reaction mixture was filtered through a pad of celite, washed with a mixture of MeOH/EtOAc (100 mL) and the combined filtrates were concentrated. The residue was dried under high vacuum overnight to provide the product 103 as pale yellow foam (5.30 g, 98%). It was directly used for the next reaction with out further purification. $^1$H NMR (DMSO-d$_6$, 400 MHz) δ=7.94(bs, 1H), 7.70-7.75(m, 1H), 7.12-7.33(m, 9H), 6.81-6.88(m, 4H), 4.50-4.64(m, 1H), 4.05-4.17(m, 1H), 3.71(m, 6H), 3.59(s, 3H), 3.19-3.40(m, 2H), 2.85-3.05(m, 2H), 2.47-2.52(m, 1H), 1.80-2.22(m, 7H), 0.89-1.50(m, 6H), 0.83(s, 9H), 0.04-0.01(m, 6H). $^{13}$C NMR DMSO-d$_6$) δ=176.23, 176.11, 171.74, 171.53, 170.98, 165.15, 162.96, 158.46, 158.33, 158.15, 145.37, 145.04, 140.04, 136.10, 135.94, 135.74, 135.64, 129.92, 129.92, 128.55, 128.24, 128.13, 127.83, 127.17, 127.01, 113.52, 113.42, 113.09, 86.25, 85.62, 70.67, 69.67, 65.50, 63.65, 60.22, 56.06, 55.44, 55.35, 55.32, 55.06, 53.96, 53.55, 51.86, 37.13, 36.22, 34.31, 32.78, 31.93, 31.17, 30.67, 29.21, 26.42, 25.94, 24.84, 24.46, 21.04, 17.81, 17.95, 14.35, −4.60, −4.65 MS. Molecular weight calculated for C$_{44}$H$_{63}$F$_3$N$_3$O$_8$Si, Cal. 789.44, Found 790.5 (MH$^+$).

Preparation of 105: N$^{10}$-(Trifluoroacetyl)pteroic acid 104 (2.30 g, 6.00 mmol) and amine 103 (5.75 g, 1.2 eq) were dissolved in DMF (60 mL, it takes about 15-20 minutes to dissolve the compounds in solution). HBTU (3.01 g, 1.3 eq.) followed by DIEA (3 mL, 3 eq.) were added and stirred for 30 minutes. Reaction was monitored by TLC (8% MeOH/DCM, PMA stain). TLC of the reaction mixture showed completion of reaction. Solvents were removed under reduced pressure and the residue extracted with DCM, washed with water and brine. The organic layer was dried over anhydrous sodium sulfate. Solvents were removed and residue was purified by chromatography (3-8% MeOH/DCM) to get the product 105 as a pale yellow solid (Yield=6.77 g, 93%). $^1$H NMR (DMSO-d$_6$, 400 MHz) δ=8.88-8.90(d, J=7.07 Hz, 1H), 8.60(bs, 1H), 7.90(d, J=8.4 Hz, 2H), 7.80(t, J=8.4 Hz, 1H), 7.60(d, J=8.06 Hz, 2H), 7.12-7.30(m, 9H), 6.80-6.89(m, 4H), 5.09(bs, 2H), 4.52-4.68(m, 1H), 4.32-4.40(m, 1H), 4.05-1.12(m, 1H), 3.71 (s, 6H), 3.62(s, 3H), 2.86-3.30(m, 6H), 1.75-2.23(m, 8H), 1.10-145(m, 6H), 0.82(s, 9H), 0.04-0.01 (m, 6H). $^{13}$C NMR DMSO-d$_6$) δ=172.38, 170.96, 170.88, 165.60, 158.11, 157.99, 145.08, 141.66, 135.77, 135.60, 134.19, 129.59, 128.74, 128.74, 128.45, 128.13, 127.78, 127.52, 113.20, 113.11, 85.24, 55.01, 54.98, 54.91, 52.46, 51.90, 45.72, 40.12, 39.92, 39.71, 39.50, 39.29, 39.08, 38.87, 25.65, 17.69, 8.68, −4.88, −4.94. MS. Molecular weight calculated for C$_{60}$H$_{72}$F$_3$N$_9$O$_{11}$Si, Cal. 1179.51, Found 1181.0 (MH$^+$).

Preparation of 106: To a solution of 105 (6.75 g, 5.72 mmol) in a mixture of DCM/Pyridine (100 mL, 1:1) DMAP (1.00 g, 1.5 eq.) was added and cooled in an ice-water bath. Isobutyric anhydride (10 mL, excess) was added and stirred overnight. The reaction was monitored by TLC. Reaction mixture was quenched with MeOH. Solvents were removed and the residue extracted with DCM, washed with water and brine; dried over anhydrous sodium sulfate. Solvents were removed and the residue was purified by chromatography (first ethyl acetate then 3-5% MeOH/DCM) to get the product 106 as pale yellow solid (Yield=6.70 g, 94%). $^1$H NMR (DMSO-d$_6$, 400 MHz) δ=11.90-12.32(m, 3H), 8.84-8.90(m, 2H), 7.96-7.90(m, 3H), 7.60-7.84(m, 3H), 7.10-7.35(m, 9H), 6.80-6.90(m, 4H), 5.20(bs, 2H), 4.50-4.67(m, 1H), 4.34-4.42 (m, 1H), 4.05-4.12(m, 1H), 3.71(s, 6H), 3.61(s, 3H), 2.86-3.30(m, 6H), 1.75-2.23(m, 6H), 1.17(d, J=7.08 Hz, 3H), 1.05 (d, J=7.08 Hz, 3H), 1.10-1.45(m, 6H), 0.82(s, 9H), 0.04-0.01 (m, 6H). $^{13}$C NMR DMSO-d$_6$) δ 180.81, 177.83, 172.37, 170.98, 170.94, 170.87, 165.56, 162.28, 159.89, 158.12, 157.99, 155.90, 155.55, 149.99, 149.87, 147.79, 145.10, 144.78, 141.79, 135.77, 135.61, 135.44, 135.35, 134.25, 130.55, 129.60, 128.71, 128.51, 127.88, 127.78, 127.53, 126.60, 117.54, 114.66, 113.19, 113.09, 85.86, 85.25, 70.35, 63.37, 59.75, 55.00, 54.97, 54.62, 54.02, 52.49, 51.89, 45.75, 38.37, 38.22, 36.79, 35.76, 35.00, 33.94, 33.12, 31.69, 30.74, 29.04, 26.30, 26.16, 25.63, 24.14, 20.74, 18.89, 18.74, 17.68, 17.65, 14.07, 8.67, −4.89, −4.96. MS. Molecular weight calculated for C$_{64}$H$_{78}$F$_3$N$_9$O$_{12}$Si, Cal. 1249.55, Found: 1248.4 (M−H)$^-$.

Preparation of 107: Compound 106 (6.70 g, 5.36 mmol) was dissolved in acetonitrile (50 mL) and Triethylamine (20 mL). To that HF/TEA (20 mL) was added and stirred for 3 hrs. The reaction was monitored by TLC (5% MeOH/DCM). TLC showed complete disappearance of starting material. Water and sodium bicarbonate solution was added to the reaction mixture and extracted with DCM. The organic layer was dried over sodium sulfate. Solvents were removed and the residue was purified by chromatography (2-5% MeOH/DCM) to get the product 107 as pale yellow solid (Yield=5.10 g, 84%). $^1$H NMR (DMSO-d$_6$, 400 MHz) δ=11.45-11.95(m, 2H), 8.81-8.95(m, 2H), 7.60-7.94(m, 5H), 7.10-7.36(m, 9H), 6.78-6.91 (m, 4H), 5.19(bs, 2H), 4.85-5.01(bs, 1H), 4.34-4.42(m, 1H), 3.71(s, 6H), 3.61(s, 3H), 2.86-3.55(m, 9H), 1.75-2.23(m, 6H), 1.16(d, J=7.08 Hz, 3H), 1.10-1.45(m, 6H), 0.95(d, J=7.08 Hz, 3H). $^{13}$C NMR DMSO-d$_6$) δ=180.36, 172.39, 170.98, 170.87, 170.34, 165.60, 160.60, 158.11, 157.98, 155.89, 155.54, 154.97, 151.03, 149.68, 147.30, 145.10, 144.76, 141.76, 135.88, 135.74, 135.49, 135.44, 134.24, 130.50, 129.62, 129.56, 128.74, 128.50, 127.88, 127.78, 127.59, 126.59, 117.54, 114.67, 113.19, 113.10, 85.78, 85.11, 68.59, 67.47, 65.18, 63.34, 59.76, 55.01, 54.98, 52.48, 51.90, 38.38, 36.29, 34.91, 34.15, 32.51, 31.67, 29.05, 26.29, 26.19, 24.18, 20.75, 18.84, 14.08, 11.07. MS. Molecular weight calculated for C$_{58}$H$_{64}$F$_3$N$_9$O$_{12}$, Cal. 1135.46, Found 1135.0 (M−H)$^-$.

Preparation of Long alkyl chain CPG 108: Hydroxy derivative 107 (0.500 g, 0.441 mmol) was dissolved in DCM (10 mL) to that Succinic anhydride (0.088 g, 2 eq) and DMAP (0.160 g, 3 eq.) were added and stirred overnight. TLC showed completion of reaction. The reaction mixture was diluted with DCM (20 mL), washed successively with cold dilute citric acid and water (2 times), dried over sodium sulfate. Solvents were removed and dried under high vacuum to get the succinate. $PPh_3$ (0.150 g, 1.3 eq.), DMAP (0.080 g, 1.5 eq.) and the succinate from the previous step were dissolved in a mixture of acetonitrile and DCM (6 mL). A solution of DTNP (0.143 g, 1.05 eq.) in DCM (1 mL) was added to the above solution. The mixture was slowly shaken for 3-4 minutes. Long chain alkyl amine-CPG (1caa CPG, 2.05 g, 133 µmol/g) was added to the mixture and gently shaken for 2 h. The CPG was filtered, successively washed with DCM, mixture of MeOH/DCM (1:9) and DCM until filtrate remained colorless and dried. The dried CPG was transferred into another flask treated with $Ac_2O$ in pyridine (25%) in the presence of TEA (1 mL) for 15 min. under gentle shaking. Finally the CPG was filtered, washed with DCM, DCM: MeOH (9:1), followed by DCM and ether. The CPG 108 was dried under vacuum overnight and the loading was measured as reported (2.14 g, loading 53.3 µmol/g).

Preparation of phosphoramidite 109: To a solution of 107 (0.20 g, 0.176 mmol) in EtOAc/DCM (4:1, 10 mL) chlorophosphonate reagent (0.086 mL, 2 eq.) was added, followed by TEA (0.53 mL, 2 eq.). After 10 minutes the solution becomes cloudy. The reaction was monitored by TLC. TLC showed reaction was complete in 30 minutes, diluted with DCM washed with sodium bicarbonate solution and dried over sodium sulfate. Solvents were removed and the residue was dissolved small amount of DCM/EtOAc mixture and precipitated the product with hexane (Yield=195 mg, 82%). MS. Molecular weight calculated for $C_{67}H_{81}F_3N_{11}O_{13}P$, Cal. 1335.57, Found. 1136.60 (M+H).

Example 2

Synthesis of Pteroic Acid Precursor 110

In another method the appropriately substituted pteroic acid precursor 110, amenable for RNA synthesis was prepared as follows.

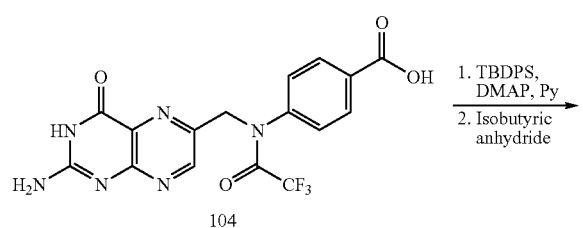

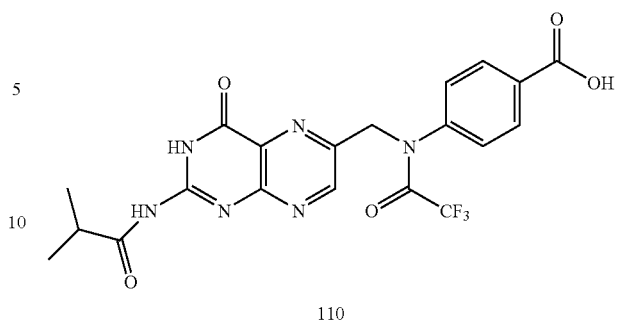

Synthesis of 4-[(2-isobutyrylamino-4-oxo-3,4-dihydro-pteridin-6-ylmethyl)-(2,2,2-trifluoroacetyl)-amino]benzoic acid 110. To a suspension of pteroic acid (25 g, 61.2 mmol) and DMAP (11.25 g, 92 mmol) in anhydrous pyridine (400 mL), TBDPS chloride (42 g, 153 mmol) was added. The reaction mixture was stirred at room temperature for 30 h after which isobutyric anhydride (14.6 g, 92 mmol) was added and the mixture was slightly warmed. An additional 60 mL of pyridine was also added and the reaction mixture was stirred at room temperature overnight. The reaction mixture became homogenous after which pyridine and other volatiles were concentrated in a rotary evaporator. The residue was stirred with EtOAc (1 L) and acetic acid (100 mL) and water (500 mL) for 24 h. The thus obtained slurry was filtered, the residue was washed with water (500 mL), EtOAc (1 L) and dried to obtain the pure product as a white solid (26.1 g, 89%). $^1$H NMR (DMSO-$d_6$, 400 MHz) δ=8.87 (s, 1H), 7.95 (d, J=8.6 Hz, 2H), 7.67 (d, J=8.6 Hz, 2H), 5.21(s, 2H), 2.79-2.74 (m, 1H), 1.12 (d, J=6.83 Hz, 6H), $^{13}$C NMR (DMSO-$d_6$) δ=180.72, 166.49, 159.25, 149.87, 147.68, 142.69, 136.34, 134.45, 130.54, 129.16, 128.86, 127.49, 34.96, 33.09, 26.52, 18.88, 18.74. $^{19}$F NMR (DMSO-$d_6$) δ—64.32. MS. Molecular weight calculated for $C_{20}H_{17}F_3N_6O_5$, Cal. 478.12, Found 479.12 (MH$^+$).

Example 3

Synthesis of Disulfide Precursor 112

In order to conjugate Folic acid to siRNA via a cleavable disulfide linker the following strategy was used. The pyridyl disulfide precursor 112 was synthesized by conjugating hydroxyprolinol derivative 101 with the NHS ester 111 as follows.

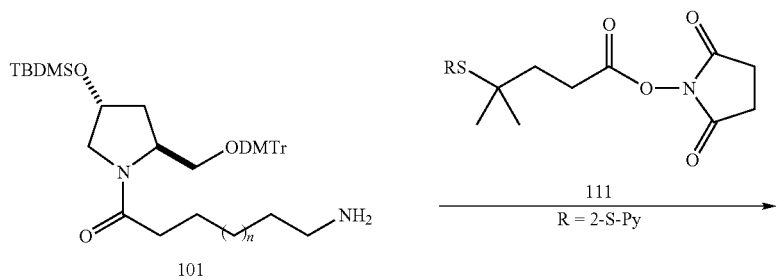

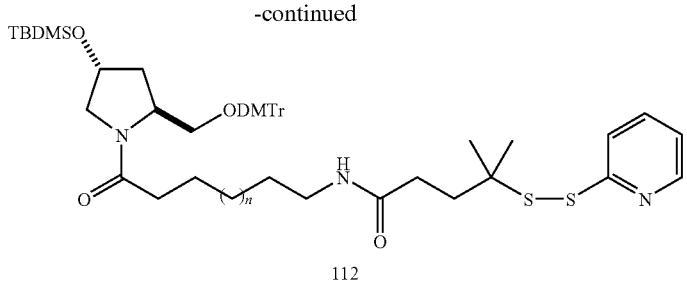

112

Synthesis of 4-methyl-4-(pyridine-2-yldisulfanyl)-pentanoic acid{6-[2-[bis-(4-methoxy-phenyl)-phenyl-methoxymethyl]-4-(tert-butyl-dimethyl-silanyloxy)-pyrrolidin-1-yl]-6-oxo-hexyl}-amide 112. To a solution of the amine 101 (3.23 g, 5 mmol) in dichloromethane (50 mL), diisopropylethylamine (1.27 g, 10 mmol) and the NHS ester 111 (1.8 g, 5 mmol) was added and the mixture was stirred at room temperature overnight. The reaction mixture was diluted with $CH_2Cl_2$ (200 mL) and the organic layer was washed with satd. $NaHCO_3$ (100 mL), water (100 mL), brine (100 mL) and dried ($Na_2SO_4$). Solvents were removed and the residue was purified by chromatography (2-5% MeOH/DCM) to get the product 112 as pale yellow foam (Yield=4.10 g, 92%). $^1$H NMR (DMSO-$d_6$, 400 MHz) δ=8.39 (d, J=4.6 Hz, 1H), 7.80-7.73 (m, 3H), 7.33-7.24 (m, 4H), 7.22-7.16 (m, 5H), 6.88-6.84 (m, 4H), 4.66-4.62 (m, 0.7H), 4.58-4.50 (m, 0.3H), 4.16-4.06 (m, 1H), 3.78-3.66 (m, 2H), 3.26-3.18 (m, 2H), 3.12-2.89 (m, 4H), 2.24-2.12 (m, 4H), 2.02-1.86 (m, 1H), 1.84-1.76 (m, 3H), 1.50-1.10 (m, 6H), 1.20 (s, 3H), 0.83 (s, 9H), 0.81 (s, 3H), 0.04-0.01 (m, 6H). $^{13}$C NMR (DMSO-$d_6$) δ=171.23, 170.91, 170.81, 160.02, 158.09, 157.96, 149.14, 145.05, 144.73, 137.51, 135.75, 135.58, 135.42, 135.32, 129.56, 127.85, 127.75, 127.50, 126.73, 126.58, 120.98, 119.22, 113.18, 113.09, 85.83, 85.23, 70.31, 69.31, 65.17, 63.34, 54.99, 54.96, 54.60, 52.19, 38.30, 36.77, 36.43, 33.92, 32.41, 31.01, 28.94, 26.87, 26.11, 25.64, 24.08, 17.66, −4.88, −4.91, −4.94. MS. Molecular weight calculated for $C_{49}H_{67}N_3O_6S_2Si$, Cal. 885.42, Found 886.42 (MH$^+$).

Example 4

Synthesis of Folate Conjugates 121 and 122

The pyridyl disulfide 112 is treated with the thiol 114 to get the disulfide 115 which on treatment with the glutamate 116 provided the amide 117. The Fmoc disulfide 117 is treated with piperidine to remove the Fmoc protecting group to give the amine 118 which on treatment with the protected pteroic acid 110 provided the couple product 119. The TBDMS protecting group in 119 is removed using HF:NEt$_3$ complex to provide the hydroxyprolinol precursor 120. The hydroxyprolinol 120 is converted to the solid support 122 via the succinate and the amidite 121 as follows.

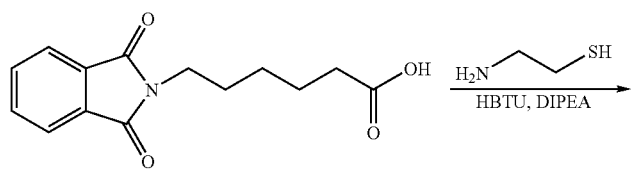

113

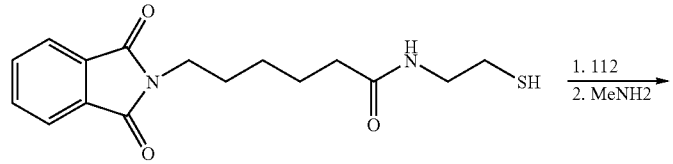

114

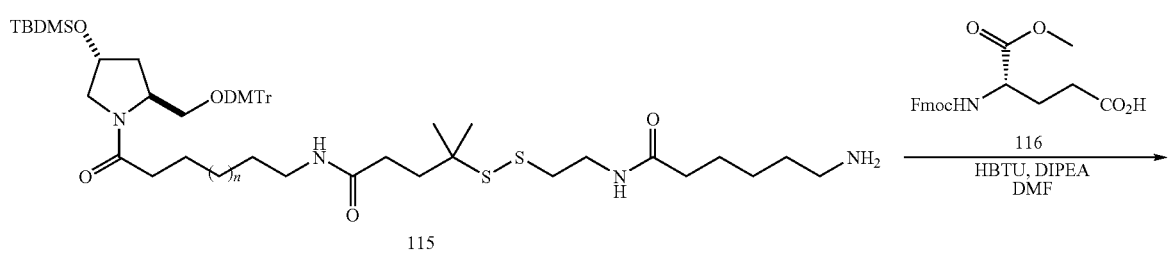

115

-continued
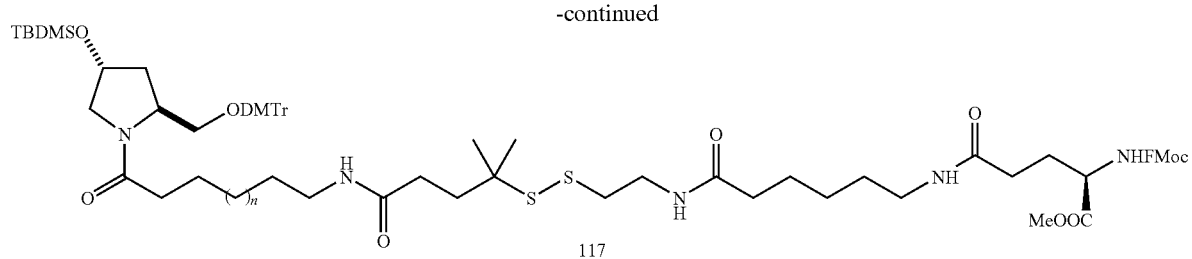
117
↓ Piperidine
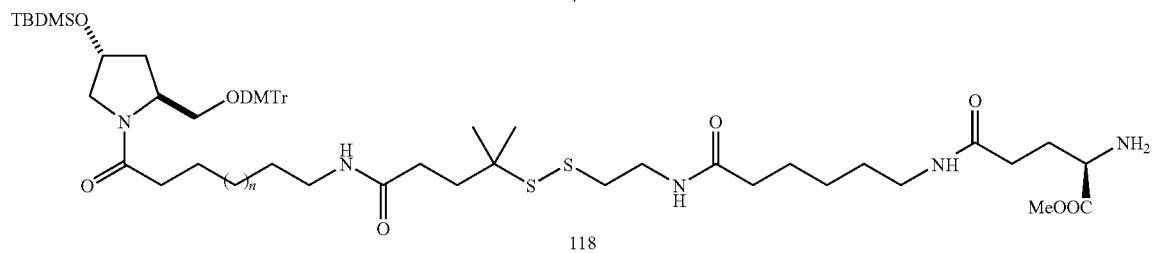
118

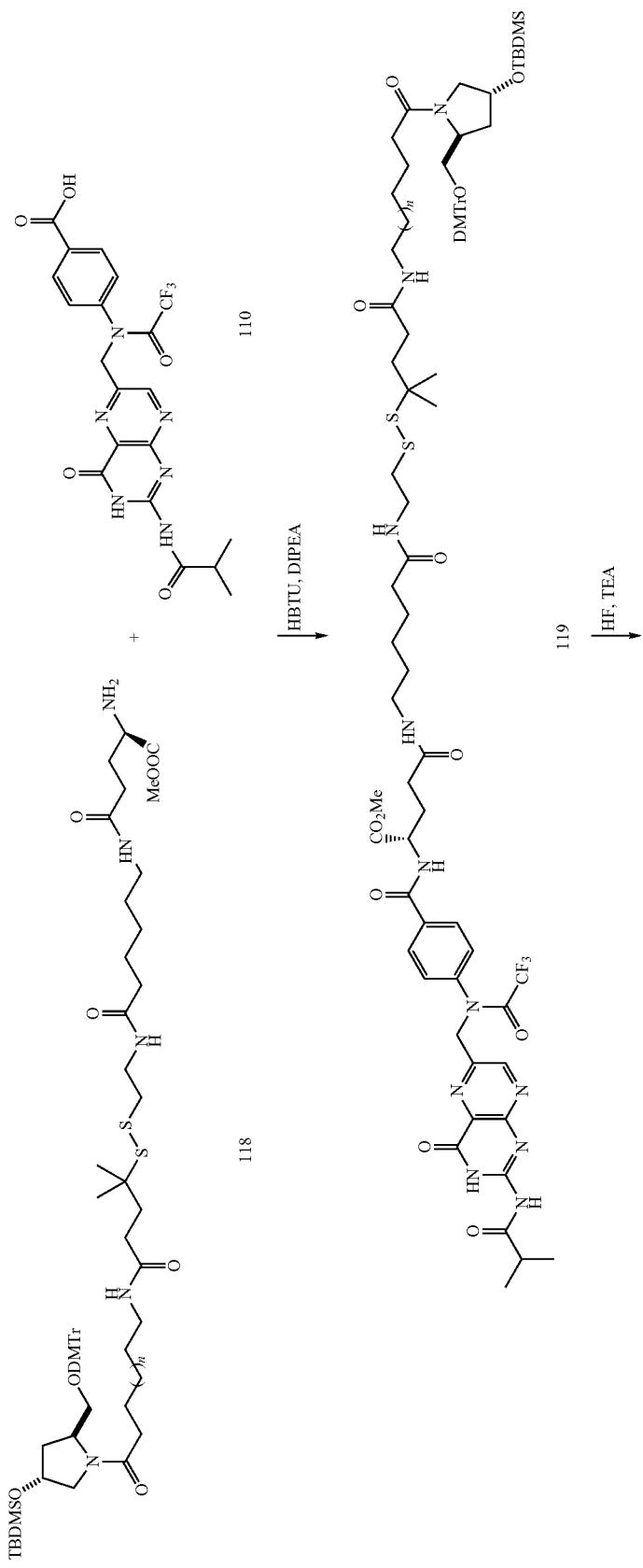

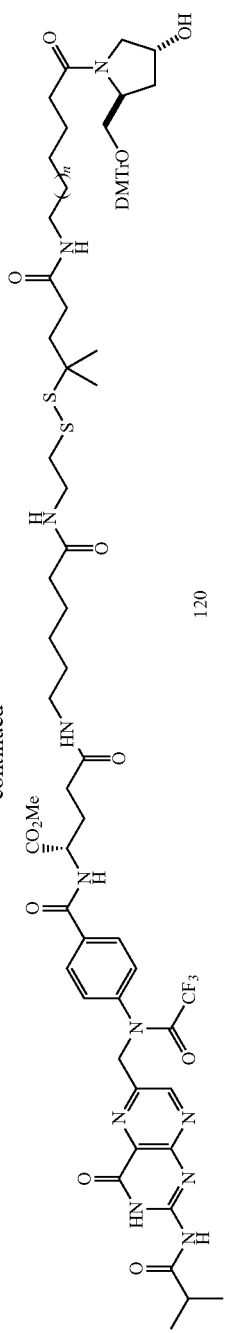
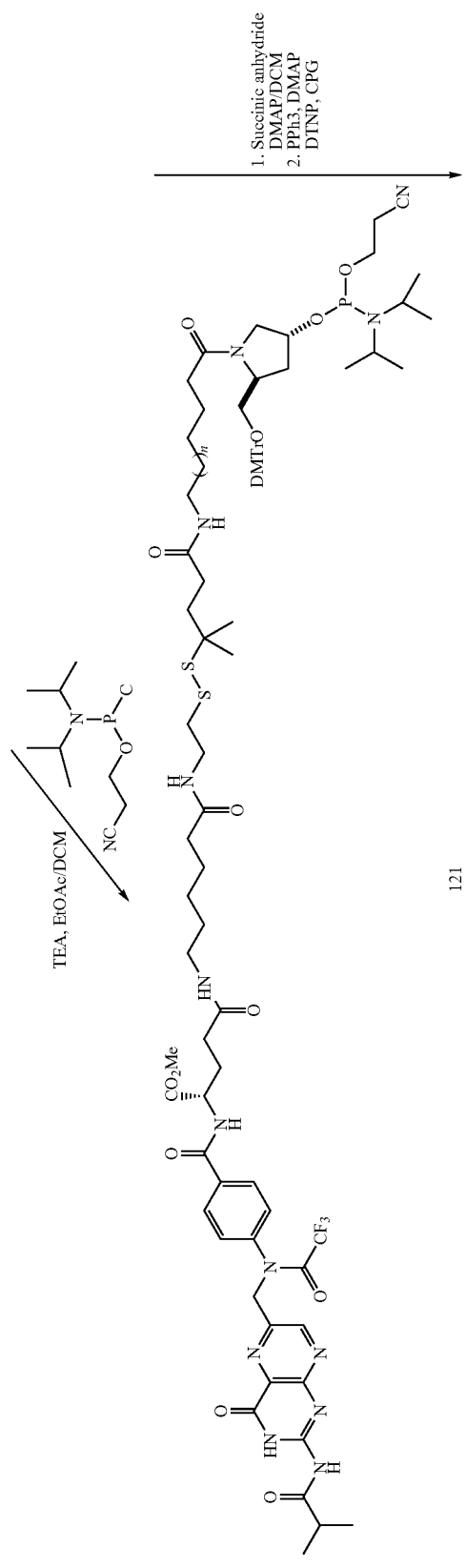
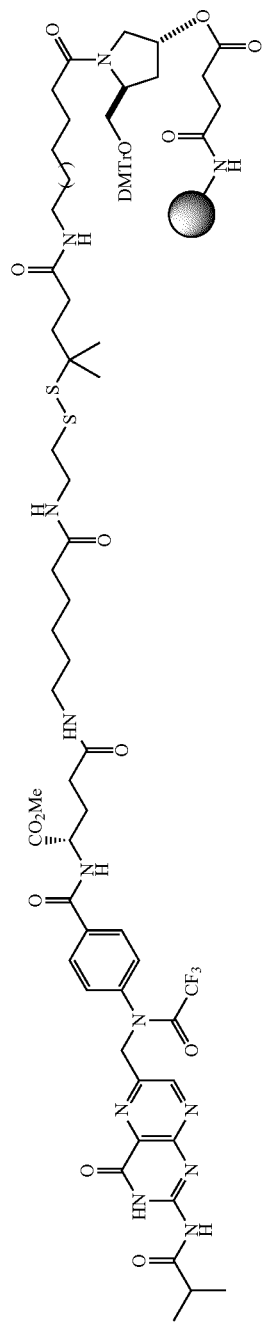

Example 5

Synthesis of Disulfide Precursor 124

In another example the folate conjugate without the stabilizing gem dimethyl group next to the disulfide link was probed. In a procedure similar to that described above for compound 112 (example 3) is used to synthesize 124 as follows.

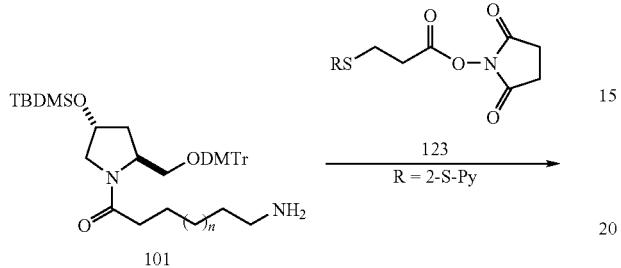

101

→ 123
R = 2-S-Py

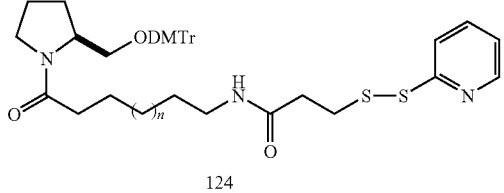

124

Example 6

Synthesis of Folate Conjugates 130 and 131

In another approach the Folic acid was conjugated to the siRNA via a disulfide link through cystine as follows.

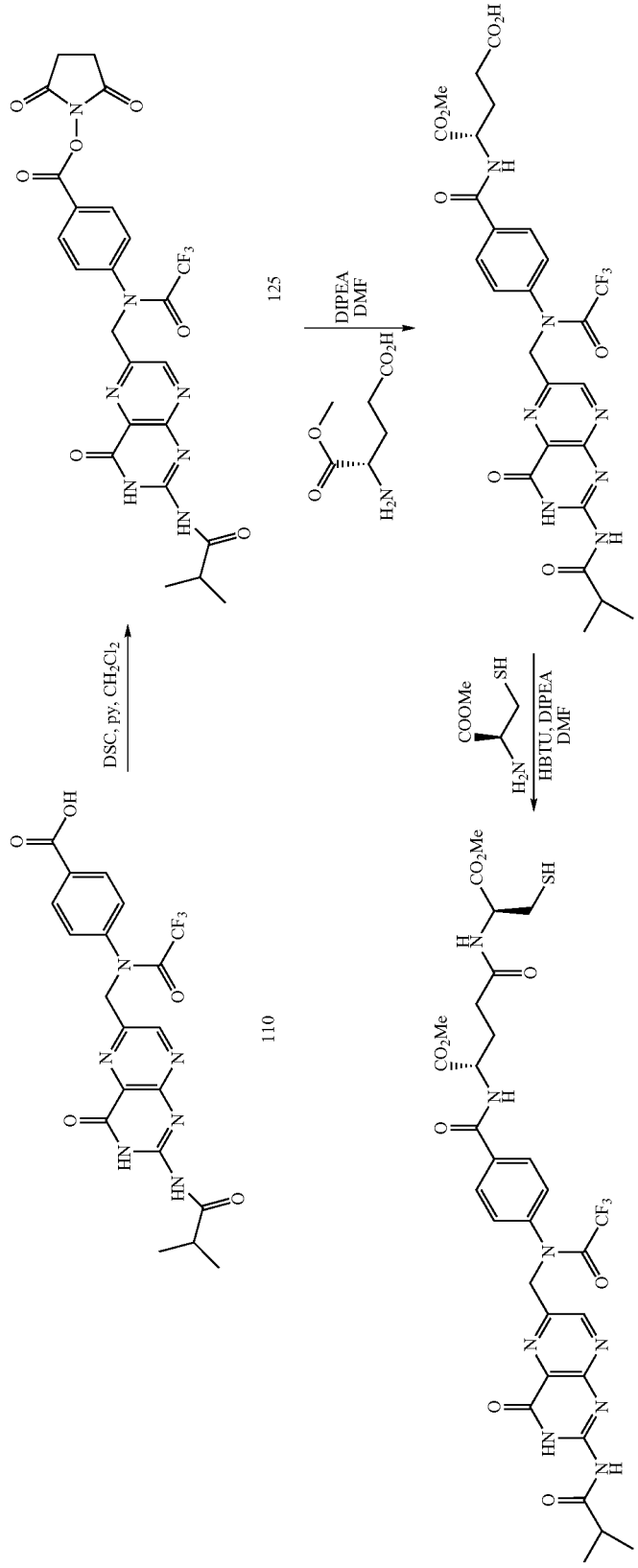
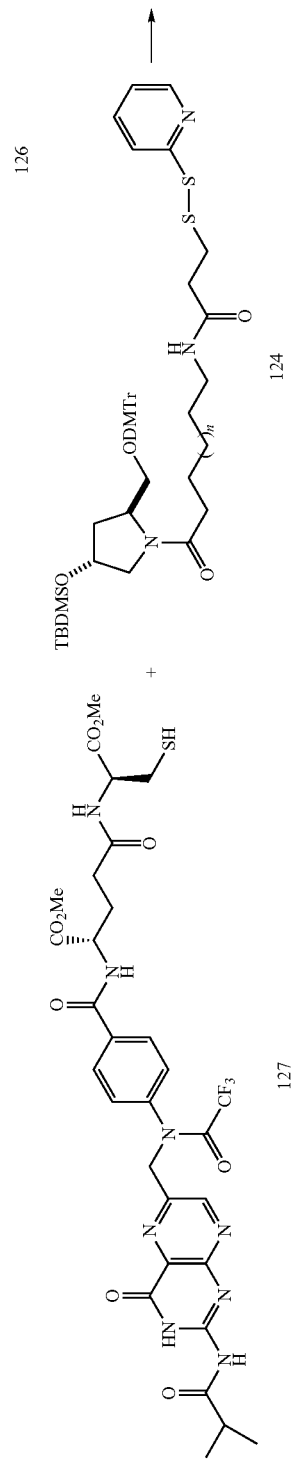

-continued
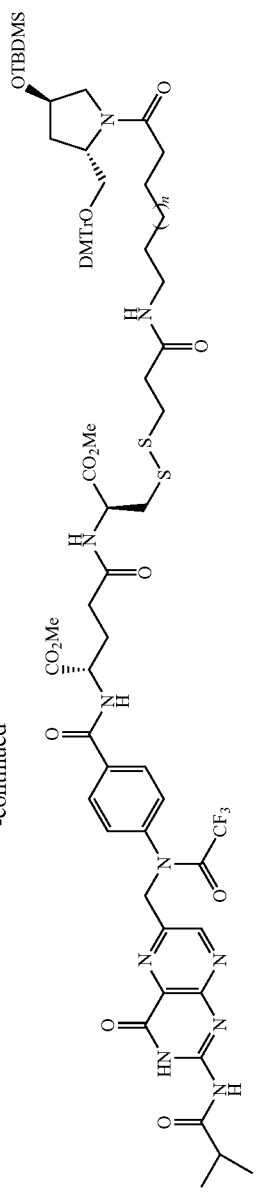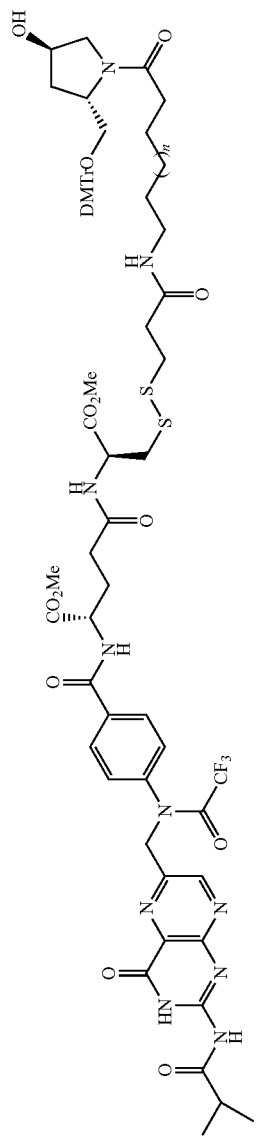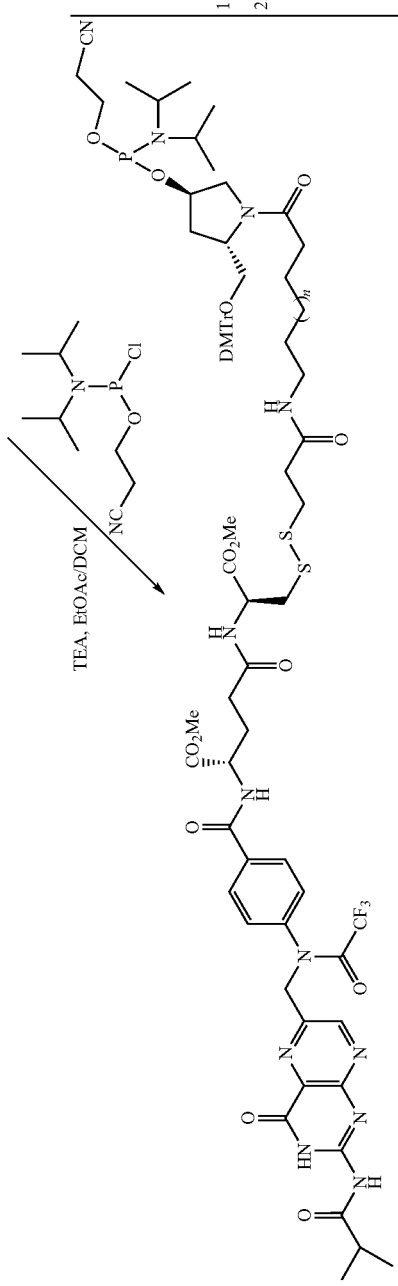

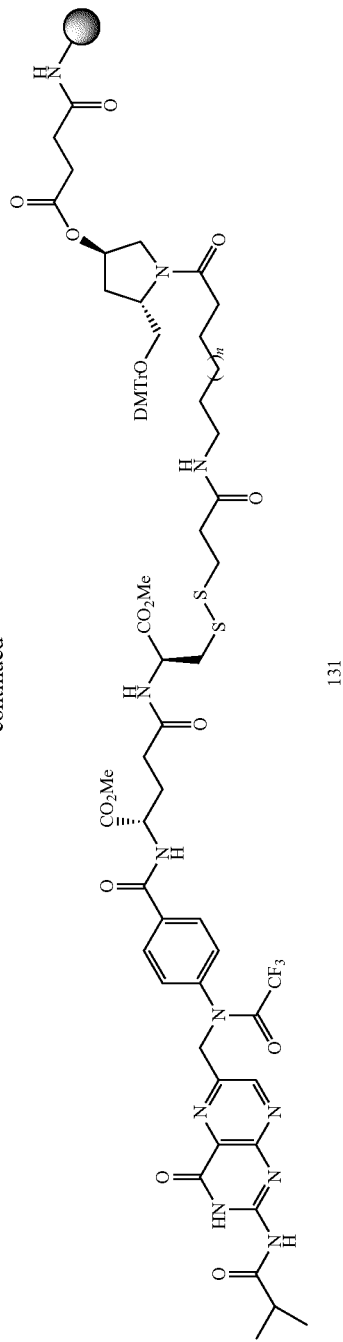

Example 7

In another embodiment the disulfide linkage was placed closer to the siRNA as follows.

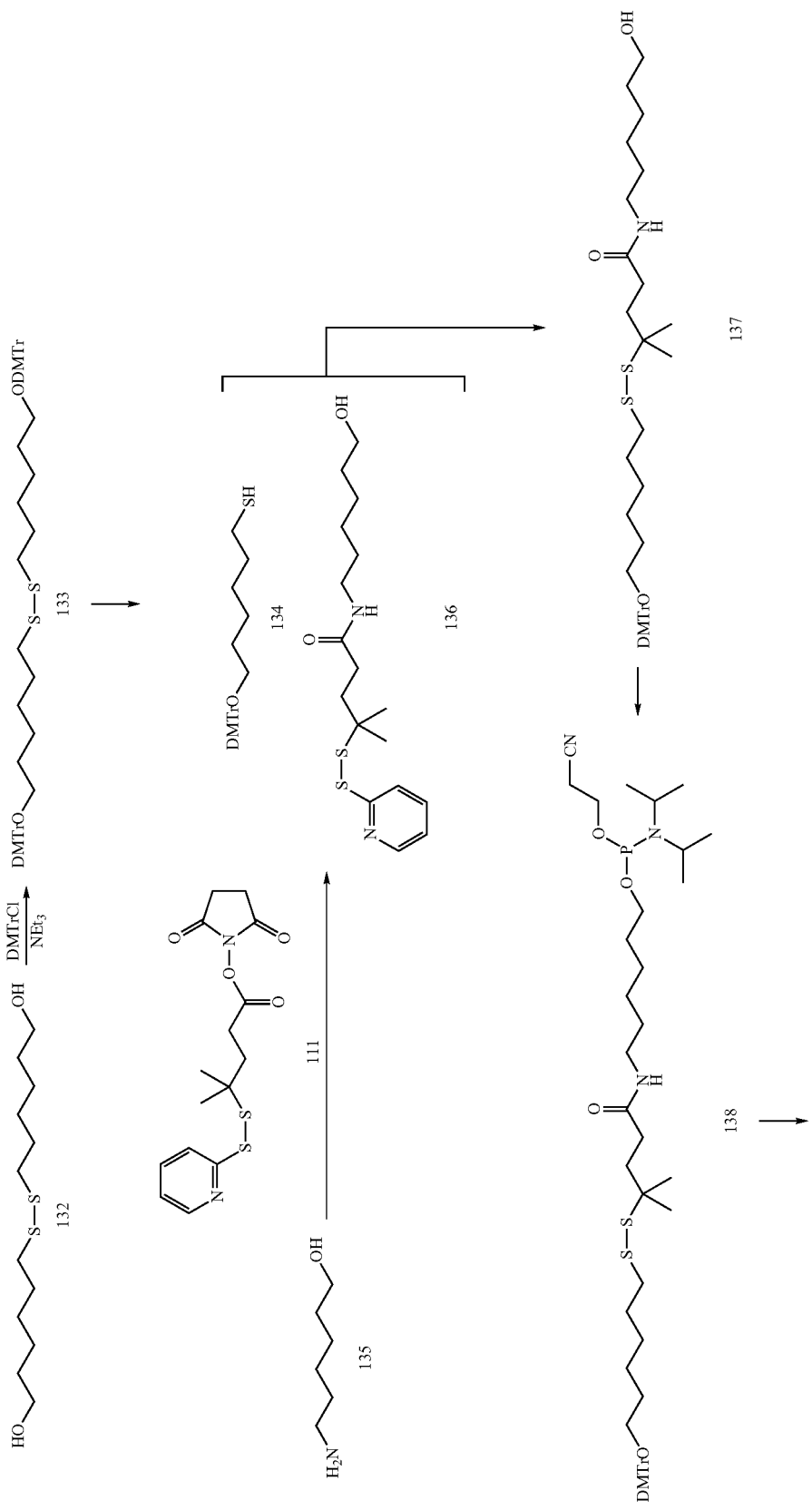

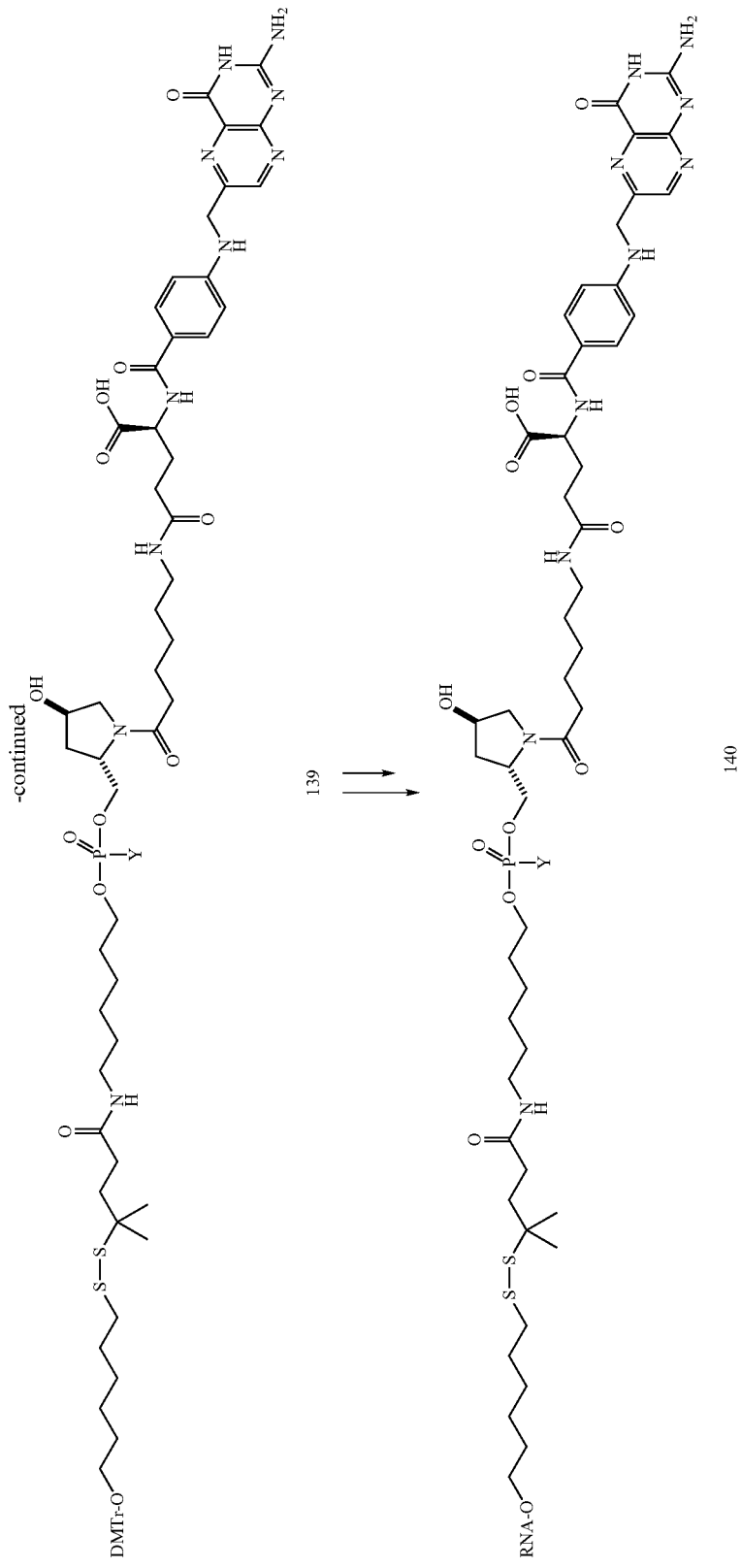

Example 8

Synthesis of Compounds Folic Acid Precursors Amenable to Oligonucleotide Synthesis In order to synthesize an appropriately substituted more versatile precursor of Folic acid amenable for RNA synthesis, the following strategy was used. In this method the protected Folic acid 110 was treated with the γ-tert-butyl, α-Me ester of glutamic acid, 142 to obtain the ester 143 which on treatment with TFA/$CH_2Cl_2$ provided the precursor 144. The precursor 144 was coupled with various amines like 145, 151, 155, 161, 165, 172 and 176 provided the couple products 146, 152, 156, 162, 166, 173 and 177 respectively. These products are then converted to solid-supports 147, 153, 157, 163, 167, 174 and 178, and phosphoramidites 148, 154, 158, 164, 168 and 175.

Synthesis of 147

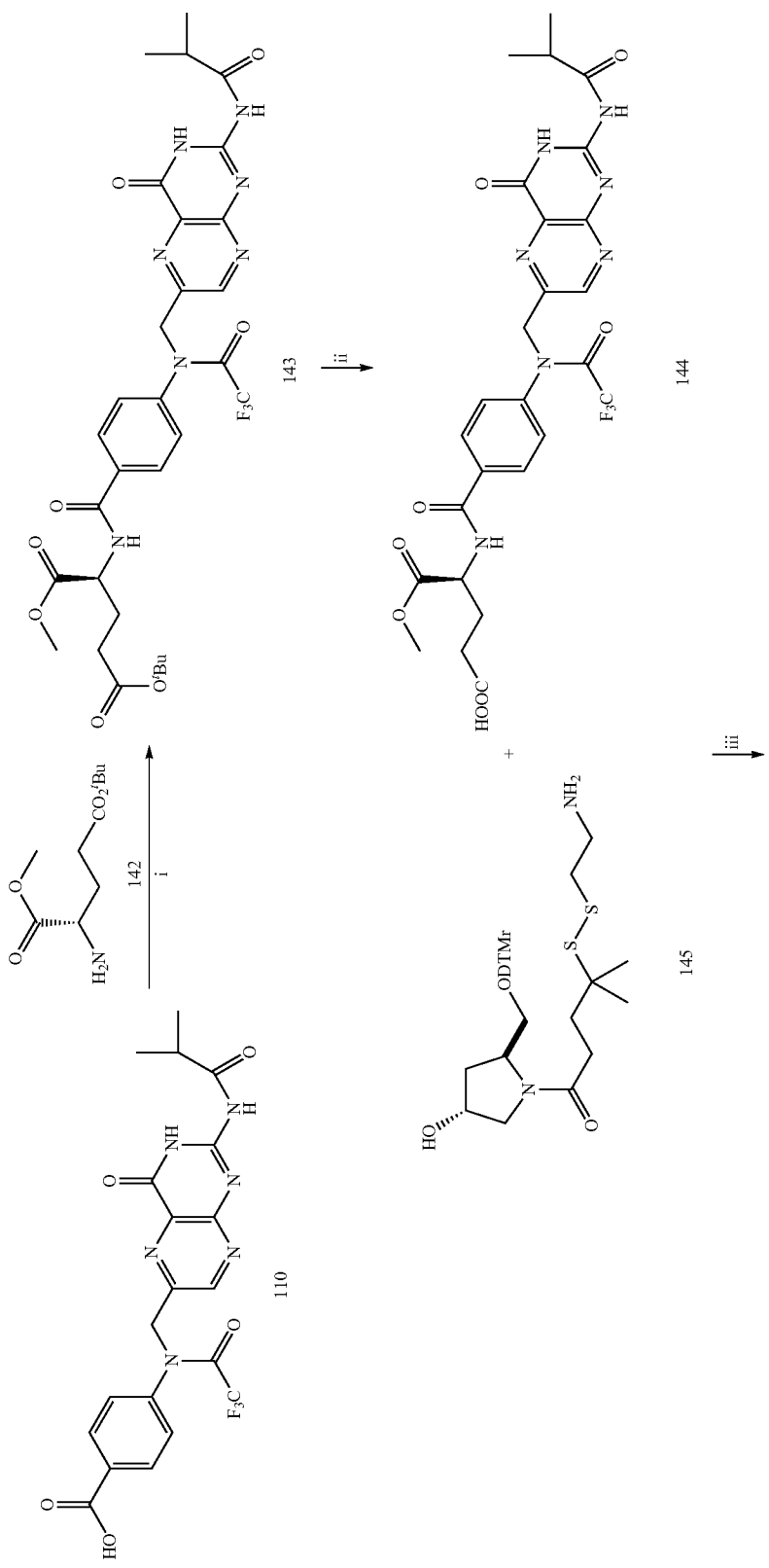

-continued
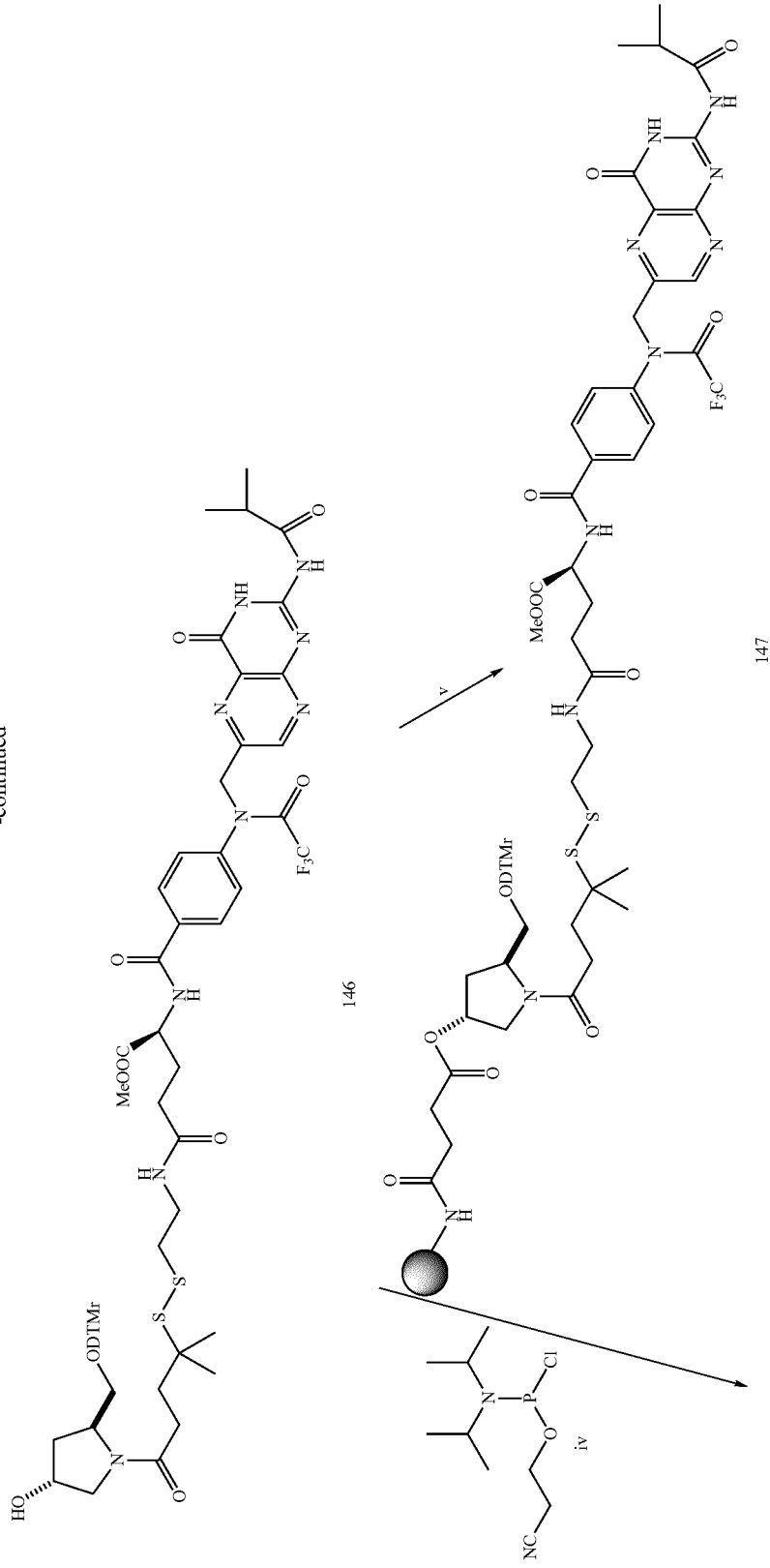

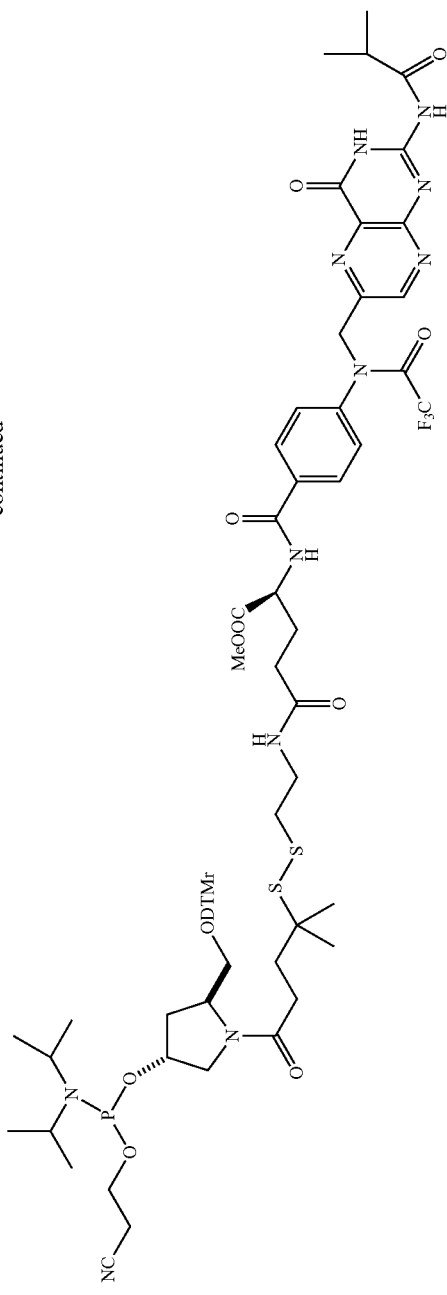
148
i), iii) HBTU, DIPEA, DMF; ii) TFA, CH$_2$Cl$_2$; iv) TEA, EtOAc/DCM; v) a) succinic anhydride, DMAP, CH$_2$Cl$_2$; b) PPh$_3$, DMAP, DTNP, CPG-NH$_2$ or Polystyrene-NH$_2$

Synthesis of 2-{4-[(2-isobutyrylamino-4-oxo-3,4-dihydro-pteridin-6-ylmethyl)-(2,2,2-trifluoroacetyl)-amino}-pentanedioic acid 5-tert-butyl ester 1-methyl ester 143

In a representative procedure, the pteroic acid precursor 110 (2.4 g, 5 mmol) was dissolved in anhydrous DMF (20 mL), HBTU (1.9 g, 1 eq.) followed by DIEA (1 mL, 5 eq.) were added and stirred for 20 minutes. To this reaction mixture the amine hydrochloride 142 (1.2 g, 1 eq) was added as a solution in DMF (6 mL). Reaction was monitored by TLC (8% MeOH/DCM, PMA stain). TLC of the reaction mixture showed completion of the reaction. The reaction mixture was slowly poured in ice with vigorous stirring. The precipitated product was filtered to get the product 143 as a white solid (Yield=2.85 g, 86%). $^1$H NMR (DMSO-$d_6$, 400 MHz) δ=12.33 (s, 1H), 11.94 (s, 1H), 8.88 (s, 1H), 8.82 (d, J=7.3 Hz, 1H), 7.90 (d, J=8.6 Hz, 2H), 7.68 (d, J=8.4 Hz, 2H), 5.22 (s, 2H), 4.46-4.40 (m, 1H), 3.62 (s, 3H), 2.86-2.73 (m, 1H), 2.32 (t, J=7.4 Hz, 2H) 2.05-1.90 (m, 2H), 1.35 (m, 9H), 1.12 (d, J=6.8 Hz, 6H). $^{13}$C NMR DMSO-$d_6$) δ=180.75, 172.13, 171.45, 165.64, 159.10, 154.80, 149.97, 149.79, 147.72, 141.75, 134.15, 130.53, 128.70, 128.49, 117.50, 114.64, 79.79, 51.96, 51.91, 34.96, 31.22, 27.68, 25.71, 18.72. MS. Molecular weight calculated for $C_{30}H_{34}F_3N_7O_8$, Cal. 677.63, Found 676.72 (M−H)−.

Synthesis of 2-{4-[(2-isobutyrylamino-4-oxo-3,4-dihydro-pteridin-6-ylmethyl)-(2,2,2-trifluoroacetyl)-amino}-pentanedioic acid 1-methyl ester 144

The ester 143 (2 g, 2.9 mmol) was dissolved in 20 mL of 50% TFA in dichloromethane and the solution was stirred at room temperature for 30 min. after which the TLC showed the complete disappearance of the starting ester. The reaction mixture was concentrated and the residue was crystallized from $CH_2Cl_2$:Hexanes (2:3) and crystallized product was filtered off and dried to obtain the pure product 144 (1.76 g, 96%) as off white powder. $^1$H NMR (DMSO-$d_6$, 400 MHz) δ=12.32 (bs, 1H), 11.94 (s, 1H), 8.88 (s, 1H), 8.84 (d, J=7.4 Hz, 1H), 7.90 (d, J=8.3 Hz, 2H), 7.69 (d, J=8.3 Hz, 2H), 5.22 (s, 2H), 4.45-4.41 (m, 1H), 3.62 (s, 3H), 2.78-2.75 (m, 1H), 2.35 (t, J=7.4 Hz, 2H) 2.07-1.92 (m, 2H), 1.12 (d, J=6.8 Hz, 6H). $^{13}$C NMR DMSO-$d_6$) δ=180.77, 173.70, 172.19, 165.70, 159.21, 155.54, 149.93, 149.84, 147.75, 141.78, 134.18, 130.53, 128.71, 128.49, 117.51, 114.64, 53.98, 52.06, 51.93, 34.97, 30.11, 25.68, 18.73. MS. Molecular weight calculated for $C_{26}H_{26}F_3N_7O_8$, Cal. 621.18, Found 620.18 (M−H)−.

Preparation of 146: $N^{10}$-(Trifluoroacetyl)pteroic acid 144 (2.30 g, 6.00 mmol) is dissolved in DMF (60 mL, it takes about 15-20 minutes to dissolve the compounds in solution). HBTU (3.01 g, 1.3 eq.) followed by DIEA (3 mL, 3 eq.) are added and stirred for 30 minutes then the amine 145 (5.75 g, 1.2 eq) is added and the reaction mixture is stirred at room temperature. Reaction is monitored by TLC (8% MeOH/DCM, PMA stain). TLC of the reaction mixture showed the completion of reaction. Solvents are removed under reduced pressure and the residue extracted with DCM, washed with water and brine. The organic layer is dried over anhydrous sodium sulfate. Solvents are removed and residue was purified by chromatography (3-8% MeOH/DCM) to get the product 146 as a foam (Yield=6.77 g, 93%). $^1$H NMR (DMSO-$d_6$, 400 MHz) δ=8.88-8.90(d, J=7.07 Hz, 1H), 8.60(bs, 1H), 7.90 (d, J=8.4 Hz, 2H), 7.80(t, J=8.4 Hz, 1H), 7.60(d, J=8.06 Hz, 2H), 7.12-7.30(m, 9H), 6.80-6.89(m, 4H), 5.09(bs, 2H), 4.52-4.68(m, 1H), 4.32-4.40(m, 1H), 4.05-1.12(m, 1H), 3.71(s, 6H), 3.62(s, 3H), 2.86-3.30(m, 6H), 1.75-2.23(m, 8H), 1.10-145(m, 6H), 0.82(s, 9H), 0.04-0.01(m, 6H). $^{13}$C NMR DMSO-$d_6$) δ=172.38, 170.96, 170.88, 165.60, 158.11, 157.99, 145.08, 141.66, 135.77, 135.60, 134.19, 129.59, 128.74, 128.74, 128.45, 128.13, 127.78, 127.52, 113.20, 113.11, 85.24, 55.01, 54.98, 54.91, 52.46, 51.90, 45.72, 40.12, 39.92, 39.71, 39.50, 39.29, 39.08, 38.87, 25.65, 17.69, 8.68, −4.88, −4.94. MS. Molecular weight calculated for $C_{60}H_{68}F_3N_9O_{12}S_2$, Cal. 1228.36, Found 1227.3 (M−H)−.

Preparation of Long alkyl chain CPG 147: Hydroxy derivative 146 (0.7 g, 0.441 mmol) was dissolved in DCM (10 mL) to that Succinic anhydride (0.088 g, 2 eq) and DMAP (0.160 g, 3 eq.) were added and stirred overnight. TLC showed completion of reaction. The reaction mixture was diluted with DCM (20 mL), washed successively with cold dilute citric acid and water (2 times), dried over sodium sulfate. Solvents were removed and dried under high vacuum to get the succinate. PPh$_3$ (0.150 g, 1.3 eq.), DMAP (0.080 g, 1.5 eq.) and the succinate from the previous step were dissolved in a mixture of acetonitrile and DCM (6 mL). A solution of DTNP (0.143 g, 1.05 eq.) in DCM (1 mL) was added to the above solution. The mixture was slowly shaken for 3-4 minutes. Long chain alkyl amine-Polystyrene (5.05 g, 250 μmol/g) was added to the mixture and gently shaken for 2 h. The CPG was filtered, successively washed with DCM, mixture of MeOH/DCM (1:9) and DCM until filtrate remained colorless and dried. The dried support was transferred into another flask treated with Ac$_2$O in pyridine (25%) in the presence of TEA (1 mL) for 15 min. under gentle shaking. Finally the CPG was filtered, washed with DCM, DCM:MeOH (9:1), followed by DCM and ether. The support 147 was dried under vacuum overnight and the loading was measured as reported (5.14 g, loading 78 μmol/g).

Synthesis of compound 153

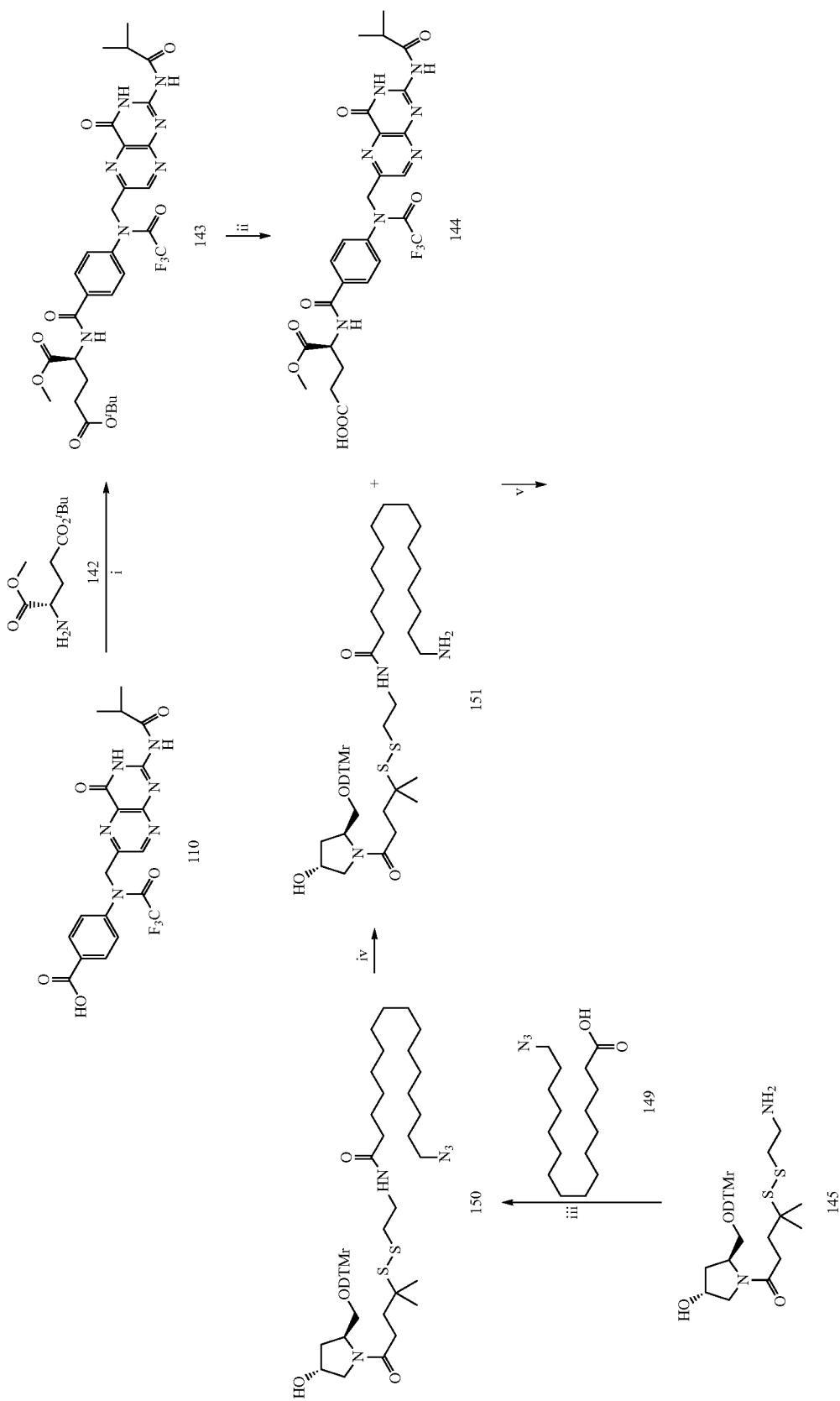

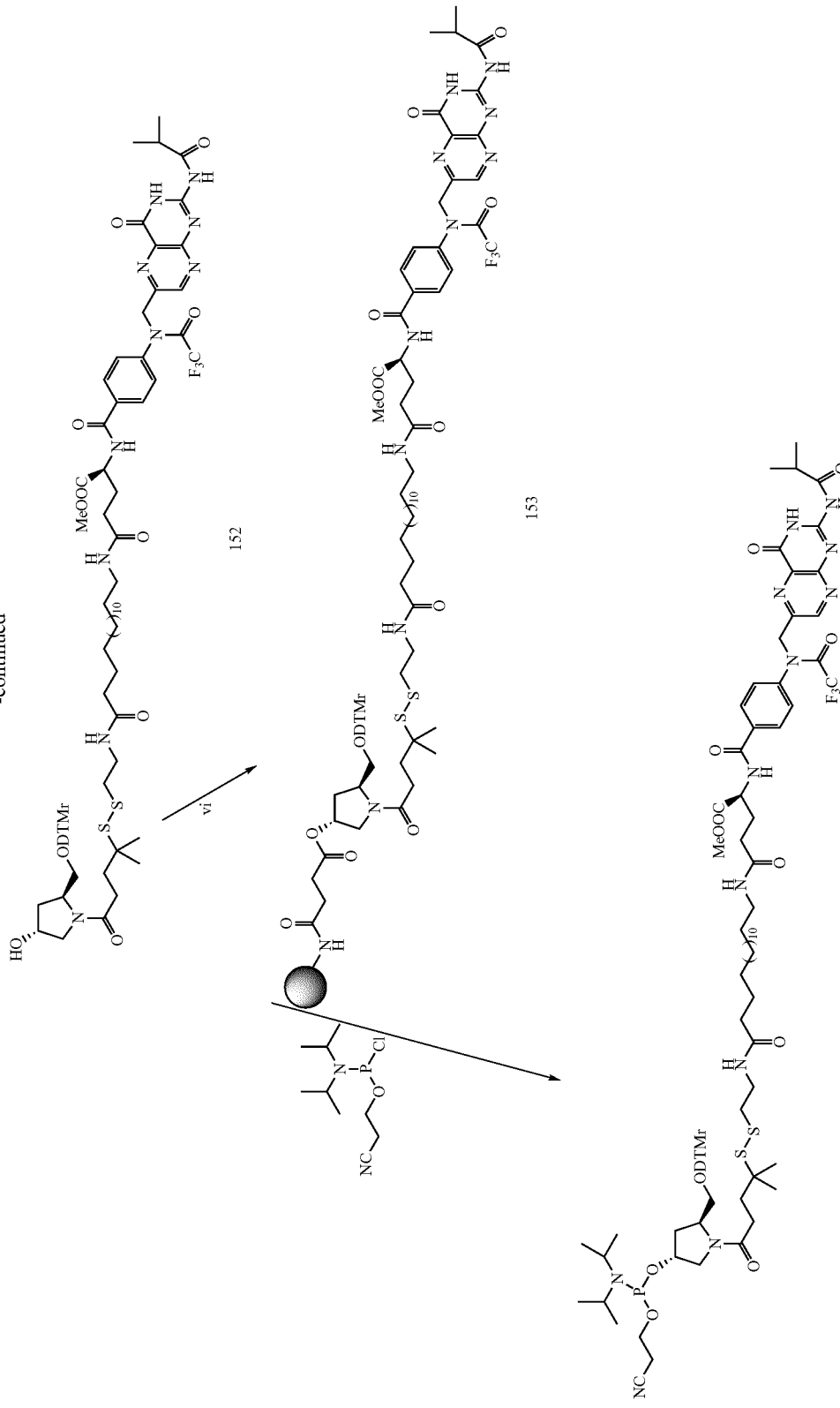

Using a similar procedure to that described above, a folate conjugated solid support with a cleavable disulfide linkage was synthesized as follows. Treatment of the protected folic acid 144 with the amine 151 provided the coupled precursor 152 as white foam. The amine 151 was prepared by coupling the amine 145 with the azido acid 149 followed by the reduction of the azide group using triphenyl phosphine in the presence of water.

Synthesis of azide 150: Using a similar procedure to that used for the synthesis of 146, coupling of the amine 145 (2 g, 3.2 mmol) with the azido acid 149 (0.9 g, 3.2 mmol) provided the coupled azide 150 (1.86 g, 64%) as a foam. $^1$H NMR (DMSO-d$_6$, 400 MHz) δ=7.94-7.90 (m, 2H), 7.30-7.25 (m, 6H), 7.24-7.14 (m, 7H), 6.87-6.84 (m, 6H), 5.22 (d, 0.7H), 4.90 (d, 0.3H) 4.39-4.13 (m, 2H), 3.72 (s, 6H), 3.30 (s, 3H), 3.55-2.86 (m, 9H), 2.23-1.75 (m, 6H), 1.16 (d, J=7.08 Hz, 3H), 1.10-1.45(m, 6H), 0.95(d, J=7.08 Hz, 3H). $^{13}$C NMR DMSO-d$_6$) δ=172.22, 170.42, 162.27, 158.06, 157.96, 145.04, 135.81, 135.71, 135.34, 129.56, 127.75, 127.56, 126.57, 113.09, 85.09, 68.55, 63.27, 54.97, 54.88, 50.57, 50.45, 35.74, 35.29, 30.74, 28.99, 28.96, 28.89, 28.86, 28.71, 28.55, 28.47, 28.19, 27.29, 26.08, 25.16. MS. Molecular weight calculated for $C_{50}H_{73}N_5O_6S_2$, Cal. 904.27, Found 905.3 (MH$^+$).

Synthesis of the amine 151. Treatment of the azide 150 (1.86 g, 2.06 mmol) with triphenyl phosphine (0.54 g, 2.1 mmol) with THF (60 mL) and water (5 mL) at room temperature followed by usual workup and column chromatography provided the pure amine 151 (1.45 g, 82%) as a foam. $^1$H NMR (DMSO-d$_6$, 400 MHz) δ=7.93-7.89 (m, 1H), 7.30-7.25 (m, 6H), 7.24-7.14 (m, 7H), 6.87-6.84 (m, 6H), 5.22 (d, 0.7H), 4.90 (d, 0.3H) 4.39-4.13 (m, 2H), 3.72 (s, 6H), 3.30 (s, 3H), 3.55-2.86 (m, 9H), 2.23-1.75 (m, 6H), 1.16(d, J=7.08 Hz, 3H), 1.10-1.45(m, 6H), 0.95(d, J=7.08 Hz, 3H). $^{13}$C NMR DMSO-d$_6$) δ=172.22, 170.42, 162.27, 158.06, 157.96, 145.04, 135.81, 135.71, 135.34, 129.56, 127.75, 127.56, 126.57, 113.09, 85.09, 68.55, 63.27, 54.97, 54.88, 50.57, 50.45, 35.74, 35.29, 30.74, 28.99, 28.96, 28.89, 28.86, 28.71, 28.55, 28.47, 28.19, 27.29, 26.08, 25.16. MS. Molecular weight calculated for $C_{50}H_{75}N_3O_6S_2$, Cal. 878.28, Found 879.26 (MH$^+$).

Synthesis of compound 152

Using a similar procedure to that used for the synthesis of 146, coupling of the amine 151 (1.45 g, 1.65 mmol) with the acid 144 (1.02 g, 1.65 mmol) provided the coupled product 152 (2 g, 81%) as a foam. $^1$H NMR (DMSO-d$_6$, 400 MHz) δ=11.65 (bs, 1H), 8.90-8.85 (m, 1H), 7.93 (d, J=6 Hz, 2H), 7.85 (m, H), 7.78 (d, J=76 Hz, 2H), 7.40-7.19 (m, 7H), 6.90-6.87 (m, 6H), 5.21 (s, 2H), 4.80-4.56 (m, 1H), 4.42-4.32 (m, 1H), 4.26-4.16 (m, 1H), 3.96-3.79 (m, 1H), 3.72 (s, 3H), 3.30-2.60 (m, 7H), 2.23-1.65 (m, 6H), 1.36-1.15 (m, 24H), 1.12 (d, J=7 Hz, 6H). $^{13}$C NMR DMSO-d$_6$) δ=180.44, 172.32, 170.98, 170.80, 170.58, 165.51, 162.27, 159.10, 158.21, 158.11, 155.53, 154.80, 149.82, 147.75, 145.60, 145.48, 141.75, 136.45, 136.38, 136.33, 136.20, 134.21, 130.51, 129.68, 128.67, 128.45, 127.89, 127.66, 126.70, 114.63, 113.27, 104.26, 85.94, 71.80, 61.70, 57.32, 56.92, 5502, 53.99, 52.57, 52.46, 51.87, 50.45, 45.67, 38.63, 38.44, 38.21, 35.74, 35.29, 30.74, 28.99, 28.96, 28.89, 28.86, 28.71, 28.55, 28.47, 28.19, 27.29, 26.08, 25.16, 18.79, 11.16. MS. Molecular weight calculated for $C_{76}H_{99}F_3N_{10}O_{13}S_2$, Cal. 1481.78, Found 1481.0 (M−H$^−$).

The hydroxyl compound 152 on treatment with succinic anhydride followed by treatment with polystyrene linked resin provided the folate coupled solid support 153 in 84 μM/g loading.

Synthesis of Compound 157

Using a similar procedure to that described above, a folate conjugated solid support with a cleavable disulfide linkage was synthesized as follows. Treatment of the protected folic acid 144 with the amine 155 provided the coupled precursor 156 as white foam.

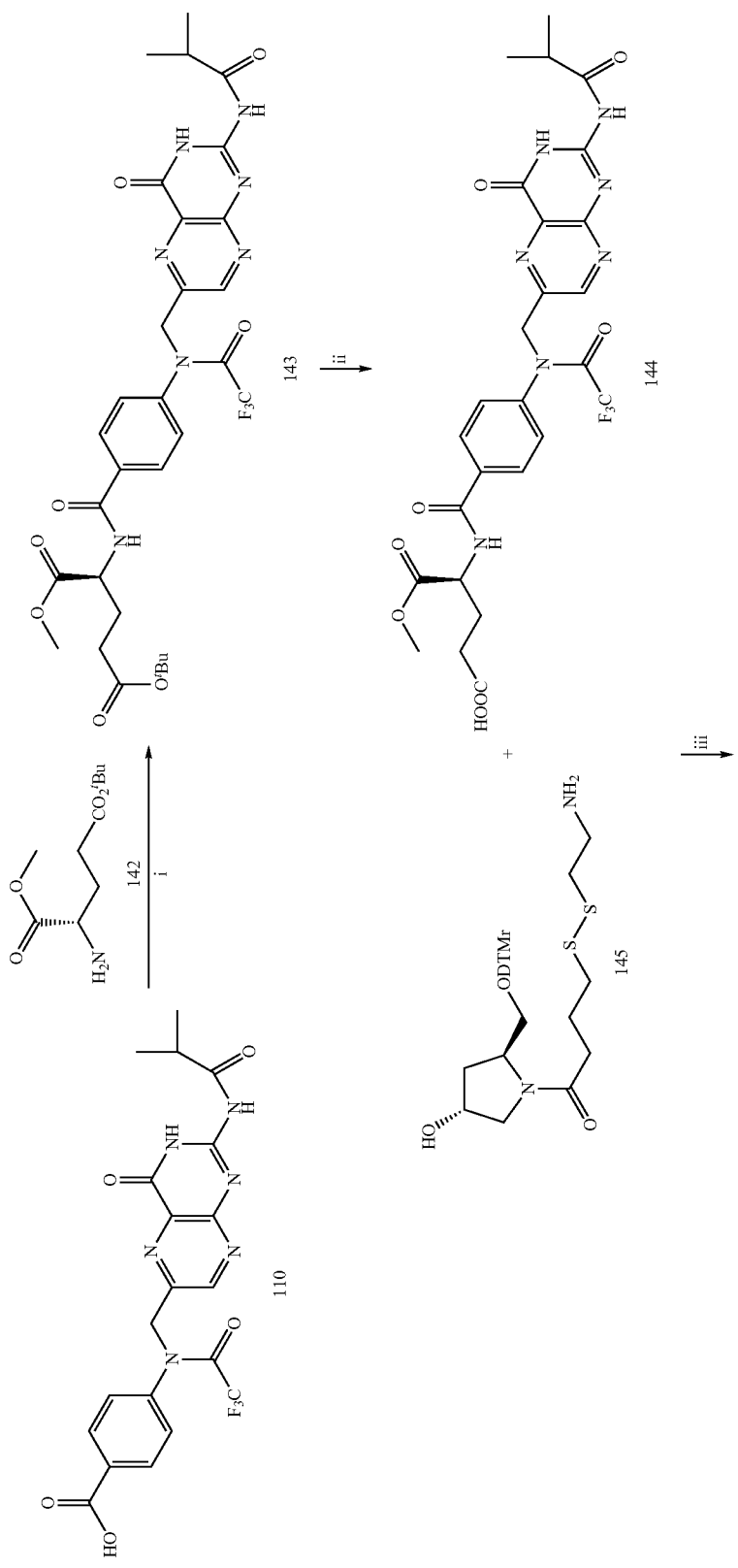

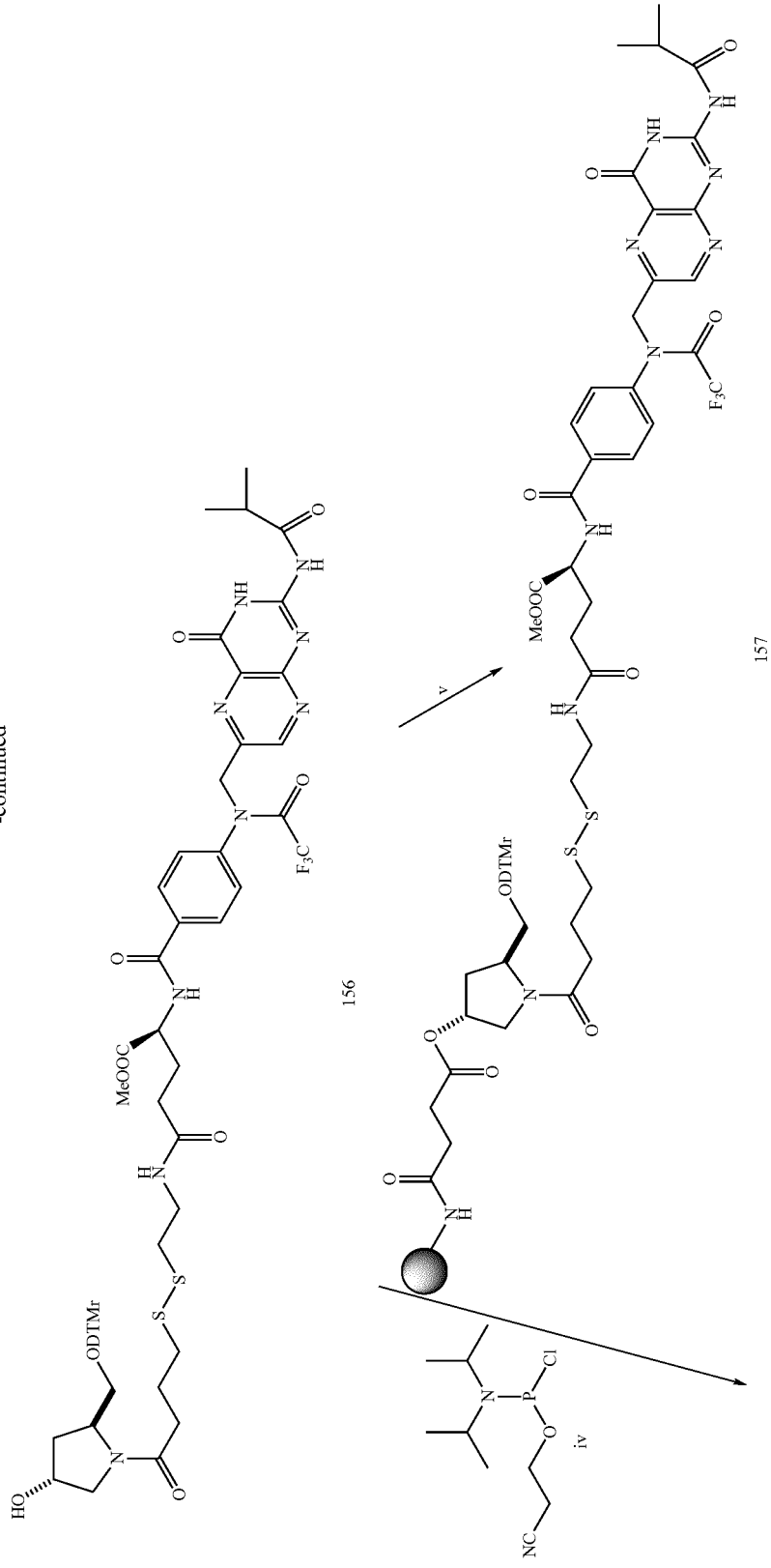

-continued
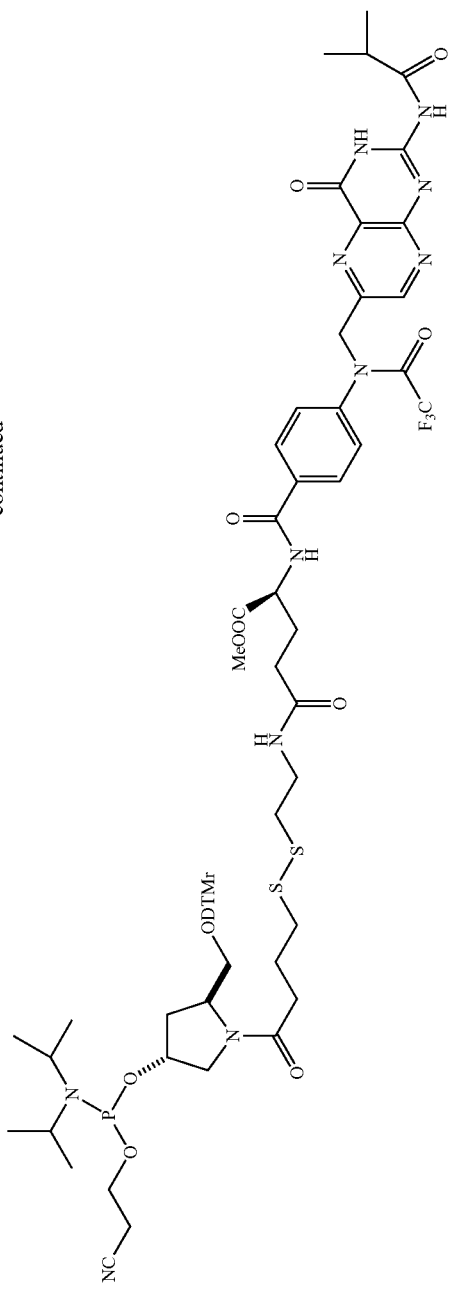
158
i), iii) HBTU, DIPEA, DMF, ii) TFA, CH₂Cl₂; iv) TEA, EtOAc/DCM; v) a) succinic anhydride, DMAP, CH₂Cl₂; b) PPh₃, DMAP, DTNP, CPG-NH₂ or Polystyrene-NH₂

Synthesis of compound 156. Using a similar procedure to that used for the synthesis of 146, coupling of the amine 155 (0.84 g, 1.45 mmol) with the acid 144 (0.875 g, 1.41 mmol) provided the coupled product 156 (1.4 g, 83%) as a foam. $^1$H NMR (DMSO-d$_6$, 400 MHz) δ=8.89-8.85 (m, 2H), 8.08-7.62 (m, 5H), 7.40-7.12 (m, 7H), 6.90-6.87 (m, 6H), 5.20 (s, 2H), 4.60-4.36 (m, 2H), 4.20-4.12 (m, 1H), 3.72 (s, 6H), 3.30-2.60 (m, 7H), 2.23-1.65 (m, 6H), 1.10 (d, J=7 Hz, 6H). $^{13}$C NMR DMSO-d$_6$) δ=180.35, 172.28, 171.32, 170.18, 165.57, 160.52, 158.08, 157.96, 154.92, 149.65, 147.27, 145.04, 144.72, 141.73, 135.83 135.70, 135.48, 134.28, 130.48, 129.57, 128.69, 128.46, 127.85, 127.75, 127.55, 126.56, 114.63, 113.19, 113.09, 109.30, 85.10, 68.55, 63.22, 54.97, 53.99, 52.38, 51.87, 45.67, 37.92, 37.18, 37.05, 36.21, 34.87, 32.50, 31.58, 26.19, 24.01, 18.80, 11.08. MS. Molecular weight calculated for $C_{58}H_{64}F_3N_9O_{12}S_2$, Cal. 1200.31, Found 1200.10 (M−H$^-$).

The hydroxyl compound 156 on treatment with succinic anhydride followed by treatment with polystyrene linked resin provided the folate coupled solid support 157 in 74 µM/g loading.

Synthesis of Compounds 163 and 164

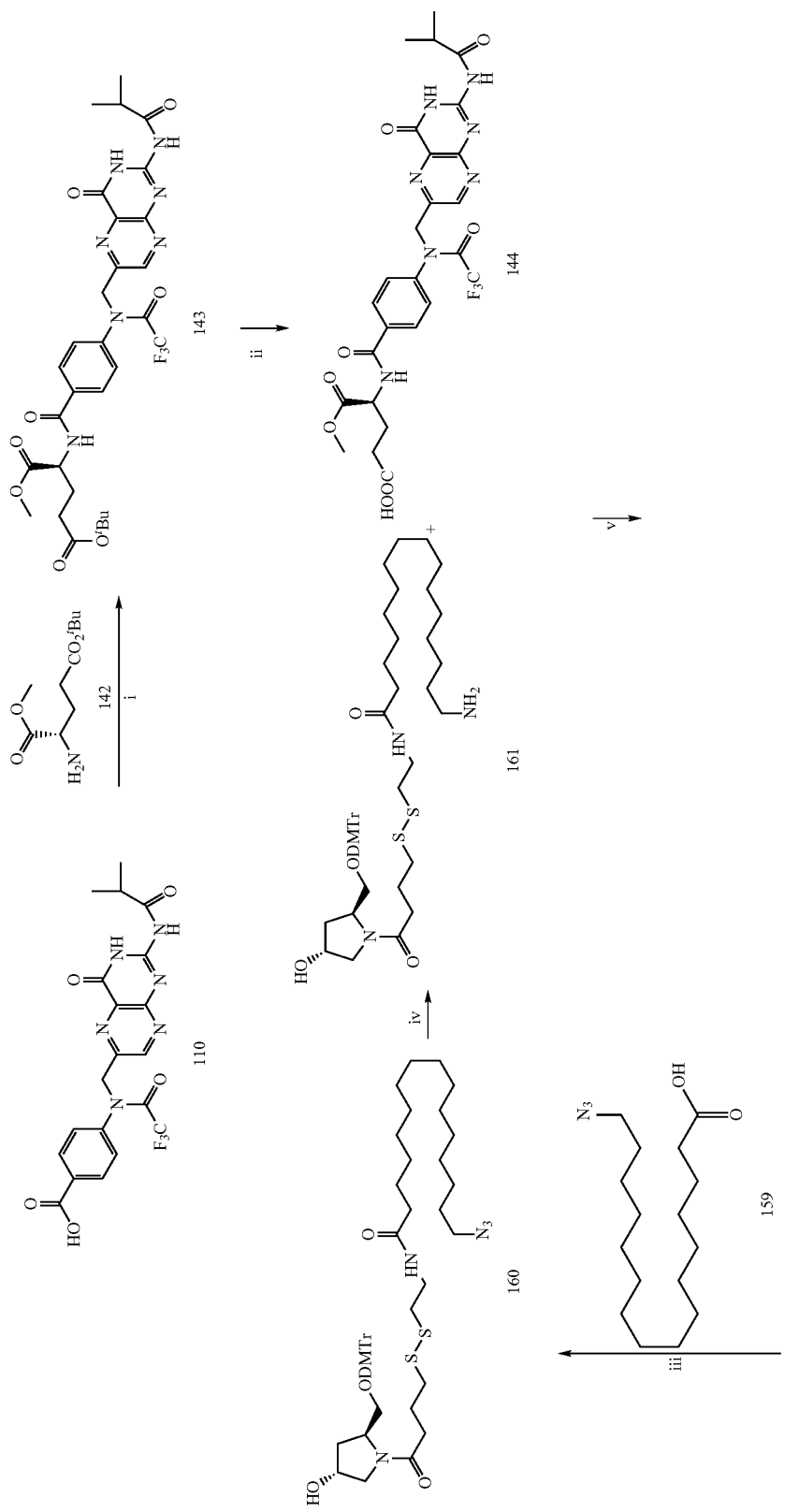

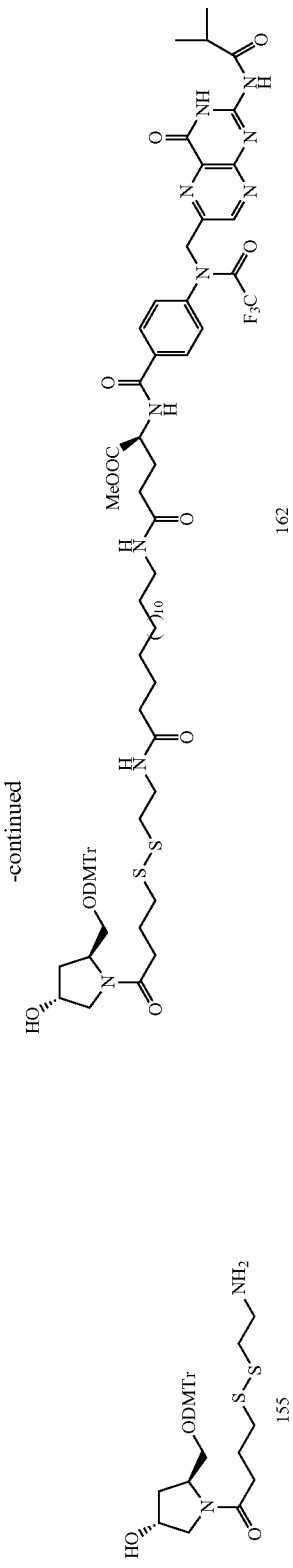
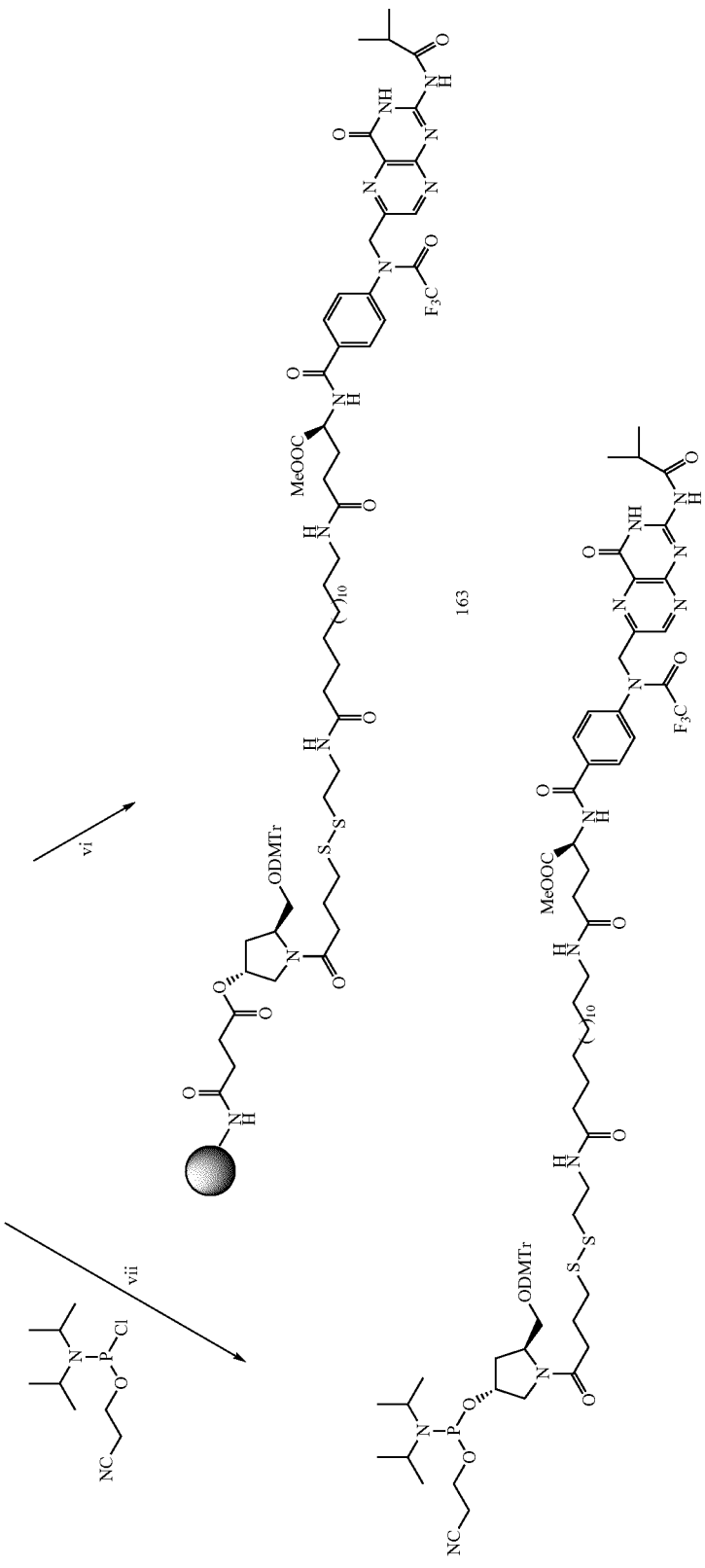
i), iii), v) HBTU, DIPEA, DMF; ii) TFA, CH₂Cl₂; iv) PPh₃, THF, H₂O; vi) a) succinic anhydride, DMAP, CH₂Cl₂; b) PPh₃, DMAP, DTNP, CPG-NH₂ or Polystyrene-NH₂

Using a similar procedure to that described above, compounds 163 and 164 are prepared. Treatment of the protected folic acid 144 with the amine 161 provided the coupled precursor 162. The precursor 162 is then converted into a phosphoramidite, 164 and solid-support 163.
Synthesis of Compound 167 and 168
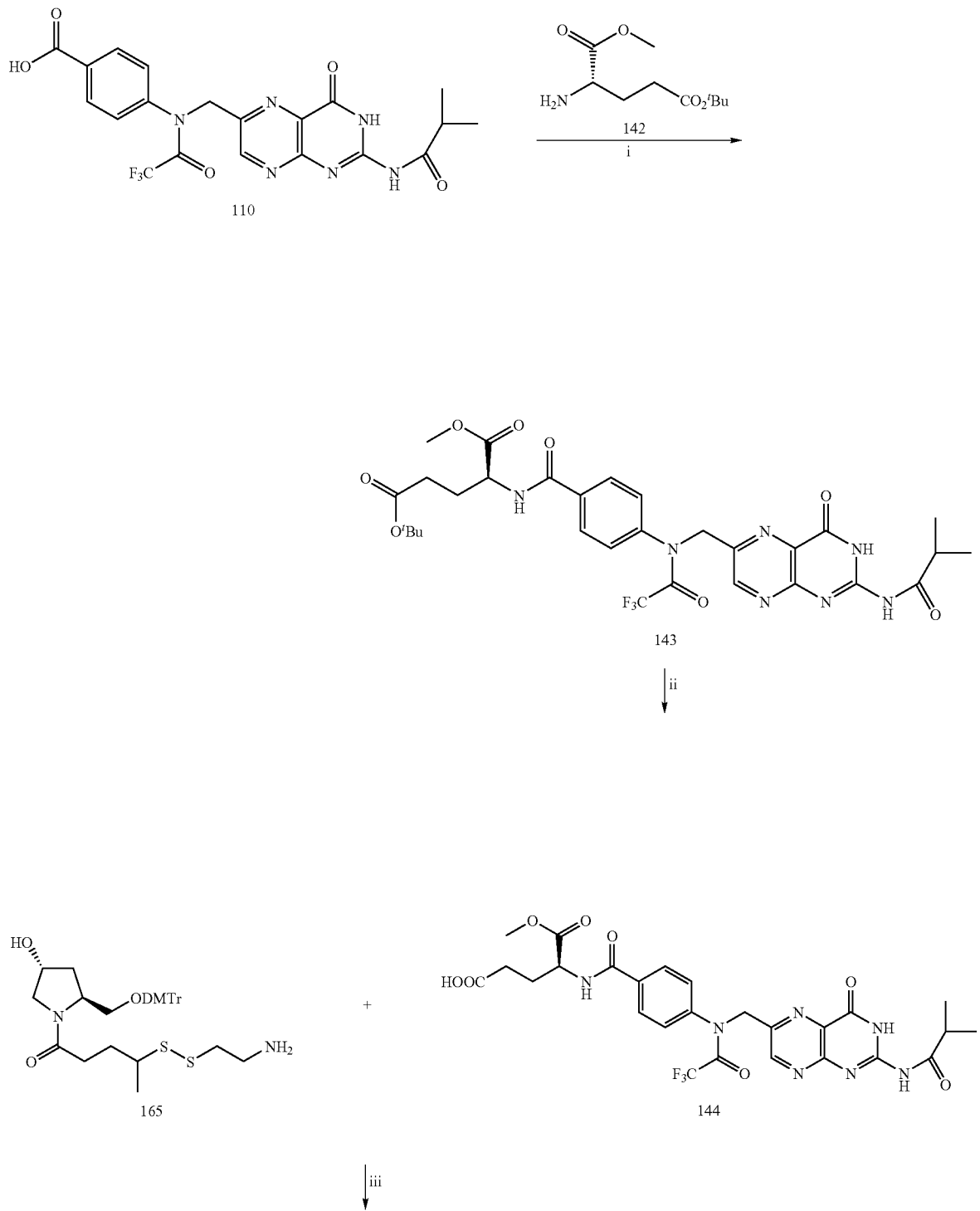

135 136
-continued
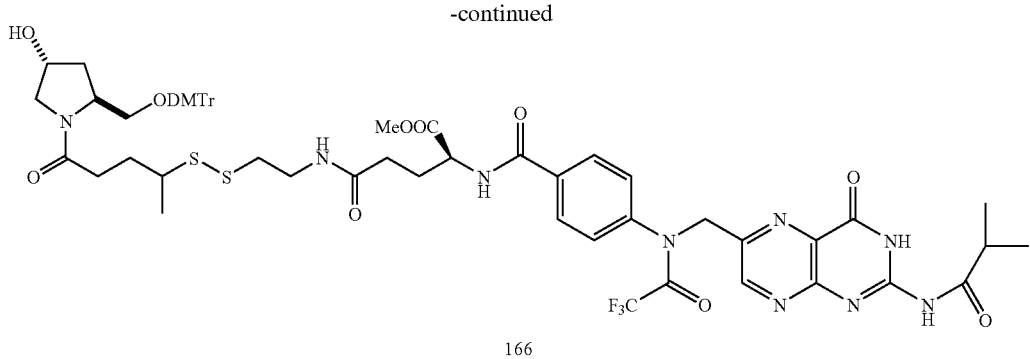
166
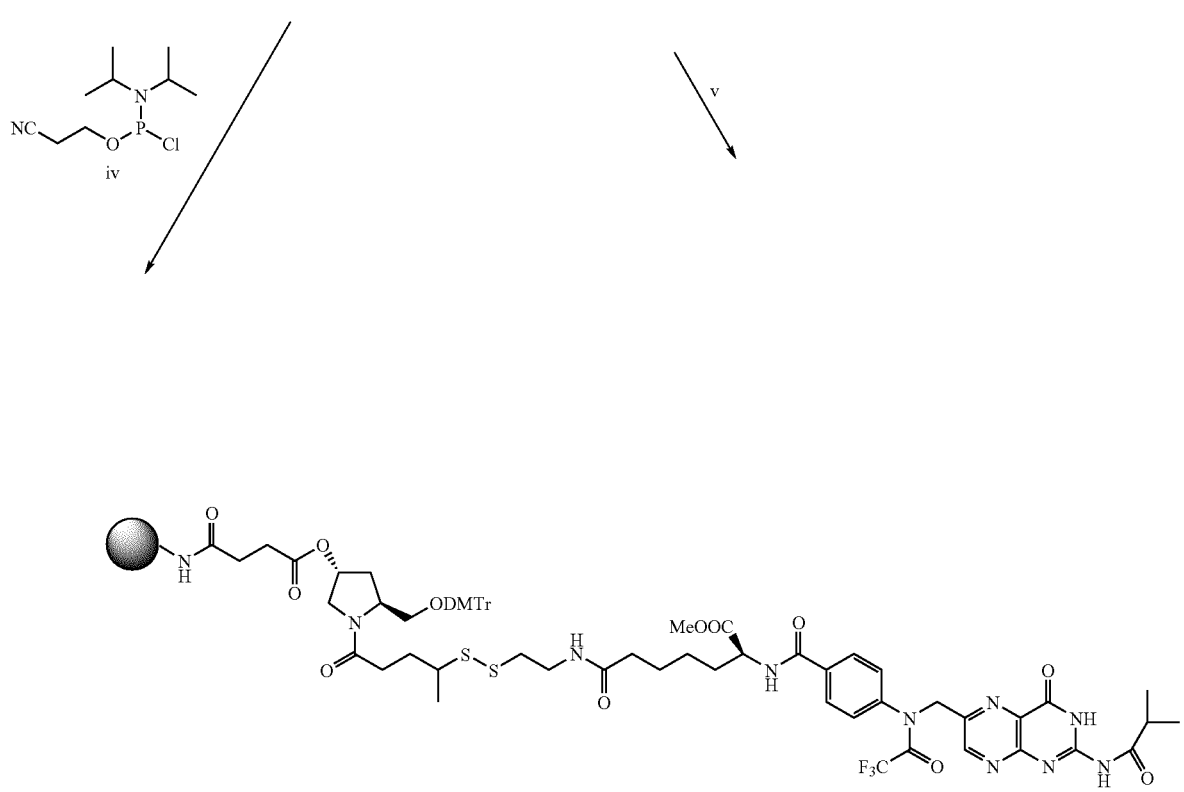
167
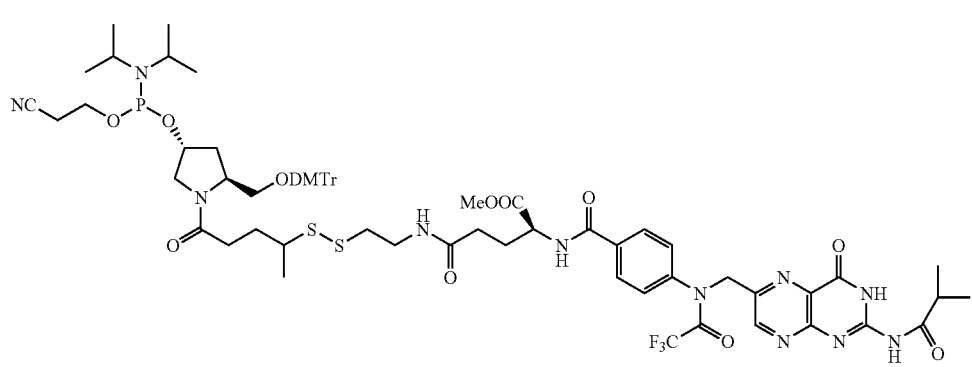
168
i), iii) HBTU, DIPEA, DMF; ii) TFA, CH₂Cl₂; iv) TEA, EtOAc/DCM; v) a) succinic anhydride, DMAP, CH₂Cl₂; b) PPh₃, DMAP, DTNP, CPG-NH₂ or Polystyrene-NH₂

Using a similar procedure to that described above, compounds 167 and 168 are prepared. Treatment of the protected folic acid 144 with the amine 165 provided the coupled precursor 166. The precursor 166 is then converted into a phosphoramidite, 168 and solid-support 167.

Synthesis of Compounds 177 and 178

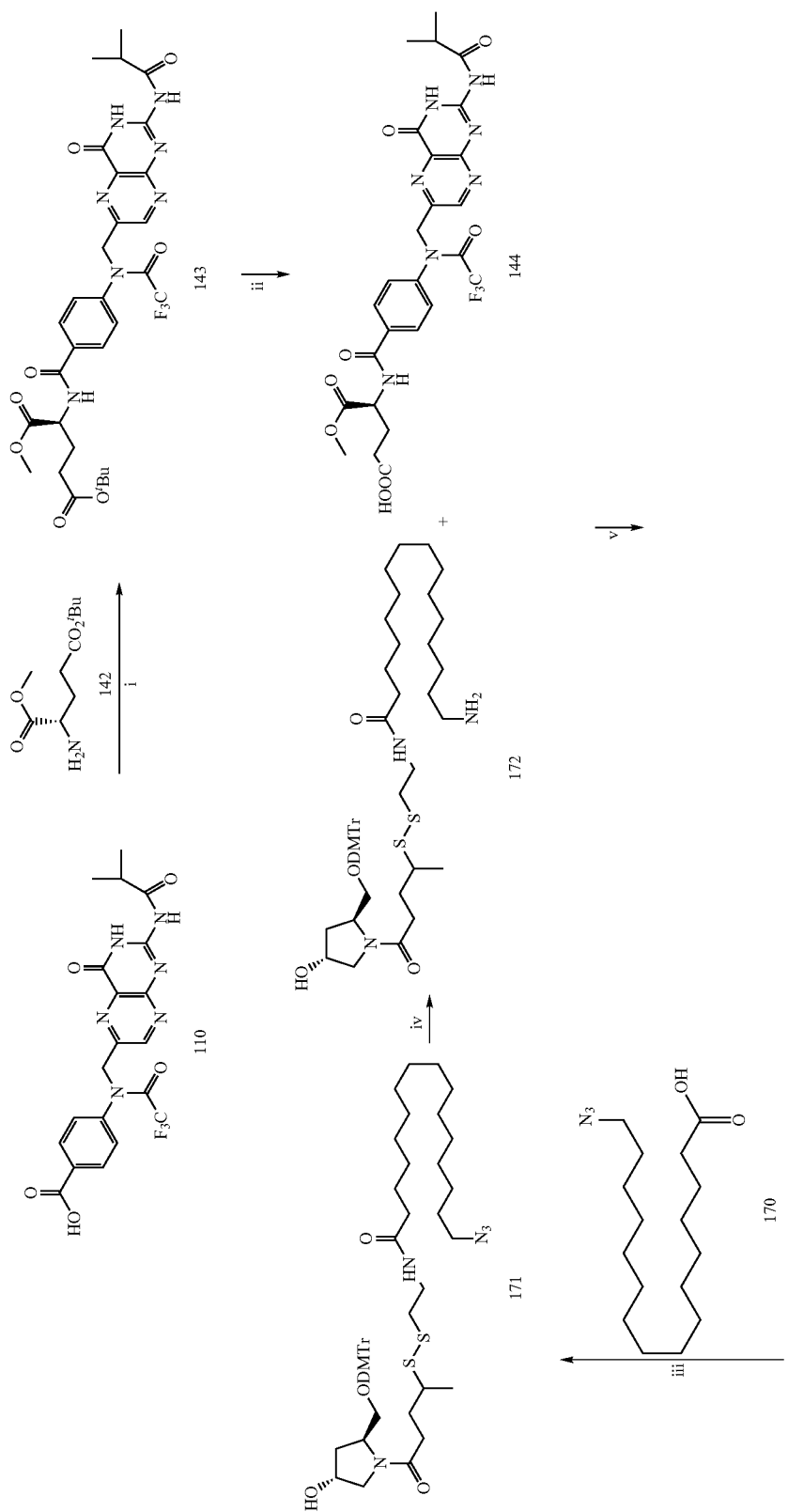

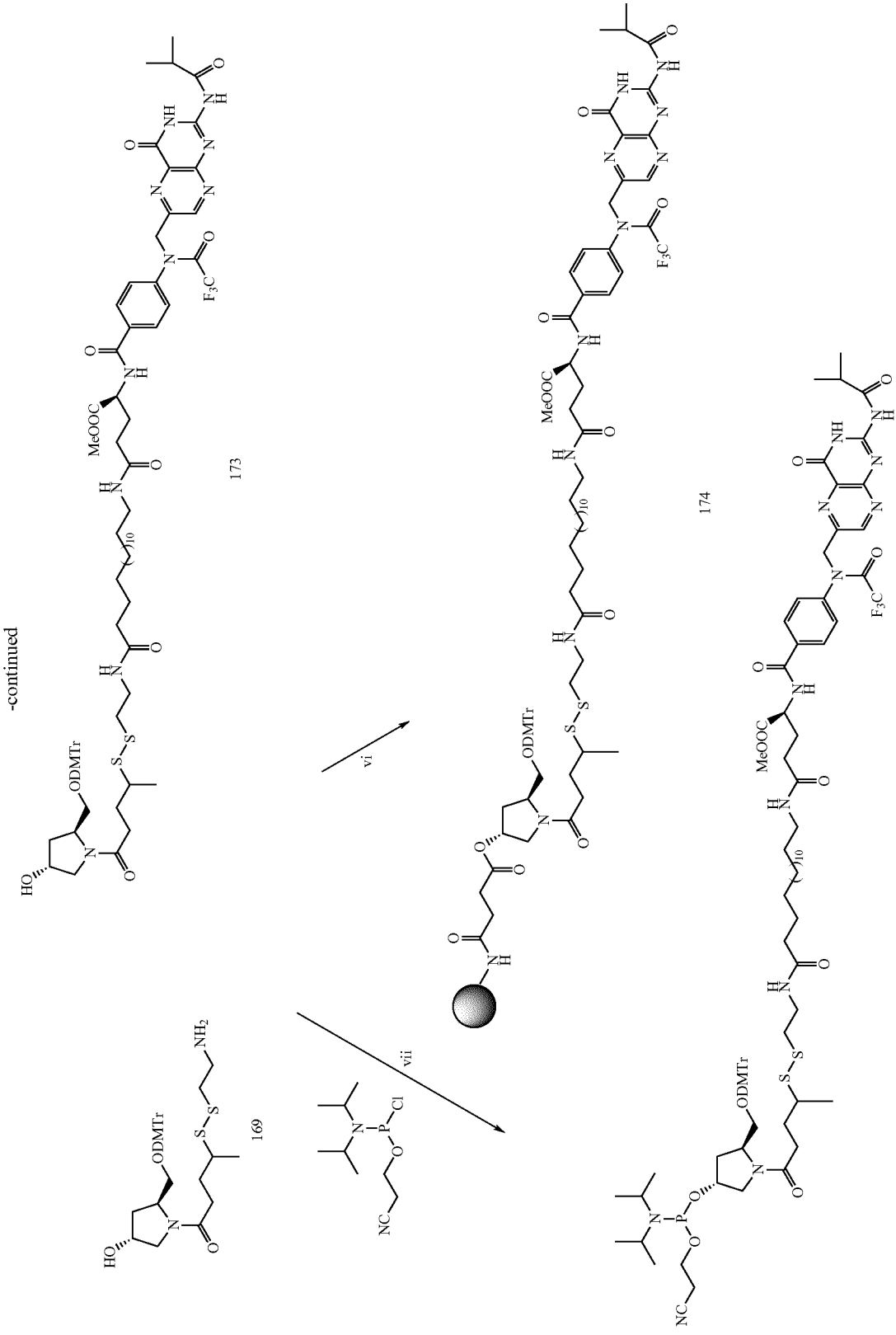

Using a similar procedure to that described above, compounds 174 and 175 are prepared. Treatment of the protected folic acid 144 with the amine 172 provided the coupled precursor 173. The precursor 173 is then converted into a phosphoramidite, 175 and solid-support 174.
Synthesis of Compounds 178
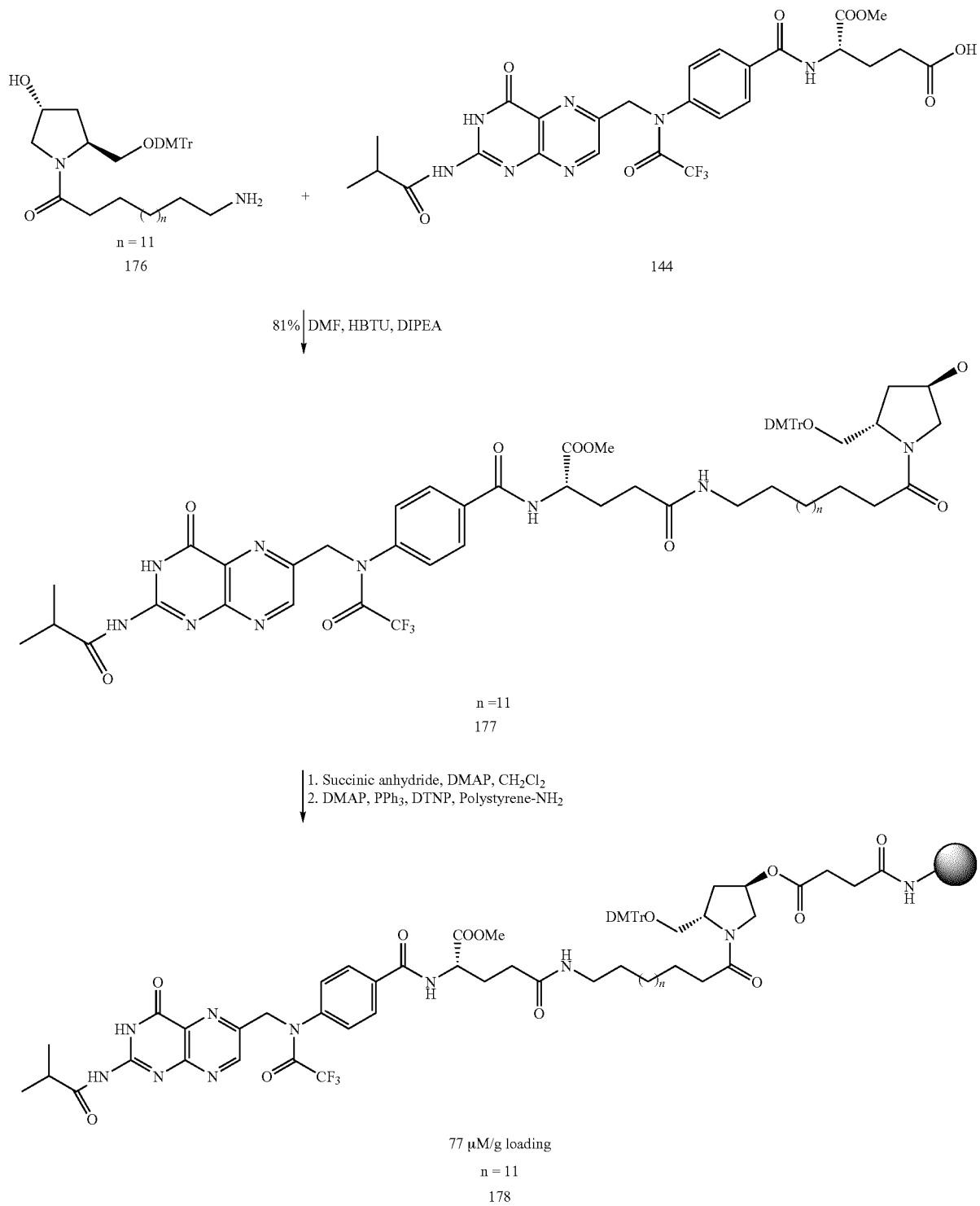

Synthesis of 4(6-{2-[bis-(4-methoxy-phenyl)-phenyl-methoxymethyl]-4-hydroxy-pyrrolidin-1-yl}-[6-oxo-hexadecylcarbamoyl)-2-{4-[(2-isobutrylamino-4-oxo-3,4-dihydro-pteridin-6-ylmethyl)-(2,2,2-trifluoro-acetyl)-amino]-benzoylamino}-butyric acid methyl ester 177

The pteroic acid precursor 144 (4.3 g, 6.92 mmol) was dissolved in anhydrous DMF (80 mL), HBTU (2.62 g, 1 eq.) followed by DIEA (2.7 g, 3 eq.) were added and stirred for 20 minutes. To this reaction mixture the amine 176 (4.65 g, 6.92 mmol) was added as a solution in DMF (20 mL). Reaction was monitored by TLC (5% MeOH/DCM, PMA stain). TLC of the reaction mixture showed completion of the reaction after 1 h. The reaction mixture was slowly poured in ice with vigorous stirring. The mixture was extracted with ethyl acetate and the combined organic layers were dried ($Na_2SO_4$) and concentrated to give the crude product. The thus obtained crude product was further purified by column chromatography (silica gel, 0-5% MeOH in DCM in the presence of 1% $NEt_3$) to obtain 177 as a white foam (Yield=5.1 g, 58%). $^1$H NMR (DMSO-$d_6$, 400 MHz) δ=11.95 (bs, 1H), 8.91-8.89 (m, 2H), 7.92 (d, J=6 Hz, 2H), 7.65 (m, H), 7.68 (d, J=76 Hz, 2H), 7.40-7.38 (m, 2H), 7.36-7.19 (m, 7H), 6.90-6.87 (m, 6H), 5.21 (s, 2H), 4.80-4.56 (m, 1H), 4.42-4.32 (m, 1H), 4.26-4.16 (m, 1H), 3.96-3.79 (m, 1H), 3.72 (s, 3H), 3.30-2.60 (m, 7H), 2.23-1.65 (m, 6H), 1.36-1.15 (m, 24H), 1.12 (d, J=7 Hz, 6H). $^{13}$C NMR DMSO-$d_6$) δ=180.76, 172.32, 170.98, 170.80, 170.58, 165.51, 162.27, 159.10, 158.21, 158.11, 155.53, 154.80, 149.82, 147.75, 145.60, 145.48, 141.75, 136.45, 136.38, 136.33, 136.20, 134.21, 130.51, 129.68, 128.67, 128.45, 127.89, 127.66, 126.70, 114.63, 113.27, 104.26, 85.94, 71.80, 61.70, 57.32, 56.92, 5502, 53.99, 52.57, 52.46, 51.87, MS. Molecular weight calculated for $C_{30}H_{34}F_3N_7O_8$, Cal. 1276.44, Found 1276.0 (M−H⁻).

Preparation of solid support 178: Hydroxy derivative 177 (5 g, 3.91 mmol) was dissolved in DCM (100 mL) to that Succinic anhydride (0.782 g, 2 eq) and DMAP (1.43 g, 3 eq.) were added and stirred overnight. TLC showed completion of reaction. The reaction mixture was diluted with DCM (100 mL), washed successively with cold dilute citric acid and water (2 times), dried over sodium sulfate. Solvents were removed and dried under high vacuum to get the crude succinate. The thus obtained crude succinate was purified by column chromatography (silica gel, 0-10% MeOH in DCM in the presence of 1% $NEt_3$ to isolate the pure succinate as a white foam (4.7 g, 93%). This succinate was dissolved in acetonitrile (100 mL) and to it $PPh_3$ (0.96 g, 1.1 eq.), DMAP (0.61 g, 1.5 eq.) were added after which a solution of DTNP (3.1 g, 1.05 eq.) in ACN (10 mL) was added to the above solution. The mixture was slowly shaken for 3-4 minutes. Long chain alkyl amine-polystyrene (30 g, 250 μmol/g) was added to the mixture and gently shaken for 2 h. The solid support was filtered, successively washed with DCM, mixture of MeOH/DCM (1:9) and DCM until filtrate remained colorless and dried. The dried support was transferred into another flask treated with $Ac_2O$ in pyridine (25%) in the presence of TEA (1 mL) for 15 min. under gentle shaking. Finally the solid support was filtered, washed with DCM, DCM:MeOH (9:1), followed by DCM and ether. The solid support 116 was dried under vacuum overnight and the loading was measured as reported (30 g, loading 72 μmol/g).

Example 9

Synthesis of Folate Conjugates with Peg Spacer

In order to introduce a hydrophilic PEG spacer the following route was used. Treatment of the commercially available PEGazido acid 179 with the hydroxyprolinol derivative 180 provided the coupled azide 181 which on treatment with triphenyl phospine in the presence of water provided the amine 182. The coupling of the amine 182 with the pteroic acid 113 to give the coupled product 183. The hydroxyl compound 183 on treatment with succinic anhydride followed by treatment with polystyrene linked resin provided the folate coupled solid support 184 in 88 μM/g loading.

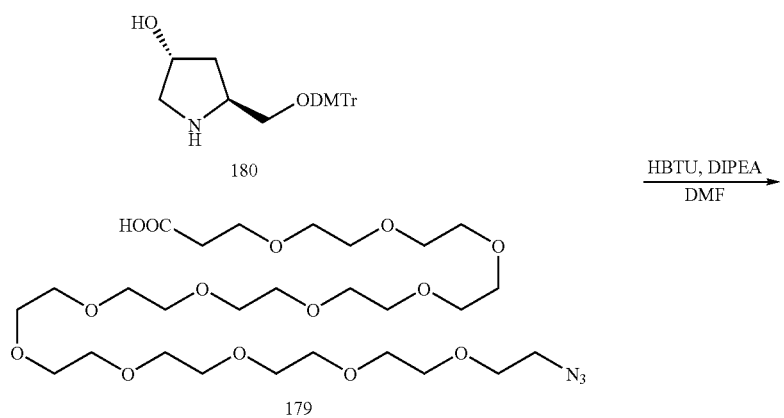

-continued

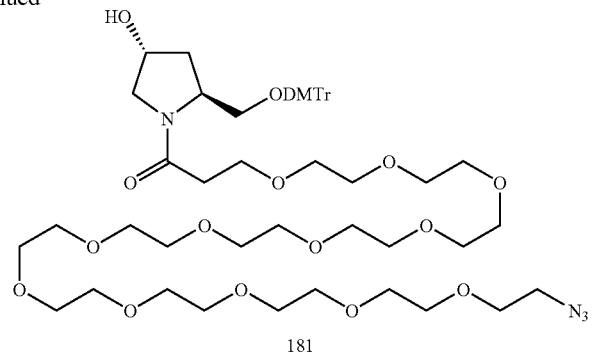
181

| PPh₃, H₂O/THF, r.t.

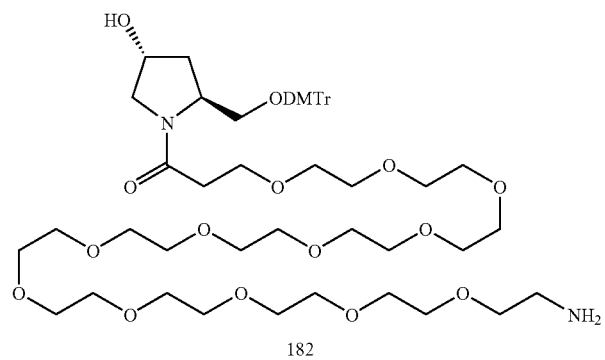
182

Preparation of Compound 181

Using a similar procedure to that used for the synthesis of 112, coupling of the amine 180 (2.1 g, 5 mmol) with the azido acid 179 (3.2 g, 5 mmol) provided the coupled azide 181 (3.26 g, 64%) as a foam. ¹H NMR (DMSO-d$_6$, 400 MHz) δ=7.94-7.90 (m, 2H), 7.30-7.25 (m, 6H), 7.24-7.14 (m, 7H), 6.87-6.84 (m, 6H), 5.22 (d, 0.7H), 4.90 (d, 0.3H) 4.39-4.13 (m, 2H), 3.72 (s, 6H), 3.56-3.54 (m, 46H), 2.23-1.75 (m, 2H), 1.71-1.66 (m, 2H). MS. Molecular weight calculated for C$_{53}$H$_{80}$N$_4$O$_{17}$, Cal. 1044.55, Found 1045.6 (MH⁺).

Synthesis of the amine 182. Treatment of the azide 181 (3.26 g, 3.12 mmol) with triphenyl phosphine (0.78 g, 3.1 mmol) with THF (60 mL) and water (5 mL) at room temperature followed by usual workup and column chromatography provided the pure amine 182 (3.45 g, 82%) as a foam. ¹H NMR (DMSO-d$_6$, 400 MHz) δ=7.93-7.89 (m, 1H), 7.30-7.25 (m, 6H), 7.24-7.14 (m, 7H), 6.87-6.84 (m, 6H), 5.22 (d, 0.7H), 4.90 (d, 0.3H) 4.39-4.13 (m, 2H), 3.72 (s, 6H), 3.30 (s, 3H), 3.55-2.86 (m, 9H), 2.23-1.75 (m, 6H), 1.16(d, J=7.08 Hz, 3H), 1.10-1.45(m, 6H), 0.95(d, J=7.08 Hz, 3H). MS. Molecular weight calculated for C$_{53}$H$_{82}$N$_2$O$_{17}$, Cal. 1119.22, Found 1120.26 (MH⁺).

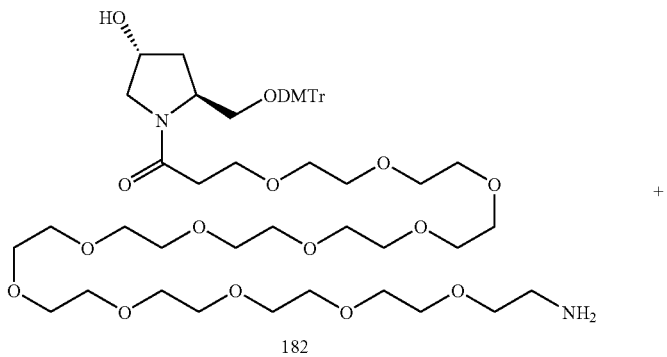
182

+

-continued

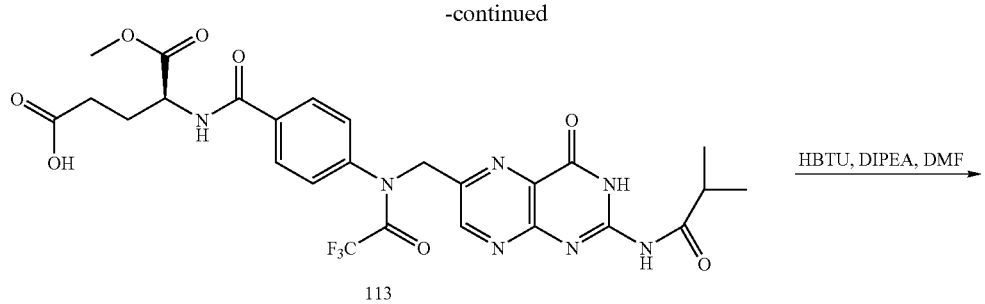

113

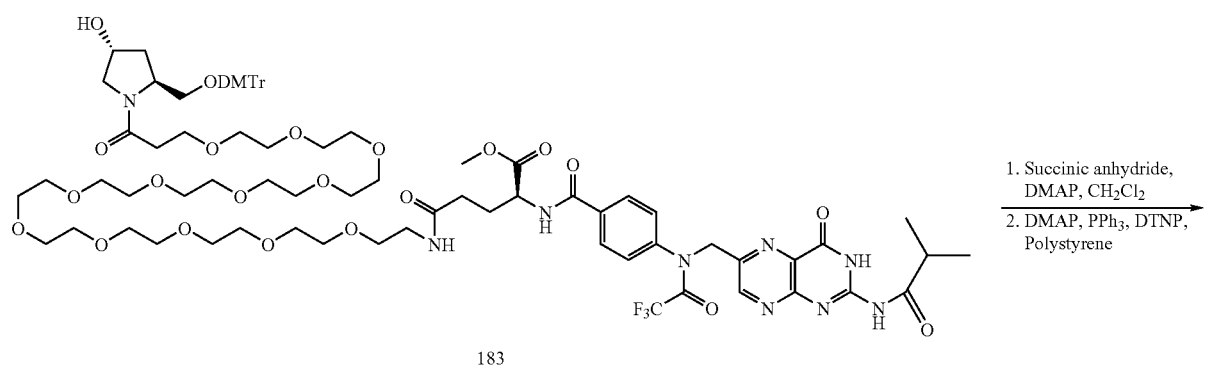

183

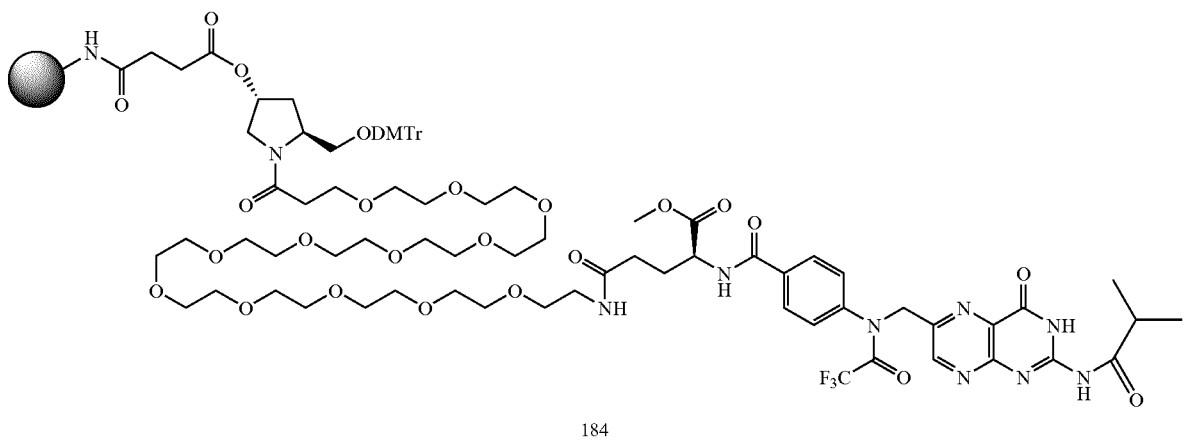

184

Synthesis of compound 183.

Using a similar procedure to that used for the synthesis of 112, coupling of the amine 182 (2.04 g, 2 mmol) with the acid 113 (1.24 g, 2 mmol) provided the coupled product 183 (1.46 g, 46%) as a foam. $^1$H NMR (DMSO-d$_6$, 400 MHz) δ=8.85 (s, 1H), 7.93 (d, J=6 Hz, 2H), 7.85 (m, H), 7.78 (d, J=76 Hz, 2H), 7.40-7.19 (m, 7H), 6.90-6.87 (m, 6H), 5.21 (s, 2H), 4.80-4.56 (m, 1H), 4.42-4.32 (m, 1H), 4.26-4.16 (m, 1H), 3.96-3.79 (m, 1H), 3.72 (s, 3H), 3.62-3.46 (m, 48H), 2.23-1.65 (m, 6H), 1.36-1.15 (m, 24H), 1.12 (d, J=7 Hz, 6H). MS. Molecular weight calculated for C$_{76}$H$_{106}$F$_3$N$_9$O$_{24}$, Cal. 1622.73, Found 1622.0 (M−H$^-$).

Example 10

Synthesis of a Folate Analogue Conjugate 199

In order to evaluate the targeting ability of the pyrrolo[2,3-d]pyrimidine-based folate analogue, the multitargeted antifolate, Alimta [(a) Bunn, P. A., Jr.; Smith, I. E., Guest Editors *Seminars Oncol.* 2002, 29 (6), Suppl. 18, 1-75. (b) Bertino, J.; Allegra, C.; Calvert, H., Guest Editors *Seminars Oncol.* 1999, 26 (2), Suppl. 6, 1-111. (c) Hanauske, A.-R.; Chen, V.; Paoletti, P.; Niyikiza, C. *The Oncologist* 2001, 6, 363-373. (d) Taylor, E. C.; Kuhnt, D.; Shih, C.; Rinzel S. M.; Grindey, G. B.; Barredo, J.; Jannatipour, M.; Moran, R. G. *J. Med. Chem.* 1992, 35, 4450-4454.] the following approach was undertaken.

The necessary building block for the conjugation to the pyrrolo[2,3-d]pyrimidine was synthesized as follows.

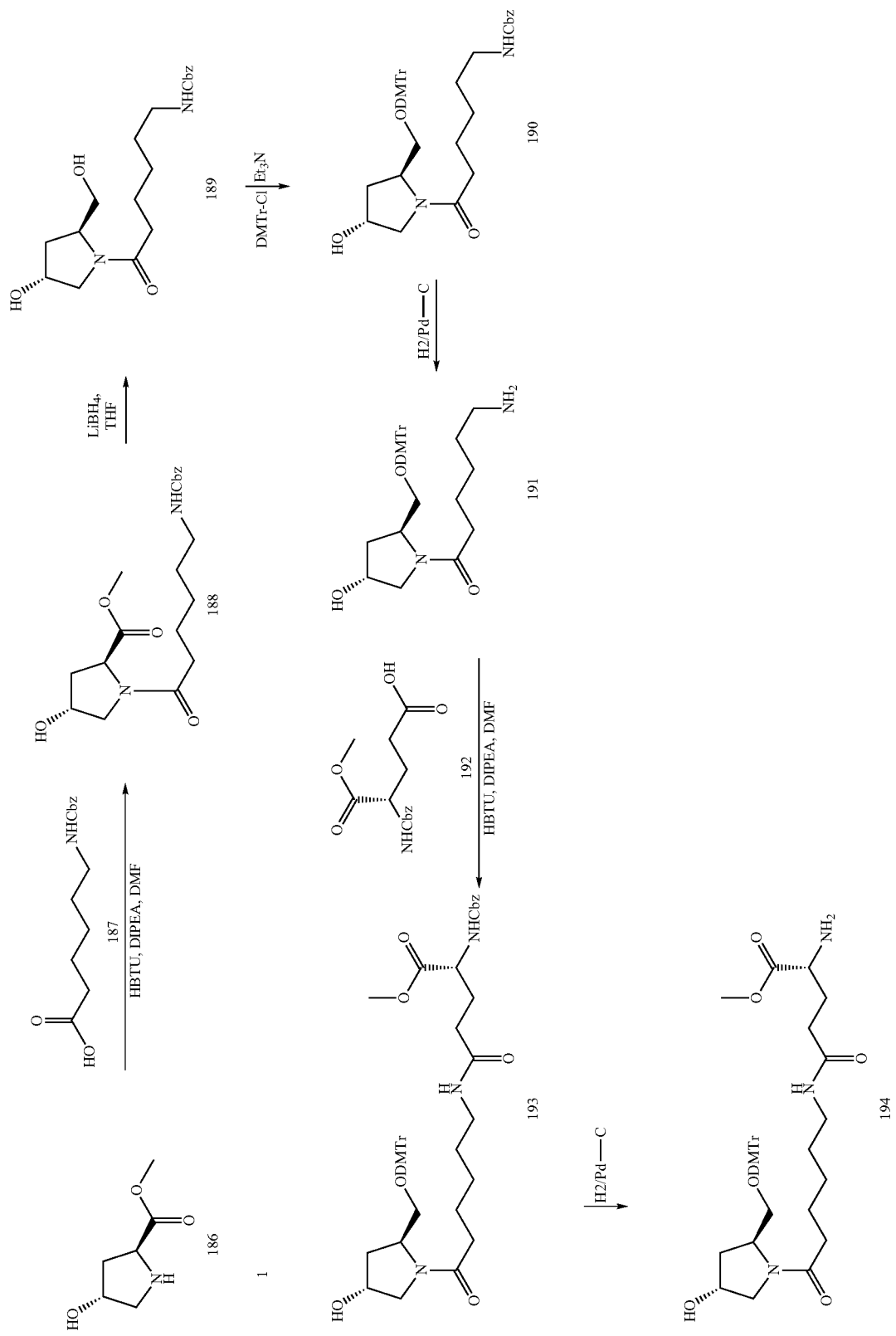

Synthesis of Compound 187

Caproic Acid (100 g, 0.7623 moles) was dissolved in 250 ml NaOH (2N) and cooled in a round bottom flask (2L). Benzyl Chloroformate (273 mL, 0.8004 moles) and 250 ml NaOH (2N) were added simultaneously at 0° C. with stirring. The progress of the reaction was monitored by TLC (about 2 hr). After completion of the reaction, the mixture was acidified with dilute HCl (10%) and extracted with EtOAc (750 mL×3). The organic layer was separated, washed well with water and dried over $Na_2SO_4$. Removal of the solvent under vacuum afforded crude 2 which was purified by column chromatography (ethyl acetate:hexane). Yield: 80 g (40%). $^1$H NMR (DMSO, 400 MHz)=7.33 (s, 5H), 5.09 (s, 2H), 4.88 (br, 1H), 3.18 (m, 2H), 2.23 (m, 2H), 1.62 (m, 2H), 1.50 (m, 2H), 1.34 (m, 2H).

Synthesis of Compound 188

Compound 187 (57.59 g, 0.2173 moles) was dissolved in 500 mL dry DCM and cooled to 0° C. in a round bottom flask (2L). This was followed with the addition of EDC.HCl (50 g, 0.2608 moles) and HOBt (33 g, 0.2173 moles). After 15 minutes of stirring at 0° C., 186 (39.46 g, 0.2173 moles) in 500 ml of dry DCM was added at 0° C. DIPEA was then added till the reaction mixture showed basic to pH. Reaction was stirred overnight at room temperature, quenched with water (500 mL) and extracted with DCM (500 mL×3). The organic layer was washed with sat. $NH_4Cl$ and dried over anhydrous $Na_2SO_4$ Removal of solvent afforded the crude compound which was purified by column chromatography (4% MeOH/DCM) using 100-200 mesh silica gel. Yield 50 g (87%). $^1$H NMR (DMSO, 400 MHz), δ=7.38 (m,5H), 7.25 (m,1H), 5.18 (s,1H), 4.99 (s,2H), 4.32-4.25 (m,2H), 3.67 (s,3H), 3.37 (m,1H), 2.97 (m,2H), 2.21 (m,2H), 2.08 (m,2H), 1.85 (m,1H), 1.46 (m,2H), 1.39 (m,2H), 1.25 (m,2H). MS $(MH)^+$: 393.35.

Synthesis of Compound 189

Compound 188 (135 g, 0.3440 moles) was dissolved in 800 mL THF in 3 L RBF. The reaction mixture was cooled to 0° C. and $LiBH_4$ (9.74 g, 0.4475 moles) in 200 mL of THF was added in portion over a span of half hour. Reaction was stirred for additional half an hr at this temperature and then at room temperature for 1.5 hr. The completion of the reaction was monitored by TLC. Reaction mixture was then cooled to 0° C. and diluted with 600 mL of water. 600 mL HCl (2N) was then added till pH was acidic. Excess of THF was removed under reduced pressure and residue was extracted with EtOAc (700 mL×3). Organic layer was separated, washed with brine and dried over $Na_2SO_4$. The solvent was stripped under reduced pressure to furnish 189 which was used directly for further reactions. Yield: 120 g (96%) $^1$H NMR (DMSO, 400 MHz), δ=7.35(m,5H), 7.31(m,1H), 4.98(s,2H), 4.27(m,1H), 4.02-3.95(m,1H), 3.47-3.22(m,6H) 2.98-2.93(m,2H), 2.15(m, 2H), 1.88(m,1H), 1.76(m,1H), 1.47(m,2H), 1.40(m,2H), 1.17 (m,2H). MS $(MH)^+$: 365.2.

Synthesis of Compound 190

To a stirring solution of 189 (2 g, 0.005494 mole), triethylamine (1.5 mL, 0.01153 moles) in DCM (10 mL), DMTr-Cl (2.047 gm, 0.006043 moles) in 10 mL DCM was added dropwise and the reaction mixture stirred overnight (14 h). Reaction mixture was concentrated and the product was purified by column chromatography (EtOAc/hexane) using 100-200 silica gel.

(Note: Few drops of TEA were added while loading the silica gel onto the column to reduce the acidic nature of silica gel). Yield 1.5 gm (41%). $^1$H NMR (DMSO, 400 MHz), δ=7.35-7.16 (m,15H), 6.87 (m,4H), 4.99 (s,2H), 4.38 (m,1H), 4.13 (m,1H), 3.72 (s,6H), 3.57 (m,1H), 3.15 (m,1H), 2.97(m, 3H), 2.19 (t,2H), 2.01 (m,1H), 1.83 (m,1H), 1.46-1.23 (m,7H). MS $(MH)^+$: 667.50.

Synthesis of Compound 191

The Cbz protected amine 190 (38 g, 0.05705 moles) was dissolved in 250 mL EtOAc/MeOH (3:1). After degassing, triethylamine (Catalytic) was added. This was followed by the addition of Pd/C (5.5 g, 15 Wt %, 10 Wt % Degussa type) and the reaction mixture was stirred for 3 hr under hydrogen atmosphere. After completion of reaction (monitored by TLC), the mixture was filtered through celite bed and washed with 300 mL (3:1 EtOAc:MeOH). Filtrate was concentrated to give crude 191 which was purified by column chromatography (5% MeOH/DCM) on 100-200 silica gel. (Note: Few drops of TEA were added while loading the silica gel onto the column to reduce the acidic nature of silica gel). Yield: 28 g (93%). $^1$H NMR (DMSO, 400 MHz), δ=7.32-7.17 (m, 9H), 6.85-6.89 (m, 4H), 4.38 (m, 1H), 4.45 (m,1H), 4.14 (m,1H), 3.76(s,6H), 3.58 (m,1H), 3.34-2.97 (m, 7H), 2.22-2.18 (m,2H), 2.02-1.98 (m,2H), 1.83 (m,1H), 1.48-1.14 (m, 4H). MS $(MH)^+$: 533.37.

Synthesis of Compound 193

To a stirring solution of 192 (1 g, 0.003386, moles) in 7 mL DCM, EDC.HCl (0.778 g, 0.004763 moles) was added at 0° C. under nitrogen atmosphere. After stirring for 5 minutes HOBt (0.518 g, 0.03385 moles) was added and the reaction mixture was stirred additionally for 15 mins. 191 (1.8 g, 0.003386 moles) in 7 mL of DCM was then added to reaction mixture at the same temperature and stirring was continued. This was followed by DIPEA till reaction mixture showed basic on pH paper (~0.7 mL). Stirring was continued overnight at room temperature. After completion of reaction, it was quenched with ice, extracted with DCM (15 mL×3) and washed with 20 mL $NH_4Cl$ solution. The organic layer was separated, dried over $Na_2SO_4$ and concentrated under reduced pressure. Purification by column chromatography (5% MeOH-DCM) using 100-200 silica gel furnished pure 193 in respectable yield. Yield: 2.3 g (85%). $^1$H NMR (DMSO, 400 MHz), δ=7.78 (m,2H), 7.36-7.16 (m, 14H), 6.85 (m,4H), 4.99 (m,2H), 4.37 (m,1H), 4.08 (m,1H), 3.72 (s,6H), 3.62-3.55 (m,4H), 3.14 (m,1H), 2.98 (m,3H), 2.50 (m,2H) 2.20-1.92 (m,8H), 1.45-1.23 (m,7H). MS $(MH)^+$: 810.49.

Synthesis of Compound 194

The Cbz protected amine 193 (63 mg, 0.077 mmoles) was dissolved in 4 mL, EtOAc:MeOH (3:1). After degassing, triethylamine (catalytic) was added. This was followed by the addition of Pd/C (9.4 mg, 15 Wt %, 10 Wt % Degussa type) and the reaction was stirred for 3 hr under hydrogen atmosphere. The progress of the reaction was monitored by TLC. After completion (5 hrs) the reaction was filtered through celite bed and washed with 15 mL (3:1 EtOAc:MeOH). The filtrate was concentrated to afford the crude product which was column purified (5% MeOH-DCM) on 100-200 silica gel. Yield: 40 mg (78%) $^1$H NMR (DMSO, 400 MHz), δ=7.77 (m,1H), 7.30 (m,4H), 7.21-7.16 (m,5H), 6.88(m,4H), 4.38 (m,1H), 4.25(m,1H), 3.72(s,6H), 3.60(m,4H), 3.33-3.16(m, 2H), 3.15(m, 1H), 2.98(m, 3H), 2.2(t, 2H), 2.12(t, 2H), 2.0(m, 2H) 1.83(m,2H), 1.6 (m,1H), 1.46(m,2H), 1.37(m,2H), 1.25 (m,4H). MS (MH)$^+$: 676.41.
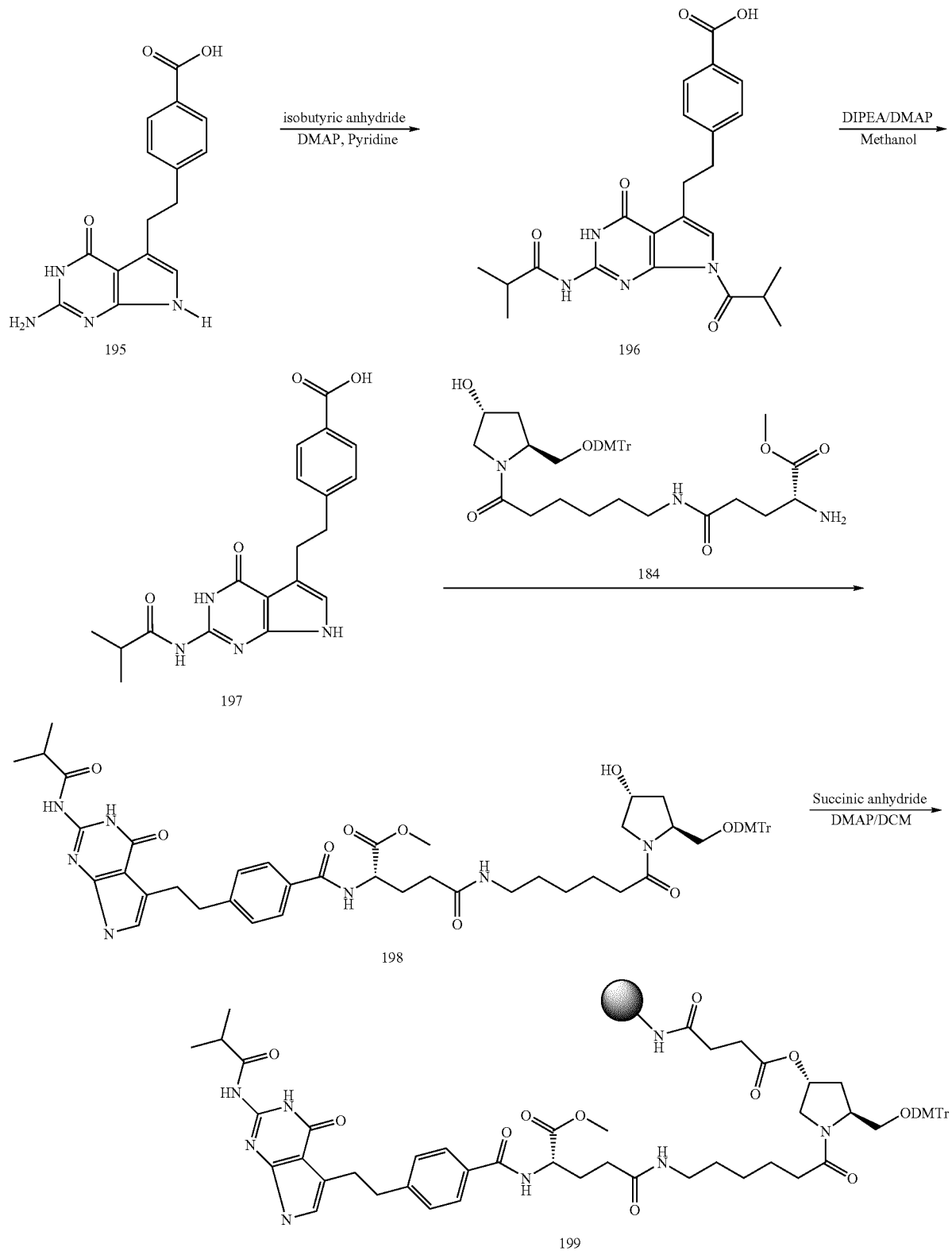

Synthesis of Compound 196

To suspension of Compound 195 (0.2 g, 0.000671 moles) in anhydrous pyridine (5 mL) was added DMAP (0.13 g, 0.0010 moles), followed by isobuytric anhydride (0.6 mL, 0.0040 moles) at room temperature. The resulting mixture was then refluxed for 4 hr. After completion of reaction (by TLC), the mixture was poured onto ice-HCl/hexane and stirred well. The resulting solid was filtered, washed with hexane and used directly for further reactions. Yield (0.1 g, 34%). $^1$H NMR (DMSO, 400 MHz): δ=12.08 (s,1H), 11.48 (s,1H), 7.85 (d,2H), 7.35 (d,2H), 7.22 (s,1H), 4.33 (m,1H), 2.98 (m,2H), 2.96 (m,2H), 2.81 (m,1H), 1.19 (d,6H), 1.14 (d,6H). $^{13}$C NMR (DMSO): 179.85, 175.21, 167.00, 156.64, 147.81, 147.34, 146.73, 129.08, 128.32, 128.14, 121.27, 116.00, 106.07, 35.02, 34.51, 33.37, 26.90, 18.72, 18.64. MS (MH)$^+$: 439.40.

Synthesis of Compound 197

To a stirring solution of 196 (0.4 g, 0.00091 moles) in 5 ml MeOH, DIPEA (0.036 mL, 0.00278 moles), was added at room temperature. (Note: After addition of DIPEA reaction mixture becomes clear). After 10 minutes DMAP (catalytic) was added to the mixture. The completion of reaction was monitored by TLC (& LCMS). MeOH was then concentrated and the residue was diluted with water (5 mL). Acidification with dilute HCl was followed by extraction with ethyl acetate. Organic layer was separated, dried over Na$_2$SO$_4$ and concentrated. The crude mixture was pure enough and was used directly for further reactions. Yield: 260 mg (54%). $^1$H NMR (DMSO, 400 MHz), δ=12.77 (bs,1H), 11.68 (s,1H), 11.34 (s,2H), 7.84 (d,2H), 7.32 (d,2H), 6.64 (s,1H), 3.01 (m,2H), 2.94 (m,2H), 2.74 (m,1H), 1.09 (d,6H). MS (MH)$^+$: 369.10.

Synthesis of Compound 198

To a solution of 197 (4 g, 0.01086 moles) in 15 mL dry DMF, HBTU (4.11 g, 0.01086 moles) and DIPEA (3.87 mL, 0.02173 moles) were added at room temperature under stirring. After half an hour, 194 (7.33 g, 0.01086 moles) in dry DMF (10 mL) was added to the solution and stirring was continued. The progress of the reaction was monitored by TLC (4 hr). After completion, the reaction mixture was poured into crushed ice and was extracted with EtOAc (100 mL×3). Organic layer was separated and dried over Na$_2$SO$_4$. Removal of solvent under reduced pressured afforded 198, which was purified by column chromatography (3% MeOH/DCM). Yield: 3.6 g (33%). $^1$H NMR (DMSO, 400 MHz), δ=11.68 (s, 1H), 11.34 (bs, 2H), 8.73 (bs, 1H), 7.83-7.77 (m, 3H), 7.29-7.16 (m, 11H), 6.87 (m, 4H), 6.63 (s, 1H), 4.99 (m, 1H), 4.37 (m, 2H), 4.12 (bs, 1H), 3.71 (bs, 6H), 3.62 (broad, 3H), 3.57 (m, 1H), 3.50 (m, 2H), 3.15 (m, 3H), 2.99 (m, 8H), 2.74 (m, 2H), 2.18 (m, 4H), 1.44-1.22 (m, 6H), 1.11 (d, 6H) 1.09 (m, 2H), 1.02 (m, 1H). MS (MH)$^+$: 1026.60

The hydroxyl compound 198 on treatment with succinic anhydride followed by treatment with polystyrene linked resin provided the folate coupled solid support 199 in 72 μM/g loading.

Example 11

Folate Building Blocks for Click-Chemistry

In order to synthesize azido functional group containing folate conjugates the following strategy was used. The azido amine tether 204 was synthesized starting from the commercially available diamine 201 as shown below.

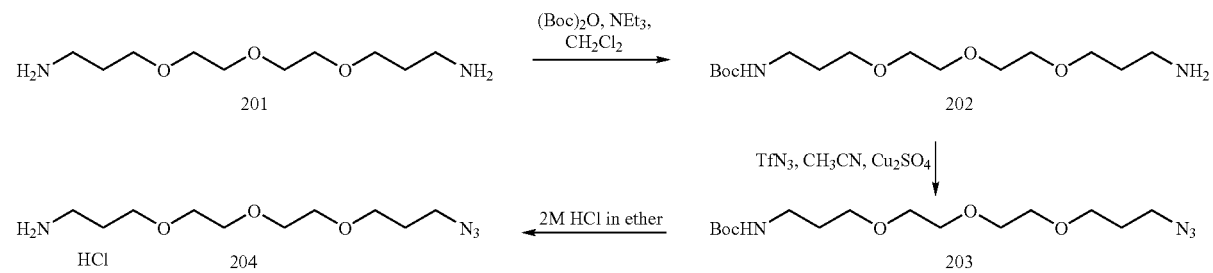

Synthesis of Amine 202

To a solution of the diamine (22 g, 0.1 mol) in dichloromethane (300 mL), triethylamine (15 mL) was added and the mixture was cooled in ice bath. To this cold solution a solution of (Boc)$_2$O in CH$_2$Cl$_2$ (100 mL) was added dropwise and the mixture was stirred overnight. The reaction mixture was washed with satd. NaHCO$_3$ (200 mL), water (300 mL), brine (300 mL) and dried (Na$_2$SO$_4$). Concentration of this organic layer followed by column purification provided the pure mono Boc amine 202 in 55% yield. MS: MW Calc. for C$_{15}$H$_{32}$N$_2$O$_5$: 320.42; Found 321.41 (MH$^+$).

Synthesis of Azide 203:

The triflic azide stock solution was prepared as reported in *Tetrahedron Letters* 47 (2006) 2382-2385. The amine (0.96 g, 3 mmol), sodium bicarbonate (0.85 mg, 10 mmol) and copper (II) sulfate pentahydrate (22 mg, 0.1 mmol) were dissolved in water (3 mL). Triflic azide stock solution (5 mL) was added, followed by the addition of methanol (20 mL) to yield a homogeneous system. The blue mixture was stirred for 30 min after which the TLC and MS showed the complete disappearance of starting amine. The reaction mixture was concentrated in a rotary evaporator and the residue was purified by chromatography on silica gel (eluent: dichloromethane-methanol) to obtain the pure azide 203 (1 g, 96%) as an oil. MS: MW Calc. for C$_{15}$H$_{30}$N$_4$O$_5$: 346.42; Found 347.41 (MH$^+$). $^1$HNMR (CDCl$_3$, 400 MHz) δ=4.68 (bs, 1H), 3.40-3.30 (m, 12H), 3.16 (t, J=6.4 Hz, 2H), 3.00-2.95 (m, 2H), 1.68-1.54 (m, 4H), 1.04 (s, 9H).

Synthesis of 204:

The azide 203 (1 g, 2.88 mmol) was dissolved in ethanol (10 mL) and to this a 2M solution of HCl in ether was added and the mixture was stirred at room temperature overnight. The MS showed the absence of starting material. The reaction mixture was concentrated and the thus obtained oil was used as such for the next reaction without further purification. MS: MW Calc. for $C_{10}H_{23}ClN_4O_3$: 246.17; Found 247.17 (MH$^+$). $^1$HNMR (DMSO-d$_6$ 400 MHz) δ=8.96 (bs, 1H), 7.92 (bs, 2H), 3.52-3.40 (m, 12H), 3.37 (t, J=6.8 Hz, 2H), 2.85-2.77 (m, 2H), 1.81-1.70 (m, 4H).

Synthesis of 205:

of water) was added and the solution was stirred at room temperature for 4 h after which the MS showed the complete disappearance of SM. The reaction mixture was acidified to pH 5 using acetic acid and the RM was diluted with ethyl acetate (100 mL). The precipitated product was filtered off and washed with water and ethyl acetate and dried under vacuo at 40° C. overnight to get the pure azide 206 (0.455 g 55%) as an orange solid. $^1$H NMR (DMSO-d$_6$, 400 MHz) δ=8.59 (s, 1H), 7.85 (bs, 1H), 7.72 (bs, 1H), 7.56 (d, J=8.4 Hz, 2H), 6.88 (bs, 1H), 6.65 (d, J=8.4 Hz, 2H), 4.45 (s, 2H), 4.00-4.02 (m, 1H), 3.50-3.33 (m, 14H), 3.04-3.00 (m, 2H),

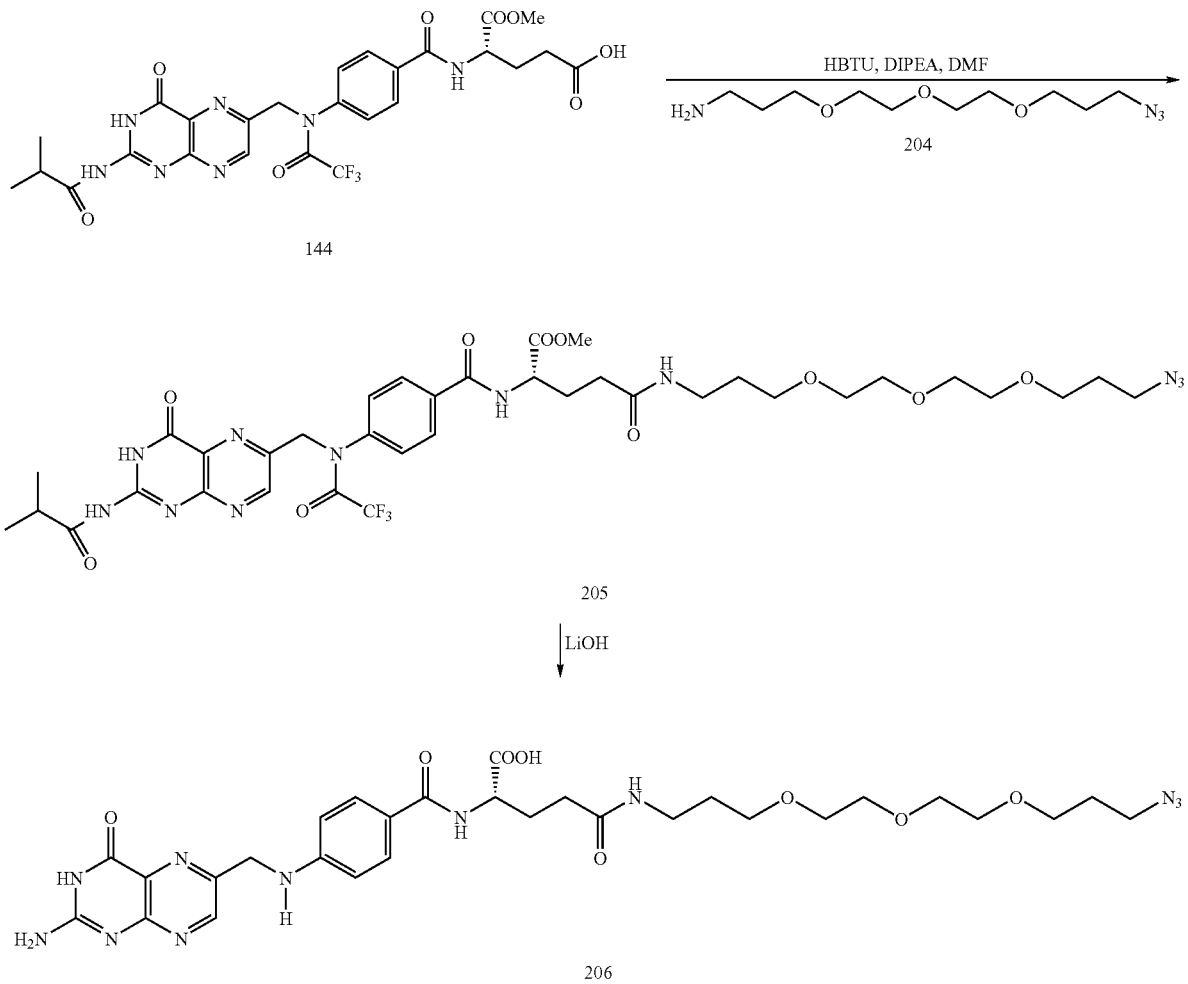

Coupling of the amine 204 (0.6 g) with the acid 144 (1.2 g) using a similar procedure to that used for the synthesis of 146 provided the coupled azide 205 (1.68 g, 93%) as a light yellow foam. $^1$HNMR (DMSO-d$_6$, 400 MHz) δ=12.34 (s, 1H), 11.95 (s, 1H), 8.89 (s, 2H), 7.92 (d, J=8.4 Hz, 2H), 7.81 (m, 1H), 7.70 (d, J=8.4 Hz, 2H), 5.22 (s, 2H), 4.40-4.34 (m, 1H), 3.62 (s, 3H), 3.50-3.31 (m, 15H), 3.09-3.00 (m, 2H), 2.80-2.72 (m, 1H), 2.20 (t, J=7.4 Hz, 2H) 2.10-1.89 (m, 2H), 1.76-1.54 (m, 4H), 1.12 (d, J=6.8 Hz, 6H). MS. Molecular weight calculated for $C_{36}H_{46}F_3N_{11}O_{10}$, Cal. 849.81, Found 850.2 (MH$^+$).

Synthesis of 206:

The azide 205 (1 g) was dissolved in THF (20 mL) and to it an aqueous solution of lithium hydroxide (100 mg in 2 mL 2.07-1.83 (m, 4H), 1.76-1.54 (m, 4H). MS. Molecular weight calculated for $C_{29}H_{39}N_{11}O_8$, Cal. 669.69, Found 668.2 (M−H$^-$).

In another embodiment, the alkyne containing folic acid is synthesized as follows. In this case the protected pteroic acid 144 was coupled with the protected lysine 207 to get the coupled product 208 which on Cbz deprotection provided the amine 209. Coupling of the amine 209 with the acid 210 provided the coupled product 211 which after purification and deprotection provided the product 212 as described below.

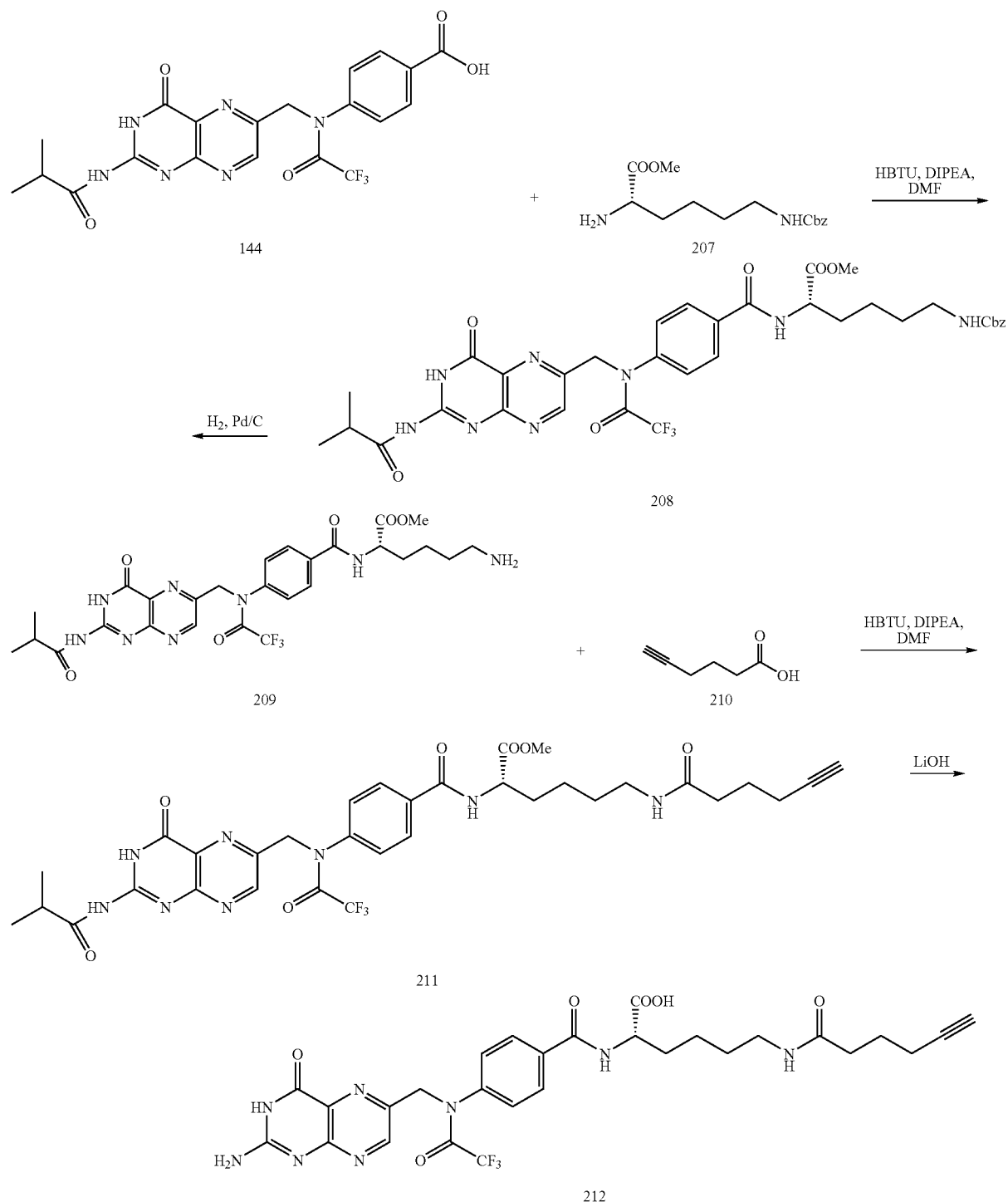

Synthesis of 208: Using a similar procedure to that used for the synthesis of 205, coupling of the acid 144 with the lysine derivative 207 provided the coupling product 208 as a white solid in 95% yield.

Synthesis of 209: The compound 208 on hydrogenation with Pd/C provided the deprotected amine 209 as a yellow solid.

Synthesis of 210: Coupling of the amine 209 with the acid 210 using a procedure to that used for the synthesis of 205 provided the couple product 210 in high yields.

Synthesis of 212: The deprotection of the protecting groups is achieved using a similar procedure as described for the synthesis of 206 to isolate the fully deprotected alkyne 212.

The synthesis of the building block 213 is then carried out as shown below.

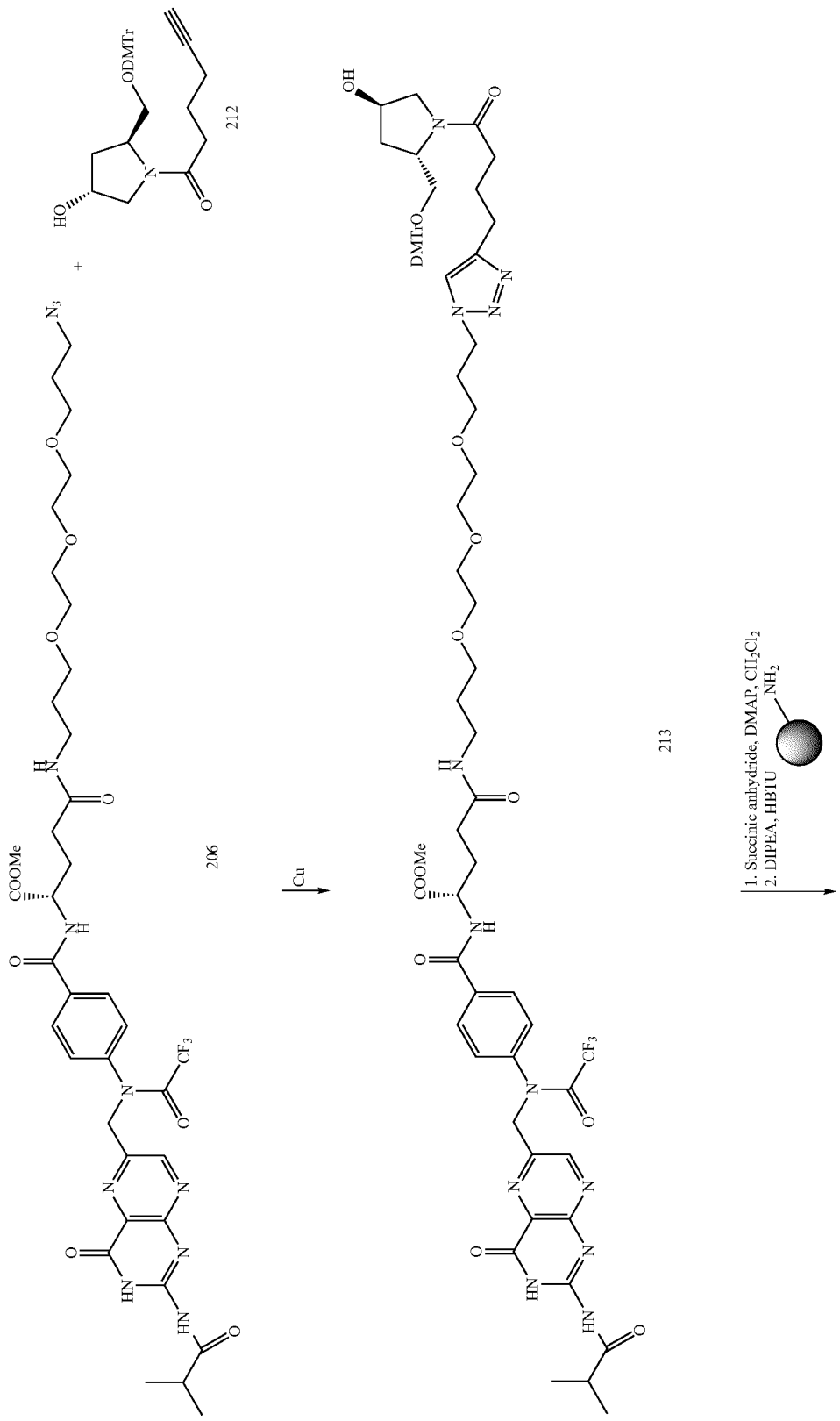

-continued
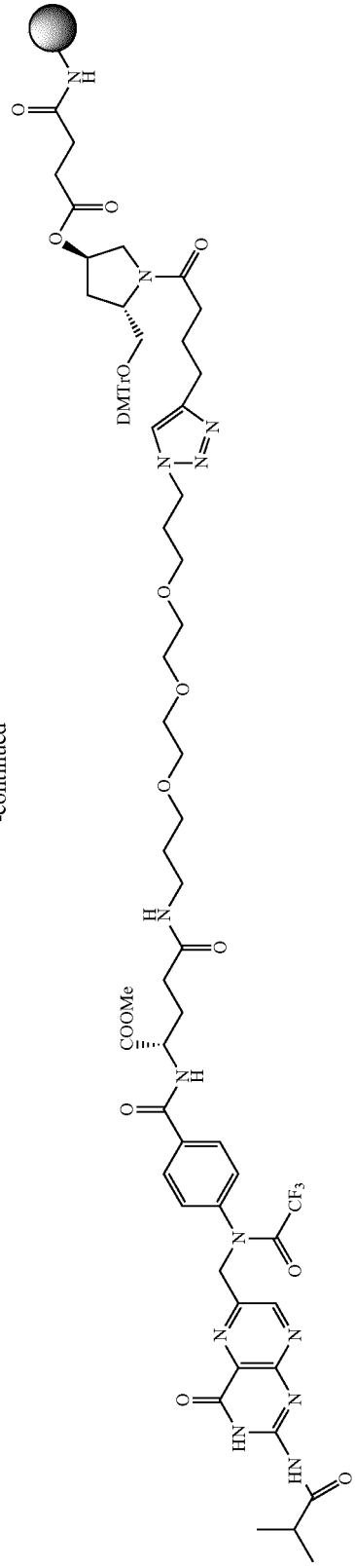
214

The building block 213 is then converted to solid-support 214 or phosphoramidite 215.

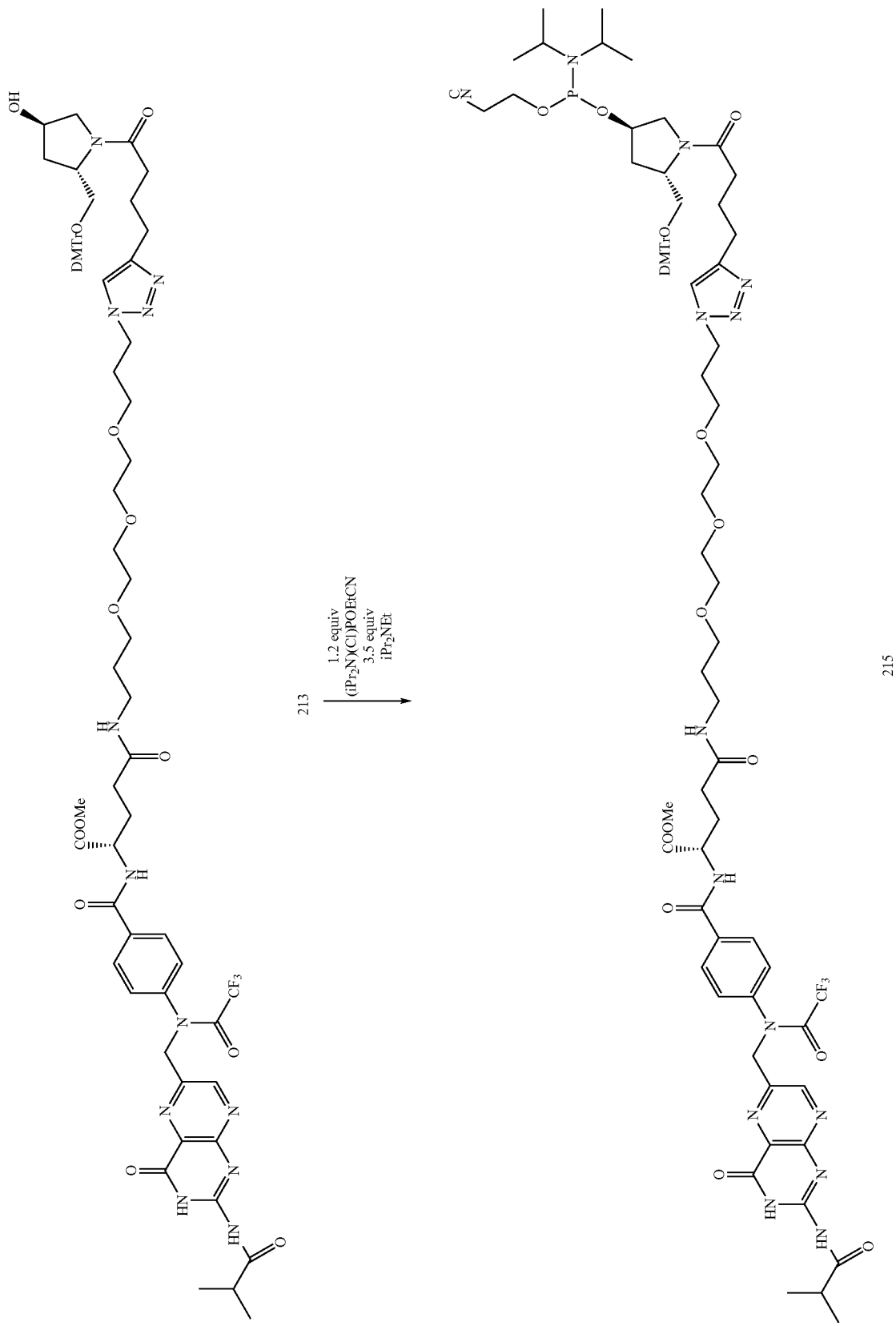

Example 12

Synthesis of Folate Conjugate 216

In order to conjugate folic acid to the 5' end of the oligo, post synthetically, the following route was developed. Treatment of folic acid 215 with DCC followed by N-hydroxysuccinimide provided the activated ester 216 in 80% yield. In a typical procedure, folic acid (5 g, 11.33 mmol) was dissolved in anhydrous DMSO (100 mL) and to this solution was added, triethyamine (2.5 mL), DCC (4.7 g, 22.6 mmol) and N-hydroxysuccinimide (2.6 g, 22.6 mmol) and the solution was stirred at room temperature in dark for 18 h. The reaction mixture was filtered and to the filtrate EtOAc (1 L) was added and the precipitated product was filtered, washed with ethyl acetate (500 mL), ether (200 mL) and dried under vacuum to isolate the product as a yellow powder. The purity of the product was found to be 83% by HPLC. This product was used as such for the coupling steps without further purification.

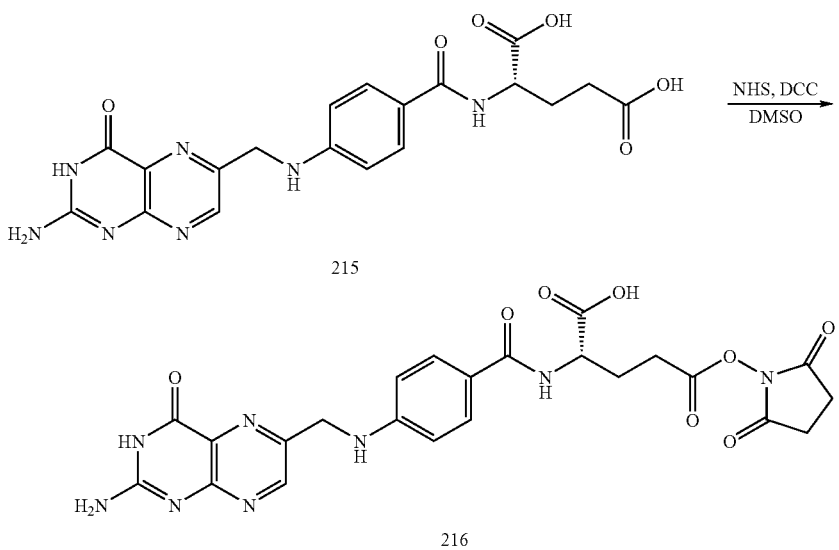

In another embodiment a cleavable acetal linkage was used in order to facilitate the release of siRNA from the targeting folate as follows.

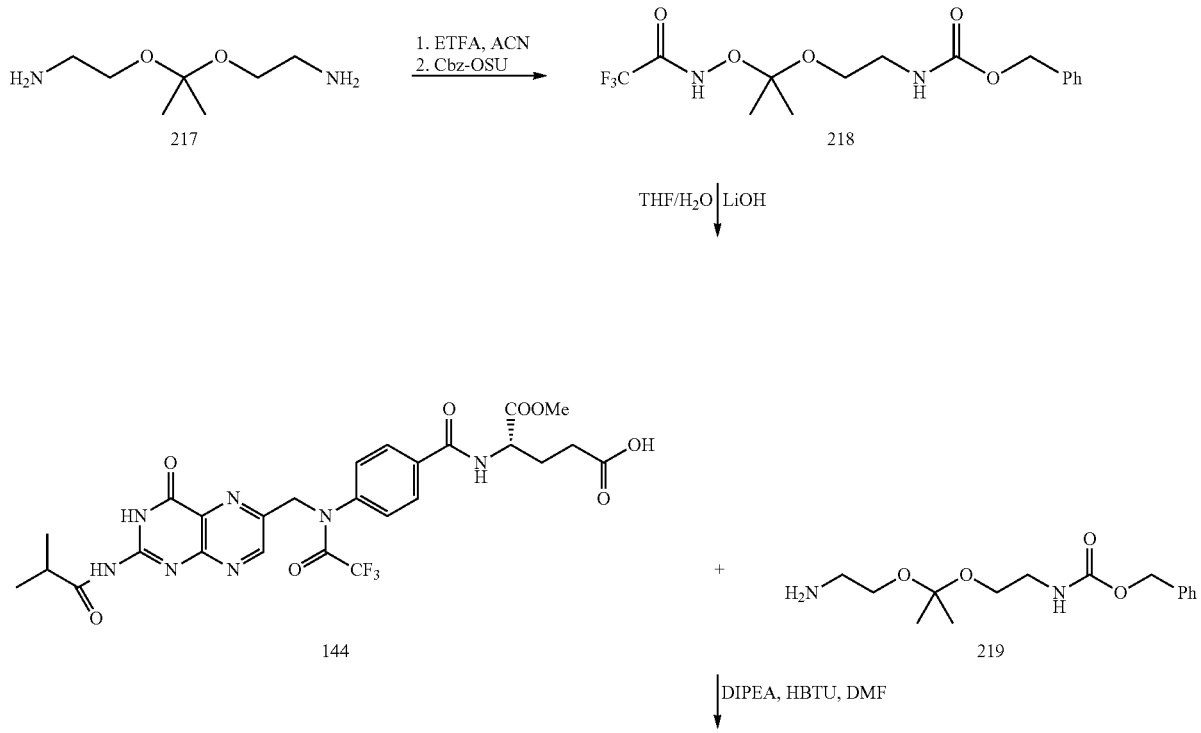

173 174
-continued
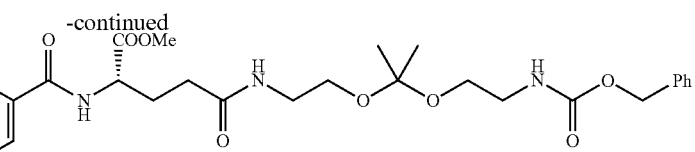
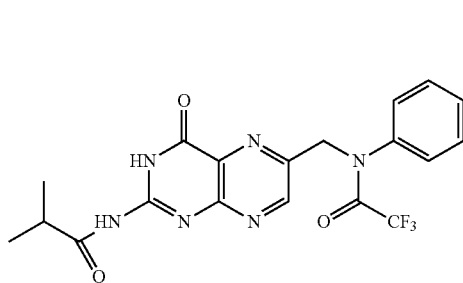
220
↓ Pd/C
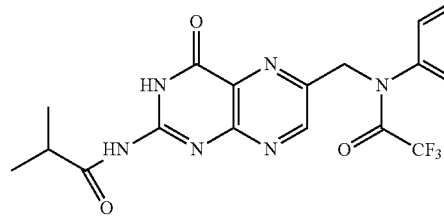
221
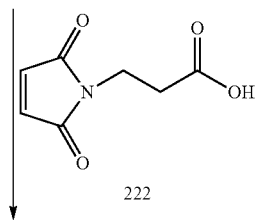
222
↓
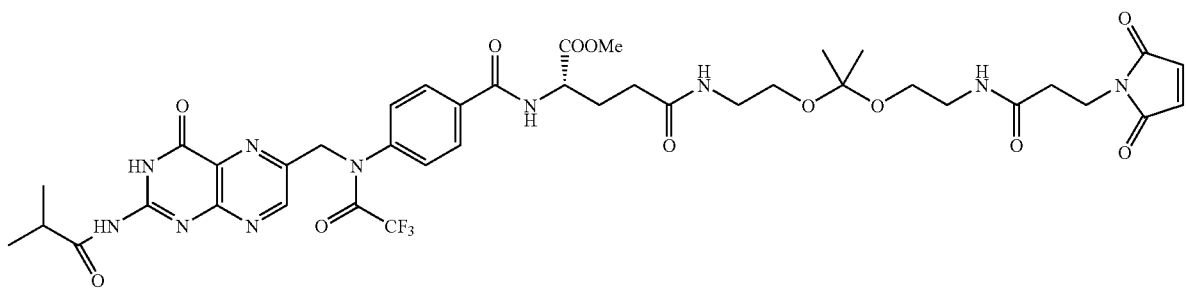
223
↓ LiOH
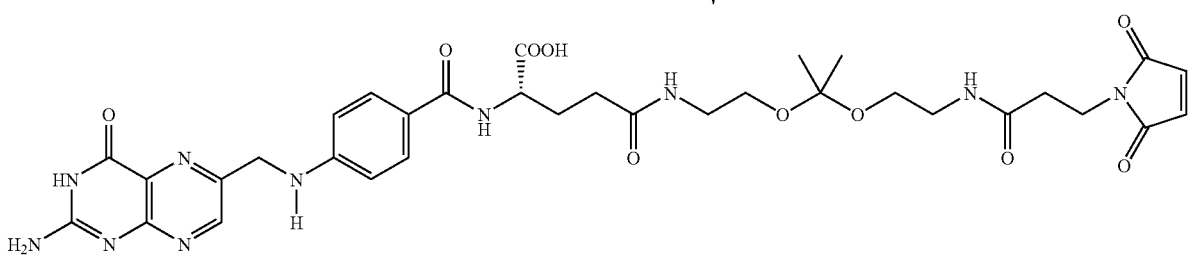
224

The ketal 217 was synthesized using a reported procedure (Paramonov, S. E.; Bachelder, E. M.; Beaudette, T. T.; Standley, S. M.; Lee, C. C.; Dashe, J.; Frechet, Jean M. J. Fully Acid-Degradable Biocompatible Polyacetal Microparticles for Drug Delivery. *Bioconjugate Chemistry* (2008), 19 (4), 911-919). The transient protection of the ketal was carried out in two steps in one pot first by treating the diamine with one equivalent of ethyltrifluoroacetate followed by one equivalent of Cbz-OSu to provide the di protected derivative 218 in 80% yield after column purification. The protected amine 218 on treatment with aqueous LiOH provided the amine 219 in quantitative yield. Coupling of this amine 219 (0.5 g) with the protected folic acid 144 (1 g) provided the coupled product 220 (1.1 g) which on hydrogenation provided the amine 221 in quantitative yield. Coupling of amine 221 was carried out with the maleimidopropionic acid 222 to give the coupled product 223 in good yields. The final deprotection of all the protecting group in 223 is carried out using ice-cold aqueous LiOH in THF to afford the precursor 224 as an orange solid.

Example 13

Synthesis of Conjugated siRNAs

Figure 2:
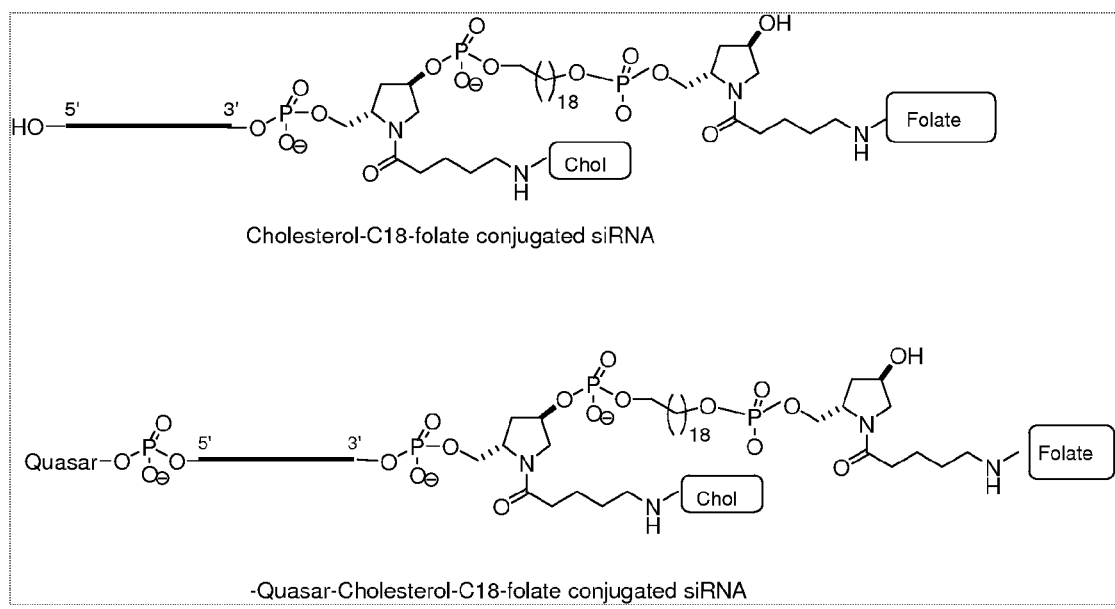
FIG. 2. Graphical representation of sequences AL-3609 and AL-3610.
Figure 3:
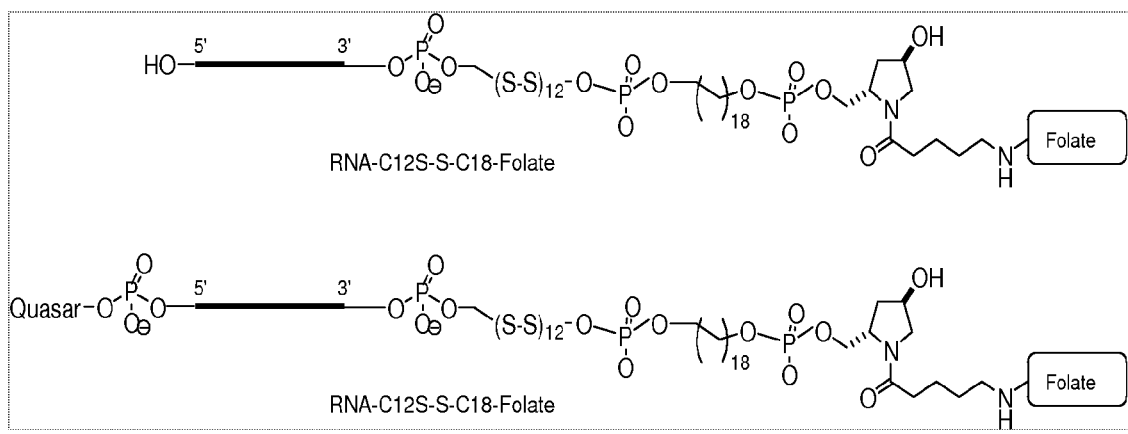
FIG. 3. Graphical representation of sequences AL-3664, AL-3665, AL-3670 and AL-3671.
Figure 4:
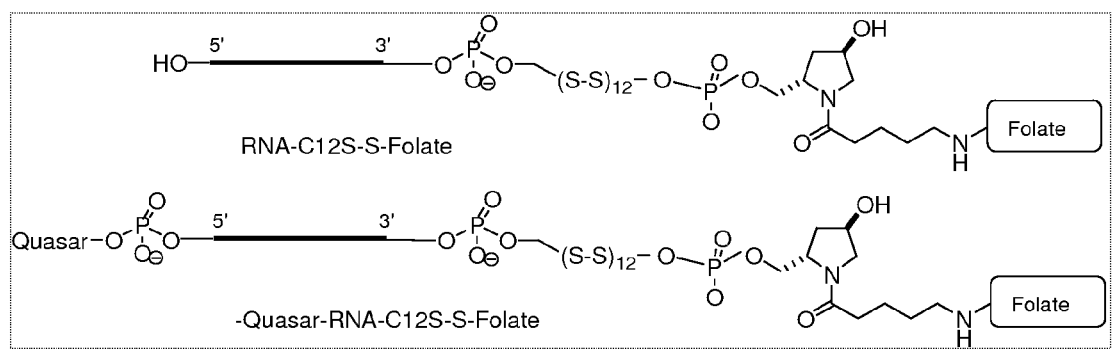
FIG. 4. Graphical representation of sequences AL-3639, AL-3640, AL-3668 and AL-3669.
Figure 5:
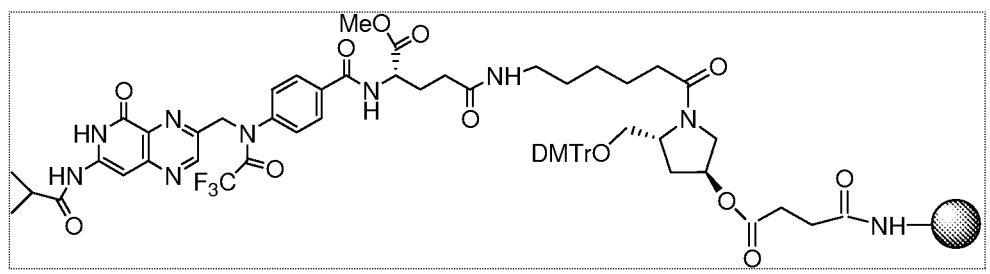
FIG. 5. Folate conjugate monomer (compound 108) used in the synthesis of oligonucleotides.
Figure 6:
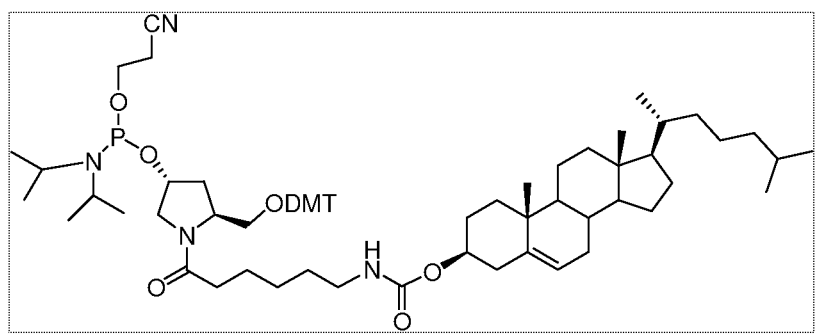
FIG. 6. Cholesterol conjugate monomer used in the synthesis of oligonucleotides.
Figure 7:
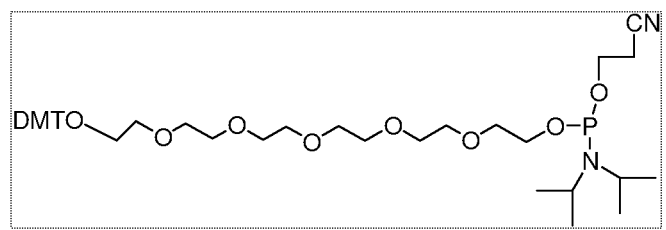
FIG. 7. C18 Spacer monomer used in the synthesis of oligonucleotides.
Figure 8:
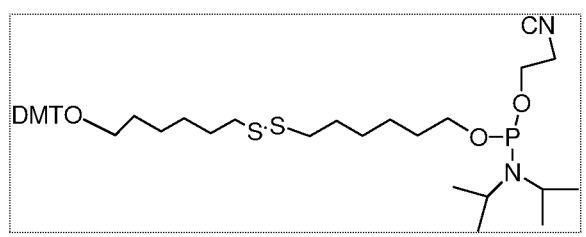
FIG. 8. 12 Disulfide linker monomer used in the synthesis of oligonucleotides.
Figure 9:
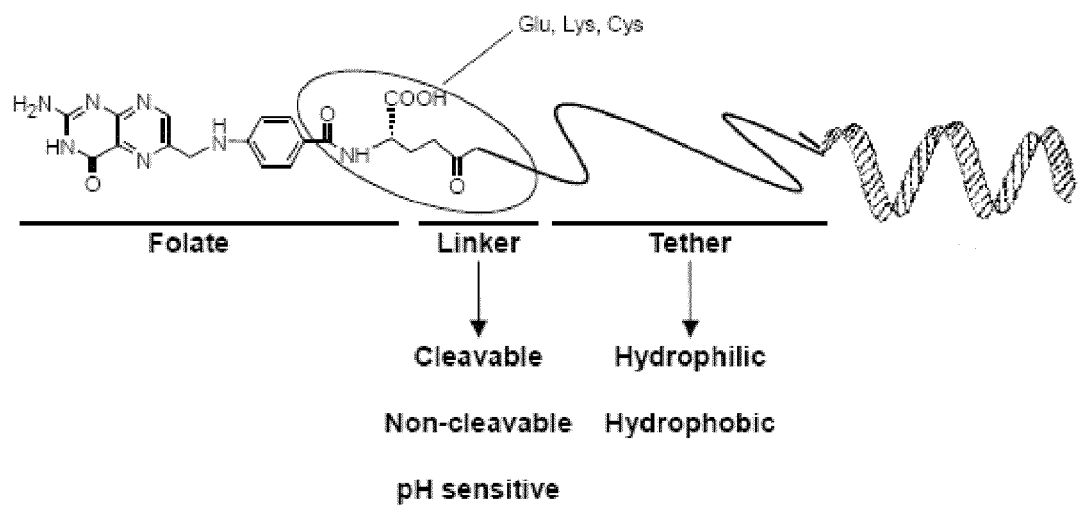
FIG. 9. A schematic view of oligonucleotide conjugate design considerations.

Synthesis of Folate Conjugated siRNA:

The 3'-folate and C6-S—S—C6-folate siRNA conjugates with and without fluorophore label and its controls and corresponding antisense strands used in this study are shown in Tables 4-7. These were individually synthesized using commercially available 5'-O-(4,4'-dimethoxytrityl)-2'-O-t-butyldimethylsilyl-3'-O-(2-cyanoethyl-N,N-diisopropyl) RNA phosphoramidite monomers of 6-N-benzoyladenosine ($A^{Bz}$), 4-N-acetylcytidine ($C^{Ac}$), 2-N-isobutyrylguanosine ($G^{iBu}$), and uridine (U), according to standard solid phase oligonucleotide synthesis protocols as previously described (1). The folate conjugated strands were synthesized using folate containing solid support. (C, FIG. 2). The introduction of cholesterol unit in the sequence was performed from a hydroxyprolinol-cholesterol phosphoramidite. Cholesterol was tethered to trans-4-hydroxyprolinol via a 6-aminohexanoate linkage to obtain a hydroxyprolinol-cholesterol moiety. 5'-end Cy-3 and Cy-5.5 (fluorophore) labeled siRNAs were synthesized from the corresponding Quasar-570 (Cy-3) phosphoramidite phosphoramidite purchased from Biosearch Technologies). The disulfide linker was introduced to the siRNA using C6-S—S—C6 phosphoramidite as purchased from Glen Res. VA. An extended 15 min coupling of 0.1M solution of phosphoramidite in anhydrous $CH_3CN$ in the presence of 5-(ethylthio)-1H-tetrazole activator to a solid bound oligonucleotide. Oxidation of the internucleotide phosphite to the phosphate was carried out using tert-butyl hydroperoxide/acetonitrile/water (10:87:3) with 10 min oxidation wait time afforded folate conjugated oligonucleotide.

Deprotection-I

After completeness of oligonucleotide synthesis, a solid support was treated with 1 M aq. piperidine for 24 h at room temperature. The solid support was washed with another portion of deprotecting reagent and combined solutions were evaporated under reduced pressure. Added a mixture of ethanolic ammonia [ammonia (28-30%): ethanol (3:1) 1.0 mL] for 8 h at 55° C. (2). The vial was cooled briefly on ice and then the ethanolic ammonia mixture was transferred to a new microfuge tube. The CPG was washed with portions of deionized water (2×0.1 mL). The combined filtrate was then put in dry ice for 10 min dried in a speed vac.

Deprotection-II (Removal of 2'-O-TBDMS Group)

The white residue obtained was resuspended in a mixture of triethylamine, triethylamine trihydrofluoride (TEA.3HF ca, 24% HF) and Dimethylsulfoxide (DMSO) (1:2:6) (3.0 mL) and heated at 65° C. for 2 h to remove the tert-butyldimethylsilyl (TBDMS) groups at the 2'-position.

Analysis of Folate Conjugated siRNA:

The Folate conjugated sequences were analyzed by high-performance liquid chromatography (HPLC) on Phenomenox C6 phenyl column. The buffer A was 50 mM TEAA, 10% Acetonitrile and Buffer B was 50 mM Sodium Acetate, 70% Acetonitrile at 65° C. in gradient of 25-80% B in 35 min HPLC Purification:

The Folate conjugated, Cy-3, Cy 5.5 and Cy-3-Folate hybrid sequences were purified by high-performance liquid chromatography (HPLC) on an in-house packed RPC-Source15 reverse-phase column. The buffers were 20 mM NaOAc in 10% $CH_3CN$ (buffer A) and 20 mM NaOAc in 70% $CH_3CN$ (buffer B). Fractions containing full-length oligonucleotides were pooled, desalted and lyophilized. Analytical HPLC, CGE and ES LC-MS established the integrity of the compounds. The unconjugated oligonucleotides were purified by anion-exchange HPLC on a TSK gel column packed in house. The buffers were 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides were pooled, desalted, and lyophilized. For duplex generation, equimolar amounts of sense and antisense strand were heated in 1×PBS at 95° C. for 5 min and slowly cooled to room temperature.

Duplex Preparation

For the preparation of duplexes, equimolar amounts of sense and antisense strand were heated in 1×PBS at 95° C. for 5 min and slowly cooled to room temperature. Integrity of the duplex was confirmed by HPLC analysis.

Synthesized oligonucleotides and duplexes are shown in Table 4-7.

TABLE 4

Oligonucleotides synthesized and evaluated

| Target | Duplex ID | SEQ ID No | S/AS | Sequence 5'-3' |
|---|---|---|---|---|
| Luc | AD-3618 | 30 | A-30678 | 5' CcAcAuGAAGcAGcACGACuUQ51sL37 |
|  |  | 31 | A-4381 | 5' AAGUCGUGCUGCUUCAUGUGgsusC |
| Luc | AD-3614 | 32 | A-30677 | 5' AccGAAAGGucuuAccGGAdTdTQ51sL37 |
|  |  | 33 | A-30674 | 5' UCCGGuAAGACCUUUCGGUdTdTsL10 |
| Luc | AD-3514 | 34 | A-30659 | 5' Q38cuuacgcugaguacuucgadTdTL37 |
|  |  | 35 | A-30660 | 5' ucgaaguacucagcguaagdTdTL8 3' |

TABLE 4-continued

Oligonucleotides synthesized and evaluated

| Target | Duplex ID | SEQ ID No | S/AS | Sequence 5'-3' |
|---|---|---|---|---|
| Luc | AD-3515 | 36 | A-30659 | 5' Q38cuuacgcugaguacuucgadTdTL37 |
| | | 37 | A-30661 | 5' ucgaaguacucagcguaagdTdT-L10 |
| GFP | AD-3615 | 38 | A-30678 | 5' CcAcAuGAAGcAGcACGACuUQ51sL37 |
| | | 39 | A-3389 | 5' AAGUCGUGCUGCUUCAUGUGgusCs-L10 |
| GFP | AD-3616 | 40 | A-30676 | 5' cuGGcuGAAuuucAGAGcAdTdTQ51sL37 |
| | | 41 | A-22826 | 5' UGCUCUGAAAUUcAGCcAGdTsdT |
| Luc | AD-3617 | 42 | A-30677 | 5' AccGAAAGGucuuAccGGAdTdTQ51sL37 |
| | | 43 | A-24775 | 5' UCCGGuAAGACCUUUCGGUdTsdT |
| CD45 | AD-3613 | 44 | A-30676 | 5' cuGGcuGAAuuucAGAGcAdTdTQ51sL37 |
| | | 45 | A-30673 | 5' UGCUCUGAAAUUcAGCcAGdTdTsL10 |
| CD45 | AD-3637 | 46 | A-22825 | 5'-cuGGcuGAAuuucAGAGcAdTsdT |
| | | 47 | A-30687 | 5' Q39UGCUCUGAAAUUcAGCcAGdTsdT |
| CD45 | AD-3638 | 48 | A-22825 | 5'-cuGGcuGAAuuucAGAGcAdTsdT |
| | | 49 | A-30695 | 5' Q39UGCUCUGAAAUUcAGCcAGdTdTsL10 |
| CD45 | AD-3639 | 50 | A-30676 | 5' cuGGcuGAAuuucAGAGcAdTdTQ51sL37 |
| | | 51 | A-30852 | 5' Q78UGCUCUGAAAUUcAGCcAGdTsdT |
| CD45 | AD-3633 | 52 | A-30676 | cuGGcuGAAuuucAGAGcAdTdTQ51sL37 |
| | | 53 | A-30821 | 5' UGCUCUGAAAUUcAGCcAGdTdTL10 |
| CD45 | AD-3634 | 54 | A-22825 | 5'-cuGGcuGAAuuucAGAGcAdTsdT |
| | | 55 | A-30821 | 5' UGCUCUGAAAUUcAGCcAGdTdTL10 |
| CD45 | AD-3635 | 56 | A-30676 | 5' cuGGcuGAAuuucAGAGcAdTdTQ51sL37 |
| | | 57 | A-30687 | 5' Q39UGCUCUGAAAUUcAGCcAGdTsdT |
| CD45 | AD-3636 | 58 | A-30676 | 5' cuGGcuGAAuuucAGAGcAdTdTQ51sL37 |
| | | 59 | A-30695 | 5' Q39UGCUCUGAAAUUcAGCcAGdTdTsL10 |
| CD45 | AD-3599 | 60 | A-30592 | 5' cuGGcuGAAuuucAGAGcAdTdTQ51L37 |
| | | 61 | A-22826 | 5' UGCUCUGAAAUUcAGCcAGdTsdT |
| CD45 | AD-18744 | 62 | A-31653 | 5' cuGGcuGAAuuucAGAGcAdTsdTL37 |
| | | 63 | A-30687 | 5' Q39UGCUCUGAAAUUcAGCcAGdTsdT |
| CD45 | AD-18218 | 64 | A-31632 | 5' cuGGcuGAAuuucAGAGcAUUZ32 |
| | | 65 | 31633 and | 5' UGCUCUGAAAUUcAGCcAGUU |
| | | 66 | 31634 | 5' Q67dAdAdCdCdGdTdGdGdTdCdAdTdGdCdTdCdC |
| GFP | AD-18219 | 67 | A-31635 | 5' CcAcAuGAAGcAGcACGACUUUUZ32 |
| | | 68 | 31636 and | 5' UGCUCUGAAAUUcAGCcAGUU |
| | | 69 | 31634 | 5' Q67dAdAdCdCdGdTdGdGdTdCdAdTdGdCdTdCdC |
| CD45 | AD-18367 | 70 | A-31653 | 5' cuGGcuGAAuuucAGAGcAdTsdTL37 |
| | | 71 | A-31015 | 5' ugcucugaaauucagccagdTsdTL63 |
| GFP | AD-18860 | 72 | A-33204 | 5' AcAuGAAGcAGcACGACuUdTdTQ11L37 |
| | | 73 | A-32594 | 5' AAGUCGUGCUGCUUCAUGUdTsdT |
| GFP | AD-18866 | 74 | A-33169 | 5' AcAuGAAGcAGcACGACuUdTsdTL37 |
| | | 75 | A-32594 | 5' AAGUCGUGCUGCUUCAUGUdTsdT |
| GFP | AD-18866 | 76 | A-33169 | 5' AcAuGAAGcAGcACGACuUdTsdTL37 |
| | | 77 | A-32594 | 5' AAGUCGUGCUGCUUCAUGUdTsdT |
| GFP | AD-18576 | 78 | A-32141 | 5' CcAcAuGAAGcAGcACGACusUL102 |
| | | 79 | A-4381 | 5' AAGUCGUGCUGCUUCAUGUGgsusC |
| GFP | AD-18578 | 80 | A-32142 | 5' CcAcAuGAAGcAGcACGACusUL103 |
| | | 81 | A-4381 | 5' AAGUCGUGCUGCUUCAUGUGgsusC |
| GFP | AD-18579 | 82 | A-32142 | 5' CcAcAuGAAGcAGcACGACusUL103 |
| | | 83 | A-32145 | 5' AAGUCGUGCUGCUUCAUGUGgsusCL10 |
| GFP | AD-18580 | 84 | A-32143 | 5' CcAcAuGAAGcAGcACGACusUL104 |
| | | 85 | A-4381 | 5' AAGUCGUGCUGCUUCAUGUGgsusC |

TABLE 4-continued

Oligonucleotides synthesized and evaluated

| Target | Duplex ID | SEQ ID No | S/AS | Sequence 5'-3' |
|---|---|---|---|---|
| GFP | AD-18581 | 86 | A-32143 | 5' CcAcAuGAAGcAGcACGACusUL104 |
|  |  | 87 | A-32145 | 5' AAGUCGUGCUGCUUCAUGUGgsusCL10 |
| GFP | AD-18747 | 88 | A-32593 | 5' AcAuGAAGcAGcACGACuUdTsdT |
|  |  | 89 | A-32592 | 5' AAGUCGUGCUGCUUCAUGUdTdTL48 |
| GFP | AD-18858 | 90 | A-33199 | 5' AcAuGAAGcAGcACGACuUdTdTL10 |
|  |  | 91 | A-32594 | 5' AAGUCGUGCUGCUUCAUGUdTsdT |
| GFP | AD-18861 | 92 | A-33205 | 5' Q11AcAuGAAGcAGcACGACuUdTsdT |
|  |  | 93 | A-32594 | 5' AAGUCGUGCUGCUUCAUGUdTsdT |
| GFP | AD-18862 | 94 | A-33199 | 5' AcAuGAAGcAGcACGACuUdTdTL10 |
|  |  | 95 | A-32592 | 5' AAGUCGUGCUGCUUCAUGUdTdTL48 |
| GFP | AD-18867 | 96 | A-33169 | 5' AcAuGAAGcAGcACGACuUdTsdTL37 |
|  |  | 97 | A-32592 | 5' AAGUCGUGCUGCUUCAUGUdTdTL48 |
| GFP | AD-19084 | 98 | A-33200 | 5' AcAuGAAGcAGcACGACuUdTdTL103 |
|  |  | 99 | A-32592 | 5' AAGUCGUGCUGCUUCAUGUdTdTL48 |
| GFP | AD-19085 | 100 | A-33201 | 5' Q11AcAuGAAGcAGcACGACuUdTdTL103 |
|  |  | 101 | A-32592 | 5' AAGUCGUGCUGCUUCAUGUdTdTL48 |
| GFP | AD-19086 | 102 | A-33203 | 5' AcAuGAAGcAGcACGACuUdTdTQ11L103 |
|  |  | 103 | A-32592 | 5' AAGUCGUGCUGCUUCAUGUdTdTL48 |
| GFP | AD-19087 | 104 | A-33201 | 5' Q11AcAuGAAGcAGcACGACuUdTdTL103 |
|  |  | 105 | A-32594 | 5' AAGUCGUGCUGCUUCAUGUdTsdT |
| GFP | AD-19088 | 106 | A-33203 | 5' AcAuGAAGcAGcACGACuUdTdTQ11L103 |
|  |  | 107 | A-32594 | 5' AAGUCGUGCUGCUUCAUGUdTsdT |
| GFP | AD-19185 | 108 | A-33054 | 5' CcAcAuGAAGcAGcACGACusUL113 |
|  |  | 109 | A-4381 | 5' AAGUCGUGCUGCUUCAUGUGgsusC |
| GFP | AD-18577 | 110 | A-32141 | 5' CcAcAuGAAGcAGcACGACusUL102 |
|  |  | 111 | A-32145 | 5' AAGUCGUGCUGCUUCAUGUGgsusCL10 |
| GFP | AD-18859 | 112 | A-33202 | 5' Q11AcAuGAAGcAGcACGACuUdTsdT |
|  |  | 113 | A-32594 | 5' AAGUCGUGCUGCUUCAUGUdTsdT |
| GFP |  | 114 | A-34122 | AcAuGAAGcAGcACGACuUdTsdTL10 |
|  |  | 115 | A-32594 | AAGUCGUGCUGCUUCAUGUdTsdT |
| GFP |  | 116 | A-34123 | AcAuGAAGcAGcACGACuUdTsdTL103 |
|  |  | 117 | A-32594 | AAGUCGUGCUGCUUCAUGUdTsdT |
| GFP |  | 118 | A-34124 | Q11AcAuGAAGcAGcACGACuUdTsdTL103 |
|  |  | 119 | A-32594 | AAGUCGUGCUGCUUCAUGUdTsdT |
| GFP |  | 120 | A-34125 | Q11AcAuGAAGcAGcACGACuUdTsdTL37 |
|  |  | 121 | A-32594 | AAGUCGUGCUGCUUCAUGUdTsdT |
| GFP |  | 122 | A-34126 | AcAuGAAGcAGcACGACuUdTsdTQ11L103 |
|  |  | 123 | A-32594 | AAGUCGUGCUGCUUCAUGUdTsdT |
| GFP |  | 124 | A-34127 | AcAuGAAGcAGcACGACuUdTsdTQ11L37 |
|  |  | 125 | A-32594 | AAGUCGUGCUGCUUCAUGUdTsdT |

Note:
Lower case = 2'-OMe, S = PS linkage, L37: = N-(folic acidcarboxamidocaproyl)-4-hydroxyprolinol (Hyp-C6-folate), L63: = Oregon Green 488-aminohexylcarboxamidocaproyl-prolinol-4-phosphate, Q8: = N-(aminocaproyl)prolinol-4-phosphate, L8: = N-(cholesterylcarboxamidocaproyl)-3-hydroxy-4-hydroxymethylpyrrolidine, Q38: = Quasar 570 phosphate (BNS-5063, Biosearch Tech), L10: =N-(cholesterylcarboxamidocaproyl)-4-hydroxyprolinol (Hyp-C6-Chol), Q39: = Quasar 705 phosphate (BNS-5067, Biosearch Tech), Q78: = Atto-610-aminohexylphosphate, L102: = N-(folate carboxamidohexadecanoylcarboxamidoethyl-dithio-1, 1-dimethylbutyryl)-4-hydroxyprolinol (Hyp-Me2S-S-C16-folate), L103: = N-(folate carboxamidoethyl-dithio-butyryl)-4-hydroxyprolinol (Hyp-S-S-folate), L104: = N-(folate carboxamidohexadecanoyl)-4-hydroxyprolinol (Hyp-C16-folate), Q11: = N-(cholesterylcarboxamidocaproyl)prolinol-4-phosphate, Q51: = 6-hydroxyhexyldithiohexyiphosphate (Thiol-Modifier C6 S-S Glen Res. 10-1936), L48: = N-(Alexa647-carboxamidocaprooyl)-4-hydroxyprolinol (Hyp-C6-Alexa647), L113: = N-(folate carboxamido-PEG12)-4-hydroxyprolinol (Hyp-PEG12-folate), Q67: = Folate-gamma-carboxamidohexyiphosphate (Folate C6), Z32: GGAGCAUGACCACGG (SEQ ID NO: 126).

TABLE 5

Oligonucleotides synthesized.

| | SEQ ID No | Sequence (5'-3') | Call Mass | Found Mass |
|---|---|---|---|---|
| AL-3435 | 127 | 5' cuG AAG Acc uGA AGA cAA uTT-s-Folate | 7529.02 | 7530.8 |
| AL-3436 | 128 | 5' AUu GUC uUc AGG UCu UcA GTT-s-Folate | 7385.76 | 7386.8 |
| AL-3437 | 129 | 5' GAA CUG UGU GUG AGA GGU CCU-s-Folate | 7499.7 | 7498.7 |
| AL-3482 | 130 | 5' GAA CUG UGU GUG AGA GGU CCU chol-s-Folate | 8203.7 | 8205.2 |
| AL-3480 | 131 | 5' cuG AAG Acc uGA AGA cAA uTT-Chol-s-Folate | 8232.3 | 8234.4 |
| AL-3481 | 132 | 5' GAA CUG UGU GUG AGA GGU CCU-Chol-s- Folate | 8203.7 | 8205.3 |
| AL-3609 | 133 | 5' CUU ACG CUG AGU ACU UCG AdTdT-Chol-C18-Folate 3' | 8369.2 | 8371.70 |
| AL-3610 | 134 | 5' Quasar CUU ACG CUG AGU ACU UCG AdTdT-Chol-C18-Folate 3' | 8989.2 | 8990.15 |
| AL-3611 | 135 | 5' CUU ACG CUG AGU ACU UCG AdTdT-C18-Chol-C18-Folate 3' | 8715.96 | 8715.30 |
| AL-3612 | 136 | 5' Quasar CUU ACG CUG AGU ACU UCG AdTdT-C18-Chol-C18-Folate 3' | 9333.96 | 9334.36 |
| AL-3639 | 137 | 5' CUU ACG CUG AGU ACU UCG ATT-C12S-S-Folate 3' | 7650.05 | 7650.26 |
| AL-3640 | 138 | 5' Quasar CUU ACG CUG AGU ACU UCG ATT-C12S-S-Folate 3' | 8270.26 | 8270.18 |
| AL-3664 | 139 | 5' CUU ACG CUG AGU ACU UCG ATT-C12S-S-C18-Folate 3' | 7994.35 | 7994.71 |
| AL-3665 | 140 | 5' Quasar CUU ACG CUG AGU ACU UCG ATT-C12S-S-C18-Folate 3' | 8614.67 | 8614.47 |
| AL-3668 | 141 | 5' cuG AAG Acc uGA AGA cAA uTT C12S-S-Folate 3' | 7841.35 | 7841.37 |
| AL-3669 | 142 | 5' Quasar cuG AAG Acc uGA AGA cAA uTT C12S-S-Folate 3' | 8461.59 | 8461.47 |
| AL-3670 | 143 | 5' cuG AAG Acc uGA AGA cAA uTT C12S-S-C18-Folate 3' | 8185.68 | 8186.05 |
| AL-3671 | 144 | 5' Quasar cuG AAG Acc uGA AGA cAA uTT C12S-S-C18-Folate 3' | 8805.99 | 8805.83 |

Quasar = Cy3; C18 = Spacer C18 linker, C12 S-S = disulfide linker, Chol = Cholesterol, lower case = 2'-o-Me, s = phosphorothioate linkage, Folate = Folate. See FIG 1-8 for a graphical representation of sequences with the associated conjugates and structure of monomers used.

TABLE 6

Oligonucleotides synthesized.

| | SEQ ID No | Sequence (5'-3') | Cal Mass | Found Mass |
|---|---|---|---|---|
| Al-30658 | 145 | 5' Cy-3 cuuacgcugaguacuucgadTdT-Hyp-NH₂ | 7786.5 | 7784.3 |
| Al-30660 | 146 | 5' ucgaaguacucagcguaagdTdT-Hyp-NH₂ 3' | 7251.1 | 7250.6 |
| Al-30659 | 147 | 5' Cy-3 cuuacgcugaguacuucgadTdT-Folate 3' | 8209.9 | 8207.8 |
| Al-30661 | 148 | 5' ucgaaguacucagcguaagdTdT-cholesterol | 76634.4 | 7663.6 |
| Al-30676 | 149 | 5' cuGGcuGAAuuucAGAGcAdTdT-C6-S-S-C6-s-Folate | 7856.4 | 7855.4 |
| Al-30677 | 150 | 5' AccGAAAGGucuuAccGGAdTdT-C6-S-S-C6-s-Folate | 7864.4 | 7863.4 |
| Al-30678 | 151 | 5' CcAcAuGAAGcAGcACGACuU-C6-S-S-C6-s-Folate | 7822.3 | 7821.2 |
| Al-30673 | 152 | 5' UGCUCUGAAAUUcAGCcAGdTdTs-cholesterol | 7379.0 | 7377.1 |
| Al-30674 | 153 | 5' UCCGGuAAGACCUUUCGGUdTdTs-cholesterol | 7357.9 | 7357.1 |
| Al-3389 | 154 | 5' AAGUCGUGCUGCUUCAUGUGgusCs-cholesterol | 8082.4 | 8081.1 |
| Al-24775 | 155 | 5' UCCGGuAAGACCUUUCGGUdTsdT | 6653.1 | 6652.3 |
| Al-4381 | 156 | 5' AAGUCGUGCUGCUUCAUGUGgsusC | 7277.5 | 7376.6 |

TABLE 6-continued

Oligonucleotides synthesized.

| SEQ ID No | Sequence (5'-3') | Cal Mass | Found Mass |
|---|---|---|---|
| Al-30687 157 | 5' Cy-5.5 UGCUCUGAAAUUcAGCcAGTsT | 7421.0 | 27420.4 |
| Al-30695 158 | 5' Cy-5.5 UGCUCUGAAAUUcAGCcAGTTs-cholesterol | 8125.9 | 8124.6 |

Hyp-NH2 = Hydroxy prolinol linker; Cy3 = Cy3 dye; Cy5.5 = Cy-5.5 dye; C6 S-S-C6 = disulfide linker; Chol = Cholesterol; lower case = 2'-O-Me; Folate = Folate; s = phosphorothioate linkage.

TABLE 7

Some more folate-conjugated duplexes.

| Al-Duplex # | SEQ ID No | Sequences | Duplex Concentration |
|---|---|---|---|
| AD-3513 | 159 | 5' Cy-3 cuuacgcugaguacuucgadTdT-Hyp-NH$_2$ | 10 mg/ml |
|  | 160 | 5' ucgaaguacucagcguaagdTdT-Hyp-NH$_2$ 3' |  |
| AD-3514 | 161 | 5' Cy-3 cuuacgcugaguacuucgadTdT-Folate 3' | 10 mg/ml |
|  | 162 | 5' ucgaaguacucagcguaagdTdT-Hyp-NH$_2$ |  |
| AD-3515 | 163 | 5' Cy-3 cuuacgcugaguacuucgadTdT-Folate | 10 mg/ml |
|  | 164 | 5' ucgaaguacucagcguaagdTdT-Hyp-Cholesterol |  |

Hyp-NH2 = Hydroxy prolinol linker; Cy3 = Cy3 dye; Chol = Cholesterol; lower case = 2'-O-Me; Folate = Folate;

Example 14

Binding Competition Assays

Figure 10:
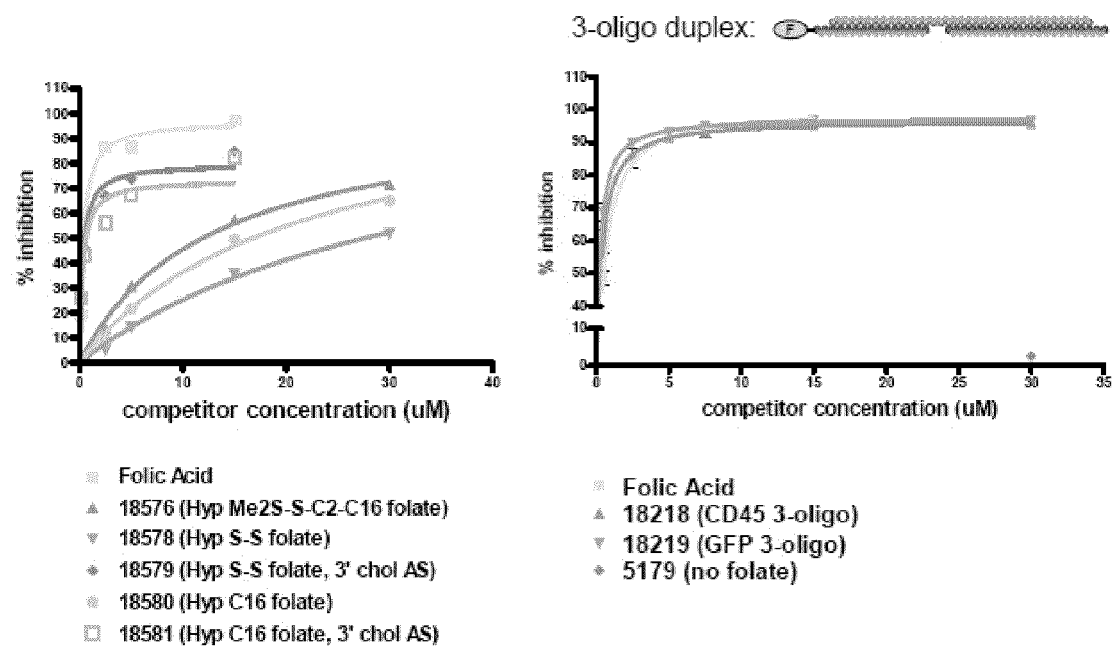
FIG. 10. Comparison of binding of various folate conjugates to folate receptor.

Folate conjugated siRNAs were incubated with KB cells in presence of FTIC-folate (PBS, on Ice). % competition for folate receptor (FR) was plotted as a measure of activity. FIG. 10 shows that different folate conjugates had different binding competition but sequence of the oligonucleotide made no difference on binding competition. The Kd were calculated from the binding assays and are reported in table 8. The 3' sense folate with cleavable or non-cleavable linkers shows lower affinity for FR than folic acid. Introduction of 3' antisense cholesterol improves binding by ~50 fold. 5' folate attached to a DNA-oligo tether binds to FR with an affinity similar to that of folic acid. FR ligands have a slow off-rate—no significant competition is observed if FITC-folate is added 1$^{st}$.

TABLE 8

Folate receptor binding of folate conjugated siRNAs

| duplex # | sense | antisense | KD (uM) |
|---|---|---|---|
| AD-18218 | 5' extended | 5' folate DNA oligo | 0.3 |
| AD-18219 | 5' extended | 5' folate DNA oligo | 0.2 |
| AD-18576 | 3'-Hyp-Me2S-S-C2-C16-folate | unconjugated | 12.5 |
| AD-18578 | 3'-Hyp-S-S-folate | unconjugated | 34.8 |
| AD-18579 | 3'-Hyp-S-S-folate | 3' chol | 0.3 |
| AD-18580 | 3'-Hyp-C16-folate | unconjugated | 20.7 |
| AD-18581 | 3'-Hyp-C16-folate sense | 3' chol | 0.3 |
| AD-3614 | 3'C6-SS-C6-Hyp folate | 3' chol | 0.2 |
| AD-3617 | 3'C6-SS-C6-Hyp folate | unconjugated | 13.7 |

Example 15

Folate GFP Duplexes, In Vitro Silencing with Transfection Reagent

Figure 11:
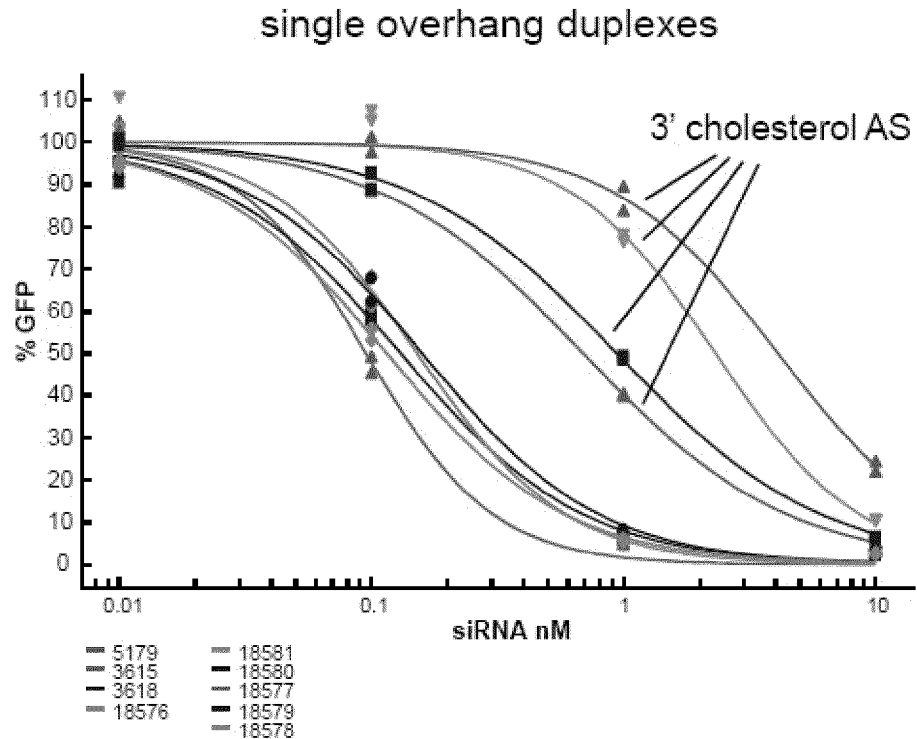
FIG. 11. Effect of folate conjugation on the silencing activity of siRNAs.
Figure 11:
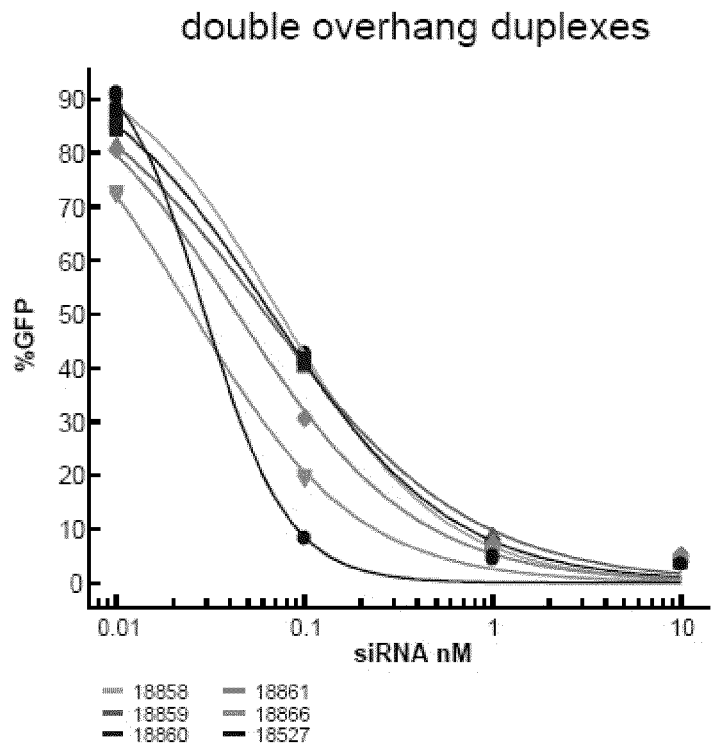

KB pEGFP clone 17 cells were used for all GFP silencing experiments. For silencing experiments with transfection reagent HiPerFect was used to transfect in the siRNAs tested and GFP expression was analyzed 72 hrs later. As seen in FIG. 11, presence of folate ligands (multiple linker designs) at the 3' of the sense strand does not significantly impact silencing activity. 3' antisense cholesterol decreased activity by 10× or greater depending on design, similar trends were observed for CD45 duplexes. Addition of 3' sense folate to 3' or 5' sense cholesterol duplex does not significantly alter silencing activity.

Example 16

Free Uptake Silencing Activity

Silencing by free uptake was evaluated in the KB-EGFP cells, a cell line stably expressing the EGFP gene. KB-EGFP cells were cultured continuously in folate free media with 10% FBS. For free uptake silencing folate-siRNA conjugates were added to KB-EGFP cells in 24-well plates in media with or without serum. For the "no serum" wells complete media (with 10% FBS) was added 4 hrs later. Cells were cultured for 72 hrs, removed from plates using Versene, washed and GFP expression quantified by flow cytometry on a LSRII instrument. Data was analyzed using the FlowJo software and median fluorescence intensity of the GFP signal was plotted. As seen in Table 9, various tethers and linker designs containing folate conjugates can be accommodated at the 3'-end of the sense strand without affecting RNAi activity. 25% silencing by free uptake is observed for folate conjugated siRNA at 5 uM concentration independent of serum. siRNAs comprising both cholesterol and folate show 40% silencing by free uptake in absence of serum at 5 uM.

TABLE 9

Free uptake of folate conjugated siRNAs

| duplex # | sense | antisense | KD (uM) | IC$_{50}$ (nM) | % free uptake silencing (5 uM, no serum) |
|---|---|---|---|---|---|
| singe overhang | | | | | |
| AD-5179 | unconjugated | unconjugated | ND | 0.09 | 0 |
| AD-3618 | 3' C6-SS-C6-Hyp folate | unconjugated | ND | 0.13 | 0 |
| AD-3615 | 3' C6-SS-C6-Hyp folate | 3' chol | ND | 0.69 | 0 |
| AD-18576 | 3'-Hyp-Me2S-S-C2-C16-folate | unconjugated | 12.5 | 0.12 | 10 |
| AD-18577 | 3'-Hyp-Me2S-S-C2-C16-folate | 3' chol | ND | 4.09 | ND |
| AD-18578 | 3'-Hyp-S-S-folate | unconjugated | 34.8 | 0.09 | 0 |
| AD-18579 | 3'-Hyp-S-S-folate | 3' chol | 0.3 | 0.80 | 20 |
| AD-18580 | 3'-Hyp-C16-folate | unconjugated | 20.7 | 0.14 | 0 |
| AD-18581 | 3'-Hyp-C16-folate sense | 3' chol | 0.3 | 2.04 | 0 |
| double overhang | | | | | |
| AD-18527 | unconjugated | unconjugated | ND | 0.03 | 0 |
| AD-18526 | unconjugated | 3' chol | ND | 2.08 | ND |
| AD-18858 | 3' cholesterol | unconjugated | ND | 0.07 | 80 |
| AD-18861 | 5' cholesterol | unconjugated | ND | 0.06 | 40 |
| AD-18859 | 5' cholesterol, 3' folate | unconjugated | ND | 0.07 | 40 |
| AD-18860 | 3' cholesterol, 3' folate | unconjugated | ND | 0.04 | 40 |
| AD-18866 | 3' Hyp-C6 folate | unconjugated | ND | 0.03 | 25 |
| 3-oligo duplex | | | | | |
| AD-18219 | 5' extended | 5' folate DNA oligo | 0.2 | 0.16 | 0 |

Example 17

Serum Stability of Folate Conjugated Oligonucleotides siRNAs comprising folate conjugates with a cleavable linker were incubated in mouse serum at 37° C. for 0, 0.5, 1, 2, 6, 16 and 24 hours. After incubation, amount of individual strands were quantified by IEX HPLC. Sense strand $t_{1/2}$ decreased by 5-78× depending on the sequence. Table 10 summarizes the $t_{1/2}$ of individual strands of tested siRNAs. For a 3' sense folate a gem-dimethyl linker duplex is more stable in serum then an unhindered disulfide linked duplex. The 3' sense folate duplex with a C16 non-cleavable linker is as stable as the unmodified parent duplex. The 3' sense folate duplexes with a Glen research disulfide linker show the lowest serum stability, however these molecules also lack the PS group in the overhang.

TABLE 10

Serum stability of folate conjugated duplexes in mouse serum
(table discloses SEQ ID NOS 165-178, respectively, in order of appearance)

| Duplex | Single Strand | Strand Type | 5-3 Full Strand | Half-life (h) |
|---|---|---|---|---|
| AD-3215 | 22825 | s | 5'-cuGGcuGAAuuucAGAGcAdTsdT | 6.58 |
|  | 22826 | as | 5' UGCUCUGAAAUUcAGCcAGdTsdT | 1.83 |
| AD-3616 | 30676 | s | 5'-cuGGcuGAAuuucAGAGcAdThT-C6-S-S-C6-folate | 1.22 |
|  | 22826 | as | UGCUCUGAAAUUcAGCcAGdTsdT | 2.90 |
| AD-5179 | 4545-b1 | s | CcAcAuGAAGcAGcACGAGusU | 15.00 |
|  | 4381-b11 | as | AAGUCGUGCUGCUUCAUGUGgsusC | 11.50 |
| AD-3618 | 30678 | s | 5' CcAcAuGAAGcAGcACGACuU-C6-S-S-C6-Folate | 0.19 |
|  | 4381 | as | AAGUCGUGCUGCUUCAUGUGgsusC | 1.59 |
| AD-18576 | 32141 | s | CcAcAUGAAGcAGcACGACusU-Hyp-Me2S-S-C16-folate | 15.36 |
|  | 4381 | as | AAGUCGUGCUGCUUCAUGUGgsusC | 8.22 |
| AD-16578 | 32142 | s | CcAcAuGAAGcAGcACGACusU-Hyp-S-S-folate | 6.39 |
|  | 4381 | as | AAGUCGUGCUGCUUGAUGUGgsusC | 4.69 |
| AD-18680 | 32143 | s | CcAcAuCAAGcAGcACGACusU-Hyp-C16-folate | 15.72 |
|  | 4381 | as | AAGUCGUGCUGCUUGAUGUGgsusC | 10.44 |

Example 18

In vivo Folate Conjugate Distribution in KB Xenograft Tumor Model

Figure 12:
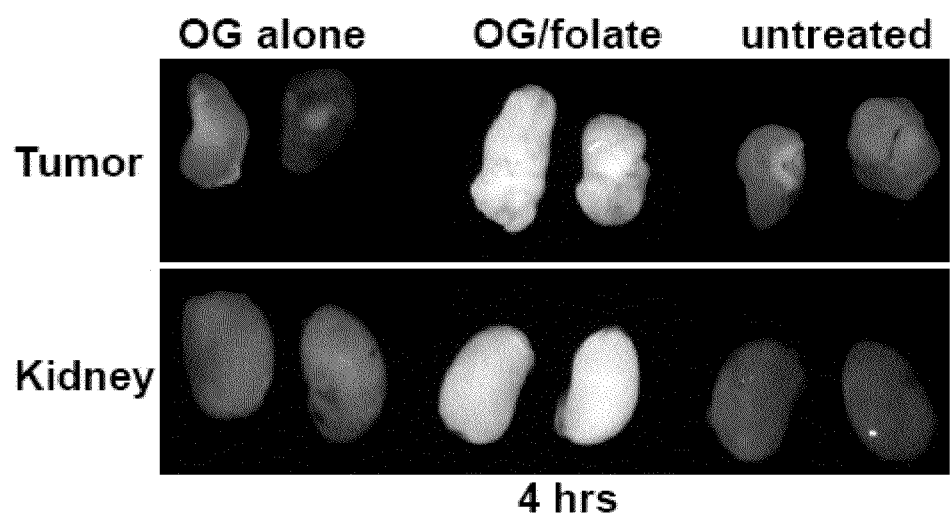
FIG. 12. In vivo targeting of folate conjugated siRNAs.
Figure 13:
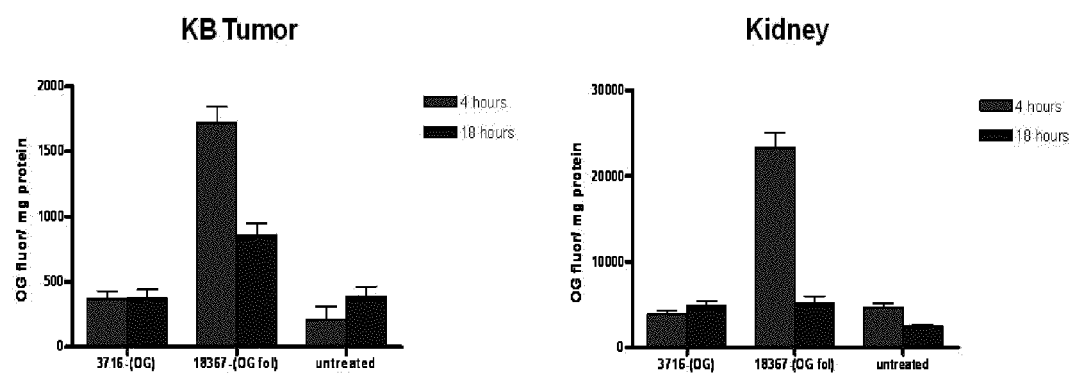
FIG. 13. Tissue levels of folate conjugated siRNAs in vivo.
Figure 14:
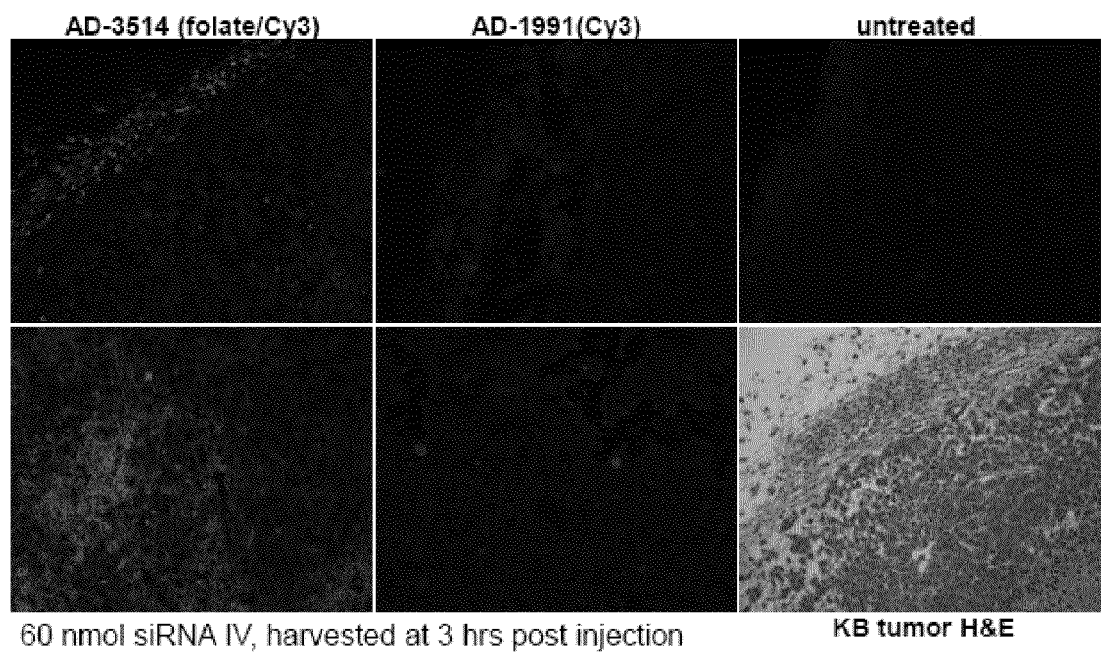
FIG. 14. Tumor distribution of folate conjugated siRNAs.
Figure 14:
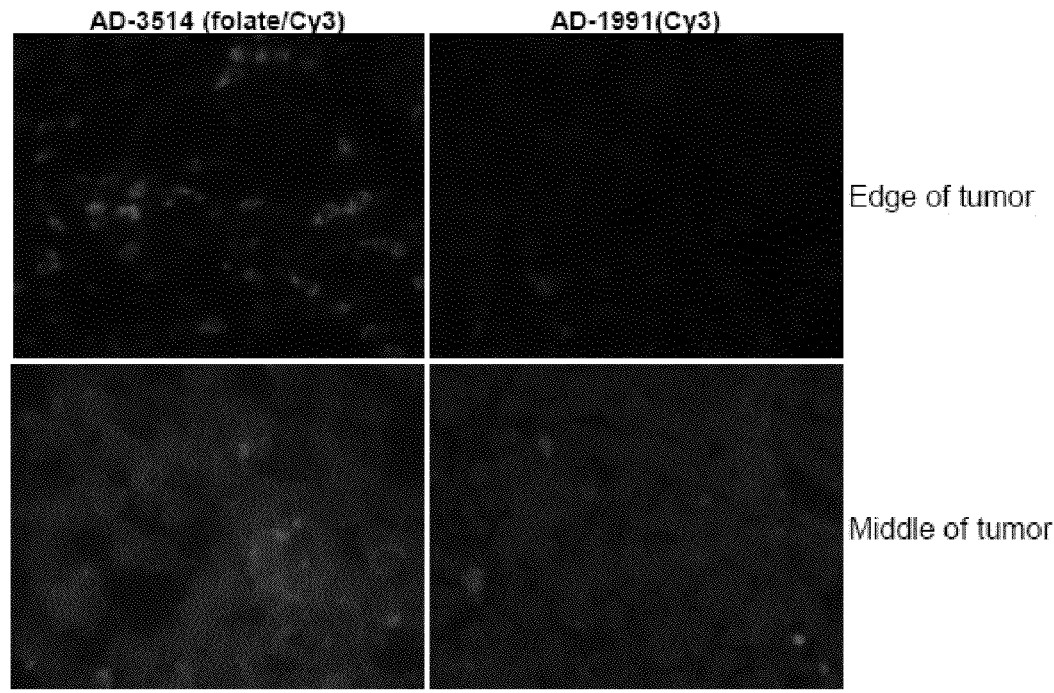

KB cells were injected subcutaneously on both flanks of Nu/Nu mice ($3 \times 10^6$ cells per site). Tumors were allowed to develop for 2 weeks. Mice were injected with 60 nmol fluorophore and folate conjugated siRNAs. Mice were saced at the desired time point and tumors and kidneys harvested for imaging on the Maestro imaging system and downstream processing. For lysate assays tissues were frozen and ground to powder using a mortar and pestle. Tissue powders (20 mg) were lysed using the Mammalian Cell Lysis Kit (Sigma). Protein concentration was quantified using the BCA assay, Oregon Green fluorescence in lysates was quantified using the Victor plate reader. For tumor sections, animals were perfused with 4% PFA upon sacrifice, tumors were harvested and cryoprotected in 30% sucrose. Tumors were sectioned by cryostat. Sections were post-fixed with PFA and stained for mouse CD11b or F4/80 macrophage markers. Sections were imaged on the Axiovision fluorescence microscope and fluorescence normalized to protein concentration. Conjugated siRNAs AD-18367 (3' non-cleavable folate sense and 3' OregonGreen antisense) and AD-3716 (3' OregonGreen antisense) were used. Figure x shows the accumulation of folate conjugated siRNA (AD-18367) in the tumor and kidney at 4 hours. FIG. 12 show tissue uptake of folate conjugated siRNA at 4 hour and 18 hours after injection. As can be seen in FIG. 13, folate conjugated siRNA was present in significant amount in the tumor after 18 hours. FIG. 14 shows the accumulation of Cy3 labeled folate conjugated siRNAs in tumors. Accumulation was only seen when the siRNA had a folate conjugate, thus confirming targeting by folate conjugates.

Figure 15:
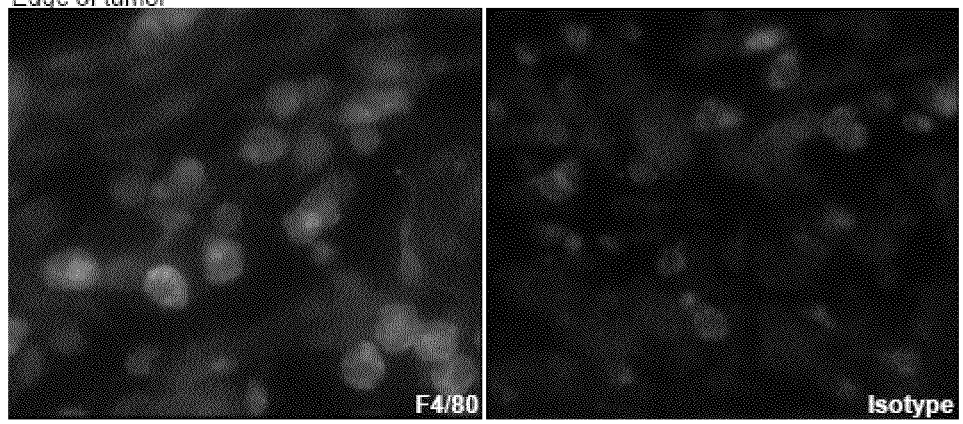
FIG. 15. Co-localization of folate conjugated siRNAs with macrophages.

Sections from a tumor treated with folate conjugated Cy3 labeled siRNA (AD-3514) were strained with an antibody to mouse F4/80 or an isotype control. Results are shown in FIG. 15.

Example 19

KB EGFP Tumors in Nude Mice

Figure 16:
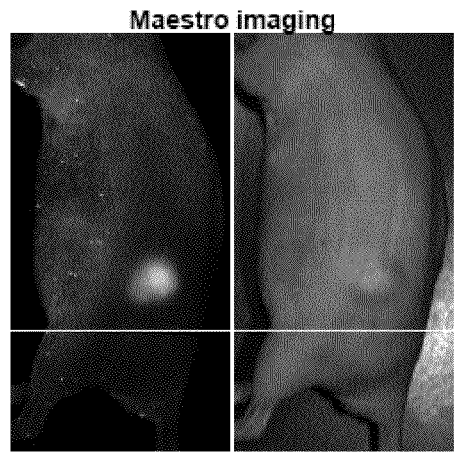
FIG. 16. Establishment of KB EGFP tumors in nude mice.
Figure 16:
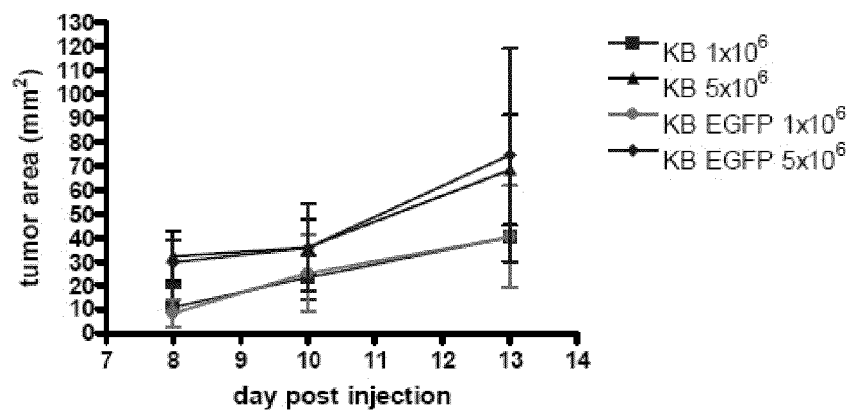
Figure 16:
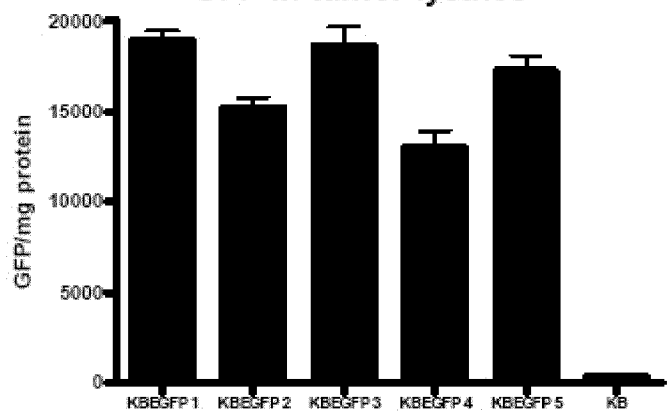
Figure 17:
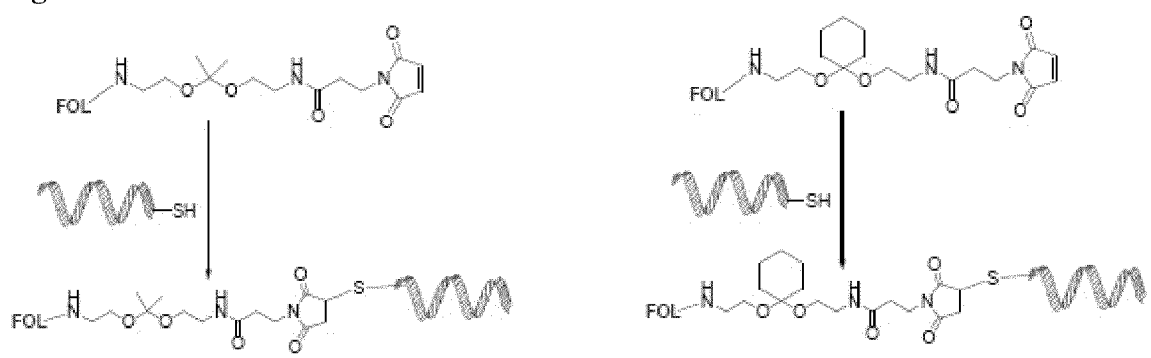
FIG. 17. Conjugates with endosomolytic linkers.

Nu/Nu mice were SC implemented with KB or KB EGFP cells. Tumors were imaged on the Maestro system. Tumor lysates were prepared to measure GFP levels. FIG. 16 shows results of tumor establishment and GFP levels in the tumors.

---

We claim:

1. An iRNA agent comprising at least one monomer having the structure shown in formula (I')

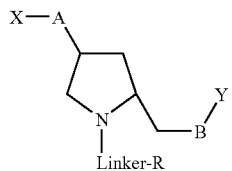

wherein:

A and B are each independently for each occurrence O, N($R^N$) or S;

X is H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, —P(Z')(Z")O-$L^6$-Q'-$L^7$-P(Z''')(Z"")O-oligonucleotide, a nucleotide, or an oligonucleotide;

Y is H, a protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a lipophile, a polymer, —P(Z')(Z")O-$L^6$-Q'-$L^7$-OP(Z''')(Z"")O-oligonucleotide, a nucleotide, or an oligonucleotide;

R is folate, a folate analog a folate mimic or a folate receptor binding ligand;

$L^6$ and $L^7$ are each independently for each occurrence —(CH$_2$)$_n$—, —C(R')(R")(CH$_2$)$_n$—, —(CH$_2$)$_n$C(R')(R")—, —(CH$_2$CH$_2$O)$_m$CH$_2$CH$_2$—, or —(CH$_2$CH$_2$O)$_m$ CH$_2$CH$_2$NH—;

Q' is NH, O, S, CH$_2$, C(O)O, C(O)NH, —NH—CH($R^a$)—C(O)—, —C(O)—CH($R^a$)—NH—, CO,

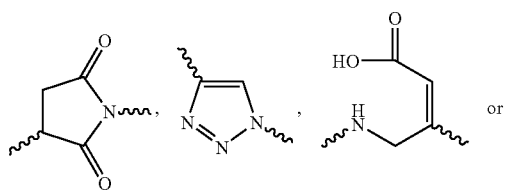

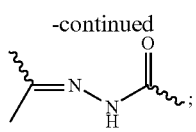

$R^a$ is H or amino acid side chain;

R' and R" are each independently H, CH$_3$, OH, SH, NH$_2$, NH(Alkyl) or N(diAlkyl);

Z', Z", Z''' and Z"" are independently O or S;

n represent independently for each occurrence 1-20; and m represent independently for each occurrence 0-50.

2. An iRNA agent comprising at least one monomer having the structure shown in formula (I)

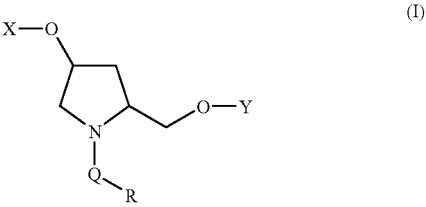

wherein:

X is H, a hydroxyl protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a polymer, —P(Z')(Z")O-$L^6$-Q'-$L^7$-OP(Z''')(Z"")O-oligonucleotide, a nucleotide, or an oligonucleotide;

Y is H, a hydroxyl protecting group, a phosphate group, a phosphodiester group, an activated phosphate group, an activated phosphite group, a phosphoramidite, a solid support, —P(Z')(Z")O-nucleoside, —P(Z')(Z")O-oligonucleotide, a lipid, a PEG, a steroid, a lipophile, a polymer, —P(Z')(Z")O-$L^6$-Q'-$L^7$-OP(Z''')(Z"")O- ligonucleotide, a nucleotide, or an oligonucleotide;

Q is a tether;

R is folate, a folate analog a folate mimic or a folate receptor binding ligand;

$L^6$ and $L^7$ are each independently for each occurrence —(CH$_2$)$_n$—, —C(R')(R")(CH$_2$)$_n$—, —(CH$_2$)$_n$C(R')(R")—, —(CH$_2$CH$_2$O)$_m$CH$_2$CH$_2$—, or —(CH$_2$CH$_2$O)$_m$ CH$_2$CH$_2$NH—;

Q' is NH, O, S, CH$_2$, C(O)O, C(O)NH, —NH—CH($R^a$)—C(O)—, —C(O)—CH($R^a$)—NH—, CO,

257

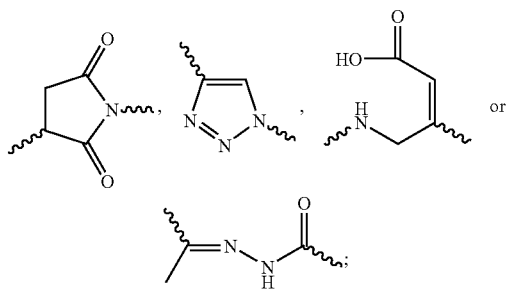

Rª is H or amino acid side chain;
R' and R" are each independently H, CH₃, OH, SH, NH₂, NH(Alkyl) or N(diAlkyl);
Z', Z", Z'" and Z"" are independently O or S;
n represent independently for each occurrence 1-20; and
m represent independently for each occurrence 0-50.

3. The iRNA agent of claim 1, wherein said iRNA agent is double stranded.
4. The iRNA agent of claim 3, wherein said monomer is at the 3'-end of one of the strands.
5. The iRNA agent of claim 4, wherein said monomer is at the 3'-end of sense strand.
6. The iRNA agent of claim 1, wherein the iRNA agent further comprises at least one monomer of formula (LI)

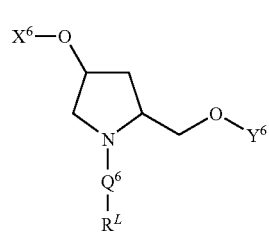

Formula (LI)

wherein X⁶ and Y⁶ are each independently H, a hydroxyl protecting group, a phosphate group, a phosphodiester group, an activated phosphate group, an activated phosphate group, a phosphoramidite, a solid support, —P(Z')(Z")O-nucleoside, —P(Z')(Z")O-oligonucleotide, a lipid, a PEG, a steroid, a polymer, —P(Z')(Z")O—R¹-Q'-R²—OP(Z'")(Z"")O-oligonucleotide, a nucleotide, or an oligonucleotide, —P(Z')(Z")-formula (I) or —P(Z')(Z")—;

Q⁶ is absent or —(P⁶-Q⁶-R⁶)ᵥ-T⁶-;
P⁶ and T⁶ are each independently for each occurrence absent, CO, NH, O, S, OC(O), NHC(O), CH₂, CH₂NH or CH₂O;
Q⁶ is independently for each occurrence absent, substituted alkylene wherein one or more methylenes can be interrupted or terminated by one or more of O, S, S(O), SO₂, N(Rᴺ), C(R')═C(R'), C≡C or C(O);
R⁶ is independently for each occurrence absent, NH, O, S, CH₂, C(O)O, C(O)NH, NHCH(Rª)C(O), —C(O)—CH (Rª)—NH—, CO, CH═N—O,

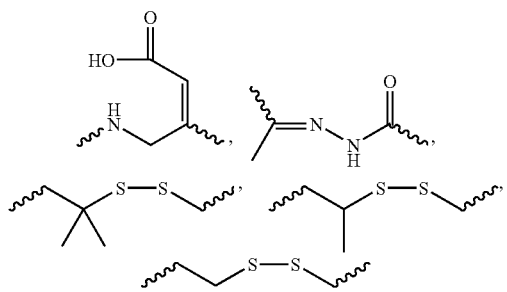

or heterocyclyl;
R' and R" are each independently H, C₁-C₆ alkyl OH, SH, N(Rᴺ)₂;
Rᴺ is independently for each occurrence methyl, ethyl, propyl, isopropyl, butyl or benzyl;
Rª is H or amino acid side chain;
Z', Z", Z'" and Z"" are each independently for each occurrence O or S;
v represent independently for each occurrence 0-20;
Rᴸ is a lipophile or a cationic lipid.

7. The RNAi agent of claim 6, wherein Rᴸ is a lipophile.
8. The RNAi agent of claim 7, wherein Rᴸ is cholesterol.
9. The RNAi agent of claim 1, wherein R is chosen from a group consisting of

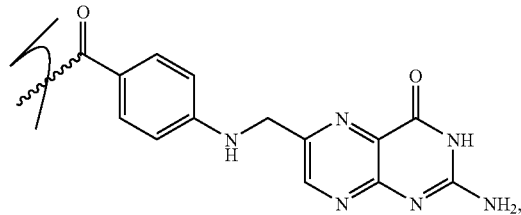

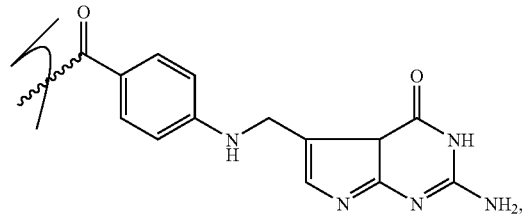

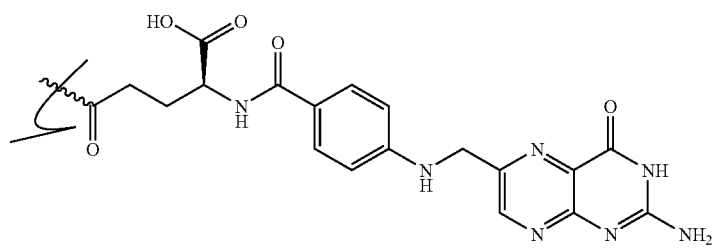

-continued
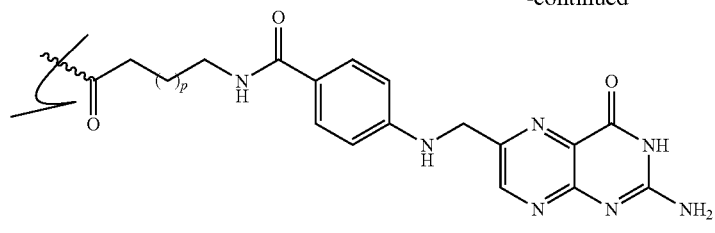
p = 1, 3, 8, 13, 19
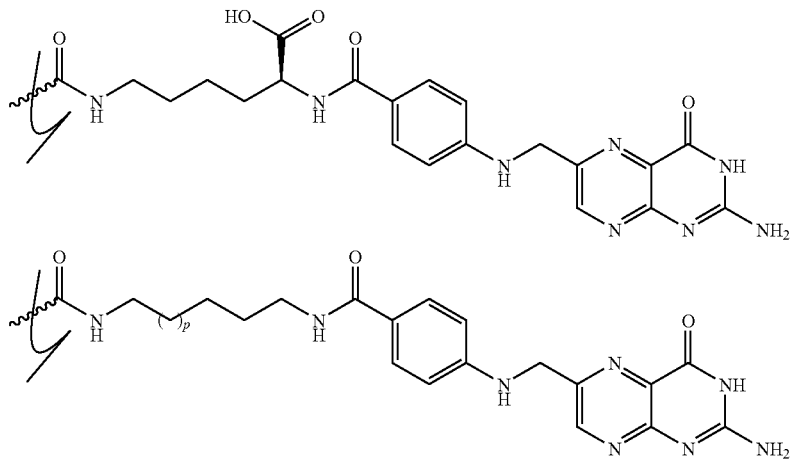
p = 1, 2, 7, 12, 18
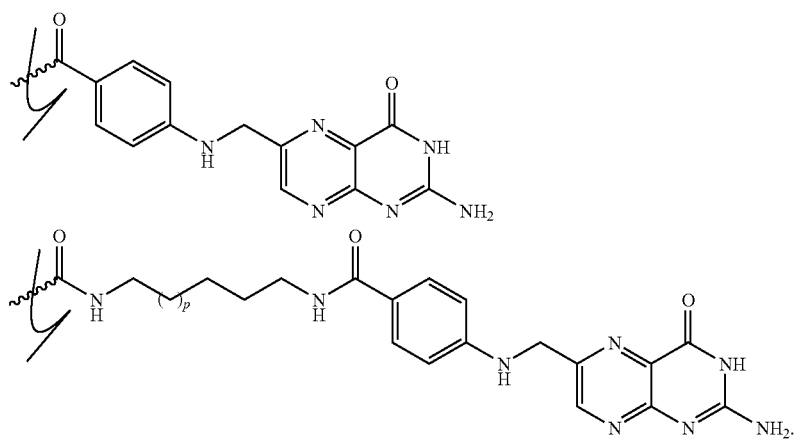
p = 1, 2, 7, 12, 18
10. The RNAi agent of claim 1, wherein said monomer is chosen from a group consisting of
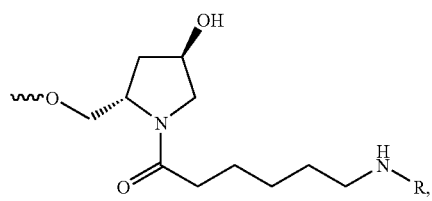 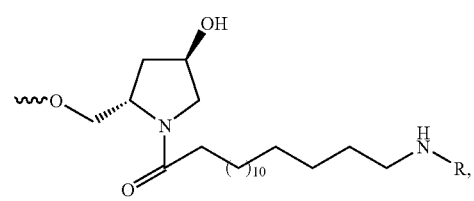

-continued

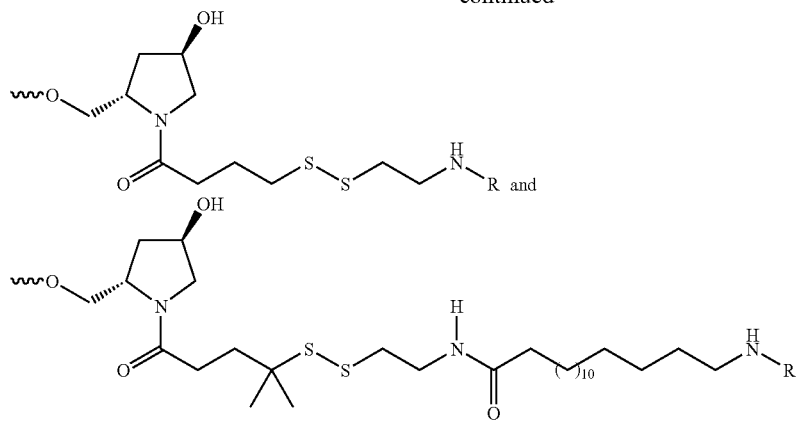

11. The RNAi agent of claim 10, wherein R is

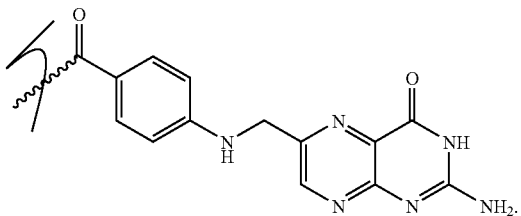

12. A method of modulating the expression of a target gene in a cell, comprising providing to said cell an iRNA agent of claim 1.

13. The method of claim 12, wherein the target gene is selected from the group consisting of CD45, GFP, Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

14. A pharmaceutical composition comprising an iRNA agent of claim 1 alone or in combination with a pharmaceutically acceptable carrier or excipient.

\* \* \* \* \*